(12) United States Patent
Zhang et al.

(10) Patent No.: US 10,006,064 B2
(45) Date of Patent: Jun. 26, 2018

(54) BIOSYNTHETIC PATHWAYS, RECOMBINANT CELLS, AND METHODS

(71) Applicant: REGENTS OF THE UNIVERSITY OF MINNESOTA, Minneapolis, MN (US)

(72) Inventors: Kechun Zhang, Minneapolis, MN (US); Mingyong Xiong, St. Paul, MN (US); Yi-Shu Tai, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days. days.

(21) Appl. No.: 14/404,125

(22) PCT Filed: Mar. 14, 2013

(86) PCT No.: PCT/US2013/031470
§ 371 (c)(1),
(2) Date: Nov. 26, 2014

(87) PCT Pub. No.: WO2013/180810
PCT Pub. Date: Dec. 5, 2013

(65) Prior Publication Data
US 2015/0140620 A1 May 21, 2015

Related U.S. Application Data

(60) Provisional application No. 61/652,505, filed on May 29, 2012.

(51) Int. Cl.
*C12P 7/62* (2006.01)
*C12N 9/10* (2006.01)

(52) U.S. Cl.
CPC .............. *C12P 7/62* (2013.01); *C12N 9/1029* (2013.01)

(58) Field of Classification Search
None
See application file for complete search history.

(56) References Cited

U.S. PATENT DOCUMENTS 8,633,002 B2 * 1/2014 Roessler .............. C12N 9/0008
435/132

FOREIGN PATENT DOCUMENTS

| CN | 101680009 A | 3/2010 |
| WO | WO 2008/119082 * | 2/2008 |
| WO | WO 2012/109534 A2 | 8/2012 |

OTHER PUBLICATIONS

Atsumi et al.,"Non-fermentative pathways for synthesis of branched-chain higher alcohols as biofuels", Nature 451(7174):86-89 (Jan. 2008).*

International Search Report and Written Opinion of PCT/US2013/031470, issued by the European Patent Office as the International Search Authority, dated Jul. 4, 2013; 13 pgs.
International Preliminary Report on Patentability of PCT/US2013/031470, issued by the International Bureau of WIPO, dated Dec. 11, 2014; 9 pgs.
Baez et al., "High-flux isobutanol production using engineered *Escherichia coli*: a bioreactor study with in situ product removal," *Appl Microbiol Biotechnol*, 2011;90(5):1681-1690.
Conner et al., "3-Methyl-1-butanol production in *Escherichia coli*: random mutagenesis and two-phase fermentation," *Appl Microbiol Biotechnol*, 2010;86(4):1155-1164.
D'Auria et al. "Characterization of an acyltransferase capable of synthesizing benzylbenzoate and other volatile esters in flowers and damaged leaves of *Clarkia breweri*," *Plant Physiol*, Sep. 2002;130(1):466-476.
Dhande et al., "Production of C5 carboxylic acids in engineered *Escherichia coli*," *Process Biochem*, Jul. 11, 2012;47:1965-1971.
Duan et al., "De novo Biosynthesis of Biodisel by *Escherichia coli* in Optimized Fed-Batch Cultivation," *PLoS One*, May 2011;6(5):e20265: 7 pgs.
Gibson et al., "Enzymatic assembly of DNA molecules up to several hundred kilobases," *Nature Methods*, May 2009:6(5):343-345.
Hashimoto et al., "Nitrile pathway involving acyl-CoA synthetase," *J Biol Chem*, Mar. 11, 2005;280(10):8660-8667.
Hoover et al, "DNAWorks: an automated method for designing oligonucleotides for PCR-based gene synthesis," *Nucleic Acids Res*, May 2002;30(10):e43: 7 pgs.
Lin et al., "Metabolic engineering of aerobic succinate production systems in *Escherichia coli* to improve process productivity and achieve the maximum theoretical succinate yield," *Metab Eng*, 2005;7(2):116-127.
Liu et al., "Quantitative analysis and engineering of fatty acid biosynthesis in *E. coli*," *Metab Eng*, 2010;12(4):378-386.
Marcheschi et al. "A synthetic recursive '+1' pathway for carbon chain elongation," *ACS Chem. Biol.*, Jan. 13, 2012;7:689-697.
National Center for Biotechnology Information, National Library of Medicine, National Institutes of Health, GenBank Locus NP_746515, Accession No. NP_746515, "bkdA1 gene product [*Pseudomonas putida* KT2440]," [online]. Bethesda, MD [retrieved on May 29, 2012]. Retrieved from the Internet: <URL:http://www.ncbi.nlm.nih.gov/protein/26991090>; 2 pgs.
National Center for Biotechnology Information, National Library of Medicine, National Institutes of Health, GenBank Locus NP_742717, Accession No. NP_742717, "acoB gene product [*Pseudomonas putida* KT2440]," [online]. Bethesda, MD [retrieved on May 29, 2012]. Retrieved from the Internet: <URL:http://www.ncbi.nlm.nih.gov/protein/26987292>; 2 pgs.

(Continued)

*Primary Examiner* — Anand U Desai
(74) *Attorney, Agent, or Firm* — Mueting, Raasch & Gebhardt, PA

(57) ABSTRACT

This disclosure describes engineered biosynthetic pathways, recombinant cells, and methods relating to biosynthesis of esters. The recombinant cells may be modified to exhibit increased biosynthesis of an ester compared to a wild-type control. The recombinant cell may be incubated in medium that includes a carbon source under conditions effective for the recombinant cell to produce an ester. This disclosure also describes a method that generally includes introducing into a host cell a heterologous polynucleotide encoding at least one polypeptide that catalyzes a step in converting a carbon source to an ester, wherein the at least one polynucleotide is operably linked to a promoter so that the modified host cell catalyzes conversion of the carbon source to an ester.

7 Claims, 4 Drawing Sheets

(56) References Cited

OTHER PUBLICATIONS

National Center for Biotechnology Information, National Library of Medicine, National Institutes of Health, GenBank Locus NP_746516, Accession No. NP_746516, "bkdA2 gene product [*Pseudomonas putida* KT2440]," [online]. Bethesda, MD [retrieved on May 29, 2012]. Retrieved from the Internet: <URL:http://www.ncbi.nlm.nih.gov/protein/26991091>; 2 pgs.

National Center for Biotechnology Information, National Library of Medicine, National Institutes of Health, GenBank Locus NP_746517, Accession No. NP_746517, "bkdB gene product [*Pseudomonas putida* KT2440]," [online]. Bethesda, MD [retrieved on May 29, 2012]. Retrieved from the Internet: <URL:http://www.ncbi.nlm.nih.gov/protein/NP_746517.1>; 2 pgs.

National Center for Biotechnology Information, National Library of Medicine, National Institutes of Health, GenBank Locus NP_746518, Accession No. NP_746518, "lpdV gene product [*Pseudomonas putida* KT2440]," [online]. Bethesda, MD [retrieved on May 29, 2012]. Retrieved from the Internet: <URL:http://www.ncbi.nlm.nih.gov/protein/26991093>; 2 pgs.

Wang et al., "Evolution of D-lactate dehydrogenase activity from glycerol dehydrogenase and its utility for D-lactate production from lignocellulose," *Proc Natl Acad Sci USA*, 2011;108(47):18920-18925.

Wang et al., "Development of a new strategy for production of medium-chain-length polyhydroxyalkanoates by recombinant *Escherichia coli* via inexpensive non-fatty acid feedstocks," *Appl Environ Microbiol*, Jan. 2012;78:519-527.

Xiong et al., "A bio-catalytic approach to aliphatic ketones," *Scientific Reports*, Mar. 13, 2012;2:1-7.

Yu et al., "Engineering artificial metabolic pathways for biosynthesis," *Curr Opin Chem Eng*, Oct. 7, 2012;1:373-379.

Zhang et al., "A synthetic metabolic pathway for production of the platform chemical isobutryric acid," *ChemSusChem*, 2011;4:1068-1070.

Zhang et al., Industrial partnership for Research in Interfacial and materials Engineering/Research Highlights, 2011; Retrieved from the Internet: URL: http://www.imprime.umn.edu/pdfs/IPrimeResearchHighlights2011.pdf [retrieved on Jun. 6, 201].

* cited by examiner

*Figure 1A*

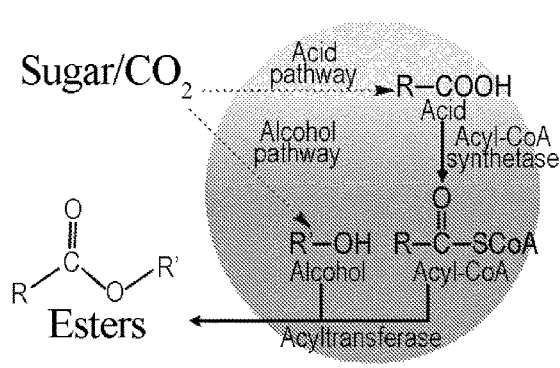

*Figure 1B*

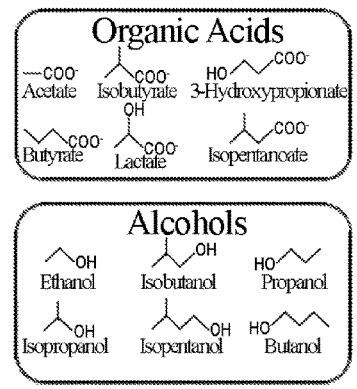

*Figure 1C*

Ester Approach to chemicals of fuels
* Neutral molecules (do not need base during fermentation)
* Low toxicity (high titer is achievable)
* Low water solubility (purification requires minimal energy input)

Properties of medium-chain ester fuels
* High energy density (compatible with existing infrastructure)
* High carbon yield and production rate (competitive against oil)
* Low heat of vaporization (better cold starting)
* Recycle $CO_2$ (carbon neutral)

SEQUENCE LISTING

<160> NUMBER OF SEQ ID NOS: 92

<210> SEQ ID NO 1
<211> LENGTH: 54
<212> TYPE: DNA
<213> ORGANISM: artificial
<220> FEATURE:
<223> OTHER INFORMATION: synthetic oligonucleotide primer

<400> SEQUENCE: 1
tgcatcgaat tcaggagaaa ttaactatga acgagtacgc cccctgcgt ttgc        54

<210> SEQ ID NO 2
<211> LENGTH: 36
<212> TYPE: DNA
<213> ORGANISM: artificial
<220> FEATURE:
<223> OTHER INFORMATION: synthetic oligonucleotide primer

<400> SEQUENCE: 2
tgcatcaagc tttcagatat gcaaggcgtg gcccag        36

<210> SEQ ID NO 3
<211> LENGTH: 60
<212> TYPE: DNA
<213> ORGANISM: artificial
<220> FEATURE:
<223> OTHER INFORMATION: synthetic oligonucleotide primer

<400> SEQUENCE: 3
tgtacggtat taatgtcgac aggagaaatt aactatgctt caactccaaa acaagaaac        60

<210> SEQ ID NO 4
<211> LENGTH: 60
<212> TYPE: DNA
<213> ORGANISM: artificial
<220> FEATURE:
<223> OTHER INFORMATION: synthetic oligonucleotide primer

<400> SEQUENCE: 4
tgatcatgcg ccatagttaa tttctcctgg atccttagac gctggcaggg gtggcctgtt        60

<210> SEQ ID NO 5
<211> LENGTH: 653
<212> TYPE: PRT
<213> ORGANISM: Pseudomonas putida

<400> SEQUENCE: 5

Met Ser Ala Ala Pro Leu Tyr Pro Val Arg Pro Glu Val Ala Ala Thr
1               5                   10                  15

Thr Leu Thr Asp Glu Ala Thr Tyr Lys Ala Met Tyr Gln Gln Ser Val
            20                  25                  30

Ile Asn Pro Asp Gly Phe Trp Arg Glu Gln Ala Gln Arg Ile Asp Trp
        35                  40                  45

Ile Lys Pro Phe Thr Lys Val Lys Gln Thr Ser Phe Asp Asp His His
    50                  55                  60

Val Asp Ile Lys Trp Phe Ala Asp Gly Thr Leu Asn Val Ser Ser Asn
65                  70                  75                  80

Cys Leu Asp Arg His Leu Glu Glu Arg Gly Asp Gln Leu Ala Ile Ile
                85                  90                  95

Trp Glu Gly Asp Asp Pro Ser Glu His Arg Asn Ile Thr Tyr Arg Glu
            100                 105                 110

-continued

Leu His Glu Gln Val Cys Lys Phe Ala Asn Ala Leu Arg Gly Gln Asp
115                 120                 125

Val His Arg Gly Asp Val Val Thr Ile Tyr Met Pro Met Ile Pro Glu
130                 135                 140

Ala Val Val Ala Met Leu Ala Cys Ala Arg Ile Gly Ala Ile His Ser
145                 150                 155                 160

Val Val Phe Gly Gly Phe Ser Pro Glu Ala Leu Ala Gly Arg Ile Ile
            165                 170                 175

Asp Cys Lys Ser Lys Val Val Ile Thr Ala Asp Glu Gly Val Arg Gly
            180                 185                 190

Gly Arg Arg Thr Pro Leu Lys Ala Asn Val Asp Leu Ala Leu Thr Asn
            195                 200                 205

Pro Glu Thr Ser Ser Val Gln Lys Ile Ile Val Cys Lys Arg Thr Gly
            210                 215                 220

Gly Asp Ile Ala Trp His Gln His Arg Asp Ile Trp Tyr Glu Asp Leu
225                 230                 235                 240

Met Lys Val Ala Ser Ser His Cys Ala Pro Lys Glu Met Gly Ala Glu
            245                 250                 255

Glu Ala Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Ala Leu Thr
            275                 280                 285

His Glu Arg Val Phe Asp Tyr Arg Pro Gly Glu Val Tyr Trp Cys Thr
290                 295                 300

Ala Asp Val Gly Trp Val Thr Gly His Ser Tyr Ile Val Tyr Gly Pro
305                 310                 315                 320

Leu Ala Asn Gly Ala Thr Thr Leu Leu Phe Glu Gly Val Pro Asn Tyr
            325                 330                 335

Pro Asp Ile Thr Arg Val Ser Lys Ile Val Asp Lys His Lys Val Asn
            340                 345                 350

Ile Leu Tyr Thr Ala Pro Thr Ala Ile Arg Ala Met Met Ala Glu Gly
            355                 360                 365

Gln Ala Ala Val Glu Gly Ala Asp Gly Ser Ser Leu Arg Leu Leu Gly
            370                 375                 380

Ser Val Gly Glu Pro Ile Asn Pro Glu Ala Trp Asn Trp Tyr Tyr Lys
385                 390                 395                 400

Thr Val Gly Lys Glu Arg Cys Pro Ile Val Asp Thr Trp Trp Gln Thr
            405                 410                 415

Glu Thr Gly Gly Ile Leu Ile Ser Pro Leu Pro Gly Ala Thr Gly Leu
            420                 425                 430

Lys Pro Gly Ser Ala Thr Arg Pro Phe Phe Gly Val Val Pro Ala Leu
            435                 440                 445

Val Asp Asn Leu Gly Asn Leu Ile Asp Gly Ala Ala Glu Gly Asn Leu
450                 455                 460

Val Ile Leu Asp Ser Trp Pro Gly Gln Ser Arg Ser Leu Tyr Gly Asp
465                 470                 475                 480

His Asp Arg Phe Val Asp Thr Tyr Phe Lys Thr Phe Arg Gly Met Tyr
            485                 490                 495

Phe Thr Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Met Gly
            515                 520                 525

Thr Ala Glu Ile Glu Ser Ala Met Val Ala His Ser Lys Val Ala Glu

```
            530                 535                 540
Ala Ala Val Val Gly Val Pro His Asp Ile Lys Gly Gln Gly Ile Tyr
545                 550                 555                 560

Val Tyr Val Thr Leu Asn Ala Gly Ile Glu Ala Ser Glu Gln Leu Arg
                565                 570                 575

Leu Glu Leu Lys Asn Trp Val Arg Lys Glu Ile Gly Pro Ile Ala Ser
                580                 585                 590

Pro Asp Val Ile Gln Trp Ala Pro Gly Leu Pro Lys Thr Arg Ser Gly
            595                 600                 605

Lys Ile Met Arg Arg Ile Leu Arg Lys Ile Ala Thr Gly Glu Tyr Asp
            610                 615                 620

Ala Leu Gly Asp Ile Ser Thr Leu Ala Asp Pro Gly Val Val Gln His
625                 630                 635                 640

Leu Ile Asp Thr His Lys Ala Met Asn Leu Ala Ser Ala
                645                 650

<210> SEQ ID NO 6
<211> LENGTH: 649
<212> TYPE: PRT
<213> ORGANISM: Vibrio furnissii

<400> SEQUENCE: 6

Met Ser Glu Ala His Ile Tyr Pro Val Lys Glu Asn Ile Lys Ala His
1               5                   10                  15

Thr His Ala Asp Asp Glu Thr Tyr Leu Ala Met Tyr Gln Gln Ser Val
            20                  25                  30

Ser Asp Pro Glu Gly Phe Trp Ser Glu His Gly Lys Ile Val Asp Trp
        35                  40                  45

Met Lys Pro Phe Thr Gln Val Lys His Thr Ser Phe Asp Thr Gly His
    50                  55                  60

Val Asp Ile Arg Trp Phe Glu Asp Gly Thr Leu Asn Val Ser Ala Asn
65              70                  75                  80

Cys Ile Asp Arg His Leu Ala Glu Arg Gly Asp Val Ala Ile Ile
            85                  90                  95

Trp Glu Gly Asp Asp Pro Ala Asp Lys Thr Leu Thr Phe Asn Glu
            100                 105                 110

Leu His Arg Asp Val Cys Arg Phe Ser Asn Ala Leu Lys Ala Gln Gly
            115                 120                 125

Val Arg Lys Gly Asp Val Val Cys Leu Tyr Met Pro Met Val Pro Glu
    130                 135                 140

Ala Ala Val Ala Met Leu Ala Cys Thr Arg Ile Gly Ala Val His Thr
145                 150                 155                 160

Val Val Phe Gly Gly Phe Ser Pro Glu Ala Leu Ala Gly Arg Ile Ile
                165                 170                 175

Asp Ser Asp Ser Lys Val Val Ile Thr Ala Asp Glu Gly Val Arg Gly
            180                 185                 190

Gly Arg Ala Val Pro Leu Lys Lys Asn Val Asp Glu Ala Leu Thr Asn
        195                 200                 205

Pro Glu Val Lys Thr Ile Ser Lys Val Ile Val Phe Lys Arg Thr Gly
    210                 215                 220

Gly Glu Val Ala Trp His Glu His Arg Asp Val Trp Trp His Asp Ala
225                 230                 235                 240

Val Ala Ala Ser Asp Val Cys Pro Pro Glu Glu Met Asn Ala Glu
                245                 250                 255
```

```
Asp Pro Leu Phe Ile Leu Tyr Thr Ser Gly Ser Thr Gly Lys Pro Lys
                260                 265                 270

Gly Val Leu His Thr Thr Gly Gly Tyr Leu Val Tyr Ala Thr Met Thr
            275                 280                 285

Phe Lys Tyr Val Phe Asp Tyr Gln Pro Gly Glu Thr Phe Trp Cys Thr
        290                 295                 300

Ala Asp Val Gly Trp Ile Thr Gly His Thr Tyr Leu Ile Tyr Gly Pro
305                 310                 315                 320

Leu Ser Asn Gly Ala Lys Thr Ile Leu Phe Glu Gly Val Pro Asn Tyr
                325                 330                 335

Pro Ser Thr Ala Arg Met Ser Glu Val Val Asp Lys His Gln Val Asn
            340                 345                 350

Ile Leu Tyr Thr Ala Pro Thr Ala Ile Arg Ala Leu Met Ala Lys Gly
        355                 360                 365

Asp Glu Ala Val Lys Gly Thr Ser Arg Ser Ser Leu Arg Ile Met Gly
370                 375                 380

Ser Val Gly Glu Pro Ile Asn Pro Glu Ala Trp Glu Trp Tyr Tyr Lys
385                 390                 395                 400

Thr Ile Gly Asn Glu Lys Ser Pro Ile Val Asp Thr Trp Trp Gln Thr
                405                 410                 415

Glu Thr Gly Gly Ile Leu Ile Thr Pro Leu Pro Gly Ala Thr Ala Leu
            420                 425                 430

Lys Pro Gly Ser Ala Thr Arg Pro Phe Phe Gly Val Gln Pro Ala Leu
        435                 440                 445

Val Asp Asn Met Gly Glu Val Ile Asp Gly Ala Ala Glu Gly Asn Leu
450                 455                 460

Val Ile Leu Asp Ser Trp Pro Gly Gln Met Arg Thr Val Tyr Gly Asp
465                 470                 475                 480

His Glu Arg Phe Glu Gln Thr Tyr Phe Ser Thr Phe Lys Gly Met Tyr
                485                 490                 495

Phe Thr Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Met Gly
        515                 520                 525

Thr Ala Glu Ile Glu Ser Ala Leu Val Ala Phe Asp Lys Ile Ala Glu
530                 535                 540

Ala Ala Val Val Gly Val Pro His Asp Ile Lys Gly Gln Ala Ile Tyr
545                 550                 555                 560

Ala Tyr Ile Thr Leu Asn Asp Gly Val Tyr Pro Ser Ala Glu Leu His
                565                 570                 575

Lys Glu Val Lys Asp Trp Val Arg Lys Glu Ile Gly Pro Ile Ala Thr
            580                 585                 590

Pro Asp Val Leu His Trp Thr Asp Ala Leu Pro Lys Thr Arg Ser Gly
        595                 600                 605

Lys Ile Met Arg Arg Ile Leu Arg Lys Ile Ala Thr Gly Asp Thr Gly
610                 615                 620

Asn Leu Gly Asp Thr Ser Thr Leu Ala Asp Pro Ser Val Val Asp Lys
625                 630                 635                 640

Leu Ile Ala Glu Lys Ala Gln Leu Val
                645

<210> SEQ ID NO 7
<211> LENGTH: 650
<212> TYPE: PRT
```

<213> ORGANISM: Shewanella halifaxensis

<400> SEQUENCE: 7

```
Met Ser Thr Gln Ser Leu Tyr Lys Val Pro Ser Glu Ile Ala Ala Asn
1               5                   10                  15

Ala Leu Val Asn Asp Glu Gln Tyr Lys Lys Met Tyr Gln Glu Ser Ile
            20                  25                  30

Val Asn Pro Glu Gly Phe Trp Arg Glu His Gly Asn Arg Ile Asp Trp
        35                  40                  45

Ile Lys Pro Phe Thr Lys Val Lys Lys Thr Ser Phe Asp Asp His Asn
    50                  55                  60

Leu Phe Ile Lys Trp Phe Tyr Asp Gly Thr Leu Asn Ala Ser Ala Asn
65                  70                  75                  80

Cys Leu Asp Arg His Leu Glu Asn Asn Ala Asp Lys Leu Ala Ile Ile
                85                  90                  95

Trp Glu Gly Asp Asp Ala Lys Asp Gln Arg Thr Leu Thr Tyr Gly Gln
            100                 105                 110

Leu His Thr Gln Val Cys Lys Phe Ala Asn Ala Leu Arg Ser Gln Gly
        115                 120                 125

Val Arg Arg Gly Asp Val Val Thr Ile Tyr Met Pro Met Val Pro Glu
    130                 135                 140

Ala Ala Val Ala Met Leu Ala Cys Ala Arg Ile Gly Ala Ile His Ser
145                 150                 155                 160

Val Val Phe Gly Gly Phe Ser Pro Asp Ser Ile Ala Ser Arg Val Ile
                165                 170                 175

Asp Gly Asn Ser Lys Val Val Ile Thr Ala Asp Glu Gly Val Arg Ala
            180                 185                 190

Gly Arg Ile Ile Pro Leu Lys Ala Asn Ile Asp Glu Ala Leu Ser His
        195                 200                 205

Pro Asp Val Asn Cys Val Glu Lys Val Ile Val Met Lys Arg Thr Gly
    210                 215                 220

Gly Asp Ile Asn Trp Val Glu Gly Arg Asp Ile Trp Trp Asp Ser Leu
225                 230                 235                 240

Met Asp Thr Ala Ser Glu His Cys Ile Ala Glu Glu Met Gly Ala Glu
                245                 250                 255

Asp Pro Leu Phe Leu Leu Tyr Thr Ser Gly Ser Thr Gly Asn Pro Lys
            260                 265                 270

Gly Val Leu His Thr Thr Gly Gly Tyr Met Val Tyr Ala Ala Met Thr
        275                 280                 285

His Glu Tyr Val Phe Asp Tyr Lys Glu Asn Glu Val Tyr Trp Cys Thr
    290                 295                 300

Ala Asp Val Gly Trp Ile Thr Gly His Ser Tyr Met Val Tyr Gly Pro
305                 310                 315                 320

Leu Ala Asn Gly Ala Thr Val Leu Ile His Glu Gly Val Pro Asn Tyr
                325                 330                 335

Pro Ser Pro Ala Arg Leu Gly Glu Met Val Asp Arg His Lys Val Asn
            340                 345                 350

Ile Leu Tyr Thr Ala Pro Thr Leu Ile Arg Ala Leu Met Ala Glu Gly
        355                 360                 365

Lys Glu Gln Phe Ala Gly Phe Asp Gly Ser Ser Leu Arg Ile Met Gly
    370                 375                 380

Ser Val Gly Glu Pro Ile Asn Pro Glu Ala Trp Arg Trp Tyr Asn Asp
385                 390                 395                 400
```

Val Ile Gly His Glu Lys Cys Pro Ile Val Asp Thr Trp Trp Gln Thr
                405                 410                 415

Glu Thr Gly Gly Ile Leu Ile Ser Pro Leu Pro Gly Ala Thr Asp Thr
            420                 425                 430

Lys Pro Gly Ser Ala Thr Arg Pro Phe Phe Gly Val Gln Pro Ala Leu
        435                 440                 445

Val Asp Asn Met Gly Asn Ile Val Asp Gly Ala Ser Glu Gly Asn Leu
    450                 455                 460

Val Ile Leu Asp Ser Trp Pro Gly Gln Met Arg Thr Val Phe Gly Asp
465                 470                 475                 480

His Asp Arg Phe Val Leu Thr Tyr Phe Lys Thr Phe Arg Gly Met Tyr
                485                 490                 495

Phe Thr Gly Asp Gly Ala Lys Arg Asp Glu Asp Gly Tyr Tyr Trp Ile
            500                 505                 510

Thr Gly Arg Val Asp Asp Val Ile Asn Val Ser Gly His Arg Leu Gly
        515                 520                 525

Thr Ala Glu Val Glu Ser Ala Leu Val Ala His Glu Phe Val Ala Glu
    530                 535                 540

Ala Ala Val Val Gly Tyr Pro His Asp Ile Lys Gly Gln Gly Ile Tyr
545                 550                 555                 560

Ala Tyr Val Thr Leu Thr Lys Gly Ser Val Glu Thr Glu Leu Arg
                565                 570                 575

Gln Glu Leu Arg Gln Trp Val Arg Lys Glu Ile Gly Ala Leu Ala Thr
            580                 585                 590

Pro Asp Leu Ile Gln Trp Ala Gly Gly Leu Pro Lys Thr Arg Ser Gly
        595                 600                 605

Lys Ile Met Arg Arg Phe Leu Arg Lys Ile Ala Ala Asn Glu Val Ser
    610                 615                 620

Asn Leu Gly Asp Ser Ser Thr Leu Ala Asp Pro Ala Val Ile Asp Thr
625                 630                 635                 640

Leu Ile Glu Thr Arg Leu Asn Arg Ser Glu
                645                 650

<210> SEQ ID NO 8
<211> LENGTH: 650
<212> TYPE: PRT
<213> ORGANISM: Aeromonas veronii

<400> SEQUENCE: 8

Met Ser Thr Gln Ser Leu Tyr Lys Val Pro Ser Glu Ile Ala Ala Asn
1               5                   10                  15

Ala Leu Val Asn Asp Glu Gln Tyr Lys Lys Met Tyr Gln Glu Ser Ile
            20                  25                  30

Val Asn Pro Glu Gly Phe Trp Arg Glu His Gly Asn Arg Ile Asp Trp
        35                  40                  45

Ile Lys Pro Phe Thr Lys Val Lys Lys Thr Ser Phe Asp Asp His Asn
    50                  55                  60

Leu Phe Ile Lys Trp Phe Tyr Asp Gly Thr Leu Asn Ala Ser Ala Asn
65                  70                  75                  80

Cys Leu Asp Arg His Leu Glu Asn Asn Ala Asp Lys Leu Ala Ile Ile
                85                  90                  95

Trp Glu Gly Asp Asp Ala Lys Asp Gln Arg Thr Leu Thr Tyr Gly Gln
            100                 105                 110

Leu His Thr Gln Val Cys Lys Phe Ala Asn Ala Leu Arg Ser Gln Gly
        115                 120                 125

```
Val Arg Arg Gly Asp Val Val Thr Ile Tyr Met Pro Met Val Pro Glu
    130                 135                 140
Ala Ala Val Ala Met Leu Ala Cys Ala Arg Ile Gly Ala Ile His Ser
145                 150                 155                 160
Val Val Phe Gly Gly Phe Ser Pro Asp Ser Ile Ala Ser Arg Val Ile
                165                 170                 175
Asp Gly Asn Ser Lys Val Val Ile Thr Ala Asp Glu Gly Val Arg Ala
            180                 185                 190
Gly Arg Ile Ile Pro Leu Lys Ala Asn Ile Asp Glu Ala Leu Ser His
        195                 200                 205
Pro Asp Val Asn Cys Val Glu Lys Val Ile Val Met Lys Arg Thr Gly
    210                 215                 220
Gly Asp Ile Asn Trp Val Glu Gly Arg Asp Ile Trp Trp Asp Ser Leu
225                 230                 235                 240
Met Asp Thr Ala Ser Glu His Cys Ile Ala Glu Glu Met Gly Ala Glu
                245                 250                 255
Asp Pro Leu Phe Leu Leu Tyr Thr Ser Gly Ser Thr Gly Asn Pro Lys
            260                 265                 270
Gly Val Leu His Thr Thr Gly Gly Tyr Met Val Tyr Ala Ala Met Thr
        275                 280                 285
His Glu Tyr Val Phe Asp Tyr Lys Glu Asn Glu Val Tyr Trp Cys Thr
    290                 295                 300
Ala Asp Val Gly Trp Ile Thr Gly His Ser Tyr Met Val Tyr Gly Pro
305                 310                 315                 320
Leu Ala Asn Gly Ala Thr Val Leu Ile His Glu Gly Val Pro Asn Tyr
                325                 330                 335
Pro Ser Pro Ala Arg Leu Gly Glu Met Val Asp Arg His Lys Val Asn
            340                 345                 350
Ile Leu Tyr Thr Ala Pro Thr Leu Ile Arg Ala Leu Met Ala Glu Gly
        355                 360                 365
Lys Glu Gln Phe Ala Gly Phe Asp Gly Ser Ser Leu Arg Ile Met Gly
    370                 375                 380
Ser Val Gly Glu Pro Ile Asn Pro Glu Ala Trp Arg Trp Tyr Asn Asp
385                 390                 395                 400
Val Ile Gly His Glu Lys Cys Pro Ile Val Asp Thr Trp Trp Gln Thr
                405                 410                 415
Glu Thr Gly Gly Ile Leu Ile Ser Pro Leu Pro Gly Ala Thr Asp Thr
            420                 425                 430
Lys Pro Gly Ser Ala Thr Arg Pro Phe Phe Gly Val Gln Pro Ala Leu
        435                 440                 445
Val Asp Asn Met Gly Asn Ile Val Asp Gly Ala Ser Glu Gly Asn Leu
    450                 455                 460
Val Ile Leu Asp Ser Trp Pro Gly Gln Met Arg Thr Val Phe Gly Asp
465                 470                 475                 480
His Asp Arg Phe Val Leu Thr Tyr Phe Lys Thr Phe Arg Gly Met Tyr
                485                 490                 495
Phe Thr Gly Asp Gly Ala Lys Arg Asp Glu Asp Gly Tyr Tyr Trp Ile
            500                 505                 510
Thr Gly Arg Val Asp Asp Val Ile Asn Val Ser Gly His Arg Leu Gly
        515                 520                 525
Thr Ala Glu Val Glu Ser Ala Leu Val Ala His Glu Phe Val Ala Glu
    530                 535                 540
```

Ala Ala Val Val Gly Tyr Pro His Asp Ile Lys Gly Gln Gly Ile Tyr
545                 550                 555                 560

Ala Tyr Val Thr Leu Thr Lys Gly Ser Val Glu Thr Glu Glu Leu Arg
            565                 570                 575

Gln Glu Leu Arg Gln Trp Val Arg Lys Glu Ile Gly Ala Leu Ala Thr
        580                 585                 590

Pro Asp Leu Ile Gln Trp Ala Gly Gly Leu Pro Lys Thr Arg Ser Gly
    595                 600                 605

Lys Ile Met Arg Arg Phe Leu Arg Lys Ile Ala Ala Asn Glu Val Ser
610                 615                 620

Asn Leu Gly Asp Ser Ser Thr Leu Ala Asp Pro Ala Val Ile Asp Thr
625                 630                 635                 640

Leu Ile Glu Thr Arg Leu Asn Arg Ser Glu
                645                 650

<210> SEQ ID NO 9
<211> LENGTH: 649
<212> TYPE: PRT
<213> ORGANISM: Aliivibrio salmonicida

<400> SEQUENCE: 9

Met Ser Asp Ile His Val Tyr Pro Val Asn Gln Asp Ile Ala Lys Asn
1               5                   10                  15

Ala His Ala Asp Glu Asp Lys Tyr Arg Glu Met Tyr Gln Gln Ser Val
            20                  25                  30

Ile Asn Pro Glu Gly Phe Trp Arg Glu His Gly Gln Ile Val Asp Trp
        35                  40                  45

Met Thr Pro Tyr Thr Lys Val Lys Asn Thr Ser Phe Asp Thr Gly His
    50                  55                  60

Val Asp Ile Lys Trp Phe Glu Asp Gly Glu Leu Asn Val Ser Ala Asn
65                  70                  75                  80

Cys Ile Asp Arg His Leu Ala Ala Arg Gly Asp Glu Val Ala Ile Ile
                85                  90                  95

Trp Glu Gly Asp Asp Pro Gln Asp Asp Ala Ser Ile Thr Phe Asn Glu
            100                 105                 110

Leu His Glu Gln Val Cys Lys Phe Ser Asn Ala Leu Lys Ser Gln Gly
        115                 120                 125

Val Arg Lys Gly Asp Val Val Cys Ile Tyr Met Pro Met Val Ala Glu
    130                 135                 140

Ala Ala Ile Ala Met Leu Ala Cys Thr Arg Ile Gly Ala Val His Thr
145                 150                 155                 160

Val Val Phe Gly Gly Phe Ser Pro Glu Ala Leu Ala Gly Arg Ile Val
                165                 170                 175

Asp Ser Asp Ala Lys Val Val Ile Thr Ala Asp Glu Gly Val Arg Gly
            180                 185                 190

Gly Arg Thr Val Pro Leu Lys Lys Asn Val Asp Asp Ala Leu Asn Asn
        195                 200                 205

Pro Glu Val Thr Thr Ile Glu Lys Val Val Phe Gln Arg Thr Gly
    210                 215                 220

Asn Asp Ile Asp Trp Asn Glu Glu Arg Asp Val Trp Trp His Glu Ala
225                 230                 235                 240

Thr Ala Val Ala Ser Ala His Cys Glu Pro Glu Ala Met Asn Ala Glu
                245                 250                 255

Asp Pro Leu Phe Ile Leu Tyr Thr Ser Gly Ser Thr Gly Lys Pro Lys
            260                 265                 270

-continued

Gly Val Leu His Thr Thr Gly Gly Tyr Leu Val Tyr Ala Ala Met Thr
            275                 280                 285
Phe Lys Tyr Ile Phe Asp Tyr Gln Glu Gly Glu Val Phe Trp Cys Thr
290                 295                 300
Ala Asp Val Gly Trp Ile Thr Gly His Thr Tyr Leu Ile Tyr Gly Pro
305                 310                 315                 320
Leu Ala Asn Gly Ala Lys Thr Ile Leu Phe Glu Gly Val Pro Asn Tyr
                325                 330                 335
Pro Ser Thr Ser Arg Met Ser Glu Val Val Asp Lys His Asn Val Asn
                340                 345                 350
Ile Leu Tyr Thr Ala Pro Thr Ala Ile Arg Ala Leu Met Ala His Gly
                355                 360                 365
Asn Asp Ala Val Glu Gly Thr Ser Arg Ser Ser Leu Arg Val Met Gly
370                 375                 380
Ser Val Gly Glu Pro Ile Asn Pro Glu Ala Trp Glu Trp Tyr Tyr Asn
385                 390                 395                 400
Thr Ile Gly Asp Ala Arg Cys Pro Ile Val Asp Thr Trp Trp Gln Thr
                405                 410                 415
Glu Thr Gly Gly Ile Leu Ile Ser Pro Leu Pro Gly Ala Thr Ala Leu
                420                 425                 430
Lys Pro Gly Ser Ala Thr Arg Pro Phe Phe Gly Val Gln Pro Ala Leu
                435                 440                 445
Val Asp Asn Met Gly Asn Leu Ile Glu Gly Ala Ala Asp Gly Asn Leu
450                 455                 460
Val Ile Thr Asp Ser Trp Pro Gly Gln Met Arg Thr Ile Tyr Gly Asp
465                 470                 475                 480
His Asp Arg Phe Glu Gln Thr Tyr Phe Ser Thr Phe Lys Gly Met Tyr
                485                 490                 495
Phe Thr Ser Asp Gly Ala Arg Arg Asp Glu Asp Gly Tyr Tyr Trp Ile
                500                 505                 510
Thr Gly Arg Val Asp Asp Val Leu Asn Val Ser Gly His Arg Met Gly
                515                 520                 525
Thr Ala Glu Val Glu Ser Ala Leu Val Ser Phe Ser Lys Ile Ala Glu
                530                 535                 540
Ala Ala Ile Val Gly Val Pro His Asp Ile Lys Gly Gln Ala Ile Tyr
545                 550                 555                 560
Ala Tyr Ile Thr Leu Asn Ser Gly Glu Tyr Pro Ser Ala Glu Leu His
                565                 570                 575
Lys Glu Val Lys Asp Trp Val Arg Lys Ile Gly Pro Ile Ala Thr
                580                 585                 590
Pro Asp Phe Leu His Trp Thr Asp Ser Leu Pro Lys Thr Arg Ser Gly
                595                 600                 605
Lys Ile Met Arg Arg Ile Leu Arg Lys Ile Ala Thr Gly Asp Thr Ser
610                 615                 620
Asn Leu Gly Asp Thr Ser Thr Leu Ala Asp Pro Ser Val Val Asn Lys
625                 630                 635                 640
Leu Ile Glu Glu Gln Arg Lys Ile Ala
            645

<210> SEQ ID NO 10
<211> LENGTH: 649
<212> TYPE: PRT
<213> ORGANISM: Photobacterium profundum

```
<400> SEQUENCE: 10

Met Ser Glu Val His Val Tyr Pro Val Asn Gln Glu Ile Ala Ala Thr
1               5                   10                  15

Ala His Val Asn Asp Glu Gln Tyr Arg Glu Met Tyr Gln Gln Ser Val
            20                  25                  30

Ile Asn Pro Glu Gly Phe Trp Arg Glu His Gly Gln Ile Val Asp Trp
        35                  40                  45

Ile Lys Pro Phe Thr Lys Val Lys His Thr Ser Phe Asp Thr Gly His
    50                  55                  60

Val Ser Val Lys Trp Phe Glu Asp Gly Thr Leu Asn Val Ser Ala Asn
65                  70                  75                  80

Cys Ile Asp Arg His Leu Ala Thr Arg Gly Asp Gln Pro Ala Ile Ile
                85                  90                  95

Trp Glu Gly Asp Asp Pro Thr Asp Ala Thr Phe Thr Tyr Asn Glu
            100                 105                 110

Leu His Glu Gln Val Cys Lys Phe Ser Asn Ala Leu Lys Ser Gln Gly
        115                 120                 125

Val Arg Lys Gly Asp Val Val Cys Leu Tyr Met Pro Met Val Ala Glu
    130                 135                 140

Ala Ala Ile Ala Met Leu Ala Cys Thr Arg Ile Gly Ala Val His Thr
145                 150                 155                 160

Ile Val Phe Gly Gly Phe Ser Pro Glu Ala Leu Ala Gly Arg Ile Val
                165                 170                 175

Asp Ser Asn Ala Lys Leu Val Ile Thr Ala Asp Glu Gly Val Arg Ala
            180                 185                 190

Gly Arg Ala Val Pro Leu Lys Lys Asn Val Asp Asp Ala Leu Ala Asn
        195                 200                 205

Lys Asn Val Thr Ser Ile Glu Lys Val Ile Val Leu Lys Arg Thr Gly
    210                 215                 220

Gly Asn Val Glu Trp His Ser Glu Arg Asp Val Trp Trp His Glu Ala
225                 230                 235                 240

Thr Ala Val Ala Ser Ser His Cys Glu Pro Glu Glu Met Asn Ala Glu
                245                 250                 255

Asp Pro Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Thr Met Thr
        275                 280                 285

Phe Lys Tyr Val Phe Asp Tyr Gln Glu Gly Asp Val Tyr Trp Cys Thr
    290                 295                 300

Ala Asp Val Gly Trp Ile Thr Gly His Ser Tyr Leu Val Tyr Gly Pro
305                 310                 315                 320

Leu Ala Asn Gly Ala Thr Thr Val Leu Phe Glu Gly Val Pro Asn Tyr
                325                 330                 335

Pro Ser Thr Ser Arg Met Ser Glu Val Val Asp Lys His Asn Val Ser
            340                 345                 350

Ile Leu Tyr Thr Ala Pro Thr Ala Ile Arg Ala Leu Met Ala Lys Gly
        355                 360                 365

Thr Glu Ala Ile Lys Gly Thr Ser Arg Ser Ser Leu Arg Ile Met Gly
    370                 375                 380

Ser Val Gly Glu Pro Ile Asn Pro Glu Ala Trp Glu Trp Tyr His His
385                 390                 395                 400

Thr Ile Gly Asp Ser Arg Cys Pro Ile Val Asp Thr Trp Trp Gln Thr
                405                 410                 415
```

```
Glu Thr Gly Gly Ile Leu Ile Thr Pro Leu Pro Gly Ala Thr Ala Leu
            420                 425                 430

Lys Pro Gly Ser Ala Thr Arg Pro Phe Phe Gly Val Gln Pro Ala Ile
            435                 440                 445

Val Asp Asn Met Gly Asn Ile Leu Glu Gly Val Ala Glu Gly Asn Leu
450                 455                 460

Val Met Val Asp Ser Trp Pro Gly Gln Met Arg Thr Leu Trp Gly Asp
465                 470                 475                 480

His Glu Arg Phe Glu Gln Thr Tyr Phe Ser Thr Phe Gln Gly Met Tyr
                485                 490                 495

Phe Thr Gly Asp Gly Ala Arg Arg Asp Glu Asp Gly Tyr Tyr Trp Ile
            500                 505                 510

Thr Gly Arg Val Asp Asp Val Leu Asn Ile Ser Gly His Arg Met Gly
            515                 520                 525

Thr Ala Glu Ile Glu Ser Ala Leu Val Ala Phe Asp Lys Ile Ala Glu
530                 535                 540

Ala Ala Ile Val Gly Val Pro His Asp Ile Lys Gly Gln Ala Ile Tyr
545                 550                 555                 560

Ala Tyr Ile Thr Leu Asn Asp Gly Glu Ile Pro Ser Ala Glu Leu His
                565                 570                 575

Lys Glu Val Lys Asp Trp Val Arg Lys Glu Ile Gly Pro Ile Ala Thr
            580                 585                 590

Pro Asp Phe Leu His Trp Thr Asp Ala Leu Pro Lys Thr Arg Ser Gly
            595                 600                 605

Lys Ile Met Arg Arg Ile Leu Arg Lys Ile Ala Thr Gly Asp Thr Gly
            610                 615                 620

Ser Leu Gly Asp Thr Ser Thr Leu Ala Asp Pro Ser Val Val Asp Lys
625                 630                 635                 640

Leu Ile Ala Glu Lys Gln Thr Ile Leu
                645

<210> SEQ ID NO 11
<211> LENGTH: 744
<212> TYPE: PRT
<213> ORGANISM: Saccharomyces cerevisiae

<400> SEQUENCE: 11

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30

Asp Glu Tyr Ile Glu Glu Leu Tyr Ser Gln Leu Pro Leu Thr Ser Tyr
        35                  40                  45

Pro Arg Tyr Lys Thr Phe Leu Lys Lys Gln Ala Val Ala Ile Ser Asn
    50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
            100                 105                 110

Gly Ser Arg Pro Ile Asp Lys Ala Thr Gly Thr Trp Glu Glu Thr Phe
        115                 120                 125

Arg Phe Glu Ser Tyr Ser Thr Val Ser Lys Arg Cys His Asn Ile Gly
```

```
                130             135             140
Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
        195                 200                 205

Thr Glu Ala Pro Ile Leu Ile Phe Ala Lys Ser Asn Met Tyr His Val
    210                 215                 220

Leu Lys Met Val Pro Asp Met Lys Phe Val Asn Thr Leu Val Cys Met
225                 230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
                260                 265                 270

Glu Gln Val Glu Gln Val Gly Cys Phe Asn Lys Ile Pro Ala Ile Pro
            275                 280                 285

Pro Thr Pro Asp Ser Leu Tyr Thr Ile Ser Phe Thr Ser Gly Thr Thr
            290                 295                 300

Gly Leu Pro Lys Gly Val Glu Met Ser His Arg Asn Ile Ala Ser Gly
305                 310                 315                 320

Ile Ala Phe Ala Phe Ser Thr Phe Arg Ile Pro Pro Asp Lys Arg Asn
                325                 330                 335

Gln Gln Leu Tyr Asp Met Cys Phe Leu Pro Leu Ala His Ile Phe Glu
            340                 345                 350

Arg Met Val Ile Ala Tyr Asp Leu Ala Ile Gly Phe Gly Ile Gly Phe
            355                 360                 365

Leu His Lys Pro Asp Pro Thr Val Leu Val Glu Asp Leu Lys Ile Leu
        370                 375                 380

Lys Pro Tyr Ala Val Ala Leu Val Pro Arg Ile Leu Thr Arg Phe Glu
385                 390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
            420                 425                 430

Gly Pro Asp Lys Ser Ile Met Asn Phe Leu Val Tyr His Arg Val Leu
        435                 440                 445

Ile Asp Lys Ile Arg Asp Ser Leu Gly Leu Ser Asn Asn Ser Phe Ile
    450                 455                 460

Ile Thr Gly Ser Ala Pro Ile Ser Lys Asp Thr Leu Leu Phe Leu Arg
465                 470                 475                 480

Ser Ala Leu Asp Ile Gly Ile Arg Gln Gly Tyr Gly Leu Thr Glu Thr
                485                 490                 495

Phe Ala Gly Val Cys Leu Ser Glu Pro Phe Glu Lys Asp Val Gly Ser
                500                 505                 510

Cys Gly Ala Ile Gly Ile Ser Ala Glu Cys Arg Leu Lys Ser Val Pro
            515                 520                 525

Glu Met Gly Tyr His Ala Asp Lys Asp Leu Lys Gly Glu Leu Gln Ile
        530                 535                 540

Arg Gly Pro Gln Val Phe Glu Arg Tyr Phe Lys Asn Pro Asn Glu Thr
545                 550                 555                 560
```

```
Ser Lys Ala Val Asp Gln Asp Gly Trp Phe Ser Thr Gly Asp Val Ala
                565                 570                 575

Phe Ile Asp Gly Lys Gly Arg Ile Ser Val Ile Asp Arg Val Lys Asn
                580                 585                 590

Phe Phe Lys Leu Ala His Gly Glu Tyr Ile Ala Pro Glu Lys Ile Glu
                595                 600                 605

Asn Ile Tyr Leu Ser Ser Cys Pro Tyr Ile Thr Gln Ile Phe Val Phe
            610                 615                 620

Gly Asp Pro Leu Lys Thr Phe Leu Val Gly Ile Val Gly Val Asp Val
625                 630                 635                 640

Asp Ala Ala Gln Pro Ile Leu Ala Ala Lys His Pro Glu Val Lys Thr
                645                 650                 655

Trp Thr Lys Glu Val Leu Val Glu Asn Leu Asn Arg Asn Lys Lys Leu
                660                 665                 670

Arg Lys Glu Phe Leu Asn Lys Ile Asn Lys Cys Thr Asp Gly Leu Gln
                675                 680                 685

Gly Phe Glu Lys Leu His Asn Ile Lys Val Gly Leu Glu Pro Leu Thr
            690                 695                 700

Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
                725                 730                 735

Ser Leu Val Lys Thr Glu Lys Leu
            740

<210> SEQ ID NO 12
<211> LENGTH: 748
<212> TYPE: PRT
<213> ORGANISM: Lachancea thermotolerans

<400> SEQUENCE: 12

Met Ser Lys Gln Asp Gly Tyr Ile Ser Leu Ser Glu Leu Ile Glu Thr
1               5                   10                  15

Asp Lys Arg Phe Gln Asn Leu Arg Glu Glu Leu Ala Val Tyr Asp Lys
                20                  25                  30

Asn Ser Lys Glu Tyr Leu Ser Asn Leu Ile Ser Lys Leu Pro Leu Thr
            35                  40                  45

Asn His Val Ser Tyr Arg Gln Phe Leu Lys Glu Gln Ala Val Ser Leu
        50                  55                  60

Glu Ser Ser Lys Lys His Gly Tyr Ser Pro Val Phe Arg Ser Ser Leu
65                  70                  75                  80

Ser Pro Glu Cys Leu Val Ser Asn Val His Pro Arg Leu Ser Thr Phe
                85                  90                  95

Phe Glu Leu Phe Asn Phe Ser Val Glu Arg Phe Pro Asp Asn Asp Cys
                100                 105                 110

Leu Gly Gln Arg Ser Gln Asp Arg Val Thr Gly His Trp Gly Gln His
            115                 120                 125

Tyr Glu Phe Glu Ser Tyr Arg Glu Ile Gln Glu Arg Ser Gln Asn Leu
        130                 135                 140

Gly Ser Gly Ile Met Thr Val Val Asn Leu Lys Arg Lys Arg Arg Phe
145                 150                 155                 160

Gly Ser Asn Asp Phe Ile Val Ser Phe Leu Ser Thr Asn Arg Lys Glu
                165                 170                 175

Trp Val Ile Ser Asp Leu Ala Cys Gln Gly Tyr Ser Leu Gly Asn Thr
```

```
              180                 185                 190
Ala Leu Tyr Glu Thr Leu Gly Leu Asp Thr Ser Glu Tyr Ile Leu Asn
              195                 200                 205

Val Thr Glu Ser Pro Val Leu Ile Leu Ser Lys Glu Asn Ile Tyr Arg
              210                 215                 220

Val Met Glu Met Val Pro Lys Leu Pro His Leu Ser Thr Ile Val Cys
225                 230                 235                 240

Met Asp Glu Leu Ser Asp Leu Glu Leu Ala Gln Leu Asn Gly Pro Leu
                    245                 250                 255

Leu Pro Gln His Thr Asn Ser Lys Gly Glu Arg Ile Ser Ile Leu Asn
                260                 265                 270

Phe Arg Gln Val Glu Arg Ile Gly Ala Ser Asn Lys Val Pro Leu Ile
            275                 280                 285

Pro Pro Thr Pro Asp Ser Leu Tyr Thr Ile Ser Phe Thr Ser Gly Thr
        290                 295                 300

Thr Gly Thr Pro Lys Gly Val Gln Met Lys Gln Ser His Val Ala Ala
305                 310                 315                 320

Ala Val Ala Phe Val Leu Ser Thr Leu Arg Met Pro Arg Leu Lys His
                    325                 330                 335

Arg Ser Gln Ala Tyr Asp Leu Cys Phe Leu Pro Leu Ala His Ile Phe
                340                 345                 350

Glu Arg Gln Ile Val Ala Phe Asp Leu Ser Ser Gly Thr Ala Ile Gly
            355                 360                 365

Phe Leu His Lys Pro Asp Pro Ser Val Leu Val Glu Asp Leu Lys Leu
        370                 375                 380

Leu Lys Pro Asp Val Phe Pro Ser Val Pro Arg Ile Leu Thr Lys Phe
385                 390                 395                 400

Glu Ala Gly Ile Lys Asn Ser Leu Gln Asn Gly Asp Gly Ser Ala Val
                    405                 410                 415

Thr Lys Asn Val Ala Ser Thr Ile Leu Asn Lys Arg Leu Glu Arg Thr
                420                 425                 430

Thr His His Gly Gly Lys Asp His Ser Ile Leu Asn Thr Val Val Phe
            435                 440                 445

His Arg Val Leu Ile Asp Lys Ile Arg Ser Ser Leu Gly Leu Glu Asn
        450                 455                 460

Leu Asp Val Val Ile Thr Gly Ser Ala Pro Ile Ser Asn Asp Thr Leu
465                 470                 475                 480

Leu Phe Met Lys Ser Ala Leu Asp Cys Gly Val Arg Gln Gly Tyr Gly
                    485                 490                 495

Leu Thr Glu Thr Phe Ala Gly Ile Cys Leu Ser Glu Ala Arg Glu Arg
                500                 505                 510

Asp Ser Gly Thr Cys Gly Gly Met Ala Val Thr Thr Glu Cys Arg Leu
            515                 520                 525

Arg Ser Ile Pro Glu Met Gly Tyr Asp Ala Glu His Asp Leu Lys Gly
        530                 535                 540

Glu Val Gln Leu Arg Gly Ser Gln Val Phe Arg Gly Tyr Tyr Lys Asn
545                 550                 555                 560

Pro Gln Glu Thr Ser Arg Ala Leu Gly Glu Asp Gly Trp Tyr Ser Thr
                    565                 570                 575

Gly Asp Val Gly Phe Ile Asp Ser Lys Gly Arg Leu Ser Ile Ile Asp
                580                 585                 590

Arg Val Lys Asn Phe Phe Lys Leu Ala Gln Gly Glu Tyr Ile Ala Pro
            595                 600                 605
```

```
Glu Lys Ile Glu Ser Val Tyr Leu Ser Ser Cys Pro Tyr Leu Thr Gln
    610                 615                 620

Ile Ser Val His Gly Asp Ser Leu Gln Thr Phe Leu Val Ala Val Ile
625                 630                 635                 640

Gly Leu Glu Leu Asp Ile Thr Ala Pro Ile Ile His Lys Lys Ile Pro
            645                 650                 655

Glu Leu Arg Gly Phe Ser Gly Lys Asp Leu Val Asp Glu Ile Asn Lys
            660                 665                 670

Ser Arg Ala His Arg Lys Ala Leu Ile Val Leu Ile Asn Ser Phe Ile
675                 680                 685

Glu Gly Leu Gln Gly Phe Glu Lys Ile His Asn Leu Tyr Val Gly Ile
    690                 695                 700

Glu Pro Leu Lys Val Thr Asp Asp Thr Ile Thr Pro Thr Leu Lys Val
705                 710                 715                 720

Lys Arg Ala Asn Ala Ala Lys His Phe Arg Lys Ile Leu Glu Asn Leu
                725                 730                 735

Tyr Glu Glu Gly Ser Leu Ile Lys Val Glu Lys Leu
            740                 745

<210> SEQ ID NO 13
<211> LENGTH: 750
<212> TYPE: PRT
<213> ORGANISM: Ashbya gossypii

<400> SEQUENCE: 13

Met Ser Asn Glu Thr Glu Val Asn Arg Tyr Pro Gly Met Gly Pro Ile
1               5                   10                  15

Ser Leu Val Glu Val Ile Arg Thr Asp Ala Arg Phe Ala Glu Leu Trp
            20                  25                  30

Lys Arg Leu Ser Leu Phe Gln Gln Gly Ser Val Glu Phe Tyr Lys Glu
        35                  40                  45

Leu Tyr Asp Asn Met Pro Leu Phe Ala Gly Met Asp Gly Met Ala Leu
    50                  55                  60

Ser Ala Pro Val Pro Gly Ser Gly Lys Lys Gly Tyr Ser Pro Val Phe
65                  70                  75                  80

Arg Asn Val Leu Val Pro Glu Gly Lys Leu Leu Ser Ala Ile Asp Glu
                85                  90                  95

Gly Val Asp Thr Gly Tyr His Val Phe Lys Leu Ser Ala Arg Met Tyr
            100                 105                 110

Pro Asp Asn His Cys Leu Gly Met Arg Ala Tyr Asp Glu Ala Thr Gly
        115                 120                 125

Lys Trp Leu Asp Glu Tyr Arg Trp Glu Thr Tyr Ser Gln Val Glu Arg
    130                 135                 140

Arg Ala Glu Asn Leu Gly Ala Gly Leu Leu Ser Val Val Asn Val Lys
145                 150                 155                 160

Arg Ser Lys Pro Leu Asp Thr Asn Asp Phe Ile Val Ala Met Met Ser
                165                 170                 175

Ala Asn Ser Lys Glu Trp Val Leu Thr Asp Leu Ala Cys Gln Thr Phe
            180                 185                 190

Ser Leu Val Asn Thr Ala Leu Tyr Glu Thr Leu Gly Pro Asn Thr Ser
        195                 200                 205

Glu Tyr Ile Met Asn Leu Thr Glu Ser Pro Val Val Val Ser Lys
    210                 215                 220

Pro Asn Leu Leu Arg Ile Phe Ala Leu Ala Ser Lys Leu Arg Ala Leu
```

-continued

```
                225                 230                 235                 240
Asn Thr Ile Val Ile Met Asp Asp Met Asp Leu Gln Glu Val Asp Arg
                    245                 250                 255
Leu Ala Ser Leu Leu Pro Val Thr Lys Asn Ala Lys Gly Glu Thr Ile
                260                 265                 270
Ser Val Leu Thr Leu Arg Gln Val Glu Lys Ile Gly Glu Leu Asn Asn
            275                 280                 285
Ile Ala Pro Ile Pro Pro Ser Pro Asp Ser Phe His Thr Ile Ser Phe
        290                 295                 300
Thr Ser Gly Thr Thr Ser Leu Pro Lys Gly Val Gln Leu Thr His Arg
305                 310                 315                 320
Ala Tyr Cys Ala Ala Leu Ala Phe Ala Cys Ser His Val Arg Cys Glu
                325                 330                 335
Pro Asn Lys Gln Arg Tyr Ala Leu Cys Leu Leu Pro Leu Thr His Ile
                340                 345                 350
Tyr Gln Arg Gln Met Thr Gly Leu Asn Leu Met His Ala Phe Gly Ile
                355                 360                 365
Gly Phe Leu His Lys Pro Asn Pro Asp Leu Phe Ile Glu Ala Met Cys
        370                 375                 380
Val Leu Arg Pro Ala Met Val Ser Leu Val Pro Arg Val Leu Thr Lys
385                 390                 395                 400
Leu Glu Ala Gly Ile Lys Asn Ser Ile Gln Gly Ala Asp Val Ser Thr
                    405                 410                 415
Phe Lys Arg Lys Leu Ala Lys Thr Val Ile Asp Ala Lys Asp Lys Arg
                420                 425                 430
Phe Ser Ala Val Ser Gly Pro Asp Asp Ser Tyr Met Asn Arg Phe Ile
            435                 440                 445
Tyr Arg Lys Ile Phe Val Asp Lys Ile Arg Asp Lys Leu Gly Phe Thr
        450                 455                 460
Asn Val Pro Leu Val Thr Thr Gly Ser Ala Pro Ile Ser Pro Glu Thr
465                 470                 475                 480
Leu Arg Phe Ile Gln Cys Ala Met Asp Ile Gly Ile Leu Gln Gly Tyr
                    485                 490                 495
Gly Leu Thr Glu Thr Phe Gly Gly Asn Phe Leu Ser Val Pro Tyr Glu
                500                 505                 510
Thr Asp Cys Gly Ser Cys Gly Pro Pro Ala Met Thr Thr Glu Val Arg
            515                 520                 525
Leu Arg Asp Val Pro Gly Met Ser Tyr Asn Ala Glu Lys Asp His Met
        530                 535                 540
Gly Glu Val Val Arg Ser Gln Gln Gln Phe Glu Arg Tyr Tyr Lys
545                 550                 555                 560
Met Pro Glu Lys Thr Ala Glu Val Leu Asp Lys Asp Gly Trp Phe Ser
                    565                 570                 575
Thr Gly Asp Val Gly Tyr Ile Asp Lys Lys Gly Arg Leu Phe Ile Thr
                580                 585                 590
Asp Arg Val Lys Asn Ile Phe Lys Leu Ser Gln Gly Glu Tyr Ile Ala
            595                 600                 605
Pro Glu Lys Val Glu Asn Cys Tyr Leu Ser Ser Cys Pro Phe Ile Thr
        610                 615                 620
Gln Ile Phe Val His Gly Asn Ser Leu Asn Asn Tyr Leu Val Gly Val
625                 630                 635                 640
Val Gly Ile Asp Val Val Pro Phe Lys Ala Ile Leu Asp Ser Arg Thr
                    645                 650                 655
```

Ser Lys Trp Ser Lys Leu Pro Leu Glu Glu Val Ile Pro Thr Ile Asn
         660                 665                 670

Lys Asp Pro Ala Leu Lys Gln Leu Thr Leu Lys Ile Ile Asn Ser Phe
            675                 680                 685

Val Thr Ala Glu Leu Gln Gly Phe Glu Lys Ile Gly Asn Leu Tyr Ala
    690                 695                 700

Asp Val Glu Pro Leu Ser Val Asp Gly Glu Thr Leu Thr Pro Thr Phe
705                 710                 715                 720

Lys Val Lys Arg Glu Val Cys Thr Lys Val Phe Lys Asp Ile Leu Ser
                725                 730                 735

Ser Leu Tyr Asp Glu Gly His Ile Leu Lys Ala Gly Lys Leu
            740                 745                 750

<210> SEQ ID NO 14
<211> LENGTH: 720
<212> TYPE: PRT
<213> ORGANISM: Candida orthopsilosis

<400> SEQUENCE: 14

Met Ala Ser Leu Phe Asn Glu Lys Pro Glu His Ile Trp Lys Thr Ile
1               5                   10                  15

Thr Glu Ser Phe Pro Leu Asp Gln Ser Val Thr Ser Arg Ala Leu Pro
            20                  25                  30

Leu Pro Asn Ser Glu Val Pro Gly Phe Ser Pro Ile Tyr Arg Asn Ala
        35                  40                  45

Tyr Ser Gln Lys Glu Leu Lys Thr Val Pro Tyr Pro Gly Ile Thr Thr
50                  55                  60

Leu His Asp Thr Phe Glu Leu Ser Val Ala Asn Asn Gly His Lys Arg
65                  70                  75                  80

Ala Leu Gly His Arg Val Lys Lys Ala Asp Gly Ser Phe Gly Glu Tyr
                85                  90                  95

Val Trp Gln Asp Tyr Lys Thr Val Gln Gln Arg Arg Asn Asn Leu Gly
            100                 105                 110

Ser Gly Ile Phe Phe Val Leu Gln Asn Asn Pro Tyr Lys Thr Asp Ser
        115                 120                 125

Glu Ala His Lys Lys Leu Lys Tyr Asp Pro Leu Ser Asp Asp Ser Phe
    130                 135                 140

Val Leu Thr Ile Phe Ala His Asn Arg Pro Glu Trp Val Leu Ala Asp
145                 150                 155                 160

Val Thr Ser Thr Ala Tyr Ser Ile Thr Asn Thr Ala Leu Tyr Asp Thr
                165                 170                 175

Leu Gly Pro Asp Thr Ser Lys Tyr Ile Leu Asn Leu Thr Glu Cys Pro
            180                 185                 190

Ile Ile Leu Cys Ser Lys Asp Lys Val Lys Ser Leu Val Glu Leu Lys
        195                 200                 205

Glu Gln Asn Pro Glu Glu Leu Ser Asn Leu Ile Cys Leu Val Ser Met
    210                 215                 220

Asp Asp Leu Thr Thr Glu Asp Ala Val Leu Lys Asn Tyr Cys His Asp
225                 230                 235                 240

His Asn Ile Ser Leu Phe Asp Tyr Lys Gln Val Glu Lys Leu Gly Glu
                245                 250                 255

Ile Asn Pro Leu Ala Pro Ile Pro Pro Lys Pro Glu Thr Lys Phe Ser
            260                 265                 270

Ile Thr Phe Thr Ser Gly Thr Thr Gly Ala Asn Pro Lys Gly Val Leu

-continued

```
                275                 280                 285
Leu Thr His Glu Thr Ala Val Ala Gly Ile Thr Phe Val Tyr Ser Gly
    290                 295                 300
Ile Thr Leu Pro Arg Ala Asp Ala Val Phe Tyr Ser Phe Leu Pro Leu
305                 310                 315                 320
Ala His Ile Tyr Glu Arg Gln Gly Ile His Phe Ala Leu Thr Tyr Gly
                325                 330                 335
Ala Ala Ile Gly Phe Pro Gln Gly Pro Ser Pro Leu Thr Leu Leu Glu
            340                 345                 350
Asp Ile Gln Val Leu Glu Pro Asp Tyr Leu Ala Leu Val Pro Arg Val
                355                 360                 365
Leu Thr Lys Leu Glu Ala Gly Ile Lys Ala Gln Thr Ile Asn Asn Asp
    370                 375                 380
Glu Lys Pro Ile Leu Lys Ser Leu Phe Thr Lys Ala Ile Asn Thr Lys
385                 390                 395                 400
Leu Ala Leu Gln Ser Asn Pro Ala Asn Glu Asn Thr Asn Pro Ser His
                405                 410                 415
Leu Leu Tyr Asp Arg Val Leu Gly Leu Leu Arg Lys Leu Gly Met
            420                 425                 430
Lys Asn Leu Lys Ile Ile Met Ser Gly Ser Ala Pro Ile Ser Pro Glu
                435                 440                 445
Thr Leu Lys Phe Leu Lys Ala Ser Leu Asn Thr Gly Val Gly Gln Gly
    450                 455                 460
Tyr Gly Met Ser Glu Thr Phe Ala Gly Val Met Ala Ser Ser Thr Phe
465                 470                 475                 480
Glu Thr Asp Ala Ser Ser Cys Gly Pro Ile Ser Val Thr Thr Glu Cys
                485                 490                 495
Lys Thr Arg Asp Leu Pro Ala Met Gly Tyr Thr Ser Lys Asp Glu Gly
            500                 505                 510
Gly Pro Arg Gly Glu Leu Leu Val Arg Gly Pro Gln Ile Phe Leu Glu
                515                 520                 525
Tyr Tyr Lys Asn Pro Glu Glu Thr Ala Lys Ser Phe Asp Glu Asp Gly
    530                 535                 540
Trp Phe Tyr Thr Gly Asp Val Ala Arg Ile Asp Ser Lys Thr Gly Arg
545                 550                 555                 560
Thr Tyr Ile Ile Asp Arg Val Lys Asn Phe Phe Lys Leu Ala Gln Gly
                565                 570                 575
Glu Tyr Val Thr Pro Glu Arg Ile Glu Asn Thr Tyr Leu Ser Cys Phe
            580                 585                 590
Pro Tyr Ile Ala Gln Leu Phe Val His Gly Asp Ser Leu Arg Thr His
                595                 600                 605
Leu Val Gly Val Val Gly Val Asp Pro Ala Ser Ile Thr Gln Tyr Ile
    610                 615                 620
Lys Gln Arg His Gly Glu Thr Ile Thr Asp Ala Ala Asp Leu Val Arg
625                 630                 635                 640
Phe Phe Gln Asp Pro Lys Arg Lys Arg Glu Leu Leu Val Asp Met Asn
                645                 650                 655
Ala Ser Leu Gly Asn Lys Leu Gln Gly Phe Glu Lys Leu His Asn Ile
            660                 665                 670
Glu Val Asp Val Glu Pro Leu Ser Val Glu Lys Asn Leu Ile Thr Pro
                675                 680                 685
Thr Met Lys Ile Lys Arg Pro Ile Cys Thr Lys Tyr Phe Lys Asp Thr
    690                 695                 700
```

```
Leu Asp Lys Leu Tyr Glu Glu Gly Ser Leu Ile Arg Asn Asp Lys Leu
705                 710                 715                 720

<210> SEQ ID NO 15
<211> LENGTH: 720
<212> TYPE: PRT
<213> ORGANISM: Scheffersomyces stipitis

<400> SEQUENCE: 15

Met Ser Leu Phe Gln Glu Asp Pro Lys Asn Ile His Asn Phe Ile Arg
1               5                   10                  15

Ala Ser Leu Pro Leu Asp Pro Lys Lys Leu Cys Glu Ser Val Pro Leu
            20                  25                  30

Pro Tyr Ser Glu Lys Pro Gly Tyr Ser Ala Val Tyr Arg Asn Lys Tyr
                35                  40                  45

Ser Val Asp Gly Leu Ile Thr Arg Pro His Pro Ser Leu Ala Thr Leu
    50                  55                  60

Phe Asp Leu His Glu Val Ala Arg Ser Gln Pro Asp Ser Pro Cys
65                  70                  75                  80

Phe Gly Val Arg His Lys Gln Ala Asp Gly Thr Tyr Gly Pro Tyr Gln
                85                  90                  95

Trp Ile Asn Tyr Gln Glu Val Tyr Asp Arg Lys Val His Phe Gly Ser
                100                 105                 110

Gly Val Phe Phe Ile Leu Gln Asn Asn Pro Tyr Arg Thr Asn Ser Pro
                115                 120                 125

Val His Gln Lys Ile His Tyr Asp Pro Gln Ala Thr Glu Ser Pro Phe
    130                 135                 140

Val Leu Ser Ile Phe Ser Ala Asn Arg Ala Glu Trp Val Thr Thr Asp
145                 150                 155                 160

Met Ala Cys Ser Ala Tyr Ser Leu Thr Ser Thr Ala Leu Tyr Asp Ser
                165                 170                 175

Leu Gly Ala Gln Thr Ser Lys Tyr Ile Leu Ser Ser Thr Glu Ser Pro
                180                 185                 190

Ile Val Val Ser Ser Lys Asp Lys Leu Lys Ser Leu Ile Lys Leu Lys
                195                 200                 205

Ala Glu Asp Pro Glu Thr Leu Ser Asn Leu Ile Thr Leu Val Ser Met
    210                 215                 220

Asp Pro Leu Asp Pro Lys Thr Asp Glu Ala Leu Val Lys Tyr Ala Asn
225                 230                 235                 240

Asp Asn Arg Ile Thr Leu Phe Asp Phe Asp Gln Val Leu Lys Leu Gly
                245                 250                 255

Glu Ile Asn Lys Leu Pro Gln Ile Pro Pro Lys Pro Glu Thr Ile Tyr
                260                 265                 270

Thr Ile Ser Phe Thr Ser Gly Thr Gly Ala Asn Pro Lys Gly Val
    275                 280                 285

Leu Leu Thr His Ala Asn Ala Val Cys Ala Val Thr Phe Cys Tyr Ser
    290                 295                 300

Asn Ile Thr Leu Pro Glu Ser Pro Thr Val Tyr Cys Phe Leu Pro Leu
305                 310                 315                 320

Ala His Ile Tyr Glu Arg Met Ser Ile Ser Phe Ala Leu Ser Met Cys
                325                 330                 335

Ala Ala Ile Gly Phe Pro Gln Ser Pro Ser Pro Leu Thr Leu Met Asp
                340                 345                 350

Asp Ile Lys His Leu Arg Pro His Phe Leu Asn Leu Val Pro Arg Val
```

```
                355                 360                 365
Tyr Thr Lys Leu Glu Ala Ala Leu Lys Ala Gln Thr Phe Asn Ser Asp
370                 375                 380

Lys Pro Ile Ile Lys Ser Leu Phe Ser Ala Ile Asn Lys Lys Met
385                 390                 395                 400

Glu Leu Gln Ala Val Glu Asp Gly Ala Gln Gly Lys His Ile Val Tyr
                405                 410                 415

Asp Gln Val Val Gln Leu Leu Arg Lys Lys Ile Gly Phe Asp Arg Leu
            420                 425                 430

Ile Ala Val Thr Thr Gly Ser Ala Pro Ile Ser Pro Glu Thr Leu Lys
                435                 440                 445

Phe Ile Lys Ala Ser Leu Asn Thr Gly Met Ser Gln Gly Tyr Gly Leu
            450                 455                 460

Thr Glu Ser Phe Ala Gly Val Cys Thr Ser Leu Lys Tyr Glu Ala Asn
465                 470                 475                 480

Pro Gly Ser Cys Gly Ala Ile Ser Ile Thr Thr Glu Met Arg Leu Arg
                485                 490                 495

Glu Val Pro Glu Met Asn Tyr His Ala His Asp Lys Gly Gly Pro Arg
            500                 505                 510

Gly Glu Leu Met Leu Arg Gly Pro Gln Ile Phe Arg Glu Tyr Phe Lys
            515                 520                 525

Asn Pro Glu Glu Thr Ala Lys Ala Ile Asp Ser Glu Gly Trp Phe Ala
530                 535                 540

Thr Gly Asp Ile Ala Arg Ile Asp Ala Thr Asn Gly Asn Arg Ile Tyr
545                 550                 555                 560

Ile Ile Asp Arg Val Lys Asn Phe Phe Lys Leu Ala Gln Gly Glu Tyr
                565                 570                 575

Ile Thr Pro Glu Lys Ile Glu Asn Thr Tyr Leu Ser Gln Phe Pro Phe
            580                 585                 590

Ile Gln Gln Leu Tyr Val His Gly Asp Pro Leu Lys Thr His Leu Val
            595                 600                 605

Ala Ile Val Gly Leu Asp Pro Ala Thr Val Asp Ser Tyr Ile Lys Arg
610                 615                 620

Lys Phe Asn Asp Ile Leu Ser Asn Gln Asp Ile Val Asp Phe Phe
625                 630                 635                 640

Arg Asn Pro Lys His Arg Leu Ala Leu Leu Glu Asp Met Asn Ser Ser
                645                 650                 655

Val Gly Gly Leu Leu Gln Gly Tyr Glu Arg Ile His Asn Ile Lys Val
            660                 665                 670

Asp Phe Asn Pro Leu Thr Ile Glu Asp Asn Val Ile Thr Pro Thr Leu
            675                 680                 685

Lys Ile Lys Arg Pro Ile Ala Val Lys Phe Phe Lys Glu Asp Phe Asp
690                 695                 700

Ala Leu Tyr Glu Glu Gly Ser Leu Ile Lys Pro Asp Ala His Lys Leu
705                 710                 715                 720
```

<210> SEQ ID NO 16
<211> LENGTH: 752
<212> TYPE: PRT
<213> ORGANISM: Debaryomyces hansenii

<400> SEQUENCE: 16

```
Met Thr Ser Ser Asp Val Tyr Asp His Gly Asp Ser Pro Tyr Val Phe
1               5                   10                  15
```

```
Lys Pro Ser Lys Thr Pro Ala Ser Gln Leu Ile Arg Asp His Leu Pro
             20                  25                  30

Leu Pro Glu Lys Met Phe Lys Asp Ser Val Ser Leu Pro Gly Thr Glu
         35                  40                  45

Lys Glu Gly Tyr Ser Ala Ile Tyr Arg Asn Lys Met Phe Pro Gly Arg
     50                  55                  60

Leu Lys Glu Ala Leu Thr Pro Glu Leu Asp Thr Tyr Arg Leu Phe
 65              70                  75                  80

Lys Asn Ser Val Leu Thr Phe Gly Asp Lys Ser Cys Leu Ala Tyr Arg
                 85                  90                  95

Lys Tyr Asp Tyr Val Asn Lys Lys Ser Ala Asp Asp Tyr Ser Phe Leu
             100                 105                 110

Thr Tyr Arg Glu Val Asp Glu Met Lys Gln Arg Tyr Gly Ser Gly Phe
         115                 120                 125

Leu Tyr Leu Leu Gln Asn Asn Pro Phe Lys Asn Ser Glu Lys Phe Glu
130                 135                 140

Ser His Arg Lys Ile Asp Asn His Val Lys Asp Tyr Lys Asn Phe Asp
145                 150                 155                 160

Ile Ser Asp Met Ser Phe Val Ala Thr Ile Tyr Ser Ala Asn Arg Met
                 165                 170                 175

Glu Trp Val Leu Ser Asp Leu Met Cys Ser Ser Tyr Ser Ile Thr Asn
             180                 185                 190

Thr Ala Leu Tyr Asp Thr Leu Gly Ala Asp Thr Ser Glu Tyr Ile Leu
         195                 200                 205

Gln Thr Thr Gln Ser Pro Val Val Ile Ala Thr Lys Glu His Val Met
     210                 215                 220

Asp Ile Val Asn Leu Lys Glu Lys Tyr Pro Glu Lys Leu Glu His Val
225                 230                 235                 240

Ile Ser Ile Val Cys Leu Asp Pro Leu Asp Leu Lys Asn Glu Thr Ser
                 245                 250                 255

Leu Ser Ala Glu Asp Gln Ala Leu Val Thr Ala Cys Lys Ser His Arg
             260                 265                 270

Ile Thr Leu Val Asp Ile Asn Gln Val Met Lys Val Gly Glu Ile Phe
         275                 280                 285

Pro Thr Pro Glu Leu Pro Pro Ser Pro Glu Thr Leu Tyr Thr Ile Ser
     290                 295                 300

Phe Thr Ser Gly Thr Thr Gly Ala His Pro Lys Gly Val Leu Leu Ser
305                 310                 315                 320

Gln Lys Ile Cys Thr Ala Gly Val Thr Phe Val Leu Thr Gln Leu Pro
                 325                 330                 335

Arg Ile Pro Asp Ala Arg Ser Phe Ser Phe Leu Pro Leu Ala His Ile
             340                 345                 350

Phe Glu Arg Gln Val Cys Ala Phe Gly Leu Ser Cys Gly Asn Cys Ile
         355                 360                 365

Gly Phe Pro Gln Asn Gly Gly Thr Pro Leu Thr Leu Ile Glu Asp Leu
     370                 375                 380

Lys Leu Phe Lys Pro Asn Tyr Met Cys Asn Val Pro Arg Val Phe Thr
385                 390                 395                 400

Lys Tyr Glu Ala Ala Ile Lys Ser Ala Thr Val Asp His Pro Thr Ser
                 405                 410                 415

Thr Phe Lys Arg Gly Ile Phe Asp Lys Val Ile Ser Thr Lys Ile Gln
             420                 425                 430

Ala Gln Glu Lys Tyr Asp Gly Ala Asp Gly Ser His Leu Val Tyr Asp
```

```
                435                 440                 445
Arg Leu Phe Leu Ser Ser Ile Arg Lys Ala Phe Gly Phe Asp Asn Met
450                 455                 460

Glu Phe Ile Val Thr Gly Ser Ala Pro Ile Ser Pro Ser Thr Val Lys
465                 470                 475                 480

Phe Leu Lys Ala Thr Leu Cys Val Gly Met Pro Gln Gly Tyr Gly Ser
                485                 490                 495

Thr Glu Ser Phe Ala Gly Phe Ala Ile Gly Ile Pro Tyr Glu Ala Glu
                500                 505                 510

Pro Gly Ser Cys Gly Ser Val Gly Val Thr Val Glu Met Lys Leu Arg
            515                 520                 525

Glu Leu Pro Ala Met Gly Tyr Asn Leu Asp Asp Pro Glu Gly Pro Arg
530                 535                 540

Gly Glu Leu Leu Leu Arg Gly Pro Gln Ile Phe Lys Gln Tyr Phe His
545                 550                 555                 560

Asn Glu Glu Thr Lys Lys Ser Phe Asp Asp Glu Gly Trp Phe His
                565                 570                 575

Thr Gly Asp Val Ala Arg Phe Ser Lys Asn Asn Gly Arg Leu Phe Ile
                580                 585                 590

Ile Asp Arg Val Lys Asn Phe Phe Lys Leu Ser Gln Gly Glu Tyr Val
            595                 600                 605

Thr Pro Glu Lys Val Glu Asn Lys Tyr Leu Ser Ser Ser Ile Leu
610                 615                 620

Asn Gln Leu Tyr Val His Gly Asp Ser Leu Arg His Phe Leu Val Gly
625                 630                 635                 640

Ile Val Gly Ile Asp Pro Glu Gly Ala Val Asn Phe Leu Val Glu Lys
                645                 650                 655

Cys Lys Val Ser Lys Ser Gln Leu Ser Ser Glu Gln Ile Leu Asn
            660                 665                 670

Glu Ile Asn Lys Lys Glu Asn Arg Glu Leu Leu Val Ala Tyr Ile Asn
            675                 680                 685

Ser Arg Ile Ser Asn Gln Leu Ser Gly Phe Glu Lys Leu His Asn Ile
690                 695                 700

Tyr Val Glu Phe Glu Pro Leu Arg Leu Asp Arg Asp Val Val Thr Ala
705                 710                 715                 720

Thr Gln Lys Leu Lys Arg Pro Ala Phe Lys Phe Lys Pro Gln
                725                 730                 735

Ile Asp Val Met Tyr Asp Glu Gly Ser Leu Val Lys Gly Pro Lys Leu
            740                 745                 750

<210> SEQ ID NO 17
<211> LENGTH: 713
<212> TYPE: PRT
<213> ORGANISM: Saccharomyces cerevisiae

<400> SEQUENCE: 17

Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ala Thr Ala
                20                  25                  30

Gln Gln Lys Lys Glu His Glu Tyr Glu His Leu Thr Ser Val Lys Ile
            35                  40                  45

Val Pro Gln Arg Pro Ile Ser Asp Arg Leu Gln Pro Ile Ala Thr
50                  55                  60
```

-continued

His Tyr Ser Pro His Leu Asp Gly Leu Gln Asp Tyr Gln Arg Leu His
 65                  70                  75                  80

Lys Glu Ser Ile Glu Asp Pro Ala Lys Phe Phe Gly Ser Lys Ala Thr
                 85                  90                  95

Gln Phe Leu Asn Trp Ser Lys Pro Phe Asp Lys Val Phe Ile Pro Asp
            100                 105                 110

Pro Lys Thr Gly Arg Pro Ser Phe Gln Asn Asn Ala Trp Phe Leu Asn
        115                 120                 125

Gly Gln Leu Asn Ala Cys Tyr Asn Cys Val Asp Arg His Ala Leu Lys
    130                 135                 140

Thr Pro Asn Lys Lys Ala Ile Ile Phe Glu Gly Asp Glu Pro Gly Gln
145                 150                 155                 160

Gly Tyr Ser Ile Thr Tyr Lys Glu Leu Leu Glu Glu Val Cys Gln Val
                165                 170                 175

Ala Gln Val Leu Thr Tyr Ser Met Gly Val Arg Lys Gly Asp Thr Val
            180                 185                 190

Ala Val Tyr Met Pro Met Val Pro Glu Ala Ile Ile Thr Leu Leu Ala
        195                 200                 205

Ile Ser Arg Ile Gly Ala Ile His Ser Val Val Phe Ala Gly Phe Ser
    210                 215                 220

Ser Asn Ser Leu Arg Asp Arg Ile Asn Asp Gly Asp Ser Lys Val Val
225                 230                 235                 240

Ile Thr Thr Asp Glu Ser Asn Arg Gly Gly Lys Val Ile Glu Thr Lys
                245                 250                 255

Arg Ile Val Asp Asp Ala Leu Arg Glu Thr Pro Gly Val Arg His Val
            260                 265                 270

Leu Val Tyr Arg Lys Thr Asn Asn Pro Ser Val Ala Phe His Ala Pro
        275                 280                 285

Arg Asp Leu Asp Trp Ala Thr Glu Lys Lys Lys Tyr Lys Thr Tyr Tyr
    290                 295                 300

Pro Cys Thr Pro Val Asp Ser Glu Asp Pro Leu Phe Leu Leu Tyr Thr
305                 310                 315                 320

Ser Gly Ser Thr Gly Ala Pro Lys Gly Val Gln His Ser Thr Ala Gly
                325                 330                 335

Tyr Leu Leu Gly Ala Leu Leu Thr Met Arg Tyr Thr Phe Asp Thr His
            340                 345                 350

Gln Glu Asp Val Phe Phe Thr Ala Gly Asp Ile Gly Trp Ile Thr Gly
        355                 360                 365

His Thr Tyr Val Val Tyr Gly Pro Leu Leu Tyr Gly Cys Ala Thr Leu
    370                 375                 380

Val Phe Glu Gly Thr Pro Ala Tyr Pro Asn Tyr Ser Arg Tyr Trp Asp
385                 390                 395                 400

Ile Ile Asp Glu His Lys Val Thr Gln Phe Tyr Val Ala Pro Thr Ala
                405                 410                 415

Leu Arg Leu Leu Lys Arg Ala Gly Asp Ser Tyr Ile Glu Asn His Ser
            420                 425                 430

Leu Lys Ser Leu Arg Cys Leu Gly Ser Val Gly Glu Pro Ile Ala Ala
        435                 440                 445

Glu Val Trp Glu Trp Tyr Ser Glu Lys Ile Gly Lys Asn Glu Ile Pro
    450                 455                 460

Ile Val Asp Thr Tyr Trp Gln Thr Glu Ser Gly Ser His Leu Val Thr
465                 470                 475                 480

Pro Leu Ala Gly Gly Val Thr Pro Met Lys Pro Gly Ser Ala Ser Phe

```
                485                 490                 495
Pro Phe Gly Ile Asp Ala Val Val Leu Asp Pro Asn Thr Gly Glu
            500                 505                 510

Glu Leu Asn Thr Ser His Ala Glu Gly Val Leu Ala Val Lys Ala Ala
            515                 520                 525

Trp Pro Ser Phe Ala Arg Thr Ile Trp Lys Asn His Asp Arg Tyr Leu
            530                 535                 540

Asp Thr Tyr Leu Asn Pro Tyr Pro Gly Tyr Tyr Phe Thr Gly Asp Gly
545                 550                 555                 560

Ala Ala Lys Asp Lys Asp Gly Tyr Ile Trp Ile Leu Gly Arg Val Asp
            565                 570                 575

Asp Val Val Asn Val Ser Gly His Arg Leu Ser Thr Ala Glu Ile Glu
            580                 585                 590

Ala Ala Ile Ile Glu Asp Pro Ile Val Ala Glu Cys Ala Val Val Gly
            595                 600                 605

Phe Asn Asp Asp Leu Thr Gly Gln Ala Val Ala Ala Phe Val Val Leu
            610                 615                 620

Lys Asn Lys Ser Ser Trp Ser Thr Ala Thr Asp Asp Glu Leu Gln Asp
625                 630                 635                 640

Ile Lys Lys His Leu Val Phe Thr Val Arg Lys Asp Ile Gly Pro Phe
                645                 650                 655

Ala Ala Pro Lys Leu Ile Ile Leu Val Asp Asp Leu Pro Lys Thr Arg
            660                 665                 670

Ser Gly Lys Ile Met Arg Arg Ile Leu Arg Lys Ile Leu Ala Gly Glu
            675                 680                 685

Ser Asp Gln Leu Gly Asp Val Ser Thr Leu Ser Asn Pro Gly Ile Val
            690                 695                 700

Arg His Leu Ile Asp Ser Val Lys Leu
705                 710

<210> SEQ ID NO 18
<211> LENGTH: 764
<212> TYPE: PRT
<213> ORGANISM: Zygosaccharomyces rouxii

<400> SEQUENCE: 18

Met Thr Val Asn Tyr Val Tyr Ala Gly Met Trp Arg Asn Leu Phe Pro
1               5                   10                  15

Glu Ser Ile Cys Arg Leu Arg Asp Lys Arg Lys Glu His Ile Pro Tyr
            20                  25                  30

Ser Met Ser Pro Ser Thr Thr Ala Thr Gly Thr Ser Pro Thr Gly Gly
        35                  40                  45

Thr Ile Gly Asp Leu Lys Ala Arg Leu Val His Ala Ala Glu Arg Glu
    50                  55                  60

Asn Thr Ser Pro Ala Thr Thr Asn Val Ser Thr Glu Lys Asp His
65                  70                  75                  80

Glu Ala Glu Thr Asn Thr Pro Thr Asp Tyr Asp His Leu Ile Ser
                85                  90                  95

Val His Thr Val Gln Gln Lys Pro Ile Thr His Arg Leu Gln Ser Glu
            100                 105                 110

Leu Ser Cys His Tyr Cys Pro His Ile Ser Gly Phe Arg Glu Tyr Glu
            115                 120                 125

Lys Leu Tyr Arg Glu Ser Ile Asp Gln Pro Ser Glu Phe Phe Gly Asn
    130                 135                 140
```

-continued

```
Lys Ala Arg Gln Phe Leu Asn Trp Phe Lys Asp Phe Asp Gln Val Phe
145                 150                 155                 160

Ile Pro Asp Pro Arg Thr Gly Lys Pro Ser Leu Asn Asn Asn Ala Trp
            165                 170                 175

Phe Leu Asn Gly Gln Thr Asn Ala Cys Tyr Asn Cys Val Asp Arg His
        180                 185                 190

Ala Leu Glu Thr Pro Asp Lys Pro Ala Ile Ile Tyr Glu Thr Asp Glu
    195                 200                 205

Pro Gly Gln Gly Tyr Thr Leu Thr Tyr Ser Glu Leu Leu Glu Gln Val
210                 215                 220

Cys Gln Leu Ala Gln Val Leu Arg Tyr Ser Met Gly Val Arg Lys Gly
225                 230                 235                 240

Asp Thr Val Ala Val Tyr Met Pro Met Ile Pro Gln Ala Val Ile Ser
                245                 250                 255

Leu Met Ala Ile Ala Arg Ile Gly Ala Ile His Ser Val Val Phe Ala
            260                 265                 270

Gly Phe Ser Cys Asn Ser Leu Arg Asp Arg Ile Asn Asp Ala Asp Ser
        275                 280                 285

His Val Val Ile Thr Thr Asp Glu Thr Lys Arg Gly Gly Lys Ile Val
    290                 295                 300

Glu Thr Lys Arg Ile Val Asp Asp Ala Leu Lys Glu Thr Pro Gly Val
305                 310                 315                 320

Ser Asn Val Leu Val Tyr Arg Arg Thr Asn Asn Pro Arg Val Pro Arg
                325                 330                 335

Gln Val Ser Arg Asp Leu Asp Trp Asp Gly Glu Leu Arg Lys Tyr Lys
            340                 345                 350

Gly Tyr Cys Pro Cys Glu Pro Val Asp Ser Glu His Pro Leu Phe Leu
        355                 360                 365

Leu Tyr Thr Ser Gly Ser Thr Gly Thr Pro Lys Gly Val Gln His Ser
    370                 375                 380

Thr Ala Gly Tyr Leu Leu Ser Ala Leu Leu Thr Met Arg Tyr Ser Phe
385                 390                 395                 400

Asp Thr His Arg Glu Asp Val Phe Phe Thr Ala Gly Asp Val Gly Trp
                405                 410                 415

Ile Thr Gly His Thr Tyr Val Val Tyr Gly Pro Leu Leu Tyr Gly Cys
            420                 425                 430

Thr Thr Leu Val Phe Glu Gly Thr Pro Ala Tyr Pro Thr Tyr Ala Arg
        435                 440                 445

Tyr Trp Asp Ile Ile Asp Gln Tyr Lys Val Thr Gln Phe Tyr Val Ala
    450                 455                 460

Pro Thr Ala Leu Arg Leu Leu Lys Arg Ala Gly Asp Ser Phe Ile Glu
465                 470                 475                 480

Gly His Ser Leu Gln Ser Leu Arg Ala Leu Gly Thr Val Gly Glu Pro
                485                 490                 495

Ile Ala Ala Glu Val Trp Glu Trp Tyr Ser Glu Lys Ile Gly Lys Asn
            500                 505                 510

Glu Leu Pro Ile Val Asp Thr Tyr Trp Gln Thr Glu Ser Gly Ser His
        515                 520                 525

Met Leu Thr Pro Met Ala Gly Gly Val Thr Pro Met Lys Pro Gly Ser
    530                 535                 540

Ala Gly Phe Pro Phe Ile Gly Ile Asp Ser Cys Ile Leu Asp Pro Thr
545                 550                 555                 560

Thr Gly Gln Glu Leu Thr Lys Pro Leu Val Glu Gly Val Leu Ala Val
```

-continued

```
                    565                 570                 575
Arg Cys Gly Trp Pro Ser Phe Ala Arg Thr Ile Trp Lys Asp His Asp
            580                 585                 590
Arg Phe Leu Asp Thr Tyr Leu Lys Pro Tyr Pro Gly Tyr Tyr Phe Thr
            595                 600                 605
Gly Asp Gly Ala Ala Arg Asp Lys Asp Gly Tyr Ile Trp Ile Leu Gly
            610                 615                 620
Arg Val Asp Asp Val Val Asn Ile Ser Gly His Arg Leu Ser Thr Ala
625                 630                 635                 640
Glu Ile Glu Ser Ala Val Leu Asp Asp Ala Ile Val Ala Glu Cys Ala
                    645                 650                 655
Val Val Gly Phe Asn Asp Asp Leu Thr Gly Gln Ala Val Ala Ala Phe
                    660                 665                 670
Val Val Leu Lys Asn Lys Ser Ser Trp Ser Thr Ala Ser Glu Glu Glu
                    675                 680                 685
Leu Leu Asp Ile Lys Lys His Leu Ile Leu Ala Val Arg Lys Asp Ile
                    690                 695                 700
Gly Pro Phe Ala Ala Pro Lys Leu Ile Val Val Asp Asp Leu Pro
705                 710                 715                 720
Lys Thr Arg Ser Gly Lys Ile Met Arg Ile Leu Arg Lys Ile Leu
                    725                 730                 735
Ala Gly Glu Cys Asp Gln Leu Gly Asp Val Ser Thr Leu Ser Asn Pro
                    740                 745                 750
Gly Val Val Arg His Leu Ile Asp Ser Val Lys Leu
                    755                 760
```

<210> SEQ ID NO 19
<211> LENGTH: 694
<212> TYPE: PRT
<213> ORGANISM: Ashbya gossypii

<400> SEQUENCE: 19

```
Met Val Thr Ser Ala Gly Val Gly His Ala Glu Tyr Asn Asn Gly Ala
1               5                   10                  15
Asp Val Gln His Ala Asp Tyr Ala His Leu Thr Ser Val Gly Gln Val
                20                  25                  30
Glu Gln Lys Pro Leu Gly Gly Arg Leu Gly Ala Leu Ala Glu Tyr Tyr
            35                  40                  45
Lys Pro Asn Val Ala Ser Met Glu Glu Tyr Arg Ala Met His Ala Gln
    50                  55                  60
Ser Ile Thr Asp Pro Ala Ala Phe Tyr Gly Glu Arg Ala Arg Thr Tyr
65                  70                  75                  80
Val Asp Trp Phe Arg Pro Phe Asp Ala Val Phe Leu Pro Gly Pro Asp
                85                  90                  95
Gly Arg Pro Ser Phe Asp Asn Asn Ala Trp Phe Val Asn Gly Gln Leu
            100                 105                 110
Asn Ala Cys Tyr Asn Leu Val Asp Arg His Ala Ala Arg Thr Pro Asp
            115                 120                 125
Lys Val Ala Ile Ile Tyr Glu Ala Asp Glu Pro Gly Glu Gly Tyr Ser
        130                 135                 140
Leu Thr Tyr Arg Glu Leu Leu Ala Gln Val Cys Lys Val Ala Gln Val
145                 150                 155                 160
Leu Gln Tyr Ser Met Gly Val Arg Lys Gly Asp Thr Val Ala Val Tyr
                165                 170                 175
```

-continued

```
Met Pro Met Ile Pro Gln Ala Leu Val Thr Leu Leu Ala Ile Ser Arg
            180                 185                 190

Ile Gly Ala Ile His Ser Val Val Phe Ala Gly Phe Ser Ser Asn Ser
        195                 200                 205

Leu Arg Asp Arg Ile Asn Asp Ala Arg Ser Glu Val Val Thr Thr
    210                 215                 220

Asp Glu Ser Lys Arg Gly Gly Lys Ile Ile Glu Thr Lys Arg Ile Val
225                 230                 235                 240

Asp Asp Ala Ile Lys Glu Thr Pro Gln Leu Arg Lys Val Leu Val Tyr
                245                 250                 255

Lys Arg Thr Cys Asn Pro Ser Val Ser Tyr Val Ala Asp Arg Asp Leu
            260                 265                 270

Asp Trp Asp Thr Glu Val Lys Lys Tyr Lys Ser Tyr Cys Pro Cys Glu
        275                 280                 285

Pro Val Asp Ser Glu His Pro Leu Phe Leu Leu Tyr Thr Ser Gly Ser
    290                 295                 300

Thr Gly Ala Pro Lys Gly Val Gln His Ser Thr Ala Gly Tyr Leu Leu
305                 310                 315                 320

Gln Ala Tyr Leu Ser Met Leu Tyr Ser Phe Asp Val His Ser Asp Asp
                325                 330                 335

Ile Phe Phe Thr Ala Gly Asp Ile Gly Trp Ile Thr Gly His Thr Tyr
            340                 345                 350

Val Val Tyr Gly Pro Leu Phe Ser Gly Cys Thr Thr Val Phe Glu
        355                 360                 365

Gly Thr Pro Ala Tyr Pro Ser Tyr Ser Arg Tyr Trp Asp Ile Ile Asp
    370                 375                 380

Lys Tyr Ser Val Thr Gln Phe Tyr Val Ala Pro Thr Ala Leu Arg Leu
385                 390                 395                 400

Leu Lys Arg Ala Gly Asp Ser Tyr Val Asp Gly Tyr Ser Leu Arg Thr
                405                 410                 415

Leu Arg Ser Leu Gly Thr Val Gly Glu Pro Ile Ala Ala Glu Val Trp
            420                 425                 430

Glu Trp Tyr Tyr Thr Val Ile Gly Lys Arg Glu Ile Pro Val Ile Asp
        435                 440                 445

Thr Tyr Trp Gln Thr Glu Ser Gly Ala His Leu Val Thr Pro Leu Ala
    450                 455                 460

Gly Gly Ser Thr Pro Met Lys Pro Gly Ser Ala Ser Phe Pro Phe Phe
465                 470                 475                 480

Gly Ile Asp Leu Ala Ile Leu Asp Pro Gln Thr Gly Glu Glu Leu Leu
                485                 490                 495

Gly Pro Asn Val Glu Gly Val Leu Ala Val Lys Gln Pro Trp Pro Ser
            500                 505                 510

Phe Thr Arg Thr Ile Trp Asn Asn His Asp Arg Tyr Leu Asp Thr Tyr
        515                 520                 525

Leu Asn Pro Tyr Lys Gly Tyr Tyr Phe Ala Gly Asp Gly Ala Ala Arg
    530                 535                 540

Asp Ser Gln Gly Phe Ile Trp Ile Leu Gly Arg Val Asp Asp Val Val
545                 550                 555                 560

Asn Val Ser Gly His Arg Leu Ser Thr Ala Glu Val Glu Ala Ala Ile
                565                 570                 575

Ile Gln Glu Ser Met Val Ala Glu Cys Ala Val Val Gly Phe Ala Asp
            580                 585                 590

Glu Leu Thr Gly Gln Ala Ile Ala Ala Phe Val Val Leu Lys Gln Lys
```

```
                    595                 600                 605
Ser Ser Trp Asn Thr Ala Ser Glu Arg Glu Leu Gln Glu Ile Lys Lys
    610                 615                 620

His Leu Ile Leu Ser Val Arg Arg Asp Ile Gly Pro Phe Ala Ala Pro
625                 630                 635                 640

Lys Leu Ile Val Leu Val Asp Asp Leu Pro Lys Thr Arg Ser Gly Lys
                645                 650                 655

Ile Met Arg Arg Ile Leu Arg Lys Ile Leu Ala Gly Glu Ala Asp Gln
                660                 665                 670

Leu Gly Asp Val Ser Thr Leu Ser Asn Pro Gly Ile Val Lys His Leu
                675                 680                 685

Ile Glu Ser Val Lys Phe
                690

<210> SEQ ID NO 20
<211> LENGTH: 683
<212> TYPE: PRT
<213> ORGANISM: Kluyveromyces lactis

<400> SEQUENCE: 20

Met Lys Ser Asn Ala Ser Ala Ala Ala Asp Gln Ile Lys Thr His
1               5                   10                  15

Glu Tyr Glu His Leu Thr Ser Val Pro Ile Val Gln Pro Leu Pro Ile
                20                  25                  30

Thr Asp Arg Leu Ser Ser Glu Ala Ala Gln Lys Tyr Lys Pro Asn Leu
            35                  40                  45

Pro Gly Gly Phe Glu Glu Tyr Lys Ser Leu His Lys Glu Ser Leu Glu
    50                  55                  60

Asn Pro Ala Lys Phe Tyr His Glu Arg Ala Gln Leu Leu Asn Trp Phe
65                  70                  75                  80

Lys Pro Tyr Asp Gln Val Phe Ile Pro Asp Thr Glu Gly Lys Pro Thr
                85                  90                  95

Phe Glu Asn Asn Ala Trp Phe Thr Asn Gly Gln Leu Asn Ala Cys Tyr
                100                 105                 110

Asn Leu Val Asp Arg His Ala Phe Thr Gln Pro Asn Lys Val Ala Ile
            115                 120                 125

Leu Tyr Glu Ala Asp Glu Pro Gly Gln Gly Tyr Ser Leu Thr Tyr Ala
    130                 135                 140

Glu Leu Leu Glu Gln Val Cys Lys Val Ala Gln Ile Leu Gln Tyr Ser
145                 150                 155                 160

Met Asn Val Lys Lys Gly Asp Thr Val Ala Val Tyr Met Pro Met Ile
                165                 170                 175

Pro Gln Ala Leu Ile Thr Leu Leu Ala Ile Thr Arg Ile Gly Ala Ile
            180                 185                 190

His Ser Val Val Phe Ala Gly Phe Ser Ser Asn Ser Leu Arg Asp Arg
        195                 200                 205

Ile Asn Asp Ala Tyr Ser Lys Thr Val Ile Thr Thr Asp Glu Ser Lys
    210                 215                 220

Arg Gly Gly Lys Thr Ile Glu Thr Lys Arg Ile Val Asp Glu Ala Leu
225                 230                 235                 240

Lys Asp Thr Pro Gln Val Thr Asn Val Leu Val Phe Lys Arg Thr His
                245                 250                 255

Asn Glu Asn Ile Lys Tyr Ile Pro Gly Arg Asp Leu Asp Trp Asp Glu
                260                 265                 270
```

-continued

```
Glu Val Lys Lys Tyr Lys Ser Tyr Thr Pro Cys Glu Pro Val Asp Ser
            275                 280                 285

Glu His Pro Leu Phe Leu Leu Tyr Thr Ser Gly Ser Thr Gly Ala Pro
290                     295                 300

Lys Gly Val Gln His Ser Thr Ala Gly Tyr Leu Leu Gln Ala Leu Leu
305                     310                 315                 320

Ser Met Lys Tyr Thr Phe Asp Ile Gln Asn Asp Asp Ile Phe Phe Thr
                    325                 330                 335

Ala Gly Asp Ile Gly Trp Ile Thr Gly His Thr Tyr Cys Val Tyr Gly
                340                 345                 350

Pro Leu Leu Gln Gly Cys Thr Thr Leu Val Phe Glu Gly Thr Pro Ala
            355                 360                 365

Tyr Pro Asn Phe Ser Arg Tyr Trp Glu Ile Val Asp Lys Tyr Gln Val
    370                 375                 380

Thr Gln Phe Tyr Val Ala Pro Thr Ala Leu Arg Leu Leu Lys Arg Ala
385                 390                 395                 400

Gly Asp Ser Phe Thr Glu Gly Phe Ser Leu Lys Ser Leu Arg Ser Leu
                    405                 410                 415

Gly Ser Val Gly Glu Pro Ile Ala Ala Glu Val Trp Glu Trp Tyr Ser
                420                 425                 430

Glu Lys Ile Gly Lys Asn Glu Leu Pro Ile Val Asp Thr Tyr Trp Gln
            435                 440                 445

Thr Glu Ser Gly Ser His Leu Val Thr Pro Leu Ala Gly Gly Ala Thr
        450                 455                 460

Pro Met Lys Pro Gly Ala Ala Phe Pro Phe Phe Gly Ile Asp Leu
465                 470                 475                 480

Ala Val Leu Asp Pro Thr Thr Gly Ile Glu Gln Thr Gly Glu His Ala
                485                 490                 495

Glu Gly Val Leu Ala Ile Lys Arg Pro Trp Pro Ser Phe Ala Arg Thr
            500                 505                 510

Ile Trp Lys Asn Asn Asp Arg Phe Leu Asp Thr Tyr Leu Lys Pro Tyr
    515                 520                 525

Pro Gly Tyr Tyr Phe Thr Gly Asp Gly Val Ala Arg Asp Lys Asp Gly
530                 535                 540

Phe Phe Trp Ile Leu Gly Arg Val Asp Asp Val Asn Val Ser Gly
545                 550                 555                 560

His Arg Leu Ser Thr Ala Glu Ile Glu Ala Ala Ile Ile Glu Asp Asp
                565                 570                 575

Met Val Ala Glu Cys Ala Val Val Gly Phe Asn Asp Glu Leu Thr Gly
                580                 585                 590

Gln Ala Val Ala Ala Phe Val Val Leu Lys Asn Lys Ser Ser Leu Thr
            595                 600                 605

Ala Ala Ser Glu Ser Glu Leu Gln Asp Ile Lys Lys His Leu Ile Ile
610                 615                 620

Thr Val Arg Lys Asp Ile Gly Pro Phe Ala Ala Pro Lys Leu Ile Val
625                 630                 635                 640

Leu Val Asp Asp Leu Pro Lys Thr Arg Ser Gly Lys Ile Met Arg Arg
                645                 650                 655

Ile Leu Arg Lys Ile Leu Ala Gly Glu Ser Asp Gln Leu Ala Thr Ser
                660                 665                 670

Pro His Tyr Pro Thr Leu Val Ser Leu Ser Thr
            675                 680
```

<210> SEQ ID NO 21
<211> LENGTH: 670
<212> TYPE: PRT
<213> ORGANISM: Ogataea parapolymorpha

<400> SEQUENCE: 21

```
Met Pro Glu Lys His Leu Glu Asn Glu His Leu Met Arg Glu Arg Ala
1               5                   10                  15

Leu Glu Pro Pro Ala Gly Phe Leu Glu Arg His Pro Ser Lys Pro Tyr
            20                  25                  30

Leu Ser Ser Leu Asp Glu Tyr Lys Lys Met Tyr Glu Glu Ser Ile Arg
        35                  40                  45

Asp Pro Gly Ser Phe Phe Gly Gly Met Ala Glu Gln His Leu Ser Trp
    50                  55                  60

Phe Lys Pro Phe Thr Val Pro Lys Val Pro Asn Ala Pro Phe Leu Lys
65                  70                  75                  80

Asp Asn Asn Gly Glu Pro Ser Ala Trp Phe Val Asp Gly Leu Asn
                85                  90                  95

Ala Cys Tyr Asn Cys Val Asp Arg Trp Ala Ile Lys Asn Pro Asp Lys
            100                 105                 110

Pro Ala Ile Ile Tyr Glu Ala Asp Glu Pro Gln Gly Glu Ile Ile
            115                 120                 125

Thr Tyr Gly Glu Leu Leu Lys Gln Val Cys Lys Val Ser Gln Val Leu
    130                 135                 140

Leu Asn Leu Gly Val Lys Lys Gly Asp Thr Val Ala Val Tyr Leu Pro
145                 150                 155                 160

Met Ile Pro Glu Ala Ile Val Thr Leu Met Ala Ile Val Arg Ile Gly
            165                 170                 175

Ala Ile His Ser Val Val Phe Ala Gly Phe Ser Ser Gly Ser Leu Arg
            180                 185                 190

Asp Arg Ile Asn Asp Ala Asn Ser Lys Val Val Ile Thr Thr Asp Glu
    195                 200                 205

Ser Lys Arg Gly Gly Lys Ile Ile Glu Thr Lys Lys Ile Val Asp Asp
    210                 215                 220

Ala Leu Leu Ala Cys Pro Gln Val Thr Asn Val Leu Val Tyr Lys Arg
225                 230                 235                 240

Thr Gly Asn Ser His Ile Pro Trp Thr Glu Gly Arg Asp Leu Trp Trp
            245                 250                 255

His Glu Glu Val Lys Lys Tyr Pro Ser Tyr Tyr Pro Ala Thr Pro Val
            260                 265                 270

Ser Ala Glu Asp Thr Leu Phe Leu Leu Tyr Thr Ser Gly Ser Thr Gly
        275                 280                 285

Lys Pro Lys Gly Ile Gln His Ser Thr Ala Gly Tyr Leu Leu Gly Ala
    290                 295                 300

Leu Leu Thr Thr Lys Tyr Val Phe Asp Val His Pro Glu Asp Ile Leu
305                 310                 315                 320

Phe Thr Ala Gly Asp Val Gly Trp Ile Thr Gly His Ser Tyr Val Val
            325                 330                 335

Tyr Gly Pro Leu Leu Asn Gly Ala Thr Thr Val Val Phe Glu Gly Thr
            340                 345                 350

Pro Ala Tyr Pro Asn Tyr Ser Arg Tyr Trp Glu Ile Val Asp Lys Tyr
        355                 360                 365

Lys Val Thr Gln Phe Tyr Val Ala Pro Thr Ala Leu Arg Leu Leu Lys
    370                 375                 380
```

-continued

Arg Ala Gly Glu Ser Tyr Ile Glu Pro Tyr Ser Leu Gln Ser Leu Arg
385                 390                 395                 400

Val Leu Gly Ser Val Gly Glu Pro Ile Ala Lys Asp Val Trp Glu Trp
            405                 410                 415

Tyr Asn Ala His Ile Gly Arg Gly Lys Ala His Ile Cys Asp Thr Tyr
            420                 425                 430

Trp Gln Thr Glu Ser Gly Ser His Leu Ile Thr Pro Leu Ala Gly Val
            435                 440                 445

Thr Pro Thr Lys Pro Gly Ser Ala Ser Leu Pro Phe Phe Gly Ile Asp
            450                 455                 460

Pro Ala Ile Ile Asp Pro Val Ser Gly Lys Glu Leu Glu Gly Asn Glu
465                 470                 475                 480

Val Glu Gly Val Leu Ala Ile Arg Ser Ser Trp Pro Ser Met Ala Arg
            485                 490                 495

Thr Ile Trp Arg Asp Tyr Ser Arg Phe Leu Asp Thr Tyr Leu Arg Pro
            500                 505                 510

Tyr His Gly Tyr Tyr Phe Ser Gly Asp Gly Ala Ala Arg Asp Lys Asp
            515                 520                 525

Gly Phe Tyr Trp Ile Leu Gly Arg Val Asp Asp Val Val Asn Val Ser
530                 535                 540

Gly His Arg Leu Ser Thr Ala Glu Ile Glu Ala Ala Leu Ile Glu His
545                 550                 555                 560

Ser Met Val Ala Glu Ser Ala Val Val Gly Phe Pro Asp Glu Leu Thr
            565                 570                 575

Gly Ser Ala Val Ala Ala Phe Val Ser Leu Lys Asn Arg Ser Ile Glu
            580                 585                 590

Asp Pro Ser Ala Ile Lys Lys Glu Leu Ile Leu Thr Val Arg Lys Glu
            595                 600                 605

Ile Gly Pro Phe Ala Ala Pro Lys Leu Ile Leu Leu Val Asn Asp Leu
610                 615                 620

Pro Lys Thr Arg Ser Gly Lys Ile Met Arg Arg Ile Leu Arg Lys Ile
625                 630                 635                 640

Leu Ser Gly Glu Glu Asp Gln Leu Gly Asp Thr Ser Thr Leu Ser Asn
            645                 650                 655

Pro Gln Val Val Ser His Leu Ile Glu Val Val Lys Ala Lys
            660                 665                 670

<210> SEQ ID NO 22
<211> LENGTH: 670
<212> TYPE: PRT
<213> ORGANISM: Meyerozyma guilliermondii

<400> SEQUENCE: 22

Met Pro Glu Ser Thr Asp His Leu Asp His Glu Lys Met Leu Asp Pro
1               5                   10                  15

Pro Lys Gly Phe Phe Glu Arg Ser Thr Ser Lys Pro Asn Leu Ala Ser
            20                  25                  30

Leu Asp Glu Tyr Lys Lys Leu Tyr Lys Gln Ser Ile Glu Asp Pro Ala
        35                  40                  45

Thr Phe Phe Gly Asn Ala Ala Lys Ser Phe Leu Asp Trp Asp Arg Pro
    50                  55                  60

Phe Asp Tyr Thr Arg Phe Pro Val Asp Pro Lys Asp Phe Lys Asn
65                  70                  75                  80

Gly Asp Ile Pro Ser Trp Phe Ile Asn Gly Gln Leu Asn Ala Ser Tyr
                85                  90                  95

```
Asn Ala Val Asp Arg Trp Ala Met Lys Asn Pro Glu Lys Pro Ala Ile
            100                 105                 110

Ile Tyr Glu Ala Asp Glu Val Asn Glu Gly Arg Thr Ile Thr Tyr Gly
            115                 120                 125

Glu Leu Leu Lys Asp Val Ser Lys Leu Ala Ala Thr Leu Thr Asn Leu
            130                 135                 140

Gly Val Lys Lys Gly Asp Ser Val Ala Val Tyr Leu Pro Met Ile Pro
145                 150                 155                 160

Glu Ala Ile Val Thr Leu Leu Ala Ile Val Arg Ile Gly Ala Leu His
                165                 170                 175

Ser Val Val Phe Ala Gly Phe Ser Ser Thr Ser Leu Arg Asp Arg Ile
            180                 185                 190

Ile Asp Ala Asp Ser Arg Ile Val Ile Thr Ala Asp Glu Ser Lys Arg
            195                 200                 205

Gly Gly Lys Thr Ile Glu Thr Lys Lys Ile Val Asp Asp Ala Leu Lys
            210                 215                 220

Glu Cys Pro His Val Arg Asn Val Leu Val Phe Lys Arg Thr Gly Asn
225                 230                 235                 240

Ser His Val Pro Phe Ser Ala Gly Arg Asp Leu Trp Trp His Asp Glu
                245                 250                 255

Leu Gln Lys Tyr Gly Pro Tyr Phe Pro Pro Val Pro Val Asn Ser Glu
            260                 265                 270

Asp Pro Leu Phe Leu Leu Tyr Thr Ser Gly Ser Thr Gly Lys Pro Lys
            275                 280                 285

Gly Val Gln His Asn Thr Ala Gly Tyr Leu Leu Gly Ala Leu Met Thr
            290                 295                 300

Ala Lys Tyr Thr Phe Asp Leu His Glu Glu Asp Ile Ile Phe Thr Ala
305                 310                 315                 320

Gly Asp Val Gly Trp Ile Thr Gly His Thr Tyr Val Val Tyr Gly Pro
                325                 330                 335

Leu Leu Cys Gly Ala Thr Thr Val Val Phe Glu Gly Thr Pro Ala Tyr
            340                 345                 350

Pro Asp Tyr Ser Arg Tyr Trp Asp Val Val Asp Lys Tyr Lys Val Asn
            355                 360                 365

Gln Phe Tyr Val Ala Pro Thr Ala Leu Arg Leu Leu Lys Arg Ala Gly
            370                 375                 380

Thr Lys Tyr Val Glu Lys His Asp Leu Ser Ser Leu Arg Val Leu Gly
385                 390                 395                 400

Ser Val Gly Glu Pro Ile Ala Ala Glu Val Trp His Trp Tyr Asn Asp
                405                 410                 415

Asn Ile Gly Arg Gly Lys Ala His Ile Val Asp Thr Tyr Trp Gln Thr
            420                 425                 430

Glu Ser Gly Ser His Leu Leu Thr Pro Leu Ala Gly Val Thr Pro Thr
            435                 440                 445

Lys Pro Gly Ser Ala Ser Leu Pro Phe Phe Gly Ile Asp Ala Arg Ile
            450                 455                 460

Leu Asp Pro Val Ser Gly Lys Asp Leu Val Asp Asn Asn Val Glu Gly
465                 470                 475                 480

Val Leu Cys Val Lys Ser Ala Trp Pro Ser Ile Thr Arg Gly Ile Tyr
                485                 490                 495

His Asp Tyr Ala Arg Tyr Ile Glu Thr Tyr Leu Lys Pro Tyr Pro Asn
            500                 505                 510
```

```
His Tyr Phe Ser Gly Asp Gly Ala Arg Asp Lys Asp Gly Phe Phe
            515                 520                 525

Trp Ile Leu Gly Arg Val Asp Asp Val Val Asn Val Ser Gly His Arg
530                 535                 540

Leu Ser Thr Ala Glu Ile Glu Ala Ala Leu Ile Glu His Glu Leu Val
545                 550                 555                 560

Gly Glu Ser Ala Val Val Gly Tyr Ala Asp Glu Leu Thr Gly Gln Ala
                565                 570                 575

Val Ala Ala Tyr Val Ser Leu Lys Ser Asn Val Glu Val Asp Asp Leu
            580                 585                 590

Glu Ala Ile Lys Lys Glu Leu Ile Leu Thr Val Arg Lys Glu Ile Gly
            595                 600                 605

Pro Phe Ala Ala Pro Lys Leu Ile Leu Leu Val Asp Asp Leu Pro Lys
            610                 615                 620

Thr Arg Ser Gly Lys Ile Met Arg Arg Ile Leu Arg Lys Val Leu Ala
625                 630                 635                 640

Gly Glu Glu Asp Gln Leu Gly Asp Ile Ser Thr Leu Ser Asn Pro Gln
                645                 650                 655

Val Val Ser Gln Val Ile Glu Val Val Lys Ala Ser Arg Lys
            660                 665                 670

<210> SEQ ID NO 23
<211> LENGTH: 572
<212> TYPE: PRT
<213> ORGANISM: Arabidopsis thaliana

<400> SEQUENCE: 23

Met Asp Asn Leu Val Leu Cys Glu Ala Asn Asn Val Pro Leu Thr Pro
1               5                   10                  15

Ile Thr Phe Leu Lys Arg Ala Ser Glu Cys Tyr Pro Asn Arg Thr Ser
            20                  25                  30

Ile Ile Tyr Gly Gln Thr Arg Phe Thr Trp Pro Gln Thr Tyr Asp Arg
        35                  40                  45

Cys Cys Arg Leu Ala Ala Ser Leu Leu Ser Leu Asn Ile Thr Arg Asn
    50                  55                  60

Asp Val Val Ser Ile Leu Ala Pro Asn Val Pro Ala Met Tyr Glu Met
65                  70                  75                  80

His Phe Ser Val Pro Met Thr Gly Ala Val Leu Asn Pro Ile Asn Thr
                85                  90                  95

Arg Leu Asp Ala Lys Thr Ile Ala Ile Ile Leu Arg His Ala Glu Pro
            100                 105                 110

Lys Ile Leu Phe Val Asp Tyr Glu Phe Ala Pro Leu Ile Gln Glu Val
        115                 120                 125

Leu Arg Leu Ile Pro Thr Asp Gln Ser Gln Ala His Pro Arg Ile Ile
    130                 135                 140

Leu Ile Asn Glu Ile Asp Ser Thr Thr Lys Pro Phe Ser Lys Glu Leu
145                 150                 155                 160

Asp Tyr Glu Gly Leu Ile Arg Lys Gly Glu Pro Thr Pro Ser Ser Ser
                165                 170                 175

Ala Ser Met Phe Arg Val His Asn Glu His Asp Pro Ile Ser Leu Asn
            180                 185                 190

Tyr Thr Ser Gly Thr Thr Ala Asp Pro Lys Gly Val Val Ile Ser His
        195                 200                 205

Arg Gly Ala Tyr Leu Ser Ala Leu Ser Ser Ile Ile Gly Trp Glu Met
    210                 215                 220
```

```
Gly Ile Phe Pro Val Tyr Leu Trp Thr Leu Pro Met Phe His Cys Asn
225                 230                 235                 240

Gly Trp Thr His Thr Trp Ser Val Ala Ala Arg Gly Gly Thr Asn Val
                245                 250                 255

Cys Ile Arg His Val Thr Ala Pro Glu Ile Tyr Lys Asn Ile Glu Leu
                260                 265                 270

His Gly Val Thr His Met Ser Cys Val Pro Thr Val Phe Arg Phe Leu
                275                 280                 285

Leu Glu Gly Ser Arg Thr Asp Gln Ser Pro Lys Ser Ser Pro Val Gln
            290                 295                 300

Val Leu Thr Gly Gly Ser Ser Pro Pro Ala Val Leu Ile Lys Lys Val
305                 310                 315                 320

Glu Gln Leu Gly Phe His Val Met His Gly Tyr Gly Leu Thr Glu Ala
                325                 330                 335

Thr Gly Pro Val Leu Phe Cys Glu Trp Gln Asp Glu Trp Asn Lys Leu
                340                 345                 350

Pro Glu His Gln Gln Met Glu Leu Gln Gln Arg Gln Gly Val Arg Asn
            355                 360                 365

Leu Thr Leu Ala Asp Val Asp Val Lys Asn Thr Lys Thr Leu Glu Ser
370                 375                 380

Val Pro Arg Asp Gly Lys Thr Met Gly Glu Ile Val Ile Lys Gly Ser
385                 390                 395                 400

Ser Leu Met Lys Gly Tyr Leu Lys Asn Pro Lys Ala Thr Ser Glu Ala
                405                 410                 415

Phe Lys His Gly Trp Leu Asn Thr Gly Asp Ile Gly Val Ile His Pro
                420                 425                 430

Asp Gly Tyr Val Glu Ile Lys Asp Arg Ser Lys Asp Ile Ile Ile Ser
            435                 440                 445

Gly Gly Glu Asn Ile Ser Ser Ile Glu Val Glu Lys Val Leu Tyr Met
450                 455                 460

Tyr Gln Gln Val Leu Glu Ala Ala Val Val Ala Met Pro His Pro Leu
465                 470                 475                 480

Trp Gly Glu Thr Pro Cys Ala Phe Val Val Leu Lys Lys Gly Asp Glu
                485                 490                 495

Glu Ser Val Thr Ser Glu Gly Asp Leu Ile Lys Tyr Cys Arg Glu Asn
                500                 505                 510

Met Pro His Phe Met Cys Pro Lys Lys Val Val Phe Phe Gln Glu Leu
            515                 520                 525

Pro Lys Asn Ser Asn Gly Lys Ile Leu Lys Ser Lys Leu Arg Asp Ile
530                 535                 540

Ala Lys Ala Leu Val Val Arg Glu Asp Asp Ala Gly Ser Lys Lys Val
545                 550                 555                 560

His Gln Arg Ser Ile Glu His Val Ser Ser Arg Leu
                565                 570

<210> SEQ ID NO 24
<211> LENGTH: 578
<212> TYPE: PRT
<213> ORGANISM: Arabidopsis thaliana

<400> SEQUENCE: 24

Met Asp Asn Leu Ala Leu Cys Glu Ala Asn Asn Val Pro Leu Thr Pro
1               5                   10                  15

Ile Thr Phe Leu Lys Arg Ala Ser Glu Cys Tyr Pro Asn Arg Thr Ser
```

```
                    20                  25                  30
Ile Ile Tyr Gly Lys Thr Arg Phe Thr Trp Pro Gln Thr Tyr Asp Arg
                35                  40                  45

Cys Cys Arg Leu Ala Ala Ser Leu Ile Ser Leu Asn Ile Gly Lys Asn
    50                  55                  60

Asp Val Val Ser Val Val Ala Pro Asn Thr Pro Ala Met Tyr Glu Met
65                  70                  75                  80

His Phe Ala Val Pro Met Ala Gly Ala Val Leu Asn Pro Ile Asn Thr
                85                  90                  95

Arg Leu Asp Ala Thr Ser Ile Ala Ala Ile Leu Arg His Ala Lys Pro
            100                 105                 110

Lys Ile Leu Phe Ile Asp Arg Ser Phe Glu Pro Leu Ala Arg Glu Ile
            115                 120                 125

Leu Gln Leu Leu Ser Ser Glu Asp Ser Asn Leu Asn Leu Pro Val Ile
            130                 135                 140

Phe Ile His Glu Ile Asp Phe Pro Lys Arg Val Ser Ser Glu Glu Ser
145                 150                 155                 160

Asp Tyr Glu Cys Leu Ile Gln Arg Gly Glu Pro Thr Pro Ser Leu Leu
                165                 170                 175

Ala Arg Met Phe Cys Ile Gln Asp Glu His Asp Pro Ile Ser Leu Asn
            180                 185                 190

Tyr Thr Ser Gly Thr Thr Ala Asp Pro Lys Gly Val Val Ile Ser His
            195                 200                 205

Arg Gly Ala Tyr Leu Ser Thr Leu Ser Ala Ile Ile Gly Trp Glu Met
            210                 215                 220

Gly Thr Cys Pro Val Tyr Leu Trp Thr Leu Pro Met Phe His Cys Asn
225                 230                 235                 240

Gly Trp Thr Phe Thr Trp Gly Thr Ala Ala Arg Gly Gly Thr Ser Val
                245                 250                 255

Cys Met Arg His Val Thr Ala Pro Glu Ile Tyr Lys Asn Ile Glu Met
            260                 265                 270

His Asn Val Thr His Met Cys Cys Val Pro Thr Val Phe Asn Ile Leu
            275                 280                 285

Leu Lys Gly Asn Ser Leu Asp Leu Ser His Arg Ser Gly Pro Val His
            290                 295                 300

Val Leu Thr Gly Gly Ser Pro Pro Ala Ala Leu Val Lys Lys Val
305                 310                 315                 320

Gln Arg Leu Gly Phe Gln Val Met His Ala Tyr Gly Leu Thr Glu Ala
                325                 330                 335

Thr Gly Pro Val Leu Phe Cys Glu Trp Gln Asp Glu Trp Asn Arg Leu
            340                 345                 350

Pro Glu Asn Gln Gln Met Glu Leu Lys Ala Arg Gln Gly Leu Ser Ile
            355                 360                 365

Leu Gly Leu Thr Glu Val Asp Val Arg Asn Lys Glu Thr Gln Glu Ser
            370                 375                 380

Val Pro Arg Asp Gly Lys Thr Met Gly Glu Ile Val Met Lys Gly Ser
385                 390                 395                 400

Ser Ile Met Lys Gly Tyr Leu Lys Asn Pro Lys Ala Thr Tyr Glu Ala
                405                 410                 415

Phe Lys His Gly Trp Leu Asn Ser Gly Asp Val Gly Val Ile His Pro
            420                 425                 430

Asp Gly His Val Glu Ile Lys Asp Arg Ser Lys Asp Ile Ile Ile Ser
            435                 440                 445
```

-continued

```
Gly Gly Glu Asn Ile Ser Ser Val Glu Val Glu Asn Ile Ile Tyr Lys
        450                 455                 460

Tyr Pro Lys Val Leu Glu Thr Ala Val Val Ala Met Pro His Pro Thr
465                 470                 475                 480

Trp Gly Glu Thr Pro Cys Ala Phe Val Val Leu Glu Lys Gly Glu Thr
                485                 490                 495

Asn Asn Glu Asp Arg Glu Asp Lys Leu Val Thr Lys Glu Arg Asp Leu
            500                 505                 510

Ile Glu Tyr Cys Arg Glu Asn Leu Pro His Phe Met Cys Pro Arg Lys
        515                 520                 525

Val Val Phe Leu Asp Glu Leu Pro Lys Asn Gly Asn Gly Lys Ile Leu
    530                 535                 540

Lys Pro Lys Leu Arg Asp Ile Ala Lys Gly Leu Val Ala Glu Asp Glu
545                 550                 555                 560

Val Asn Val Arg Ser Lys Val Gln Arg Pro Val Glu His Phe Thr Ser
                565                 570                 575

Arg Leu
```

<210> SEQ ID NO 25
<211> LENGTH: 586
<212> TYPE: PRT
<213> ORGANISM: Populus trichocarpa

<400> SEQUENCE: 25

```
Met Asp Gln Leu Leu Lys Cys Asp Ala Asn Tyr Val Pro Leu Thr Pro
1               5                   10                  15

Ile Thr Phe Leu Lys Arg Ala Asn Ala Val Tyr Ala Asn Arg Thr Ser
            20                  25                  30

Val Ile Tyr Glu Gly Thr Arg Phe Thr Trp Ser Gln Thr Tyr Glu Arg
        35                  40                  45

Cys Cys Arg Leu Ala Asp Ser Leu Arg Ser Leu Asn Val Gly Lys Asn
    50                  55                  60

Asp Val Val Ser Val Leu Ala Pro Asn Ile Pro Ala Val Tyr Glu Met
65                  70                  75                  80

His Phe Ala Val Pro Met Ala Gly Ala Val Leu Asn Thr Ile Asn Ile
                85                  90                  95

Arg Leu Asp Ala Lys Asn Ile Ala Thr Ile Leu Ser His Ser Gly Ala
            100                 105                 110

Lys Val Phe Phe Val Asp Tyr Gln Tyr Lys Glu Leu Ala Ser Lys Ala
        115                 120                 125

Leu Ser Phe Leu Asp Gly Ala Val Pro Ser Ile Ile Ala Cys Ile Asp
    130                 135                 140

Asp Ile Asp Thr Pro Thr Gly Val Gln Phe Gly Gln Leu Glu Tyr Glu
145                 150                 155                 160

Gln Leu Val Gln Arg Gly Asn Pro Gly Tyr Thr Gly Glu Leu Val Gln
                165                 170                 175

Asp Glu Trp Asp Pro Ile Ala Leu Asn Tyr Thr Ser Gly Thr Thr Ser
            180                 185                 190

Ala Pro Lys Gly Val Val Tyr Ser His Arg Gly Ala Tyr Leu Ser Ser
        195                 200                 205

Leu Ser Leu Ile Leu Gly Trp Glu Met Gly Asn Ala Pro Val Tyr Leu
    210                 215                 220

Trp Ser Leu Pro Met Phe His Cys Asn Gly Trp Thr Phe Thr Trp Gly
225                 230                 235                 240
```

```
Val Ala Ala Arg Gly Gly Thr Asn Val Cys Ile Arg Asn Thr Ser Ala
                245                 250                 255

Lys Asp Met Tyr His Asn Ile Ala Glu His Ala Val Thr His Met Cys
            260                 265                 270

Cys Ala Pro Ile Val Phe Asn Val Leu Leu Glu Ala Arg Pro His Glu
        275                 280                 285

Arg Arg Glu Ile Thr Ser Pro Val Glu Ile Leu Thr Gly Gly Ala Pro
    290                 295                 300

Pro Pro Ala Ser Leu Leu Gln Asp Ile Glu Arg Leu Gly Phe His Val
305                 310                 315                 320

Thr His Ala Tyr Gly Leu Thr Glu Ala Thr Gly Pro Ala Leu Val Cys
                325                 330                 335

Glu Trp Gln Lys Lys Trp Asn Lys Leu Pro Gln Gln Asp Gln Ala Lys
            340                 345                 350

Leu Lys Ala Arg Gln Gly Ile Ser Ile Leu Thr Leu Ala Asp Ala Asp
        355                 360                 365

Val Lys Asp Leu Asp Thr Met Val Ser Val Pro Arg Asp Gly Lys Thr
    370                 375                 380

Met Gly Glu Ile Val Leu Arg Gly Ser Ser Ile Met Lys Gly Tyr Phe
385                 390                 395                 400

Lys Asp Pro Glu Ala Thr Ser Lys Ala Phe Arg Asn Gly Trp Phe Ala
                405                 410                 415

Thr Gly Asp Val Gly Val Ile His Pro Asp Gly Tyr Leu Glu Ile Lys
            420                 425                 430

Asp Arg Ser Lys Asp Val Ile Ile Ser Gly Gly Glu Asn Ile Ser Ser
        435                 440                 445

Val Glu Leu Glu Ser Val Leu Tyr Arg His Pro Arg Val Leu Glu Ala
    450                 455                 460

Ala Val Val Ala Met Pro His Pro Lys Trp Gly Glu Ser Pro Cys Ala
465                 470                 475                 480

Phe Ile Ser Val Lys Lys Asn Ser Asn Gly Asp Thr Asn Asp Val Lys
                485                 490                 495

Glu Ser Asp Ile Ile Ala Tyr Cys Lys Lys Asn Leu Pro His Phe Thr
            500                 505                 510

Val Pro Lys Arg Val Glu Phe Met Ala Glu Leu Pro Lys Thr Ser Thr
        515                 520                 525

Gly Lys Ile Gln Lys Phe Gln Leu Arg Ala Leu Ala Gln Asn Phe Val
    530                 535                 540

Val Asn Glu Ile Leu Pro Ser Lys Lys Ile Asn Gly His Ser Gln Pro
545                 550                 555                 560

Ser Ala Ser Gly Arg Val Asn Thr Glu Val Thr Glu Tyr Ala Gln Gly
                565                 570                 575

His Glu Gln Val Leu Ala Leu Ser Arg Leu
            580                 585

<210> SEQ ID NO 26
<211> LENGTH: 578
<212> TYPE: PRT
<213> ORGANISM: Zea mays

<400> SEQUENCE: 26

Met Asp Gln Leu Pro Lys Arg Pro Ala Asn Tyr Val Pro Leu Ser Pro
1               5                   10                  15

Val Gly Phe Leu Pro Arg Ala Asn Ala Val Tyr Gly Asp Arg Thr Ser
```

```
            20                  25                  30
Val Ile Tyr Arg Gly Val Arg Phe Thr Trp Arg Gln Thr Tyr Ala Arg
            35                  40                  45

Cys Arg Arg Leu Ala Ser Ala Leu Leu Ser Leu Gly Val Val Arg Arg
 50                  55                  60

Gly Asp Val Val Ser Val Leu Ala Pro Asn Val Pro Ala Met Tyr Glu
 65                  70                  75                  80

Met His Phe Ala Val Pro Met Ala Gly Ala Val Leu Asn Thr Ile Asn
                 85                  90                  95

Thr Arg Leu Asp Ala Ala Ala Val Ala Thr Ile Leu Arg His Ser Gly
                100                 105                 110

Ala Lys Leu Phe Phe Val Asp Tyr Asp Tyr Val Arg Leu Ala Ser Asp
                115                 120                 125

Ala Leu Arg Leu Leu Asp Ala Ala Asp Val Pro Leu Val Ala Val Ile
                130                 135                 140

Asp Asp Ile His Ser Pro Thr Gly Ala Arg Leu Gly Glu Leu Glu Tyr
145                 150                 155                 160

Glu Ala Leu Leu Ala His Gly Asp Pro Asp Ala Asp Leu Pro Pro Leu
                165                 170                 175

Gln Asp Glu Trp Asp Ala Val Thr Leu Ser Tyr Thr Ser Gly Thr Thr
                180                 185                 190

Ser Ala Pro Lys Gly Val Val Tyr Ser His Arg Gly Ala Tyr Leu Ser
                195                 200                 205

Thr Thr Ser Leu Leu Leu Gln Trp Gly Val Pro Ala Glu Pro Val Tyr
                210                 215                 220

Leu Trp Thr Leu Pro Met Phe His Cys Asn Gly Trp Thr Phe Thr Trp
225                 230                 235                 240

Gly Met Ala Ala Arg Gly Gly Val Asn Val Cys Ile Arg Asp Ala Arg
                245                 250                 255

Pro Ala Asp Ile Tyr Arg Ala Ile Ala Arg His Arg Val Thr His Met
                260                 265                 270

Cys Cys Ala Pro Val Val Phe Ser Ile Leu Leu Asp Gly Asp Gly Asp
                275                 280                 285

Ser Asp Gly Ala Ala Arg Gln Leu Gln Ala Pro Val His Val Leu Thr
290                 295                 300

Gly Gly Ala Pro Pro Ala Ala Leu Leu Glu Arg Val Glu Arg Ile
305                 310                 315                 320

Gly Phe Asn Val Thr His Ala Tyr Gly Leu Thr Glu Ala Thr Gly Pro
                325                 330                 335

Ala Leu Ala Cys Glu Trp Arg Asp Gln Trp Asp Arg Leu Pro Leu Pro
                340                 345                 350

Glu Arg Ala Arg Leu Lys Ala Arg Gln Gly Val Ser Val Leu Ser Leu
                355                 360                 365

Ala Asp Ala Asp Val Lys Asn Ala Asp Thr Met Leu Ser Val Pro Arg
                370                 375                 380

Asp Gly Arg Thr Val Gly Glu Ile Val Leu Arg Gly Ser Ser Val Met
385                 390                 395                 400

Lys Gly Tyr Leu Asn Asn Pro Glu Ala Asn Glu Ser Ala Phe Arg Ala
                405                 410                 415

Gly Trp Phe Leu Thr Gly Asp Val Gly Val Val His Pro Asp Gly Tyr
                420                 425                 430

Ile Glu Ile Lys Asp Arg Ser Lys Asp Val Ile Ile Ser Gly Gly Glu
                435                 440                 445
```

```
Asn Ile Cys Ser Lys Glu Leu Glu Glu Val Leu Phe Arg His Pro Ala
        450                 455                 460

Val Ala Asp Ala Ala Val Ala Met Pro His Pro Arg Trp Gly Glu
465                 470                 475                 480

Thr Pro Cys Ala Phe Val Val Pro Arg Asp Lys Ala Ala Val Leu Ser
                    485                 490                 495

Glu Gly Asp Val Leu Ala Phe Cys Ser Lys Arg Met Ala Arg Phe Met
                500                 505                 510

Val Pro Lys Lys Val Glu Val Gly Ala Leu Pro Arg Asn Ala Leu
            515                 520                 525

Gly Lys Val Glu Lys Val Lys Leu Arg Glu Ala Ala Arg Lys Leu Ala
        530                 535                 540

Pro Thr Val Ala Ala Gln Lys Pro Lys Ala Lys Thr Thr Thr Val
545                 550                 555                 560

Gly Gly Arg Arg Asp Gly Gln Pro Val Ala His Val Met Ala Val Ser
                565                 570                 575

Arg Leu

<210> SEQ ID NO 27
<211> LENGTH: 563
<212> TYPE: PRT
<213> ORGANISM: Medicago truncatula

<400> SEQUENCE: 27

Met Asn Gln Leu Thr Arg Asn Gln Ala Asn Ser Thr Ala Leu Thr Pro
1               5                   10                  15

Leu Thr Phe Leu Glu Arg Ala Ala Thr Val Tyr Gly Asn Ser Ile Ser
                20                  25                  30

Ile Ile Tyr Asn Asn Thr Ser Phe Thr Trp Ser Gln Thr His Lys Arg
            35                  40                  45

Cys Leu Gln Leu Ala Ser Ser Leu Ser Ser Leu Gly Ile Gln Lys Gly
        50                  55                  60

Asp Val Val Ser Val Leu Ser Pro Asn Thr Pro Ala Met Tyr Glu Leu
65                  70                  75                  80

His Phe Ser Val Pro Met Ser Gly Ala Ile Leu Asn Asn Leu Asn Phe
                85                  90                  95

Arg Leu Asp His Lys Thr Leu Ser Val Leu Leu Ile His Ser Glu Ser
                100                 105                 110

Lys Leu Ile Phe Val Asp Ile Leu Ser Leu Ser Leu Thr Leu Asn Ala
            115                 120                 125

Leu Ser Leu Phe Pro Thr Asn Ile Gln Gln Pro Lys Leu Val Leu Ile
        130                 135                 140

Met Asp Glu Thr Leu Ala Pro His Gln Ile Pro Pro Leu Pro Lys Asn
145                 150                 155                 160

Val Asn Ile Ile Asn Thr Tyr Glu Gly Leu Val Ala Lys Gly Asp Pro
                165                 170                 175

Tyr Phe Lys Trp Ile Arg Pro Asp Ser Glu Trp Asp Pro Ile Thr Leu
                180                 185                 190

Asn Tyr Thr Ser Gly Thr Thr Ser Ser Pro Lys Gly Val Val His Cys
            195                 200                 205

His Arg Ala Thr Phe Ile Val Ser Leu Asp Ser Leu Ile Asp Trp Ser
        210                 215                 220

Val Pro Val Gln Pro Val Phe Leu Trp Thr Leu Pro Met Phe His Ser
225                 230                 235                 240
```

```
Asn Gly Trp Ser Tyr Pro Trp Ala Met Ala Val Gly Gly Ile Asn
            245                 250                 255

Ile Cys Thr Arg Arg Thr Asp Ala Pro Thr Ile Tyr Thr Leu Ile Glu
            260                 265                 270

Ser His Gly Val Thr His Met Cys Ala Ala Pro Val Val Leu Asn Met
            275                 280                 285

Leu Ser Asn Phe Asn Lys Thr Glu Pro Leu Lys Lys Pro Val His Val
290                 295                 300

Leu Thr Gly Gly Ser Ser Pro Pro Thr Ala Ile Leu Thr Arg Ala Glu
305                 310                 315                 320

Arg Leu Gly Phe Glu Val Ser His Gly Phe Gly Met Thr Glu Val Ile
                325                 330                 335

Gly Val Ile Val Ser Cys Ala Trp Lys Arg Glu Trp Asp Arg Phe Pro
                340                 345                 350

Ala Thr Glu Lys Ala Arg Met Lys Ala Arg Gln Gly Val Arg Lys Val
                355                 360                 365

Gly Val Ala Glu Val Asp Val Val Gly Pro Thr Gly Glu Ser Val Lys
            370                 375                 380

Asn Asp Gly Val Thr Val Gly Glu Ile Val Lys Gly Ala Cys Val
385                 390                 395                 400

Met Leu Gly Tyr Phe Lys Asp Glu Ile Ala Thr Ser Gln Cys Ile Lys
                405                 410                 415

Lys Asn Gly Trp Phe Tyr Thr Gly Asp Val Ala Val Met His Glu Asp
                420                 425                 430

Gly Tyr Leu Glu Ile Lys Asp Arg Ser Lys Asp Leu Ile Ile Ser Gly
                435                 440                 445

Gly Glu Asn Met Ser Ser Val Glu Val Glu Gly Val Leu Tyr Met His
            450                 455                 460

Ser Ala Val Lys Glu Ala Ala Val Val Ala Arg Pro Asp Asp Phe Trp
465                 470                 475                 480

Gly Glu Thr Pro Cys Gly Phe Val Ser Leu Lys Asp Glu Leu Lys Lys
                485                 490                 495

Asn Asp Ile Pro Thr Asp Asn Glu Ile Lys Glu Phe Cys Lys Glu Lys
                500                 505                 510

Leu Pro His Phe Met Met Pro Lys Thr Ile Val Phe Met Lys Glu Leu
                515                 520                 525

Pro Lys Thr Ser Thr Gly Lys Val Gln Lys His Val Leu Arg Lys Val
            530                 535                 540

Ala Lys Lys Met Gly Ser Leu Ser Leu Pro Pro Pro Arg Leu Ile
545                 550                 555                 560

Ser Arg Ile

<210> SEQ ID NO 28
<211> LENGTH: 542
<212> TYPE: PRT
<213> ORGANISM: Marinobacter algicola

<400> SEQUENCE: 28

Met Asn Ser Ile Phe Asp Lys Gly Leu Glu Pro Thr Asp Ala Asn Asn
1               5                   10                  15

Ala Thr Leu Thr Pro Leu Asp Phe Leu Ala Arg Thr Ala Ser Val Tyr
            20                  25                  30

Pro Glu Tyr Pro Ala Val Ile His Gly Ala Thr Arg Arg Asn Trp Gln
        35                  40                  45
```

-continued

```
Gln Thr Tyr Glu Arg Cys Arg Arg Leu Ala Ser Ala Leu Ala Asp Arg
     50                  55                  60

Gly Val Gly Lys Gly Asp Thr Val Ala Ala Met Leu Pro Asn Ile Pro
 65                  70                  75                  80

Pro Met Leu Glu Cys His Phe Gly Ile Pro Met Leu Gly Ala Val Leu
                 85                  90                  95

Asn Ala Leu Asn Thr Arg Leu Asp Ala Lys Ala Ile Ala Phe Met Leu
             100                 105                 110

Glu His Gly Glu Ala Lys Val Leu Ile Ala Asp Arg Glu Phe Gly Asp
         115                 120                 125

Val Ile Asn Glu Ala Val Gly Met Leu Asp Asn Pro Pro Gln Val Ile
     130                 135                 140

Asp Val Asn Asp Pro Glu Phe Ser Gly Ala Gly Thr Gln Val Ser Asp
145                 150                 155                 160

Leu Asp Tyr Asp Ala Phe Val Ala Ser Gly Asp Pro Ala Phe Asp Trp
                165                 170                 175

Gln Met Pro Ala Asp Glu Trp Asp Ala Ile Ser Leu Cys Tyr Thr Ser
            180                 185                 190

Gly Thr Thr Gly Asn Pro Lys Gly Val Val Tyr His His Arg Gly Ala
        195                 200                 205

Tyr Glu Asn Ala Met Gly Asn Gln Ala Val Trp Ser Met Gly Met His
    210                 215                 220

Pro Val Tyr Leu Trp Thr Leu Pro Met Phe His Cys Asn Gly Trp Cys
225                 230                 235                 240

Phe Pro Trp Thr Ile Thr Ala Phe Ala Gly Thr His Val Cys Leu Arg
                245                 250                 255

Lys Val Glu Pro Glu Lys Ile Leu Gln Leu Ile Ser Glu His Lys Val
            260                 265                 270

Ser His Met Cys Gly Ala Pro Ile Val Leu Asn Thr Leu Leu Gly Ala
        275                 280                 285

Ser Glu Ala Ala Lys Ser Ser Phe Ser His Thr Val Gln Ala Met Thr
    290                 295                 300

Ala Gly Ala Ala Pro Pro Ala Lys Val Ile Glu Ala Ile Glu Asn Met
305                 310                 315                 320

Gly Phe Arg Val Thr His Val Tyr Gly Leu Thr Glu Val Tyr Gly Pro
                325                 330                 335

Val Thr Val Cys Ala Trp Lys Ser Glu Trp Asp Asp Leu Pro Val Glu
            340                 345                 350

Asp Arg Ala Arg Ile Lys Ala Arg Gln Gly Val Arg Tyr His Thr Leu
        355                 360                 365

Ala Gly Met Met Val Gly Asp Pro Glu Thr Met Glu Ala Val Pro Lys
    370                 375                 380

Asp Gly Asn Thr Ile Gly Glu Ile Phe Leu Arg Gly Asn Thr Val Met
385                 390                 395                 400

Lys Gly Tyr Leu Lys Asn Pro Lys Ala Thr Glu Glu Ala Phe Arg Gly
                405                 410                 415

Gly Trp Phe His Thr Gly Asp Leu Ala Val Trp His Ala Asp Gly Tyr
            420                 425                 430

Ala Glu Ile Lys Asp Arg Leu Lys Asp Ile Ile Ser Gly Gly Glu
        435                 440                 445

Asn Ile Ser Thr Ile Glu Val Glu Asp Val Leu Tyr Arg His Pro Asp
    450                 455                 460
```

```
Ile Leu Glu Ala Ala Val Ala Arg Pro Asp Glu Lys Trp Gly Glu
465                 470                 475                 480

Thr Pro Cys Ala Phe Val Thr Leu Lys Pro Glu Ala Gly Glu Val Ser
                485                 490                 495

Glu Asp Asp Ile Ile Ala Phe Cys Arg Glu Arg Met Ala Lys Phe Lys
                500                 505                 510

Val Pro Lys Thr Ile Val Phe Ser Glu Leu Pro Lys Thr Ser Thr Gly
                515                 520                 525

Lys Ile Gln Lys Phe Val Leu Arg Asp Asp Ala Lys Lys Leu
                530                 535                 540

<210> SEQ ID NO 29
<211> LENGTH: 459
<212> TYPE: PRT
<213> ORGANISM: Pseudomonas putida

<400> SEQUENCE: 29

Met Gln Gln Ile Ile Gln Thr Thr Leu Leu Ile Ile Gly Gly Gly Pro
1               5                   10                  15

Gly Gly Tyr Val Ala Ala Ile Arg Ala Gly Gln Leu Gly Ile Pro Thr
                20                  25                  30

Val Leu Val Glu Gly Gln Ala Leu Gly Gly Thr Cys Leu Asn Ile Gly
            35                  40                  45

Cys Ile Pro Ser Lys Ala Leu Ile His Val Ala Glu Gln Phe His Gln
    50                  55                  60

Ala Ser Arg Phe Thr Glu Pro Ser Pro Leu Gly Ile Ser Val Ala Ser
65                  70                  75                  80

Pro Arg Leu Asp Ile Gly Gln Ser Val Thr Trp Lys Asp Gly Ile Val
                85                  90                  95

Asp Arg Leu Thr Thr Gly Val Ala Ala Leu Leu Lys Lys His Gly Val
                100                 105                 110

Lys Val Val His Gly Trp Ala Lys Val Leu Asp Gly Lys Gln Val Glu
            115                 120                 125

Val Asp Gly Gln Arg Ile Gln Cys Glu His Leu Leu Leu Ala Thr Gly
    130                 135                 140

Ser Ser Ser Val Glu Leu Pro Met Leu Pro Leu Gly Gly Pro Val Ile
145                 150                 155                 160

Ser Ser Thr Glu Ala Leu Ala Pro Lys Thr Leu Pro Gln His Leu Val
                165                 170                 175

Val Val Gly Gly Gly Tyr Ile Gly Leu Glu Leu Gly Ile Ala Tyr Arg
                180                 185                 190

Lys Leu Gly Ala Gln Val Ser Val Val Glu Ala Arg Glu Arg Ile Leu
            195                 200                 205

Pro Thr Tyr Asp Ser Glu Leu Thr Ala Pro Val Ala Glu Ser Leu Lys
    210                 215                 220

Lys Leu Gly Ile Ala Leu His Leu Gly His Ser Val Glu Gly Tyr Glu
225                 230                 235                 240

Asn Gly Cys Leu Leu Ala Ser Asp Gly Lys Gly Gln Leu Arg Leu
                245                 250                 255

Glu Ala Asp Gln Val Leu Val Ala Val Gly Arg Arg Pro Arg Thr Lys
            260                 265                 270

Gly Phe Asn Leu Glu Cys Leu Asp Leu Lys Met Asn Gly Ala Ala Ile
    275                 280                 285

Ala Ile Asp Glu Arg Cys His Thr Ser Met His Asn Val Trp Ala Ile
    290                 295                 300
```

```
Gly Asp Val Ala Gly Glu Pro Met Leu Ala His Arg Ala Met Ala Gln
305                 310                 315                 320

Gly Glu Met Val Ala Glu Ile Ile Ala Gly Lys Ala Arg Arg Phe Glu
            325                 330                 335

Pro Thr Ala Ile Ala Ala Val Cys Phe Thr Asp Pro Glu Val Val Val
            340                 345                 350

Val Gly Lys Thr Pro Glu Gln Ala Ser Gln Gln Gly Leu Asp Cys Ile
        355                 360                 365

Val Ala Gln Phe Pro Phe Ala Ala Asn Gly Arg Ala Met Ser Leu Glu
    370                 375                 380

Ser Lys Ser Gly Phe Val Arg Val Val Ala Arg Arg Asp Asn His Leu
385                 390                 395                 400

Ile Val Gly Trp Gln Ala Val Gly Val Ala Val Ser Glu Leu Ser Thr
                405                 410                 415

Ala Phe Ala Gln Ser Leu Glu Met Gly Ala Cys Leu Glu Asp Val Ala
            420                 425                 430

Gly Thr Ile His Ala His Pro Thr Leu Gly Glu Ala Val Gln Glu Ala
        435                 440                 445

Ala Leu Arg Ala Leu Gly His Ala Leu His Ile
    450                 455

<210> SEQ ID NO 30
<211> LENGTH: 456
<212> TYPE: PRT
<213> ORGANISM: Saccharomyces cerevisiae

<400> SEQUENCE: 30

Met Phe Arg Ser Gly Tyr Tyr Pro Thr Val Thr Pro Ser His Trp Gly
1               5                   10                  15

Tyr Asn Gly Thr Val Lys His Val Leu Gly Glu Lys Gly Thr Lys Ser
                20                  25                  30

Leu Ala Phe Arg Asp Ser Lys Arg Gln Ile Pro Leu His Glu Phe Val
            35                  40                  45

Thr Lys His Val Pro Thr Leu Lys Asp Gly Ala Asn Phe Arg Leu Asn
        50                  55                  60

Ser Leu Leu Phe Thr Gly Tyr Leu Gln Thr Leu Tyr Leu Ser Ala Gly
65                  70                  75                  80

Asp Phe Ser Lys Lys Phe Gln Val Phe Tyr Gly Arg Glu Ile Ile Lys
                85                  90                  95

Phe Ser Asp Gly Gly Val Cys Thr Ala Asp Trp Val Met Pro Glu Trp
            100                 105                 110

Glu Gln Thr Tyr Ser Leu Asn Ala Glu Lys Ala Ser Phe Asn Glu Lys
        115                 120                 125

Gln Phe Ser Asn Asp Glu Lys Ala Thr His Pro Lys Gly Trp Pro Arg
    130                 135                 140

Leu His Pro Arg Thr Arg Tyr Leu Ser Ser Glu Glu Leu Glu Lys Cys
145                 150                 155                 160

His Ser Lys Gly Tyr Ser Tyr Pro Leu Val Val Leu His Gly Leu
                165                 170                 175

Ala Gly Gly Ser His Glu Pro Leu Ile Arg Ala Leu Ser Glu Asp Leu
            180                 185                 190

Ser Lys Val Gly Asp Gly Lys Phe Gln Val Val Leu Asn Ala Arg
        195                 200                 205

Gly Cys Ser Arg Ser Lys Val Thr Thr Arg Arg Ile Phe Thr Ala Leu
```

```
              210                 215                 220
His Thr Gly Asp Val Arg Glu Phe Leu Asn His Gln Lys Ala Leu Phe
225                 230                 235                 240

Pro Gln Arg Lys Ile Tyr Ala Val Gly Thr Ser Phe Gly Ala Ala Met
                245                 250                 255

Leu Thr Asn Tyr Leu Gly Glu Glu Gly Asp Asn Cys Pro Leu Asn Ala
                260                 265                 270

Ala Val Ala Leu Ser Asn Pro Trp Asp Phe Val His Thr Trp Asp Lys
                275                 280                 285

Leu Ala His Asp Trp Trp Ser Asn His Ile Phe Ser Arg Thr Leu Thr
                290                 295                 300

Gln Phe Leu Thr Arg Thr Val Lys Val Asn Met Asn Glu Leu Gln Val
305                 310                 315                 320

Pro Glu Asn Phe Glu Val Ser His Lys Pro Thr Val Glu Lys Pro Val
                325                 330                 335

Phe Tyr Thr Tyr Thr Arg Glu Asn Leu Glu Lys Ala Glu Lys Phe Thr
                340                 345                 350

Asp Ile Leu Glu Phe Asp Asn Leu Phe Thr Ala Pro Ser Met Gly Leu
                355                 360                 365

Pro Asp Gly Leu Thr Tyr Tyr Arg Lys Ala Ser Ser Ile Asn Arg Leu
                370                 375                 380

Pro Asn Ile Lys Ile Pro Thr Leu Ile Ile Asn Ala Thr Asp Asp Pro
385                 390                 395                 400

Val Thr Gly Glu Asn Val Ile Pro Tyr Lys Gln Ala Arg Glu Asn Pro
                405                 410                 415

Cys Val Leu Leu Cys Glu Thr Asp Leu Gly Gly His Leu Ala Tyr Leu
                420                 425                 430

Asp Asn Glu Ser Asn Ser Trp Leu Thr Lys Gln Ala Ala Glu Phe Leu
                435                 440                 445

Gly Ser Phe Asp Glu Leu Val Leu
                450                 455

<210> SEQ ID NO 31
<211> LENGTH: 354
<212> TYPE: PRT
<213> ORGANISM: Saccharomyces cerevisiae

<400> SEQUENCE: 31

Met Phe Arg Ser Gly Tyr Tyr Pro Thr Val Thr Pro Ser His Trp Gly
1               5                   10                  15

Tyr Asn Gly Thr Val Lys His Val Leu Gly Glu Lys Gly Thr Arg Ser
                20                  25                  30

Leu Ala Phe Arg Asp Ser Lys Arg Gln Ile Pro Leu His Glu Phe Val
                35                  40                  45

Thr Lys His Val Pro Thr Leu Lys Asp Gly Ala Asn Phe Arg Leu Asn
                50                  55                  60

Ser Leu Leu Phe Thr Gly Tyr Leu Gln Thr Leu Tyr Leu Ser Ala Gly
65                  70                  75                  80

Asp Phe Ser Lys Lys Phe Gln Val Phe Tyr Gly Arg Glu Ile Ile Lys
                85                  90                  95

Phe Ser Asp Gly Gly Val Cys Thr Ala Asp Trp Val Met Pro Glu Trp
                100                 105                 110

Glu Gln Thr Tyr Ser Leu Asn Ala Glu Lys Ala Ser Phe Asn Glu Lys
                115                 120                 125
```

```
Gln Phe Ser Asn Asp Glu Lys Ala Thr His Pro Lys Gly Trp Pro Arg
    130                 135                 140

Leu His Pro Arg Thr Arg Tyr Leu Ser Ser Glu Glu Leu Glu Lys Cys
145                 150                 155                 160

His Ser Lys Gly Tyr Ser Tyr Pro Leu Val Val Leu His Gly Leu
                165                 170                 175

Ala Gly Gly Ser His Glu Pro Leu Ile Arg Ala Leu Ser Glu Asp Leu
                180                 185                 190

Ser Lys Val Gly Asp Gly Lys Phe Gln Val Val Leu Asn Ala Arg
            195                 200                 205

Gly Cys Ser Arg Ser Lys Val Thr Thr Arg Arg Ile Phe Thr Ala Leu
    210                 215                 220

His Thr Gly Asp Val Arg Glu Phe Leu Asn His Gln Lys Ala Leu Phe
225                 230                 235                 240

Pro Gln Arg Lys Ile Tyr Ala Val Gly Thr Ser Phe Gly Ala Ala Met
                245                 250                 255

Leu Thr Asn Tyr Leu Gly Glu Glu Gly Asp Asn Cys Pro Leu Asn Ala
            260                 265                 270

Ala Val Ala Leu Ser Asn Pro Trp Asp Phe Val His Thr Trp Asp Lys
    275                 280                 285

Leu Ala His Asp Trp Trp Ser Asn His Ile Phe Ser Arg Thr Leu Thr
290                 295                 300

Gln Phe Leu Thr Arg Thr Val Lys Val Asn Met Asn Glu Leu Gln Val
305                 310                 315                 320

Pro Glu Asn Phe Glu Val Ser His Lys Pro Thr Val Gly Lys Pro Ser
                325                 330                 335

Phe Ile Arg Ile Pro Glu Lys Ile Trp Lys Arg Leu Lys Asn Leu Gln
            340                 345                 350

Thr Tyr

<210> SEQ ID NO 32
<211> LENGTH: 444
<212> TYPE: PRT
<213> ORGANISM: Lachancea thermotolerans

<400> SEQUENCE: 32

Met Pro Leu Pro Ile Phe Asn Pro Phe His Trp Gly Tyr His Gly Thr
1               5                   10                  15

Ile Glu Gln Val Ser Asn Pro Asn Gly Thr Val Ala Leu Thr Leu Lys
            20                  25                  30

Asp Glu Lys Lys Pro Val Gln Phe Ser Asp Phe Val Ser Arg Glu Ile
        35                  40                  45

Pro Gly Leu Lys Asp Lys Ala Lys Phe Glu Val Asn Pro Leu Leu Phe
    50                  55                  60

Thr Gly Tyr Leu Gln Thr Leu Tyr Leu Gly Gly Ala Asp Phe Ser Lys
65                  70                  75                  80

Ser Phe Pro Val Tyr Tyr Gly Arg Glu Ile Val Lys Phe Ser Asp Gly
                85                  90                  95

Gly Ile Cys Thr Ala Asp Trp Val Met Lys Ser Trp Lys Ser Lys Tyr
            100                 105                 110

Gly Ala Asp Thr Ser Ser Phe Lys Thr Asp Glu Gln Ala Thr His Pro
        115                 120                 125

Glu Asn Trp Pro Arg Leu His Pro Arg Thr Arg Phe Leu Glu Glu Ser
    130                 135                 140
```

Glu Lys Lys Asp Val His Asn Ser Glu Lys Pro Leu Val Val Leu
145                 150                 155                 160

His Gly Leu Ala Gly Ser His Glu Pro Ile Ile Arg Ser Leu Thr
            165                 170                 175

Gln Asp Leu Ser Asn Ala Gly Asp Ser Lys Phe Asp Val Val Leu
        180                 185                 190

Asn Cys Arg Gly Cys Ala Arg Ser Lys Ile Thr Thr Arg Lys Leu Phe
    195                 200                 205

Tyr Ala Val Phe Thr Ser Asp Ile Arg Glu Phe Ile Ala Arg Glu Lys
    210                 215                 220

Ala Arg His Pro Ser Arg Lys Ile Tyr Ala Val Gly Phe Ser Phe Gly
225                 230                 235                 240

Ala Thr Met Leu Gly His Tyr Leu Gly Glu Glu Gly Lys Ala Pro
            245                 250                 255

Ile Glu Ala Ala Ser Phe Leu Cys Asn Pro Trp Asp Leu Tyr Gln Ser
            260                 265                 270

Ala Leu Lys Met Asn Gln Asp Trp Trp Ser Arg Asn Leu Phe Ser Lys
    275                 280                 285

Asn Ile Ala Gln Phe Leu Ile Arg Leu Val Lys Val Asn Ile Lys Glu
290                 295                 300

Leu Glu Phe Lys Glu Gly Asp Val Met Pro Ala Glu Pro Ala Ser Leu
305                 310                 315                 320

Glu His Pro Ser Phe Cys Val Phe Thr Ser Lys Asn Leu Arg Lys Ala
            325                 330                 335

Arg Glu Phe Gly Ser Thr Ala Glu Phe Asp Asn Leu Phe Thr Ala Pro
            340                 345                 350

Cys Leu Gly Phe Asp Asn Ala Met Asp Tyr Tyr Lys Ala Cys Gly Ser
            355                 360                 365

Ile His Gln Leu Pro Asn Ile Lys Val Pro Ser Leu Ile Ile Asn Ser
            370                 375                 380

Lys Asp Asp Pro Val Val Gly Glu Asp Ser Ile Pro Tyr Lys Cys Ala
385                 390                 395                 400

Lys Glu Ser Asp Asn Leu Val Leu Cys Val Ser Asp Leu Gly Gly His
            405                 410                 415

Leu Ala Phe Leu Asp Lys Lys Tyr Asn Ser Trp Ala Thr Ser Lys Ile
            420                 425                 430

Ala Ala Phe Phe Asp Lys Phe Glu Glu Leu Val Gln
            435                 440

<210> SEQ ID NO 33
<211> LENGTH: 451
<212> TYPE: PRT
<213> ORGANISM: Zygosaccharomyces rouxii

<400> SEQUENCE: 33

Met Ser Asn Leu Pro Ile Ile Asn Pro Phe His Trp Gly Ser Arg Gly
1               5                   10                  15

Thr Leu Lys His Thr Ser Ala Pro Ser Gly Thr Thr Lys Leu Thr Leu
            20                  25                  30

Asn His Asp Lys Thr Lys Ile Asp Phe Gln His Phe Val Ser Gln Tyr
        35                  40                  45

Val Pro Ala Leu Lys Asp Gly Ser Lys Phe Lys Leu Asn Asn Phe Leu
    50                  55                  60

Phe Thr Gly Ile Leu Gln Thr Met Tyr Leu Ser Gly Ala Asp Tyr Thr
65                  70                  75                  80

```
Lys Trp Phe Pro Val Phe Tyr Gly Arg Glu Ile Leu Glu Leu Ser Asp
                85                  90                  95

Gly Gly Val Cys Thr Val Asp Asn Val Met Val Ser Trp Glu Glu Lys
            100                 105                 110

Tyr Gln Leu Arg Gln Asn Ser Gly Ser Phe Asn Lys Leu Glu Phe Glu
        115                 120                 125

Lys Asp Glu Lys Asp Thr His Pro Gln Asn Trp Pro Arg Leu Gln Ala
130                 135                 140

Arg Thr Arg Tyr Leu Thr Ala Lys Glu Leu Ala Glu Val His Gly Asp
145                 150                 155                 160

Gln Arg Pro Leu Val Val Val Leu His Gly Leu Ala Gly Gly Ser His
                165                 170                 175

Glu Thr Ile Ile Arg Ser Leu Thr Ser Lys Leu Ser Lys Ile Asp Gly
            180                 185                 190

Gly Lys Phe Gln Val Ala Val Leu Asn Cys Arg Gly Cys Ala Arg Ser
        195                 200                 205

Lys Ile Thr Asn Lys Lys Leu Phe Ser Ala Phe Gln Thr Gly Asp Leu
    210                 215                 220

Lys Glu Tyr Leu Ala Arg Glu Lys Ser Arg Asn Pro Asn Arg Lys Ile
225                 230                 235                 240

Tyr Ala Val Gly Phe Ser Phe Gly Ala Ser Leu Leu Ala Asn Tyr Leu
                245                 250                 255

Gly Glu Thr Gly Ser Glu Ser Asn Leu Thr Ala Ala Val Thr Leu Cys
            260                 265                 270

Cys Pro Trp Asp Phe Leu Leu Cys Ala Glu Lys Met Lys Lys Asp Tyr
        275                 280                 285

Trp Ser Lys Asn Leu Phe Ser Lys Ala Ile Thr Gln Phe Leu Val Arg
    290                 295                 300

Leu Val Lys Val Asn Met Gly Glu Leu Glu Ser Pro Glu Gly Ser Lys
305                 310                 315                 320

Pro Glu Phe Gln Pro Asp Ile Glu Asn Pro Cys Leu Tyr Met Cys Thr
                325                 330                 335

Lys Ser Asn Leu Glu Arg Ala Lys Ser Phe Thr Gln Met Leu Glu Phe
            340                 345                 350

Asp Gly Thr Phe Thr Ala Pro Ser Met Gly Phe Ser Ser Ala Glu Glu
        355                 360                 365

Tyr Tyr Arg Ala Gly Ser Ala Ile Asn Asn Leu His Lys Val Gln Val
    370                 375                 380

Pro Thr Leu Ile Ile Asn Ser Thr Asp Asp Pro Ile Ile Asp Ala Ser
385                 390                 395                 400

Ser Ile Pro Tyr Ser Gln Val Lys Met Asn Pro Asn Leu Leu Leu Leu
                405                 410                 415

Ala Thr Asp Leu Gly Gly His Leu Ala Tyr Leu Asp Glu Thr Trp Asp
            420                 425                 430

Ser Trp Met Asn Thr His Ile Ala Ser Phe Phe Ser Thr Phe Asp Glu
        435                 440                 445

Phe Leu Val
    450

<210> SEQ ID NO 34
<211> LENGTH: 450
<212> TYPE: PRT
<213> ORGANISM: Ashbya gossypii
```

<400> SEQUENCE: 34

```
Met Gly Leu Pro Thr Phe Ala Pro Arg Ser Trp Gly Tyr Arg Gly Thr
1               5                   10                  15

Ile Thr His Arg Pro His Glu Glu Gly Leu Val Lys Leu Pro Leu Lys
                20                  25                  30

Asp Lys Glu Lys Glu Pro Val Thr Leu Ser Asp Leu Leu Asn Glu His
            35                  40                  45

Val Pro Glu Leu Lys Asp Gly Ala Arg Phe Tyr Leu His Pro Tyr Leu
50                  55                  60

Tyr Asn Gly Ile Leu Gln Thr Met Tyr Leu Tyr Gly Ala Asp Phe Ser
65                  70                  75                  80

Gln Gln Tyr Lys Pro Phe Tyr Gly Arg Glu Ile Val Ser Tyr Ser Asp
                85                  90                  95

Gly Gly Val Ser Thr Ala Asp Trp Ala Met Arg Glu Trp Asp Asp Leu
            100                 105                 110

Tyr Ala Ala Pro Glu Gly Tyr Asn Lys Glu Lys Phe Asp Ala Asp Ala
            115                 120                 125

Ala Lys Thr His Pro Glu Asn Trp Pro Arg Leu Gln Pro Asn Thr Arg
130                 135                 140

Phe Leu Asp Glu Glu Glu Leu Ala Lys Ile Pro Lys Asp Thr Arg Pro
145                 150                 155                 160

Leu Ile Val Val Ala His Gly Leu Ala Gly Ser His Glu Asn Ile
                165                 170                 175

Ile Arg Ala Leu Val Thr Glu Leu Leu Ser Val Gly Asn Gly Gln Phe
            180                 185                 190

Asn Val Val Leu Asn Ser Arg Gly Cys Ala Arg Ser Lys Ile Ala
            195                 200                 205

Asn Lys Lys Leu Phe Ser Ala Phe His Thr Met Asp Ile Arg Glu Phe
        210                 215                 220

Ile Asn Arg Glu His Ala Arg Gln Pro Glu Arg Lys Ile Tyr Gly Leu
225                 230                 235                 240

Gly Phe Ser Phe Gly Ser Val Ile Phe Gly Asn Tyr Leu Gly Glu Glu
                245                 250                 255

Gly Asp Lys Ser Pro Leu Ser Gly Ala Val Cys Cys Ala Gly Pro Trp
            260                 265                 270

Asp Met Phe Ala Ser Ser Lys Met Leu Asn Asp Asp Phe Trp Ile Ser
            275                 280                 285

Arg Leu Phe Gly Lys Asn Leu Val Lys His Leu Ser Arg Leu Leu His
        290                 295                 300

Val Asn Arg Lys Glu Leu Glu Tyr Asp Gly Ser Lys Gly Asp Asp Val
305                 310                 315                 320

Glu Asp Ala Ser Pro Thr Asn Pro Ala Ser His Ile Phe Thr Lys Glu
                325                 330                 335

Asn Leu Ala Arg Ala Ser Thr Met Ala Cys Thr Arg Asp Phe Asp Asn
            340                 345                 350

Phe Phe Thr Ala Pro Ala Leu Gly Phe Lys Asn Ala Asn Asp Tyr Tyr
            355                 360                 365

Lys Ala Ala Ser Pro Val Asn Ile Val Gly Lys Ile Arg Val Pro Thr
        370                 375                 380

Leu Leu Ile Asn Ala Leu Asp Asp Pro Met Val Gly Ala Glu Gly Phe
385                 390                 395                 400

Leu Pro Ile Glu Lys Leu Arg Ser Asn Lys His Ile Leu Leu Cys Thr
                405                 410                 415
```

Thr Asp Ile Gly Gly His Leu Ala Tyr Leu Asp Lys Asn Tyr Thr Pro
                420                 425                 430

Trp Met Ala Gly Arg Val Ala Glu Phe Leu Ser Lys Met Asp Thr Leu
            435                 440                 445

Val Ala
    450

<210> SEQ ID NO 35
<211> LENGTH: 426
<212> TYPE: PRT
<213> ORGANISM: Debaryomyces hansenii

<400> SEQUENCE: 35

Met Val Phe Pro Trp Gly Phe Arg Ser Asn Val Lys Ile His Gln Ser
1               5                   10                  15

Asn Ser Asp Lys Ser Ile Asp Leu Pro Leu Arg Asn Gly Glu Lys Thr
                20                  25                  30

Ile Lys Tyr Ala Asp Phe Ile Lys Asp Glu Leu Pro Ile Ile Asp Glu
            35                  40                  45

Lys Glu Lys Leu Trp Leu Asn Pro Leu Leu Phe Asn Gly Leu Leu Gln
50                  55                  60

Thr Leu Tyr Tyr Ser Ser Ala Asn Leu Ser His Lys Phe Gln Val Tyr
65                  70                  75                  80

Tyr Gly Arg Glu Ile Phe Thr Tyr Glu Asp Gly Gly Val Cys Ser Ile
                85                  90                  95

Asp His Val Ile Pro Gln Pro Glu Asn Thr Glu Glu Phe Lys Ala Leu
            100                 105                 110

His Asp Lys Thr Leu Pro Glu Gly Trp Pro Lys Leu His Pro Arg Ser
        115                 120                 125

Arg Tyr Phe Ser Asn Glu Glu Leu Glu Gln Val Asn Ser Pro Ser Glu
    130                 135                 140

Gly Ser Gln Ser Thr Lys Pro Ile Cys Val Val Leu His Gly Leu Ala
145                 150                 155                 160

Gly Gly Ser His Glu Pro Leu Ile Arg Asn Leu Ala Glu Tyr Leu Ser
                165                 170                 175

Thr Gly Lys Asn Glu Asn Lys Trp Asp Thr Leu Val Ile Asn Ser Arg
            180                 185                 190

Gly Cys Cys Arg Thr Lys Ile Thr Asn Gly Lys Leu Phe Thr Ala Leu
        195                 200                 205

Ser Thr Gly Asp Ile His Glu Val Leu Val Glu Leu Lys Lys Arg Asn
    210                 215                 220

Pro Asn Arg Pro Ile Tyr Thr Val Gly Phe Ser Phe Gly Ala Ala Ile
225                 230                 235                 240

Leu Ala Asn Tyr Leu Ala Glu Ile Lys Asp Asp Thr Met Ile Thr Ala
                245                 250                 255

Ala Cys Leu Val Gly Cys Pro Trp Asp Leu Ile Asp Ser Ala Tyr His
            260                 265                 270

Ile Glu Lys Ser Trp Ser Gly Ser Tyr Leu Phe Asn Pro Ala Leu Thr
        275                 280                 285

Ser Phe Leu Asn Lys Leu Val Lys Asn Asn Phe Thr Glu Leu Asn His
    290                 295                 300

His Asn Pro Glu Leu Phe Asn Glu Glu Asn Leu Lys Arg Gly Met Lys
305                 310                 315                 320

Gln Thr Lys Thr Trp Gln Phe Asp Ser Val Tyr Thr Cys His Thr Ile

```
                    325                 330                 335
Gly Tyr Ser Asn Pro Phe Glu Tyr Tyr Arg Asp Ala Ser Pro Val Asn
                340                 345                 350
Arg Ile Ser Lys Ile His Thr Pro Thr Leu Ile Leu Asn Ser Thr Asp
                355                 360                 365
Asp Pro Ala Val Gly Val Arg Leu Pro Trp Met Glu Val Glu Asn Asn
            370                 375                 380
Pro His Leu Cys Met Val Glu Thr Asp Leu Gly Gly His Leu Gly Tyr
385                 390                 395                 400
Val Gln Ser Ser Gly Lys Phe Trp Cys Val Gln Leu Val Glu Glu Phe
                405                 410                 415
Phe Ala Lys Phe Asp Glu Leu Ile Ala Ser
                420                 425

<210> SEQ ID NO 36
<211> LENGTH: 456
<212> TYPE: PRT
<213> ORGANISM: Clarkia breweri

<400> SEQUENCE: 36

Met Ala His Asp Gln Ser Leu Ser Phe Glu Val Cys Arg Arg Lys Pro
1               5                   10                  15
Glu Leu Ile Arg Pro Ala Lys Gln Thr Pro His Glu Phe Lys Lys Leu
            20                  25                  30
Ser Asp Val Glu Asp Gln Glu Gly Leu Arg Phe Gln Ile Pro Val Ile
        35                  40                  45
Gln Phe Tyr Lys His Asn Asn Glu Ser Met Gln Glu Arg Asp Pro Val
    50                  55                  60
Gln Val Ile Arg Glu Gly Ile Ala Arg Ala Leu Val Tyr Tyr Tyr Pro
65                  70                  75                  80
Phe Ala Gly Arg Leu Arg Glu Val Asp Gly Arg Lys Leu Val Val Glu
                85                  90                  95
Cys Thr Gly Glu Gly Val Met Phe Ile Glu Ala Asp Ala Asp Val Thr
            100                 105                 110
Leu Glu Gln Phe Gly Asp Ala Leu Gln Pro Pro Phe Pro Cys Phe Asp
        115                 120                 125
Gln Leu Leu Phe Asp Val Pro Gly Ser Gly Gly Ile Leu Asp Ser Pro
    130                 135                 140
Leu Leu Leu Ile Gln Val Thr Arg Leu Lys Cys Gly Ser Phe Ile Phe
145                 150                 155                 160
Ala Leu Arg Leu Asn His Thr Met Ala Asp Ala Ala Gly Ile Val Leu
                165                 170                 175
Phe Met Lys Ala Val Gly Glu Met Ala Arg Gly Ala Ala Thr Pro Ser
            180                 185                 190
Thr Leu Pro Val Trp Asp Arg His Ile Leu Asn Ala Arg Val Pro Pro
        195                 200                 205
Gln Val Thr Phe Asn His Arg Glu Tyr Glu Glu Val Lys Gly Thr Ile
    210                 215                 220
Phe Thr Pro Phe Asp Asp Leu Ala His Arg Ser Phe Phe Phe Gly Ser
225                 230                 235                 240
Thr Glu Ile Ser Ala Met Arg Lys Gln Ile Pro Pro His Leu Arg Ser
                245                 250                 255
Cys Ser Thr Thr Ile Glu Val Leu Thr Ala Cys Leu Trp Arg Cys Arg
            260                 265                 270
```

```
Thr Leu Ala Ile Lys Pro Asn Pro Asp Glu Val Arg Met Ile Cys
            275                 280                 285

Ile Val Asn Ala Arg Ser Lys Phe Asn Pro Pro Leu Pro Asp Gly Tyr
290                 295                 300

Tyr Gly Asn Ala Phe Ala Ile Pro Ala Ala Val Thr Thr Ala Gly Lys
305                 310                 315                 320

Leu Cys Asn Asn Pro Leu Gly Phe Ala Leu Glu Leu Ile Arg Lys Ala
                325                 330                 335

Lys Arg Glu Val Thr Glu Tyr Met His Ser Val Ala Asp Leu Met
            340                 345                 350

Val Ala Thr Gly Arg Pro His Phe Thr Val Val Asn Thr Tyr Leu Val
            355                 360                 365

Ser Asp Val Thr Arg Ala Gly Phe Gly Glu Val Asp Phe Gly Trp Gly
370                 375                 380

Glu Ala Val Tyr Gly Gly Pro Ala Lys Gly Val Gly Val Ile Pro
385                 390                 395                 400

Gly Val Thr Ser Phe Tyr Ile Pro Leu Arg Asn Arg Gln Gly Glu Lys
                405                 410                 415

Gly Ile Val Leu Pro Ile Cys Leu Pro Ser Ala Ala Met Glu Ile Phe
            420                 425                 430

Ala Glu Ala Leu Asn Asn Thr Leu Asn Gly Lys Glu Ile Glu Ile Ala
            435                 440                 445

Lys His Phe Thr Gln Ser Ser Leu
            450                 455

<210> SEQ ID NO 37
<211> LENGTH: 460
<212> TYPE: PRT
<213> ORGANISM: Petunia x hybrida

<400> SEQUENCE: 37

Met Asp Ser Lys Gln Ser Ser Glu Leu Val Phe Thr Val Arg Arg Gln
1               5                   10                  15

Glu Pro Glu Leu Ile Ala Pro Ala Lys Pro Thr Pro Arg Glu Thr Lys
            20                  25                  30

Phe Leu Ser Asp Ile Asp Asp Gln Glu Gly Leu Arg Phe Gln Ile Pro
        35                  40                  45

Val Ile Asn Phe Tyr Arg Lys Asp Ser Ser Met Gly Gly Lys Asp Pro
50                  55                  60

Val Glu Val Ile Lys Lys Ala Ile Ala Glu Thr Leu Val Phe Tyr Tyr
65                  70                  75                  80

Pro Phe Ala Gly Arg Leu Arg Glu Gly Asn Asp Arg Lys Leu Met Val
                85                  90                  95

Asp Cys Thr Gly Glu Gly Val Met Phe Val Glu Ala Asn Ala Asp Val
            100                 105                 110

Thr Leu Glu Glu Phe Gly Asp Glu Leu Gln Pro Pro Phe Pro Cys Leu
        115                 120                 125

Glu Glu Leu Leu Tyr Asp Val Pro Gly Ser Ala Gly Val Leu His Cys
130                 135                 140

Pro Leu Leu Leu Ile Gln Val Thr Arg Leu Arg Cys Gly Gly Phe Ile
145                 150                 155                 160

Phe Ala Leu Arg Leu Asn His Thr Met Ser Asp Ala Pro Gly Leu Val
                165                 170                 175

Gln Phe Met Thr Ala Val Gly Glu Met Ala Arg Gly Ala Thr Ala Pro
            180                 185                 190
```

Ser Thr Leu Pro Val Trp Cys Arg Glu Leu Leu Asn Ala Arg Asn Pro
            195                 200                 205

Pro Gln Val Thr Cys Thr His His Glu Tyr Glu Glu Val Pro Asp Thr
    210                 215                 220

Lys Gly Thr Leu Ile Pro Leu Asp Asp Met Val His Arg Ser Phe Phe
225                 230                 235                 240

Phe Gly Pro Thr Glu Val Ser Ala Leu Arg Arg Phe Val Pro Pro His
                245                 250                 255

Leu His Asn Cys Ser Thr Phe Glu Val Leu Thr Ala Ala Leu Trp Arg
            260                 265                 270

Cys Arg Thr Ile Ser Ile Lys Pro Asp Pro Glu Glu Val Arg Val
            275                 280                 285

Leu Cys Ile Val Asn Ala Arg Ser Arg Phe Asn Pro Gln Leu Pro Ser
        290                 295                 300

Gly Tyr Tyr Gly Asn Ala Phe Ala Phe Pro Val Ala Val Thr Thr Ala
305                 310                 315                 320

Glu Lys Leu Cys Lys Asn Pro Leu Gly Tyr Ala Leu Glu Leu Val Lys
                325                 330                 335

Lys Thr Lys Ser Asp Val Thr Glu Glu Tyr Met Lys Ser Val Ala Asp
            340                 345                 350

Leu Met Val Ile Lys Gly Arg Pro His Phe Thr Val Val Arg Thr Tyr
            355                 360                 365

Leu Val Ser Asp Val Thr Arg Ala Gly Phe Gly Glu Val Asp Phe Gly
        370                 375                 380

Trp Gly Lys Ala Val Tyr Gly Gly Pro Ala Lys Gly Gly Val Gly Ala
385                 390                 395                 400

Ile Pro Gly Val Ala Ser Phe Tyr Ile Pro Phe Arg Asn Lys Lys Gly
                405                 410                 415

Glu Asn Gly Ile Val Val Pro Ile Cys Leu Pro Gly Phe Ala Met Glu
            420                 425                 430

Lys Phe Val Lys Glu Leu Asp Ser Met Leu Lys Gly Asp Ala Gln Leu
        435                 440                 445

Asp Asn Lys Lys Tyr Ala Phe Ile Thr Pro Ala Leu
    450                 455                 460

<210> SEQ ID NO 38
<211> LENGTH: 460
<212> TYPE: PRT
<213> ORGANISM: Nicotiana tabacum

<400> SEQUENCE: 38

Met Asp Ser Lys Gln Ser Ser Glu Leu Val Phe Thr Val Arg Arg Gln
1               5                   10                  15

Lys Pro Glu Leu Ile Ala Pro Ala Lys Pro Thr Pro Arg Glu Thr Lys
            20                  25                  30

Phe Leu Ser Asp Ile Asp Asp Gln Glu Gly Leu Arg Phe Gln Ile Pro
        35                  40                  45

Val Ile Gln Phe Tyr His Lys Asp Ser Ser Met Gly Arg Lys Asp Pro
    50                  55                  60

Val Lys Val Ile Lys Lys Ala Ile Ala Glu Thr Leu Val Phe Tyr Tyr
65                  70                  75                  80

Pro Phe Ala Gly Arg Leu Arg Glu Gly Asn Gly Arg Lys Leu Met Val
                85                  90                  95

Asp Cys Thr Gly Glu Gly Ile Met Phe Val Glu Ala Asp Ala Asp Val

```
            100                 105                 110
Thr Leu Glu Gln Phe Gly Asp Glu Leu Gln Pro Pro Phe Pro Cys Leu
        115                 120                 125

Glu Glu Leu Leu Tyr Asp Val Pro Asp Ser Ala Gly Val Leu Asn Cys
    130                 135                 140

Pro Leu Leu Leu Ile Gln Val Thr Arg Leu Arg Cys Gly Gly Phe Ile
145                 150                 155                 160

Phe Ala Leu Arg Leu Asn His Thr Met Ser Asp Ala Pro Gly Leu Val
                165                 170                 175

Gln Phe Met Thr Ala Val Gly Glu Met Ala Arg Gly Gly Ser Ala Pro
            180                 185                 190

Ser Ile Leu Pro Val Trp Cys Arg Glu Leu Leu Asn Ala Arg Asn Pro
        195                 200                 205

Pro Gln Val Thr Cys Thr His His Glu Tyr Asp Glu Val Arg Asp Thr
    210                 215                 220

Lys Gly Thr Ile Ile Pro Leu Asp Asp Met Val His Lys Ser Phe Phe
225                 230                 235                 240

Phe Gly Pro Ser Glu Val Ser Ala Leu Arg Arg Phe Val Pro His His
                245                 250                 255

Leu Arg Lys Cys Ser Thr Phe Glu Leu Leu Thr Ala Val Leu Trp Arg
            260                 265                 270

Cys Arg Thr Met Ser Leu Lys Pro Asp Pro Glu Glu Val Arg Ala
        275                 280                 285

Leu Cys Ile Val Asn Ala Arg Ser Arg Phe Asn Pro Pro Leu Pro Thr
    290                 295                 300

Gly Tyr Tyr Gly Asn Ala Phe Ala Phe Pro Val Ala Val Thr Thr Ala
305                 310                 315                 320

Ala Lys Leu Ser Lys Asn Pro Leu Gly Tyr Ala Leu Glu Leu Val Lys
                325                 330                 335

Lys Thr Lys Ser Asp Val Thr Glu Glu Tyr Met Lys Ser Val Ala Asp
            340                 345                 350

Leu Met Val Leu Lys Gly Arg Pro His Phe Thr Val Val Arg Thr Phe
        355                 360                 365

Leu Val Ser Asp Val Thr Arg Gly Gly Phe Gly Glu Val Asp Phe Gly
    370                 375                 380

Trp Gly Lys Ala Val Tyr Gly Gly Pro Ala Lys Gly Gly Val Gly Ala
385                 390                 395                 400

Ile Pro Gly Val Ala Ser Phe Tyr Ile Pro Phe Lys Asn Lys Lys Gly
                405                 410                 415

Glu Asn Gly Ile Val Val Pro Ile Cys Leu Pro Gly Phe Ala Met Glu
            420                 425                 430

Thr Phe Val Lys Glu Leu Asp Gly Met Leu Lys Val Asp Ala Pro Leu
        435                 440                 445

Val Asn Ser Asn Tyr Ala Ile Ile Arg Pro Ala Leu
    450                 455                 460

<210> SEQ ID NO 39
<211> LENGTH: 461
<212> TYPE: PRT
<213> ORGANISM: Verbena x hybrida

<400> SEQUENCE: 39

Met Ala Gln Asn Asn Thr Leu Leu Thr Phe Thr Val Arg Arg Asn Glu
1               5                   10                  15
```

```
Pro Glu Leu Ile Ala Pro Ala Lys Pro Thr Pro Arg Glu Leu Lys Pro
                20                  25                  30

Leu Ser Asp Ile Asp Asp Gln Glu Gly Leu Arg Phe Gln Ile Pro Val
        35                  40                  45

Ile Gln Phe Tyr Arg His Asp Pro Lys Met Arg Asn Lys Asn Pro Ala
50                  55                  60

Arg Val Ile Arg Glu Ala Leu Ala Lys Val Leu Val Phe Tyr Tyr Pro
65                  70                  75                  80

Phe Ala Gly Arg Leu Lys Glu Gly Pro Ala Lys Lys Leu Met Val Asp
                85                  90                  95

Cys Ser Gly Glu Gly Val Leu Phe Ile Glu Ala Glu Ala Asp Val Thr
            100                 105                 110

Leu Asn Gln Phe Gly Asp Ala Leu Gln Pro Pro Phe Pro Cys Leu Glu
            115                 120                 125

Glu Leu Leu Tyr Asp Val Pro Gly Ser Gly Gly Val Leu Asp Ser Pro
            130                 135                 140

Leu Leu Leu Ile Gln Val Thr Arg Leu Leu Cys Gly Gly Phe Ile Phe
145                 150                 155                 160

Ala Leu Arg Leu Asn His Thr Met Ser Asp Ala Pro Gly Leu Val Gln
                165                 170                 175

Phe Met Thr Ala Leu Gly Glu Met Ala Gln Gly Ala Pro Arg Pro Ser
            180                 185                 190

Ile Leu Pro Val Trp Gln Arg Glu Leu Leu Phe Ala Arg Val Gln Pro
            195                 200                 205

His Val Thr Cys Thr His Glu Tyr Asp Glu Val Lys Asp Thr Lys
            210                 215                 220

Gly Thr Ile Ile Pro Leu Asp Asp Met Ala His Arg Ser Phe Phe Phe
225                 230                 235                 240

Gly Pro Thr Glu Val Ala Ala Leu Arg Arg Phe Val Pro Ser Ser Leu
                245                 250                 255

Gln Lys Cys Ser Thr Phe Glu Val Leu Thr Ala Cys Leu Trp Arg Cys
            260                 265                 270

Arg Thr Ile Ala Leu Lys Pro Asp Pro Glu Glu Glu Met Arg Ile Ile
            275                 280                 285

Cys Ile Val Asn Ala Arg Ala Lys Phe Asn Pro Pro Leu Pro Lys Gly
            290                 295                 300

Tyr Tyr Gly Asn Gly Phe Ala Phe Pro Val Ala Ile Ser Arg Ala Gly
305                 310                 315                 320

Asp Leu Ser Thr Lys Pro Leu Gly His Ala Leu Lys Leu Val Met Gln
                325                 330                 335

Ala Lys Asn Ala Val Asn Asp Glu Tyr Met Arg Ser Leu Thr Asp Leu
            340                 345                 350

Met Val Ile Lys Gly Arg Pro His Phe Thr Val Val Arg Ser Tyr Leu
            355                 360                 365

Val Ser Asp Val Thr Arg Ala Gly Phe Asp Ala Val Asp Phe Gly Trp
            370                 375                 380

Gly Asn Ala Ala Tyr Gly Gly Pro Ala Lys Gly Val Gly Ala Ile
385                 390                 395                 400

Pro Gly Val Ala Ser Phe Tyr Ile Pro Phe Thr Asn His Lys Gly Glu
                405                 410                 415

Thr Gly Ile Val Leu Pro Ile Cys Leu Pro Asn Ala Ala Met Glu Thr
            420                 425                 430

Phe Val Lys Glu Leu Asn Asn Met Leu Ala Lys Gly Asn Asn Asp Gln
```

```
                 435                 440                 445
Val Leu Lys Glu His Asn Tyr Asn Val Leu Ser Arg Leu
    450                 455                 460

<210> SEQ ID NO 40
<211> LENGTH: 463
<212> TYPE: PRT
<213> ORGANISM: Vasconcellea cundinamarcensis

<400> SEQUENCE: 40

Met Ala Glu Lys Ala Ser Ser Leu Met Phe Asn Val Arg Arg His Glu
1               5                   10                  15

Pro Glu Leu Ile Thr Pro Ala Lys Pro Thr Pro Arg Glu Ile Lys Leu
            20                  25                  30

Leu Ser Asp Ile Asp Asp Gln Asp Gly Leu Arg Phe Gln Val Pro Ile
        35                  40                  45

Ile Gln Phe Tyr Lys Asn Asn Ser Ser Met Gln Gly Lys Asn Pro Ala
    50                  55                  60

Lys Ile Ile Lys Ser Ala Leu Ala Glu Thr Leu Val His Tyr Tyr Pro
65                  70                  75                  80

Leu Ala Gly Arg Leu Arg Glu Gly Phe Gly Arg Lys Leu Met Val Glu
                85                  90                  95

Cys Thr Gly Glu Gly Ile Leu Phe Ile Glu Ala Asp Ala Asp Val Thr
            100                 105                 110

Leu His Glu Phe Gly Asp Asp Leu Pro Pro Pro Phe Pro Cys Leu Val
        115                 120                 125

Glu Leu Leu Tyr Asp Val Pro Gly Ser Ser Gly Ile Ile Asp Thr Pro
    130                 135                 140

Leu Leu Leu Ile Gln Val Thr Arg Leu Lys Cys Gly Gly Phe Ile Phe
145                 150                 155                 160

Ala Leu Arg Leu Asn His Thr Met Ser Asp Ala Ser Gly Leu Val Gln
                165                 170                 175

Phe Met Thr Ala Val Gly Glu Met Ala Arg Gly Gln Arg Ser Leu Ser
            180                 185                 190

Ile Gln Pro Val Trp Glu Arg His Leu Leu Asn Ala Arg Asp Pro Pro
        195                 200                 205

Arg Val Thr His Ile His His Glu Tyr Asp Asp Leu Glu Asp Thr Lys
    210                 215                 220

Gly Thr Ile Ile Pro Leu Asp Asp Met Val His Arg Ser Phe Phe Phe
225                 230                 235                 240

Gly Pro Ser Glu Met Ala Ala Ile Arg Arg Leu Val Pro Ala His Phe
                245                 250                 255

His Arg Ser Thr Thr Ser Glu Val Leu Thr Ala Tyr Leu Trp Arg Cys
            260                 265                 270

Tyr Thr Ile Ala Leu Gln Pro Asp Pro Glu Glu Glu Met Arg Val Ile
        275                 280                 285

Cys Val Val Asn Ser Arg Thr Lys Leu Asn Pro Pro Leu Pro Thr Gly
    290                 295                 300

Phe Tyr Gly Asn Gly Ile Ala Phe Pro Ala Ala Ile Ser Gln Ala Lys
305                 310                 315                 320

Lys Ile Cys Glu Asn Pro Phe Gly Tyr Thr Leu Gln Leu Val Lys Gln
                325                 330                 335

Thr Lys Val Asp Val Thr Glu Gly Tyr Met Arg Ser Ala Ala Asp Leu
            340                 345                 350
```

```
Met Ala Met Lys Gly Arg Pro His Phe Thr Val Val Arg Arg Tyr Met
            355                 360                 365

Val Ser Asp Val Thr Arg Ala Gly Phe Gly Leu Val Asp Phe Gly Trp
    370                 375                 380

Gly Arg Pro Glu Pro Val Tyr Gly Gly Pro Ala Lys Gly Gly Val Gly
385                 390                 395                 400

Pro Ile Pro Gly Val Thr Ser Phe Phe Val Pro Phe Lys Asn Arg Lys
                405                 410                 415

Gly Glu Lys Gly Ile Val Val Pro Thr Cys Leu Pro Thr Pro Ala Met
            420                 425                 430

Glu Arg Phe Ala Lys Leu Met Asn Glu Ile Leu Gln Asn Gln Leu Leu
            435                 440                 445

Val Ser Ala Glu Glu Asn Lys Ser Val Phe Ile Val Ser Ala Ile
    450                 455                 460

<210> SEQ ID NO 41
<211> LENGTH: 447
<212> TYPE: PRT
<213> ORGANISM: Vanda hybrid cultivar

<400> SEQUENCE: 41

Met Ala Ser Ser Thr Leu His Phe Ser Val Arg Arg Pro Pro Gln
1               5                   10                  15

Leu Val Ala Pro Ala Ser Pro Thr Pro Arg Glu Leu Lys Arg Leu Ser
            20                  25                  30

Asp Ile Asp Asp Gln Glu Gly Leu Arg Phe Gln Ile Pro Val Ile Gln
        35                  40                  45

Phe Tyr Arg His Glu Pro Ala Met Ala Gly Gln Asn Pro Ala Ser Val
    50                  55                  60

Ile Arg Asp Ala Leu Ala Arg Thr Leu Val Phe Tyr Tyr Pro Phe Ala
65                  70                  75                  80

Gly Arg Leu Arg Glu Gly Ala Gly Lys Lys Leu Phe Val Asp Cys Thr
                85                  90                  95

Gly Glu Gly Val Leu Phe Ile Glu Ala Glu Ala Asp Val Lys Leu Lys
            100                 105                 110

Asp Phe Gly Asp Ala Leu His Pro Pro Phe Pro Cys Leu Glu Glu Leu
        115                 120                 125

Leu Phe Asp Val Asp Gly Ser Ser Ala Val Leu Asn Thr Pro Leu Leu
    130                 135                 140

Leu Ile Gln Val Thr Leu Leu Ser Cys Gly Gly Phe Ile Leu Ala Leu
145                 150                 155                 160

Arg Leu Asn His Thr Met Ser Asp Ala Pro Gly Leu Val Gln Leu Met
                165                 170                 175

Thr Ala Val Gly Glu Leu Ala Arg Gly Ser Ser Pro Ser Val Ile
            180                 185                 190

Pro Val Trp Arg Arg Glu Leu Leu Glu Ala Arg Pro Ser Pro Ala Pro
        195                 200                 205

Phe Phe Pro His Pro Glu Tyr Glu Gln Val Pro Asp Thr Glu Gly Thr
    210                 215                 220

Ile Thr Pro Leu Asp Asn Thr Ala His Arg Ser Phe Ile Phe Gly Pro
225                 230                 235                 240

Arg Glu Ile Ser Ile Leu Arg Ser Arg Leu Pro Ser Gln Leu Arg Gly
                245                 250                 255

Ala Ser Ser Thr Phe Asp Ile Leu Thr Ala Cys Val Trp Arg Ser Arg
            260                 265                 270
```

```
Thr Arg Ala Leu Gln Pro Ala Asp Pro Lys Glu Asn Phe Arg Ile Ile
        275                 280                 285

Cys Ile Val Asn Ile Arg Gly Arg Ile Asn Pro Leu Pro Ser Gly
290                 295                 300

Phe Tyr Gly Asn Ala Phe Gly Leu Pro Val Ala Ile Ala Thr Ala Gly
305                 310                 315                 320

Glu Leu Cys Ser Arg Pro Leu Asp Tyr Ala Val Glu Leu Val Lys Arg
                325                 330                 335

Ala Lys Ser Gln Val Ser Gly Asp Tyr Leu His Ser Val Ala Asp Tyr
                340                 345                 350

Met Val Met Lys Gly Arg Pro His Phe Thr Val Val Arg Thr Tyr Val
                355                 360                 365

Ile Ser Asp Leu Thr Arg Ala Gly Phe Gly Asp Val Asp Phe Gly Trp
            370                 375                 380

Gly Lys Pro Val Tyr Gly Pro Ala Lys Gly Val Gly Val Ser
385                 390                 395                 400

Pro Gly Val Phe Asn Phe Phe Ile Pro Phe Val Asn Ala Ser Gly Glu
                    405                 410                 415

Lys Gly Ile Val Val Pro Ile Cys Leu Pro Pro Ala Met Arg Arg
                420                 425                 430

Phe Val Ala Glu Ile Gln Ser Leu Leu Ser Ala Gln Ser Ala Leu
                435                 440                 445

<210> SEQ ID NO 42
<211> LENGTH: 459
<212> TYPE: PRT
<213> ORGANISM: Cucumis melo

<400> SEQUENCE: 42

Met Ala Ser Ser Leu Val Phe Gln Val Gln Arg Ser Gln Pro Gln Leu
1               5                   10                  15

Ile Pro Pro Ser Asp Pro Thr Pro His Glu Phe Lys Gln Leu Ser Asp
                20                  25                  30

Ile Asp Asp Gln Glu Gly Leu Arg Phe Gln Ile Pro Val Ile Gln Phe
            35                  40                  45

Tyr Arg His Asp Pro Arg Met Ala Gly Thr Asp Pro Ala Arg Val Ile
50                  55                  60

Lys Glu Ala Ile Ala Lys Ala Leu Val Phe Tyr Tyr Pro Phe Ala Gly
65                  70                  75                  80

Arg Leu Arg Glu Gly Pro Gly Arg Lys Leu Phe Val Glu Cys Thr Gly
                85                  90                  95

Glu Gly Val Met Phe Ile Glu Ala Asp Ala Asp Val Ser Leu Glu Gln
                100                 105                 110

Phe Gly Asp Ala Leu Gln Pro Pro Phe Pro Cys Leu Glu Glu Pro Leu
            115                 120                 125

Phe Asp Val Pro Asn Ser Ser Gly Val Leu Asp Cys Pro Leu Leu Leu
130                 135                 140

Ile Gln Val Thr Arg Leu Lys Cys Gly Gly Phe Ile Phe Ala Leu Arg
145                 150                 155                 160

Leu Asn His Thr Met Ser Asp Ala Ser Gly Leu Val Gln Phe Met Met
                165                 170                 175

Ala Val Gly Glu Met Ala Arg Gly Ala Thr Ala Pro Ser Val Arg Pro
                180                 185                 190

Val Trp Gln Arg Ala Leu Leu Asn Ala Arg Asp Pro Pro Lys Val Thr
```

```
            195                 200                 205
    Cys His His Arg Glu Tyr Asp Glu Val Val Asp Thr Lys Gly Thr Ile
        210                 215                 220

Ile Pro Leu Asp Asp Met Ala His Arg Ser Phe Phe Gly Pro Ser
    225                 230                 235                 240

Glu Ile Ser Ala Ile Arg Lys Ala Leu Pro Ser His Leu Arg Gln Cys
                    245                 250                 255

Ser Ser Phe Glu Val Leu Thr Ala Cys Leu Trp Arg Phe Arg Thr Ile
                260                 265                 270

Ser Leu Gln Pro Asp Pro Glu Glu Val Arg Val Leu Cys Ile Val
                275                 280                 285

Asn Ser Arg Ser Lys Phe Asn Pro Pro Leu Pro Thr Gly Tyr Tyr Gly
        290                 295                 300

Asn Ala Phe Ala Phe Pro Val Ala Leu Thr Thr Ala Gly Lys Leu Cys
    305                 310                 315                 320

Gln Asn Pro Leu Gly Tyr Ala Leu Glu Leu Val Arg Lys Ala Lys Ala
                    325                 330                 335

Asp Val Thr Glu Asp Tyr Met Lys Ser Val Ala Asp Leu Met Val Ile
                340                 345                 350

Lys Gly Arg Pro His Phe Thr Val Arg Thr Tyr Leu Val Ser Asp
                355                 360                 365

Val Thr Arg Ala Gly Phe Glu Asp Val Asp Phe Gly Trp Gly Lys Ala
        370                 375                 380

Met Tyr Gly Gly Pro Ala Lys Gly Val Gly Ala Ile Pro Gly Val
    385                 390                 395                 400

Ala Ser Phe Tyr Ile Pro Phe Lys Asn Lys Lys Gly Glu Arg Gly Ile
                    405                 410                 415

Leu Val Pro Leu Cys Leu Pro Ala Pro Ala Met Glu Arg Phe Val Lys
                420                 425                 430

Glu Leu Asp Ala Leu Leu Lys Ala Gly Lys Thr Ile Asp Gly Val Asp
                435                 440                 445

Asn Lys Lys Pro Leu Phe Ile Ala Ser Ala Leu
        450                 455

<210> SEQ ID NO 43
<211> LENGTH: 460
<212> TYPE: PRT
<213> ORGANISM: Petunia x hybrida

<400> SEQUENCE: 43

Met Asp Ser Lys Gln Ser Ser Glu Leu Val Phe Thr Val Arg Arg Gln
    1               5                   10                  15

Glu Pro Glu Leu Ile Ala Pro Lys Pro Thr Pro Arg Glu Thr Lys
                    20                  25                  30

Phe Leu Ser Asp Ile Asp Asp Gln Glu Gly Leu Arg Phe Gln Ile Pro
                35                  40                  45

Val Ile Asn Phe Tyr Arg Lys Asp Ser Ser Met Gly Gly Lys Asp Pro
        50                  55                  60

Val Glu Val Ile Lys Lys Ala Ile Ala Glu Thr Leu Val Phe Tyr Tyr
    65                  70                  75                  80

Pro Phe Ala Gly Arg Leu Arg Glu Gly Asn Asp Arg Lys Leu Met Val
                    85                  90                  95

Asp Cys Thr Gly Glu Gly Val Met Phe Val Glu Ala Asn Ala Asp Val
                100                 105                 110
```

Thr Leu Glu Glu Phe Gly Asp Glu Leu Gln Pro Pro Phe Pro Cys Leu
            115                 120                 125

Glu Glu Leu Leu Tyr Asp Val Pro Gly Ser Ala Gly Val Leu His Cys
    130                 135                 140

Pro Leu Leu Ile Gln Val Thr Arg Leu Arg Cys Gly Phe Ile
145                 150                 155                 160

Phe Ala Leu Arg Leu Asn His Thr Met Ser Asp Ala Pro Gly Leu Val
                165                 170                 175

Gln Phe Met Thr Ala Val Gly Glu Met Ala Arg Gly Ala Thr Ala Pro
            180                 185                 190

Ser Thr Leu Pro Val Trp Cys Arg Glu Leu Leu Asn Ala Arg Asn Pro
    195                 200                 205

Pro Gln Val Thr Cys Thr His His Glu Tyr Glu Val Pro Asp Thr
210                 215                 220

Lys Gly Thr Leu Ile Pro Leu Asp Asp Met Val His Arg Ser Phe Phe
225                 230                 235                 240

Phe Gly Pro Thr Glu Val Ser Ala Leu Arg Arg Phe Val Pro Pro His
                245                 250                 255

Leu His Asn Cys Ser Thr Phe Glu Val Leu Thr Ala Ala Leu Trp Arg
            260                 265                 270

Cys Arg Thr Ile Ser Ile Lys Pro Asp Pro Glu Glu Glu Val Arg Val
    275                 280                 285

Leu Cys Ile Val Asn Ala Arg Ser Arg Phe Asn Pro Gln Leu Pro Ser
    290                 295                 300

Gly Tyr Tyr Gly Asn Ala Phe Ala Phe Pro Val Ala Val Thr Thr Ala
305                 310                 315                 320

Glu Lys Leu Cys Lys Asn Pro Leu Gly Tyr Ala Leu Glu Leu Val Lys
                325                 330                 335

Lys Thr Lys Ser Asp Val Thr Glu Glu Tyr Met Lys Ser Val Ala Asp
            340                 345                 350

Leu Met Val Ile Lys Gly Arg Pro His Phe Thr Val Val Arg Thr Tyr
    355                 360                 365

Leu Val Ser Asp Val Thr Arg Ala Gly Phe Gly Glu Val Asp Phe Gly
370                 375                 380

Trp Gly Lys Ala Val Tyr Gly Pro Ala Lys Gly Val Gly Ala
385                 390                 395                 400

Ile Pro Gly Val Ala Ser Phe Tyr Ile Pro Phe Arg Asn Lys Lys Gly
                405                 410                 415

Glu Asn Gly Ile Val Val Pro Cys Leu Pro Gly Phe Ala Met Glu
            420                 425                 430

Lys Phe Val Lys Glu Leu Asp Ser Met Leu Lys Gly Asp Ala Gln Leu
    435                 440                 445

Asp Asn Lys Lys Tyr Ala Phe Ile Thr Pro Ala Leu
450                 455                 460

<210> SEQ ID NO 44
<211> LENGTH: 460
<212> TYPE: PRT
<213> ORGANISM: Nicotiana tabacum

<400> SEQUENCE: 44

Met Asp Ser Lys Gln Ser Ser Glu Leu Val Phe Thr Val Arg Arg Gln
1               5                   10                  15

Lys Pro Glu Leu Ile Ala Pro Ala Lys Pro Thr Pro Arg Glu Ile Lys
            20                  25                  30

```
Phe Leu Ser Asp Ile Asp Asp Gln Glu Gly Leu Arg Phe Gln Ile Pro
            35                  40                  45

Val Ile Gln Phe Tyr His Lys Asp Ser Ser Met Gly Arg Lys Asp Pro
 50                  55                  60

Val Lys Val Ile Lys Lys Ala Ile Ala Glu Thr Leu Val Phe Tyr Tyr
 65                  70                  75                  80

Pro Phe Ala Gly Arg Leu Arg Glu Gly Asn Gly Arg Lys Leu Met Val
                 85                  90                  95

Asp Cys Thr Gly Glu Gly Ile Met Phe Val Glu Ala Asp Ala Asp Val
                100                 105                 110

Thr Leu Glu Gln Phe Gly Asp Glu Leu Gln Pro Pro Phe Pro Cys Leu
            115                 120                 125

Glu Glu Leu Leu Tyr Asp Val Pro Asp Ser Ala Gly Val Leu Asn Cys
            130                 135                 140

Pro Leu Leu Ile Gln Val Thr Arg Leu Arg Cys Gly Gly Phe Ile
145                 150                 155                 160

Phe Ala Leu Arg Leu Asn His Thr Met Ser Asp Ala Pro Gly Leu Val
                165                 170                 175

Gln Phe Met Thr Ala Val Gly Glu Met Ala Arg Gly Ala Ser Ala Pro
            180                 185                 190

Ser Ile Leu Pro Val Trp Cys Arg Glu Leu Leu Asn Ala Arg Asn Pro
            195                 200                 205

Pro Gln Val Thr Cys Thr His His Glu Tyr Asp Glu Val Arg Asp Thr
            210                 215                 220

Lys Gly Thr Ile Ile Pro Leu Asp Asp Met Val His Lys Ser Phe Phe
225                 230                 235                 240

Phe Gly Pro Ser Glu Val Ser Ala Leu Arg Arg Phe Val Pro His His
                245                 250                 255

Leu Arg Lys Cys Ser Thr Phe Glu Leu Leu Thr Ala Val Leu Trp Arg
            260                 265                 270

Cys Arg Thr Met Ser Leu Lys Pro Asp Pro Glu Glu Val Arg Ala
            275                 280                 285

Leu Cys Ile Val Asn Ala Arg Ser Arg Phe Asn Pro Pro Leu Pro Thr
            290                 295                 300

Gly Tyr Tyr Gly Asn Ala Phe Ala Phe Pro Val Ala Val Thr Thr Ala
305                 310                 315                 320

Ala Lys Leu Ser Lys Asn Pro Leu Gly Tyr Ala Leu Glu Leu Val Lys
                325                 330                 335

Lys Thr Lys Ser Asp Val Thr Glu Glu Tyr Met Lys Ser Val Ala Asp
            340                 345                 350

Leu Met Val Leu Lys Gly Arg Pro His Phe Thr Val Val Arg Thr Phe
            355                 360                 365

Leu Val Ser Asp Val Thr Arg Gly Gly Phe Gly Glu Val Asp Phe Gly
            370                 375                 380

Trp Gly Lys Ala Val Tyr Gly Gly Pro Ala Lys Gly Val Gly Ala
385                 390                 395                 400

Ile Pro Gly Val Ala Ser Phe Tyr Ile Pro Phe Lys Asn Lys Lys Gly
                405                 410                 415

Glu Asn Gly Ile Val Val Pro Ile Cys Leu Pro Gly Phe Ala Met Glu
                420                 425                 430

Thr Phe Val Lys Glu Leu Asp Gly Met Leu Lys Val Asp Ala Pro Leu
            435                 440                 445
```

Asp Asn Ser Asn Tyr Ala Ile Ile Arg Pro Ala Leu
    450                 455                 460

<210> SEQ ID NO 45
<211> LENGTH: 460
<212> TYPE: PRT
<213> ORGANISM: Populus trichocarpa

<400> SEQUENCE: 45

Met Ala Ser Ser Pro Ala Ser Leu Leu Phe Lys Val His Arg Arg Glu
1               5                   10                  15

Pro Glu Leu Ile Lys Pro Ala Lys Pro Thr Pro His Glu Phe Lys Leu
            20                  25                  30

Leu Ser Asp Ile Asp Asp Gln Glu Gly Leu Arg Phe His Ile Pro Val
        35                  40                  45

Met Gln Phe Tyr Arg Asn Asn Pro Ser Met Gln Gly Lys Asp Pro Val
    50                  55                  60

Lys Ile Ile Arg Glu Ala Leu Ala Lys Thr Leu Val Phe Tyr Tyr Pro
65                  70                  75                  80

Phe Ala Gly Arg Leu Arg Glu Gly Pro Asn Arg Lys Leu Met Val Glu
                85                  90                  95

Cys Thr Gly Glu Gly Ile Leu Phe Ile Glu Ala Asp Ala Asp Val Thr
            100                 105                 110

Leu Glu Gln Phe Gly Asp Ala Leu Gln Pro Pro Phe Pro Cys Leu Glu
        115                 120                 125

Glu Leu Leu Phe Asp Val Pro Gly Ser Gly Val Leu Asn Cys Pro
    130                 135                 140

Leu Leu Leu Ile Gln Val Thr Arg Leu Lys Cys Gly Gly Phe Leu Phe
145                 150                 155                 160

Ala Leu Arg Leu Asn His Thr Met Ser Asp Ala Val Gly Leu Val Gln
                165                 170                 175

Phe Met Ala Ala Val Gly Glu Met Ala Arg Gly Ala Asn Ala Pro Ser
            180                 185                 190

Val Pro Ala Val Trp Glu Arg Gln Val Leu Asn Ala Ser Asp Pro Pro
        195                 200                 205

Arg Val Thr Cys Thr His Arg Glu Tyr Glu Glu Val Ala Asp Thr Lys
    210                 215                 220

Gly Thr Ile Ile Pro Leu Asp Asp Met Ala His Arg Ser Phe Phe
225                 230                 235                 240

Gly Pro Ser Glu Met Ser Ala Leu Arg Lys Phe Val Pro Pro His Leu
                245                 250                 255

Ser His Cys Ser Thr Phe Glu Ile Leu Thr Ala Cys Leu Trp Lys Cys
            260                 265                 270

Arg Thr Ile Ala Leu Gln Pro Asp Pro Thr Glu Glu Met Arg Ile Leu
        275                 280                 285

Cys Ile Val Asn Ala Arg Glu Lys Phe Asn Pro Pro Leu Pro Arg Gly
    290                 295                 300

Tyr Tyr Gly Asn Gly Phe Ala Phe Pro Val Ala Val Ala Thr Ala Glu
305                 310                 315                 320

Glu Leu Ser Lys Asn Pro Phe Gly Tyr Ala Leu Glu Leu Val Arg Lys
                325                 330                 335

Ala Lys Ala Asp Val Thr Glu Glu Tyr Met Arg Ser Val Ser Ser Leu
            340                 345                 350

Met Val Ile Lys Gly Arg Pro His Phe Thr Val Val Arg Ala Tyr Leu
        355                 360                 365

```
Val Ser Asp Leu Arg Arg Ala Gly Phe Glu Glu Val Asp Phe Gly Trp
    370                 375                 380

Gly Asn Ala Ile Tyr Gly Gly Ala Ala Lys Gly Val Gly Ala Ile
385                 390                 395                 400

Pro Gly Val Ala Ser Phe Tyr Ile Pro Phe Thr Asn Lys Lys Gly Glu
                405                 410                 415

Asn Gly Val Val Val Pro Phe Cys Leu Pro Ala Pro Ala Met Glu Arg
            420                 425                 430

Phe Val Lys Glu Leu Asp Gly Met Leu Lys Asp Gln Thr Val Ser
        435                 440                 445

Ala Gln Thr Lys Ser Lys Phe Ile Val Ser Ser Leu
    450                 455                 460

<210> SEQ ID NO 46
<211> LENGTH: 459
<212> TYPE: PRT
<213> ORGANISM: Glycine max

<400> SEQUENCE: 46

Met Asp Thr Ser Leu Val Phe Thr Val Arg Arg Ser Glu Ala Glu Leu
1               5                   10                  15

Ile Ala Pro Ala Lys Pro Thr Pro Arg Glu Val Lys Leu Leu Ser Asp
            20                  25                  30

Ile Asp Asp Gln Asp Gly Leu Arg Phe Gln Ile Pro Val Ile Gln Phe
        35                  40                  45

Tyr Arg His Asp Pro Ser Met Ala Gly Lys Asp Pro Val Asp Val Ile
    50                  55                  60

Arg Lys Ala Val Ala Lys Thr Leu Val Phe Tyr Tyr Pro Phe Ala Gly
65                  70                  75                  80

Arg Leu Arg Glu Gly Leu Gly Arg Lys Leu Met Val Asp Cys Thr Gly
                85                  90                  95

Glu Gly Val Leu Phe Ile Glu Ala Asp Ala Asp Val Thr Leu Lys Gln
            100                 105                 110

Phe Gly Asp Ala Leu Gln Pro Pro Phe Pro Cys Trp Glu Glu Leu Leu
        115                 120                 125

Tyr Asp Val Pro Gly Ser Gln Gly Val Leu Asn Thr Pro Leu Leu Leu
    130                 135                 140

Ile Gln Val Thr Arg Leu Lys Cys Gly Gly Phe Ile Leu Ala Val Arg
145                 150                 155                 160

Leu Asn His Thr Met Ser Asp Ala Ala Gly Leu Val Gln Phe Met Ser
                165                 170                 175

Ala Leu Gly Glu Ile Ala Arg Gly Arg Gln Glu Pro Ser Ile Pro Pro
            180                 185                 190

Val Trp Arg Arg Glu Leu Leu Asn Ala Arg Asp Pro Pro Arg Val Thr
        195                 200                 205

Cys Thr His Arg Glu Tyr Glu His Val Pro Asp Thr Lys Gly Thr Ile
    210                 215                 220

Ile Pro Leu Asp His Met Ala His Arg Ser Phe Phe Phe Gly Pro Ser
225                 230                 235                 240

Glu Val Ala Ala Ile Arg Ser Leu Ile Pro Gln Thr Asp Gln Arg Cys
                245                 250                 255

Ser Asn Phe Glu Val Leu Thr Ala Cys Leu Trp Arg Cys Arg Thr Ile
            260                 265                 270

Ala Leu Gln Pro Asp Lys Asp Glu Glu Val Arg Ile Leu Cys Ile Val
```

```
            275                 280                 285
Asn Ala Arg Ser Lys Phe Asp Pro Pro Leu Pro Ser Gly Tyr Tyr Gly
    290                 295                 300

Asn Ala Phe Ala Phe Pro Val Ala Val Thr Thr Ala Gly Lys Leu Cys
305                 310                 315                 320

Asp Asn Pro Leu Gly Tyr Ala Leu Glu Leu Val Arg Lys Ala Lys Ala
                325                 330                 335

Asp Val Thr Glu Glu Tyr Met His Ser Val Ala Asp Leu Met Val Thr
            340                 345                 350

Lys Gly Arg Pro His Phe Thr Val Val Arg Ser Tyr Leu Val Ser Asp
        355                 360                 365

Val Thr Arg Ala Gly Phe Gly Asn Ile Glu Phe Gly Trp Gly Lys Ala
    370                 375                 380

Val Tyr Gly Gly Pro Ala Lys Gly Gly Val Gly Ala Ile Pro Gly Val
385                 390                 395                 400

Ala Ser Phe Tyr Ile Pro Phe Lys Asn Ala Lys Gly Glu Glu Gly Leu
                405                 410                 415

Val Ile Pro Val Cys Leu Pro Ser Glu Ala Met Glu Arg Phe Gln Lys
            420                 425                 430

Glu Leu Asp Cys Val Leu Asn His His Ile Val Gln Pro Ser Ala Ile
        435                 440                 445

Ala Pro Asn Ser Arg Phe Ile Val Ser Leu
    450                 455

<210> SEQ ID NO 47
<211> LENGTH: 461
<212> TYPE: PRT
<213> ORGANISM: Clitoria ternatea

<400> SEQUENCE: 47

Met Ala Thr Ser Thr Ser Ser Ser Leu Met Phe Gln Val Gln Lys
1               5                   10                  15

Arg Glu Ala Glu Leu Ile Ala Pro Ala Lys Pro Thr Pro Arg Glu Val
            20                  25                  30

Lys Leu Leu Ser Asp Ile Asp Asp Gln Glu Gly Leu Arg Phe Gln Ile
        35                  40                  45

Pro Val Ile Gln Phe Tyr Arg Tyr Asn Glu Thr Met Ala Gly Lys Asp
    50                  55                  60

Pro Val Glu Val Ile Arg Lys Ala Leu Ala Lys Thr Leu Val Phe Tyr
65                  70                  75                  80

Tyr Pro Phe Ala Gly Arg Leu Arg Glu Gly Pro Gly Arg Lys Leu Met
                85                  90                  95

Val Asp Cys Thr Gly Glu Gly Val Leu Phe Ile Glu Ala His Ala Asp
            100                 105                 110

Val Thr Leu Gln Gln Phe Gly Asp Ser Leu Gln Pro Phe Pro Gly
        115                 120                 125

Leu Asp His Leu Leu Tyr Asn Leu Pro Asn Ser Asp Gly Val Leu Asn
    130                 135                 140

Ser Pro Leu Leu Leu Ile Gln Val Thr Arg Leu Lys Cys Gly Gly Phe
145                 150                 155                 160

Ile Leu Ala Leu Arg Leu Asn His Thr Met Ser Asp Ala Ala Gly Leu
                165                 170                 175

Val Gln Phe Met Ser Ala Val Gly Glu Ile Ala Arg Gly Met Glu Glu
            180                 185                 190
```

```
Pro Ser Ile Pro Pro Val Trp Arg Arg Glu Leu Leu Asn Ala Arg Asn
        195                 200                 205

Pro Pro Lys Val Thr Cys Thr His Arg Glu Tyr Glu Gln Val Pro Asp
    210                 215                 220

Ser Lys Gly Thr Ile Ile Pro Leu Asp Asp Met Ala His Arg Ser Phe
225                 230                 235                 240

Phe Phe Gly Pro Ala Glu Ile Ser Ala Ile Arg Arg Leu Ile Pro Ala
                245                 250                 255

Gln Gln Gln Arg Gln Cys Ser Asn Phe Glu Ile Leu Thr Ala Cys Leu
            260                 265                 270

Trp Arg Cys Arg Thr Ile Ala Leu Gln Pro Asp Ser Asp Glu Glu Val
        275                 280                 285

Arg Ile Leu Cys Ile Val Asn Ala Arg Gly Lys Phe Asn Pro Pro Leu
    290                 295                 300

Pro Ala Gly Tyr Tyr Gly Asn Ala Phe Ala Phe Pro Val Ala Val Thr
305                 310                 315                 320

Thr Ala Gly Lys Leu Cys Gly Asn Pro Leu Gly Tyr Ala Leu Glu Leu
                325                 330                 335

Val Arg Lys Ala Lys Gly Asp Val Ser Glu Glu Tyr Met His Ser Leu
            340                 345                 350

Ala Asp Leu Met Val Thr Lys Gly Arg Pro His Phe Thr Val Val Arg
        355                 360                 365

Ser Tyr Leu Val Ser Asp Val Thr Arg Ala Gly Phe Gly Asp Val Asp
    370                 375                 380

Phe Gly Trp Gly Lys Pro Val Tyr Gly Gly Pro Ala Lys Gly Gly Val
385                 390                 395                 400

Gly Ala Ile Pro Gly Val Ala Ser Phe Tyr Ile Pro Phe Arg Asn Ser
                405                 410                 415

Lys Gly Glu Glu Gly Leu Val Ile Pro Val Cys Leu Pro Ser Gln Ala
            420                 425                 430

Met Asp Arg Phe Val Arg Glu Leu Asp Thr Ile Leu Asn His His Leu
        435                 440                 445

Gln Pro Pro Pro Lys Ser Pro Leu Val Leu Ser Leu
    450                 455                 460

<210> SEQ ID NO 48
<211> LENGTH: 460
<212> TYPE: PRT
<213> ORGANISM: Petunia x hybrida

<400> SEQUENCE: 48

Met Asp Ser Lys Gln Ser Ser Glu Leu Val Phe Thr Val Arg Arg Gln
1               5                   10                  15

Glu Pro Glu Leu Ile Ala Pro Ala Lys Pro Thr Pro Arg Glu Thr Lys
            20                  25                  30

Phe Leu Ser Asp Ile Asp Asp Gln Gly Leu Arg Phe Gln Ile Pro
        35                  40                  45

Val Ile Asn Phe Tyr Arg Lys Asp Ser Ser Met Gly Gly Lys Asp Pro
    50                  55                  60

Val Glu Val Ile Lys Lys Ala Ile Ala Glu Thr Leu Val Phe Tyr Tyr
65                  70                  75                  80

Pro Phe Ala Gly Arg Leu Arg Glu Gly Asn Asp Arg Lys Leu Met Val
                85                  90                  95

Asp Cys Thr Gly Glu Gly Val Met Phe Val Glu Ala Asn Ala Asp Val
            100                 105                 110
```

```
Thr Leu Glu Glu Phe Gly Asp Glu Leu Gln Pro Pro Phe Pro Cys Leu
        115                 120                 125

Glu Glu Leu Leu Tyr Asp Val Pro Gly Ser Ala Gly Val Leu His Cys
        130                 135                 140

Pro Leu Leu Ile Gln Val Thr Arg Leu Arg Cys Gly Gly Phe Ile
145                 150                 155                 160

Phe Ala Leu Arg Leu Asn His Thr Met Ser Asp Ala Pro Gly Leu Val
                165                 170                 175

Gln Phe Met Thr Ala Val Gly Glu Met Ala Arg Gly Ala Thr Ala Pro
            180                 185                 190

Ser Thr Leu Pro Val Trp Cys Arg Glu Leu Leu Asn Ala Arg Asn Pro
        195                 200                 205

Pro Gln Val Thr Cys Thr His His Glu Tyr Glu Glu Val Pro Asp Thr
        210                 215                 220

Lys Gly Thr Leu Ile Pro Leu Asp Asp Met Val His Arg Ser Phe Phe
225                 230                 235                 240

Phe Gly Pro Thr Glu Val Ser Ala Leu Arg Arg Phe Val Pro Pro His
                245                 250                 255

Leu His Asn Cys Ser Thr Phe Glu Val Leu Thr Ala Ala Leu Trp Arg
            260                 265                 270

Cys Arg Thr Ile Ser Ile Lys Pro Asp Pro Glu Glu Glu Val Arg Val
        275                 280                 285

Leu Cys Ile Val Asn Ala Arg Ser Arg Phe Asn Pro Gln Leu Pro Ser
        290                 295                 300

Gly Tyr Tyr Gly Asn Ala Phe Ala Phe Pro Val Ala Val Thr Thr Ala
305                 310                 315                 320

Glu Lys Leu Cys Lys Asn Pro Leu Gly Tyr Ala Leu Glu Leu Val Lys
                325                 330                 335

Lys Thr Lys Ser Asp Val Thr Glu Glu Tyr Met Lys Ser Val Ala Asp
            340                 345                 350

Leu Met Val Ile Lys Gly Arg Pro His Phe Thr Val Arg Thr Tyr
        355                 360                 365

Leu Val Ser Asp Val Thr Arg Ala Gly Phe Gly Glu Val Asp Phe Gly
        370                 375                 380

Trp Gly Lys Ala Val Tyr Gly Gly Pro Ala Lys Gly Val Gly Ala
385                 390                 395                 400

Ile Pro Gly Val Ala Ser Phe Tyr Ile Pro Phe Arg Asn Lys Lys Gly
                405                 410                 415

Glu Asn Gly Ile Val Val Pro Ile Cys Leu Pro Gly Phe Ala Met Glu
            420                 425                 430

Lys Phe Val Lys Glu Leu Asp Ser Met Leu Lys Gly Asp Ala Gln Leu
        435                 440                 445

Asp Asn Lys Lys Tyr Ala Phe Ile Thr Pro Ala Leu
450                 455                 460

<210> SEQ ID NO 49
<211> LENGTH: 460
<212> TYPE: PRT
<213> ORGANISM: Nicotiana tabacum

<400> SEQUENCE: 49

Met Asp Ser Lys Gln Ser Ser Glu Leu Val Phe Thr Val Arg Arg Gln
1               5                   10                  15

Lys Pro Glu Leu Ile Ala Pro Ala Lys Pro Thr Pro Arg Glu Thr Lys
```

-continued

```
             20                  25                  30
Phe Leu Ser Asp Ile Asp Gln Glu Gly Leu Arg Phe Gln Ile Pro
             35                  40                  45
Val Ile Gln Phe Tyr His Lys Asp Ser Ser Met Gly Arg Lys Asp Pro
 50                  55                  60
Val Lys Val Ile Lys Lys Ala Ile Ala Glu Thr Leu Val Phe Tyr Tyr
 65                  70                  75                  80
Pro Phe Ala Gly Arg Leu Arg Glu Gly Asn Gly Arg Lys Leu Met Val
                     85                  90                  95
Asp Cys Thr Gly Glu Gly Ile Met Phe Val Glu Ala Asp Ala Asp Val
                    100                 105                 110
Thr Leu Glu Gln Phe Gly Asp Glu Leu Gln Pro Pro Phe Pro Cys Leu
                    115                 120                 125
Glu Glu Leu Leu Tyr Asp Val Pro Asp Ser Ala Gly Val Leu Asn Cys
                    130                 135                 140
Pro Leu Leu Ile Gln Val Thr Arg Leu Arg Cys Gly Gly Phe Ile
145                 150                 155                 160
Phe Ala Leu Arg Leu Asn His Thr Met Ser Asp Ala Pro Gly Leu Val
                    165                 170                 175
Gln Phe Met Thr Ala Val Gly Glu Met Ala Arg Gly Gly Ser Ala Pro
                    180                 185                 190
Ser Ile Leu Pro Val Trp Cys Arg Glu Leu Leu Asn Ala Arg Asn Pro
                    195                 200                 205
Pro Gln Val Thr Cys Thr His His Glu Tyr Asp Glu Val Arg Asp Thr
                    210                 215                 220
Lys Gly Thr Ile Ile Pro Leu Asp Asp Met Val His Lys Ser Phe Phe
225                 230                 235                 240
Phe Gly Pro Ser Glu Val Ser Ala Leu Arg Arg Phe Val Pro His His
                    245                 250                 255
Leu Arg Lys Cys Ser Thr Phe Glu Leu Leu Thr Ala Val Leu Trp Arg
                    260                 265                 270
Cys Arg Thr Met Ser Leu Lys Pro Asp Pro Glu Glu Glu Val Arg Ala
                    275                 280                 285
Leu Cys Ile Val Asn Ala Arg Ser Arg Phe Asn Pro Pro Leu Pro Thr
                    290                 295                 300
Gly Tyr Tyr Gly Asn Ala Phe Ala Phe Pro Val Ala Val Thr Thr Ala
305                 310                 315                 320
Ala Lys Leu Ser Lys Asn Pro Leu Gly Tyr Ala Leu Glu Leu Val Lys
                    325                 330                 335
Lys Thr Lys Ser Asp Val Thr Glu Glu Tyr Met Lys Ser Val Ala Asp
                    340                 345                 350
Leu Met Val Leu Lys Gly Arg Pro His Phe Thr Val Val Arg Thr Phe
                    355                 360                 365
Leu Val Ser Asp Val Thr Arg Gly Gly Phe Gly Glu Val Asp Phe Gly
                    370                 375                 380
Trp Gly Lys Ala Val Tyr Gly Gly Pro Ala Lys Gly Val Gly Ala
385                 390                 395                 400
Ile Pro Gly Val Ala Ser Phe Tyr Ile Pro Phe Lys Asn Lys Lys Gly
                    405                 410                 415
Glu Asn Gly Ile Val Val Pro Ile Cys Leu Pro Gly Phe Ala Met Glu
                    420                 425                 430
Thr Phe Val Lys Glu Leu Asp Gly Met Leu Lys Val Asp Ala Pro Leu
                    435                 440                 445
```

Val Asn Ser Asn Tyr Ala Ile Ile Arg Pro Ala Leu
    450                 455                 460

<210> SEQ ID NO 50
<211> LENGTH: 459
<212> TYPE: PRT
<213> ORGANISM: Cucumis melo

<400> SEQUENCE: 50

Met Ala Ser Ser Leu Val Phe Gln Val Gln Arg Ser Gln Pro Gln Leu
1               5                   10                  15

Ile Pro Pro Ser Asp Pro Thr Pro His Glu Phe Lys Gln Leu Ser Asp
            20                  25                  30

Ile Asp Asp Gln Glu Gly Leu Arg Phe Gln Ile Pro Val Ile Gln Phe
        35                  40                  45

Tyr Arg His Asp Pro Arg Met Ala Gly Thr Asp Pro Ala Arg Val Ile
    50                  55                  60

Lys Glu Ala Ile Ala Lys Ala Leu Val Phe Tyr Tyr Pro Phe Ala Gly
65                  70                  75                  80

Arg Leu Arg Glu Gly Pro Gly Arg Lys Leu Phe Val Glu Cys Thr Gly
                85                  90                  95

Glu Gly Val Met Phe Ile Glu Ala Asp Ala Asp Val Ser Leu Glu Gln
            100                 105                 110

Phe Gly Asp Ala Leu Gln Pro Pro Phe Pro Cys Leu Glu Glu Pro Leu
        115                 120                 125

Phe Asp Val Pro Asn Ser Ser Gly Val Leu Asp Cys Pro Leu Leu Leu
130                 135                 140

Ile Gln Val Thr Arg Leu Lys Cys Gly Gly Phe Ile Phe Ala Leu Arg
145                 150                 155                 160

Leu Asn His Thr Met Ser Asp Ala Ser Gly Leu Val Gln Phe Met Met
                165                 170                 175

Ala Val Gly Glu Met Ala Arg Gly Ala Thr Ala Pro Ser Val Arg Pro
            180                 185                 190

Val Trp Gln Arg Ala Leu Leu Asn Ala Arg Asp Pro Pro Lys Val Thr
        195                 200                 205

Cys His His Arg Glu Tyr Asp Glu Val Val Asp Thr Lys Gly Thr Ile
210                 215                 220

Ile Pro Leu Asp Asp Met Ala His Arg Ser Phe Phe Gly Pro Ser
225                 230                 235                 240

Glu Ile Ser Ala Ile Arg Lys Ala Leu Pro Ser His Leu Arg Gln Cys
                245                 250                 255

Ser Ser Phe Glu Val Leu Thr Ala Cys Leu Trp Arg Phe Arg Thr Ile
            260                 265                 270

Ser Leu Gln Pro Asp Pro Glu Glu Glu Val Arg Val Leu Cys Ile Val
        275                 280                 285

Asn Ser Arg Ser Lys Phe Asn Pro Pro Leu Pro Thr Gly Tyr Tyr Gly
    290                 295                 300

Asn Ala Phe Ala Phe Pro Val Ala Leu Thr Thr Ala Gly Lys Leu Cys
305                 310                 315                 320

Gln Asn Pro Leu Gly Tyr Ala Leu Glu Leu Val Arg Lys Ala Lys Ala
                325                 330                 335

Asp Val Thr Glu Asp Tyr Met Lys Ser Val Ala Asp Leu Met Val Ile
            340                 345                 350

Lys Gly Arg Pro His Phe Thr Val Val Arg Thr Tyr Leu Val Ser Asp

```
                    355                 360                 365
Val Thr Arg Ala Gly Phe Glu Asp Val Asp Phe Gly Trp Gly Lys Ala
            370                 375                 380
Met Tyr Gly Gly Pro Ala Lys Gly Val Gly Ala Ile Pro Gly Val
385                 390                 395                 400
Ala Ser Phe Tyr Ile Pro Phe Lys Asn Lys Gly Glu Arg Gly Ile
                405                 410                 415
Leu Val Pro Leu Cys Leu Pro Ala Pro Ala Met Glu Arg Phe Val Lys
            420                 425                 430
Glu Leu Asp Ala Leu Leu Lys Ala Gly Lys Thr Ile Asp Gly Val Asp
                435                 440                 445
Asn Lys Lys Pro Leu Phe Ile Ala Ser Ala Leu
            450                 455

<210> SEQ ID NO 51
<211> LENGTH: 461
<212> TYPE: PRT
<213> ORGANISM: Clitoria ternatea

<400> SEQUENCE: 51

Met Ala Thr Ser Thr Ser Ser Ser Leu Met Phe Gln Val Gln Lys
1               5                   10                  15
Arg Glu Ala Glu Leu Ile Ala Pro Ala Lys Pro Thr Pro Arg Glu Val
                20                  25                  30
Lys Leu Leu Ser Asp Ile Asp Asp Gln Glu Gly Leu Arg Phe Gln Ile
            35                  40                  45
Pro Val Ile Gln Phe Tyr Arg Tyr Asn Glu Thr Met Ala Gly Lys Asp
50                  55                  60
Pro Val Glu Val Ile Arg Lys Ala Leu Ala Lys Thr Leu Val Phe Tyr
65                  70                  75                  80
Tyr Pro Phe Ala Gly Arg Leu Arg Glu Gly Pro Gly Arg Lys Leu Met
                85                  90                  95
Val Asp Cys Thr Gly Glu Gly Val Leu Phe Ile Glu Ala His Ala Asp
                100                 105                 110
Val Thr Leu Gln Gln Phe Gly Asp Ser Leu Gln Pro Pro Phe Pro Gly
            115                 120                 125
Leu Asp His Leu Leu Tyr Asn Leu Pro Asn Ser Asp Gly Val Leu Asn
130                 135                 140
Ser Pro Leu Leu Leu Ile Gln Val Thr Arg Leu Lys Cys Gly Gly Phe
145                 150                 155                 160
Ile Leu Ala Leu Arg Leu Asn His Thr Met Ser Asp Ala Ala Gly Leu
                165                 170                 175
Val Gln Phe Met Ser Ala Val Gly Glu Ile Ala Arg Gly Met Glu Glu
            180                 185                 190
Pro Ser Ile Pro Pro Val Trp Arg Arg Glu Leu Leu Asn Ala Arg Asn
            195                 200                 205
Pro Pro Lys Val Thr Cys Thr His Arg Glu Tyr Glu Gln Val Pro Asp
            210                 215                 220
Ser Lys Gly Thr Ile Ile Pro Leu Asp Asp Met Ala His Arg Ser Phe
225                 230                 235                 240
Phe Phe Gly Pro Ala Glu Ile Ser Ala Ile Arg Arg Leu Ile Pro Ala
                245                 250                 255
Gln Gln Gln Arg Gln Cys Ser Asn Phe Glu Ile Leu Thr Ala Cys Leu
            260                 265                 270
```

```
Trp Arg Cys Arg Thr Ile Ala Leu Gln Pro Asp Ser Asp Glu Glu Val
            275                 280                 285

Arg Ile Leu Cys Ile Val Asn Ala Arg Gly Lys Phe Asn Pro Pro Leu
        290                 295                 300

Pro Ala Gly Tyr Tyr Gly Asn Ala Phe Ala Phe Pro Val Ala Val Thr
305                 310                 315                 320

Thr Ala Gly Lys Leu Cys Gly Asn Pro Leu Gly Tyr Ala Leu Glu Leu
                325                 330                 335

Val Arg Lys Ala Lys Gly Asp Val Ser Glu Glu Tyr Met His Ser Leu
            340                 345                 350

Ala Asp Leu Met Val Thr Lys Gly Arg Pro His Phe Thr Val Val Arg
        355                 360                 365

Ser Tyr Leu Val Ser Asp Val Thr Arg Ala Gly Phe Gly Asp Val Asp
    370                 375                 380

Phe Gly Trp Gly Lys Pro Val Tyr Gly Gly Pro Ala Lys Gly Gly Val
385                 390                 395                 400

Gly Ala Ile Pro Gly Val Ala Ser Phe Tyr Ile Pro Phe Arg Asn Ser
                405                 410                 415

Lys Gly Glu Glu Gly Leu Val Ile Pro Val Cys Leu Pro Ser Gln Ala
            420                 425                 430

Met Asp Arg Phe Val Arg Glu Leu Asp Thr Ile Leu Asn His His Leu
        435                 440                 445

Gln Pro Pro Lys Ser Pro Leu Val Leu Ser Ser Leu
    450                 455                 460

<210> SEQ ID NO 52
<211> LENGTH: 460
<212> TYPE: PRT
<213> ORGANISM: Populus trichocarpa

<400> SEQUENCE: 52

Met Ala Ser Ser Pro Ala Ser Leu Leu Phe Lys Val His Arg Arg Glu
1               5                   10                  15

Pro Glu Leu Ile Lys Pro Ala Lys Pro Thr Pro His Glu Phe Lys Leu
            20                  25                  30

Leu Ser Asp Ile Asp Asp Gln Glu Gly Leu Arg Phe His Ile Pro Val
        35                  40                  45

Met Gln Phe Tyr Arg Asn Asn Pro Ser Met Gln Gly Lys Asp Pro Val
    50                  55                  60

Lys Ile Ile Arg Glu Ala Leu Ala Lys Thr Leu Val Phe Tyr Tyr Pro
65                  70                  75                  80

Phe Ala Gly Arg Leu Arg Glu Gly Pro Asn Arg Lys Leu Met Val Glu
                85                  90                  95

Cys Thr Gly Glu Gly Ile Leu Phe Ile Glu Ala Asp Ala Asp Val Thr
            100                 105                 110

Leu Glu Gln Phe Gly Asp Ala Leu Gln Pro Pro Phe Pro Cys Leu Glu
        115                 120                 125

Glu Leu Leu Phe Asp Val Pro Gly Ser Ser Gly Val Leu Asn Cys Pro
    130                 135                 140

Leu Leu Leu Ile Gln Val Thr Arg Leu Lys Cys Gly Gly Phe Leu Phe
145                 150                 155                 160

Ala Leu Arg Leu Asn His Thr Met Ser Asp Ala Val Gly Leu Val Gln
                165                 170                 175

Phe Met Ala Ala Val Gly Glu Met Ala Arg Gly Ala Asn Ala Pro Ser
            180                 185                 190
```

```
Val Pro Ala Val Trp Glu Arg Gln Val Leu Asn Ala Ser Asp Pro Pro
            195                 200                 205

Arg Val Thr Cys Thr His Arg Glu Tyr Glu Glu Val Ala Asp Thr Lys
        210                 215                 220

Gly Thr Ile Ile Pro Leu Asp Asp Met Ala His Arg Ser Phe Phe
225                 230                 235                 240

Gly Pro Ser Glu Met Ser Ala Leu Arg Lys Phe Val Pro Pro His Leu
            245                 250                 255

Ser His Cys Ser Thr Phe Glu Ile Leu Thr Ala Cys Leu Trp Lys Cys
        260                 265                 270

Arg Thr Ile Ala Leu Gln Pro Asp Pro Thr Glu Glu Met Arg Ile Leu
            275                 280                 285

Cys Ile Val Asn Ala Arg Glu Lys Phe Asn Pro Pro Leu Pro Arg Gly
        290                 295                 300

Tyr Tyr Gly Asn Gly Phe Ala Phe Pro Val Ala Val Ala Thr Ala Glu
305                 310                 315                 320

Glu Leu Ser Lys Asn Pro Phe Gly Tyr Ala Leu Glu Leu Val Arg Lys
            325                 330                 335

Ala Lys Ala Asp Val Thr Glu Glu Tyr Met Arg Ser Val Ser Ser Leu
        340                 345                 350

Met Val Ile Lys Gly Arg Pro His Phe Thr Val Val Arg Ala Tyr Leu
            355                 360                 365

Val Ser Asp Leu Arg Arg Ala Gly Phe Glu Glu Val Asp Phe Gly Trp
        370                 375                 380

Gly Asn Ala Ile Tyr Gly Gly Ala Ala Lys Gly Val Gly Ala Ile
385                 390                 395                 400

Pro Gly Val Ala Ser Phe Tyr Ile Pro Phe Thr Asn Lys Lys Gly Glu
            405                 410                 415

Asn Gly Val Val Val Pro Phe Cys Leu Pro Ala Pro Ala Met Glu Arg
        420                 425                 430

Phe Val Lys Glu Leu Asp Gly Met Leu Lys Asp Asp Gln Thr Val Ser
            435                 440                 445

Ala Gln Thr Lys Ser Lys Phe Ile Val Ser Ser Leu
        450                 455                 460

<210> SEQ ID NO 53
<211> LENGTH: 459
<212> TYPE: PRT
<213> ORGANISM: Vitis vinifera

<400> SEQUENCE: 53

Met Ala Pro Pro Pro Ser Leu Val Phe Ser Val Arg Arg Ser Lys Pro
1               5                   10                  15

Glu Leu Val Ala Pro Ala Lys Pro Thr Pro His Glu Phe Lys Pro Leu
            20                  25                  30

Ser Asp Ile Asp Asp Gln Glu Gly Leu Arg Phe Gln Ile Pro Val Ile
        35                  40                  45

Gln Phe Tyr Lys Lys Val Pro Ser Met His Gly Arg Asp Pro Ala Lys
    50                  55                  60

Val Ile Lys Asp Ala Val Ala Arg Ala Leu Val Phe Tyr Tyr Pro Phe
65                  70                  75                  80

Ala Gly Arg Leu Arg Glu Glu Ala Gly Arg Lys Leu Val Val Glu Cys
            85                  90                  95

Thr Gly Glu Gly Ile Val Phe Ile Glu Ala Asp Ala Asp Val Thr Leu
```

```
                    100                 105                 110
Glu Gln Phe Gly Asp Ala Leu Gln Pro Pro Phe Pro Gly Leu Glu Glu
            115                 120                 125

Leu Ile Tyr Asp Ala Pro Gly Ser Gly Gly Val Leu Asn Ser Pro Leu
130                 135                 140

Leu Leu Ile Gln Val Thr Arg Leu Gln Cys Gly Gly Phe Ile Phe Gly
145                 150                 155                 160

Leu Arg Leu Asn His Thr Met Ser Asp Ala Ala Gly Leu Val Gln Phe
                165                 170                 175

Met Ser Ala Val Gly Glu Met Ala Arg Gly Ala Ser Ala Pro Ser Ile
            180                 185                 190

Pro Pro Val Trp Arg Arg Asp Leu Leu Asn Ala Arg Asp Pro Pro Arg
            195                 200                 205

Val Thr Arg Thr His His Glu Tyr Asp Glu Val Ala Asp Thr Lys Gly
        210                 215                 220

Thr Ile Ile Pro Leu Asp Asp Met Glu His Arg Ser Phe Phe Phe Gly
225                 230                 235                 240

Pro Thr Glu Phe Ala Ala Leu Arg Arg Leu Leu Ser Pro His Leu Arg
                245                 250                 255

Thr Cys Ser Thr Phe Glu Leu Leu Thr Ala Cys Leu Trp Arg Cys Arg
            260                 265                 270

Thr Ile Ala Leu Arg Pro Asp Pro Glu Glu Glu Val Arg Val Leu Cys
        275                 280                 285

Ile Val Asn Ala Arg Ser Arg Leu Gln Pro Pro Leu Pro Ala Gly Tyr
    290                 295                 300

Tyr Gly Asn Val Phe Gly Phe Pro Val Ala Leu Ser Ser Ala Gly Lys
305                 310                 315                 320

Leu Cys Arg Asn Pro Leu Glu Tyr Ala Leu Asp Leu Val Lys Gly Ala
                325                 330                 335

Lys Asn Ser Val Asp Gln Glu Tyr Met Lys Ser Val Ala Asp Leu Met
            340                 345                 350

Val Ser Thr Gly Arg Arg His Phe Thr Val Val Arg Ser Tyr Leu Val
        355                 360                 365

Ser Asp Leu Thr Arg Ala Gly Phe Gly Asp Val Asp Phe Gly Trp Gly
    370                 375                 380

Lys Ala Val Tyr Gly Gly Ala Lys Gly Gly Val Gly Ala Ile Pro
385                 390                 395                 400

Gly Val Ala Ser Phe Tyr Ile Pro Phe Arg Asn His Lys Gly Glu Asp
                405                 410                 415

Gly Ile Val Val Pro Phe Cys Leu Pro Ala Ala Ala Met Glu Ile Phe
            420                 425                 430

Val Lys Glu Leu Asn Ser Leu Leu Lys Glu Glu His Pro Leu Pro Ser
        435                 440                 445

Asn Lys Ser Ser Thr Phe Ile Ile Ser Ala Leu
    450                 455

<210> SEQ ID NO 54
<211> LENGTH: 455
<212> TYPE: PRT
<213> ORGANISM: Malus x domestica

<400> SEQUENCE: 54

Met Met Ser Phe Ser Val Leu Gln Val Lys Arg Leu Gln Pro Glu Leu
1               5                   10                  15
```

```
Ile Thr Pro Ala Lys Ser Thr Pro Gln Glu Thr Lys Phe Leu Ser Asp
             20                  25                  30

Ile Asp Asp Gln Glu Ser Leu Arg Val Gln Ile Pro Ile Ile Met Cys
         35                  40                  45

Tyr Lys Asp Asn Pro Ser Leu Asn Lys Asn Arg Asn Pro Val Lys Ala
     50                  55                  60

Ile Arg Glu Ala Leu Ser Arg Ala Leu Val Tyr Tyr Pro Leu Ala
65                   70                  75                  80

Gly Arg Leu Arg Glu Gly Pro Asn Arg Lys Leu Val Val Asp Cys Asn
                 85                  90                  95

Gly Glu Gly Ile Leu Phe Val Glu Ala Ser Ala Asp Val Thr Leu Glu
                100                 105                 110

Gln Leu Gly Asp Lys Ile Leu Pro Pro Cys Pro Leu Leu Glu Glu Phe
            115                 120                 125

Leu Tyr Asn Phe Pro Gly Ser Asp Gly Ile Ile Asp Cys Pro Leu Leu
        130                 135                 140

Leu Ile Gln Val Thr Cys Leu Thr Cys Gly Gly Phe Ile Leu Ala Leu
145                 150                 155                 160

Arg Leu Asn His Thr Met Cys Asp Ala Ala Gly Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ala Arg Asp Pro Arg Ile
        195                 200                 205

Thr Cys Ala His His Glu Tyr Glu Asp Val Ile Gly His Ser Asp Gly
210                 215                 220

Ser Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
            275                 280                 285

Val Ser Cys Ile Val Asn Ala Arg Gly Lys His Asn Asn Val Arg Leu
        290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Gln Tyr Ser Ser Thr Gly
        355                 360                 365

Ser Tyr Leu Ile Val Ser Asp Asn Thr Arg Val Gly Phe Gly Asp Val
    370                 375                 380

Asn Phe Gly Trp Gly Gln Pro Val Phe Ala Gly Pro Val Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Cys Asn
```

Asn Leu Arg Ser Thr Ser Gln
    450             455

<210> SEQ ID NO 55
<211> LENGTH: 442
<212> TYPE: PRT
<213> ORGANISM: Pyrus communis

<400> SEQUENCE: 55

Met Met Ser Leu Ser Val Leu Gln Val Lys Arg Leu Gln Pro Glu Leu
1               5                   10                  15

Ile Thr Pro Ala Lys Pro Thr Pro Gln Glu Thr Lys Phe Leu Ser Asp
            20                  25                  30

Ile Asp Asp Gln Glu Gly Leu Arg Phe Gln Leu Pro Val Ile Met Cys
        35                  40                  45

Tyr Lys Asp Asn Pro Ser Leu Asn Lys Asn Arg Asn Pro Ile Lys Val
    50                  55                  60

Ile Lys Glu Ala Leu Ser Arg Ala Leu Val Tyr Tyr Pro Leu Ala
65                  70                  75                  80

Gly Arg Leu Arg Glu Gly Pro Asn Arg Lys Leu Met Val Asn Cys Asn
                85                  90                  95

Gly Glu Gly Ile Leu Phe Val Glu Ala Ser Ala Asp Val Thr Leu Glu
            100                 105                 110

Gln Leu Gly Asp Lys Ile Leu Pro Pro Cys Pro Leu Leu Glu Glu Phe
        115                 120                 125

Leu Phe Asn Phe Pro Gly Ser Asp Gly Ile Ile Gly Cys Pro Leu Leu
130                 135                 140

Leu Val Gln Val Thr Cys Leu Thr Cys Gly Gly Phe Ile Leu Ala Leu
145                 150                 155                 160

Arg Leu Asn His Thr Met Cys Asp Ala Thr Gly Leu Leu Met Phe Leu
                165                 170                 175

Thr Ala Ile Thr Glu Met Gly Arg Gly Ala Asp Ala Pro Ser Ile Leu
            180                 185                 190

Pro Val Trp Glu Arg Glu Leu Leu Phe Ala Arg Asp Pro Pro Arg Ile
        195                 200                 205

Thr Cys Ala His Tyr Glu Tyr Glu Asp Val Ile Asp His Ser Asp Gly
    210                 215                 220

Ser Tyr Ala Phe Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Val Leu Lys Ile Asn Pro Lys Gln Ala Val Arg
        275                 280                 285

Val Ser Cys Ile Val Asn Ala Arg Gly Lys His Asn Asn Val His Ile
    290                 295                 300

Pro Leu Gly Tyr Tyr Gly Asn Ala Phe Ala Phe Pro Ala Ala Val Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

```
Ala Asp Leu Leu Val Leu Arg Gly Arg Pro Gln Tyr Ser Thr Gly
            355                 360                 365

Ser Tyr Leu Ile Val Ser Asp Asn Thr Arg Ala Gly Phe Gly Asp Val
370                 375                 380

Asn Phe Gly Trp Gly Gln Pro Val Phe Ala Gly Pro Ala Lys Ala Leu
385                 390                 395                 400

Asp Leu Ile Ser Phe Tyr Val Gln His Lys Asn Asn Ile Glu Asp Gly
            405                 410                 415

Ile Leu Val Pro Met Cys Leu Pro Ser Ser Ala Met Glu Arg Phe Gln
            420                 425                 430

Gln Glu Leu Glu Arg Ile Thr Thr Gly Thr
            435                 440

<210> SEQ ID NO 56
<211> LENGTH: 451
<212> TYPE: PRT
<213> ORGANISM: Vitis vinifera

<400> SEQUENCE: 56

Met Ala Ser Ser Trp Ser Pro Leu Val Phe Ser Val Lys Arg Cys Ala
1               5                   10                  15

Pro Glu Phe Val Arg Pro Thr Asn Leu Thr Pro Arg Glu Val Lys Gln
            20                  25                  30

Leu Ser Asp Ile Asp Asp Gln Glu Gly Leu Arg Phe Gln Ile Pro Val
        35                  40                  45

Ile Met Phe Tyr Pro Asn Asn Pro Leu Met Lys Gly Lys Asp Pro Val
    50                  55                  60

Lys Val Ile Arg Glu Ala Leu Gly Lys Ala Leu Val Tyr Tyr Tyr Pro
65                  70                  75                  80

Phe Ala Gly Arg Leu Ile Glu Gly Asp Asn Arg Lys Leu Met Val Asp
                85                  90                  95

Cys Thr Gly Glu Gly Val Leu Phe Ile Glu Ala Asp Ala Asp Thr Thr
            100                 105                 110

Leu Glu Asn Leu Gly Asp Ala Ile Gln Pro Met Cys Pro Cys Phe Glu
        115                 120                 125

Glu Leu Leu Tyr Asp Val Pro Gly Ser Gly Gly Ile Leu Gly Ser Pro
    130                 135                 140

Leu Ile Leu Ile Gln Val Thr Arg Leu Arg Cys Gly Gly Phe Ile Phe
145                 150                 155                 160

Ala Leu Arg Leu Asn His Thr Met Ser Asp Ala Leu Gly Leu Ile Gln
                165                 170                 175

Phe Leu Asn Ala Ile Ser Glu Met Ala Gln Gly Leu Ser Val Pro Ser
            180                 185                 190

Leu Leu Pro Ile Trp Glu Arg Glu Leu Leu Asn Ala Arg Asn Pro Pro
        195                 200                 205

Arg Ile Thr Arg Ile His His Glu Tyr Glu Glu Val Thr Asn Asn Lys
    210                 215                 220

Gly Thr Leu Met Ala Met Asp Glu Asn Asn Leu Val His Arg Ser Phe
225                 230                 235                 240

Phe Phe Gly Pro Lys Glu Ile Arg Ala Leu Arg Asn Arg Leu Pro Ala
                245                 250                 255

Ser Leu Gly Ala Cys Ser Thr Phe Glu Val Leu Thr Ala Tyr Val Trp
            260                 265                 270

Arg Cys Arg Thr Ile Ala Phe Ala Val Asp Pro Asp Glu Val Val Arg
        275                 280                 285
```

```
Ile Ser Cys Leu Ile Asn Met Arg Gly Lys Arg Gly Phe Asp Leu Pro
    290                 295                 300
Pro Gly Tyr Tyr Gly Asn Ala Phe Val Tyr Pro Ala Ser Ile Thr Lys
305                 310                 315                 320
Ala Gly Met Leu Cys Lys Asn Pro Leu Glu Tyr Ala Ile Arg Leu Leu
                325                 330                 335
Lys Lys Ala Lys Ala Glu Met Ser Gln Glu Tyr Ile Lys Ser Val Ala
            340                 345                 350
Asp Leu Met Val Ile Lys Gly Arg Pro Ser Phe Thr Gln Pro Gly Asn
        355                 360                 365
Tyr Phe Val Ser Asp Val Thr Arg Ala Gly Phe Gly Glu Val Asn Phe
    370                 375                 380
Gly Trp Gly Lys Pro Val Tyr Gly Gly Leu Ala Arg Ala Leu Ser Ile
385                 390                 395                 400
Ile Ser Phe Cys Thr Arg Phe Arg Asn Ser Lys Gly Glu Gly Asn
                405                 410                 415
Val Ile Pro Ile Cys Leu Pro Pro Val Met Glu Arg Phe Glu Gln
            420                 425                 430
Glu Leu Lys Arg Met Thr Lys Glu Ala Glu Pro Val Leu Ile Lys
        435                 440                 445
Ser Met Leu
    450
```

<210> SEQ ID NO 57
<211> LENGTH: 460
<212> TYPE: PRT
<213> ORGANISM: Petunia x hybrida

<400> SEQUENCE: 57

```
Met Asp Ser Lys Gln Ser Ser Glu Leu Val Phe Thr Val Arg Arg Gln
1               5                   10                  15
Glu Pro Glu Leu Ile Ala Pro Ala Lys Pro Thr Pro Arg Glu Thr Lys
            20                  25                  30
Phe Leu Ser Asp Ile Asp Asp Gln Glu Gly Leu Arg Phe Gln Ile Pro
        35                  40                  45
Val Ile Asn Phe Tyr Arg Lys Asp Ser Ser Met Gly Gly Lys Asp Pro
    50                  55                  60
Val Glu Val Ile Lys Lys Ala Ile Ala Glu Thr Leu Val Phe Tyr Tyr
65                  70                  75                  80
Pro Phe Ala Gly Arg Leu Arg Glu Gly Asn Asp Arg Lys Leu Met Val
                85                  90                  95
Asp Cys Thr Gly Glu Gly Val Met Phe Val Glu Ala Asn Ala Asp Val
            100                 105                 110
Thr Leu Glu Glu Phe Gly Asp Glu Leu Gln Pro Pro Phe Pro Cys Leu
        115                 120                 125
Glu Glu Leu Leu Tyr Asp Val Pro Gly Ser Ala Gly Val Leu His Cys
    130                 135                 140
Pro Leu Leu Leu Ile Gln Val Thr Arg Leu Arg Cys Gly Gly Phe Ile
145                 150                 155                 160
Phe Ala Leu Arg Leu Asn His Thr Met Ser Asp Ala Pro Gly Leu Val
                165                 170                 175
Gln Phe Met Thr Ala Val Gly Glu Met Ala Arg Gly Ala Thr Ala Pro
            180                 185                 190
Ser Thr Leu Pro Val Trp Cys Arg Glu Leu Leu Asn Ala Arg Asn Pro
```

```
            195                 200                 205
Pro Gln Val Thr Cys Thr His His Glu Tyr Glu Val Pro Asp Thr
210                 215                 220
Lys Gly Thr Leu Ile Pro Leu Asp Asp Met Val His Arg Ser Phe Phe
225                 230                 235                 240
Phe Gly Pro Thr Glu Val Ser Ala Leu Arg Arg Phe Val Pro Pro His
                245                 250                 255
Leu His Asn Cys Ser Thr Phe Glu Val Leu Thr Ala Ala Leu Trp Arg
            260                 265                 270
Cys Arg Thr Ile Ser Ile Lys Pro Asp Pro Glu Glu Glu Val Arg Val
        275                 280                 285
Leu Cys Ile Val Asn Ala Arg Ser Arg Phe Asn Pro Gln Leu Pro Ser
    290                 295                 300
Gly Tyr Tyr Gly Asn Ala Phe Ala Phe Pro Val Ala Val Thr Thr Ala
305                 310                 315                 320
Glu Lys Leu Cys Lys Asn Pro Leu Gly Tyr Ala Leu Glu Leu Val Lys
                325                 330                 335
Lys Thr Lys Ser Asp Val Thr Glu Glu Tyr Met Lys Ser Val Ala Asp
            340                 345                 350
Leu Met Val Ile Lys Gly Arg Pro His Phe Thr Val Arg Thr Tyr
        355                 360                 365
Leu Val Ser Asp Val Thr Arg Ala Gly Phe Gly Glu Val Asp Phe Gly
    370                 375                 380
Trp Gly Lys Ala Val Tyr Gly Gly Pro Ala Lys Gly Val Gly Ala
385                 390                 395                 400
Ile Pro Gly Val Ala Ser Phe Tyr Ile Pro Phe Arg Asn Lys Lys Gly
                405                 410                 415
Glu Asn Gly Ile Val Val Pro Ile Cys Leu Pro Gly Phe Ala Met Glu
            420                 425                 430
Lys Phe Val Lys Glu Leu Asp Ser Met Leu Lys Gly Asp Ala Gln Leu
        435                 440                 445
Asp Asn Lys Lys Tyr Ala Phe Ile Thr Pro Ala Leu
    450                 455                 460

<210> SEQ ID NO 58
<211> LENGTH: 456
<212> TYPE: PRT
<213> ORGANISM: Citrus sinensis

<400> SEQUENCE: 58

Met Val Phe Thr Phe Ser Gln Gly Leu Leu Val Thr Arg Lys Ala Pro
1               5                   10                  15
Glu Leu Ile Val Pro Glu Arg Pro Thr Pro Arg Glu Val Lys Gln Ile
            20                  25                  30
Ser Asp Ile Asp Asp Gln Glu Ser Leu Arg Phe Gln Ile Pro Leu Leu
        35                  40                  45
Phe Phe Tyr Lys Asn Asp Pro Ser Pro Ser Met Gln Gly Arg Asp Pro
    50                  55                  60
Val Lys Val Ile Arg Glu Ala Ile Ser Lys Ala Leu Val Phe Tyr Tyr
65                  70                  75                  80
Pro Leu Ala Gly Arg Leu Lys Glu Gly Tyr Asn Arg Lys Leu Met Val
                85                  90                  95
Glu Cys Asn Ala Glu Gly Val Leu Phe Ile Glu Ala Asp Ala Asn Phe
            100                 105                 110
```

```
Thr Leu Glu Gln Leu Arg Asp Asp Val Gln Pro Pro Cys Pro Tyr Leu
            115                 120                 125

Asn Gln Leu Ile Tyr Asp Val Pro Gly Ser Glu Gly Ile Leu Gly Cys
130                 135                 140

Pro Leu Leu Ile Gln Val Thr Arg Leu Thr Cys Gly Gly Phe Ile
145                 150                 155                 160

Phe Ala Ile Arg Phe Asn His Thr Met Cys Asp Ala Phe Gly Leu Val
                165                 170                 175

Gln Phe Leu Lys Ala Ile Glu Asp Met Ala Arg Gly Glu Arg Ser Pro
            180                 185                 190

Thr Leu Phe Pro Ile Trp Gln Arg Leu Ile Leu Asn Ala Arg Asn Pro
        195                 200                 205

Pro Gln Val Thr Cys Ile His His Glu Tyr Asp Glu Ile Asn Thr Asn
    210                 215                 220

Glu Val Pro Ser Asp Asn Met Ala His Lys Ser Phe Phe Ser Leu
225                 230                 235                 240

Lys Gly Ile Lys Ala Leu Arg Asn Gln Leu Pro Phe Gln Leu Lys Asp
                245                 250                 255

Cys Ser Thr Phe Glu Leu Leu Leu Ala Phe Leu Trp Lys Cys Arg Thr
            260                 265                 270

Ile Ala Leu Lys Leu Gln Pro Glu Glu Ile Ala Lys Val Cys Cys Ile
        275                 280                 285

Val Asn Val Arg Gly Lys Ser Tyr Glu Met Asp Ile Pro Pro Gly Tyr
    290                 295                 300

Tyr Gly Asn Ala Phe Thr Phe Ser Ala Val Cys Ser Lys Ala Glu Gln
305                 310                 315                 320

Leu Cys Lys Asn Pro Ile Gly Tyr Ala Val Glu Leu Val Lys Lys Ala
                325                 330                 335

Lys Ala Gln Met Asn Glu Glu Tyr Ile Arg Ser Ala Ala Asp Leu Met
            340                 345                 350

Val Ile Lys Gly Arg Arg Ile Lys Phe Ser Thr Arg Gly Asn Phe Ile
        355                 360                 365

Val Ser Asp Leu Arg Asn Val Gly Leu Gly Asp Val Asp Phe Gly Trp
    370                 375                 380

Gly Lys Pro Ile Tyr Ala Gly Thr Ala Gly Ala Val Ala Val Ile Ser
385                 390                 395                 400

Phe Phe Thr Lys Tyr Gln Asn Lys Asn Gly Glu Pro Gly Ile Leu Val
                405                 410                 415

Pro Ile Cys Leu Pro Gln Ser Ala Met Glu Arg Leu Gln Glu Glu Leu
            420                 425                 430

Lys Gly Leu Met Ile Gln Gly Ser Ala Glu Asp Leu Cys Asn Ile Asn
        435                 440                 445

Gln Thr Gln Ile Phe Ser Lys Leu
    450                 455

<210> SEQ ID NO 59
<211> LENGTH: 458
<212> TYPE: PRT
<213> ORGANISM: Ricinus communis

<400> SEQUENCE: 59

Met Ala Leu Pro Pro Pro Pro Phe Thr Phe Ala Val Arg Arg Ser Pro
1               5                   10                  15

Pro Glu Leu Ile Val Pro Ala Arg Pro Thr Pro Arg Glu Leu Lys Lys
            20                  25                  30
```

-continued

```
Val Ser Asp Ile Asp Asp Gln Glu Gly Leu Arg Phe Gln Ile Ser Phe
        35              40                  45
Val Met Phe Tyr Arg Ser Leu Pro Ser Met Lys Gly Arg Asp Pro Val
 50              55                  60
Glu Ile Ile Arg Lys Ala Leu Ser Glu Ala Leu Val Phe Tyr Tyr Pro
 65              70                  75              80
Phe Ala Gly Arg Leu Ile Glu Gly Pro Asn Arg Lys Leu Ile Val Asp
                 85                  90                  95
Cys Asn Gly Glu Gly Ile Leu Phe Ile Glu Ala Asp Ala Asp Ile Thr
                100                 105                 110
Ile Glu Gln Leu Gly Asp Ser Met Gln Pro Pro Cys Pro Cys Ile Glu
            115                 120                 125
Glu Leu Leu Tyr Asp Val Pro Gly Ser Ser Gly Ile Ile Gly Cys Pro
        130                 135                 140
Leu Leu Leu Ile Gln Ile Thr Arg Leu Ala Cys Gly Gly Phe Val Phe
145                 150                 155                 160
Ala Val Arg Leu Asn His Val Met Ser Asp Ser Val Gly Leu Ala Lys
                165                 170                 175
Phe Phe Lys Ala Thr Gly Glu Ile Ala Lys Gly Ala Cys Met Pro Ser
                180                 185                 190
Leu Phe Pro Val Trp Gln Arg Glu Ile Leu Ser Ala Arg Asn Pro Pro
            195                 200                 205
Gln Val Thr His Lys Leu Glu Glu Tyr Glu Glu Ile Lys His Thr Asp
        210                 215                 220
Asp Lys Ser Ile Leu Thr Leu Asp Ser Pro Asp Met Val Gln Arg Ala
225                 230                 235                 240
Phe Phe Phe Gly Pro Lys Glu Met Arg Ser Leu Arg Arg Gln Leu Pro
                245                 250                 255
Ser His Leu Arg Asn Cys Ser Ser Phe Glu Met Leu Ala Ala Cys Leu
                260                 265                 270
Trp Arg Cys Arg Thr Ile Ala Phe Asp Ile Pro Pro Asn Glu Val Val
            275                 280                 285
Arg Leu Ser Cys Ile Met Asn Val Arg Gly Lys Lys Gly Leu Gln Leu
        290                 295                 300
Pro Asp Gly Tyr Cys Gly Asn Ser Phe Ile Phe Pro Ala Val Leu Ser
305                 310                 315                 320
Arg Ala Glu His Leu Cys Lys Asn Pro Leu Gly Tyr Ala Val Glu Leu
                325                 330                 335
Val Arg Lys Ser Lys Ser Lys Met Ser Glu Glu Tyr Ile Arg Ser Thr
                340                 345                 350
Ile Asp Leu Met Glu Ile Lys Gly Arg Pro His Tyr Val Thr Ala Trp
            355                 360                 365
Asn Leu Leu Leu Val Asp Met Ser His Val Gly Leu Ala Asp Val Asp
        370                 375                 380
Phe Gly Trp Gly Asn Pro Val Tyr Phe Gly Pro Thr Gly Ser Phe Pro
385                 390                 395                 400
Asn Ile Ser Met Phe Ser Arg Phe Lys Asn Ser Lys Gly Glu Asn Gly
                405                 410                 415
Phe Val Val Pro Met Trp Leu Pro Arg Thr Val Met Glu Lys Phe Gln
                420                 425                 430
Asp Glu Phe Leu Lys Met Thr Glu Glu Ser Ala Glu Asn Leu Asn Asp
            435                 440                 445
```

```
Ala Arg Arg Gln Arg Ile Ile Ser Thr Leu
    450                 455

<210> SEQ ID NO 60
<211> LENGTH: 452
<212> TYPE: PRT
<213> ORGANISM: Fragaria x ananassa

<400> SEQUENCE: 60

Met Glu Lys Ile Glu Val Ser Ile Asn Ser Lys His Thr Ile Lys Pro
1               5                   10                  15

Ser Thr Ser Ser Thr Pro Leu Gln Pro Tyr Lys Leu Thr Leu Leu Asp
            20                  25                  30

Gln Leu Thr Pro Pro Ala Tyr Val Pro Ile Val Phe Phe Tyr Pro Ile
                35                  40                  45

Thr Asp His Asp Phe Asn Leu Pro Gln Thr Leu Ala Asp Leu Arg Gln
        50                  55                  60

Ala Leu Ser Glu Thr Leu Thr Leu Tyr Tyr Pro Leu Ser Gly Arg Val
65                  70                  75                  80

Lys Asn Asn Leu Tyr Ile Asp Asp Phe Glu Glu Gly Val Pro Tyr Leu
                85                  90                  95

Glu Ala Arg Val Asn Cys Asp Met Thr Asp Phe Leu Arg Leu Arg Lys
            100                 105                 110

Ile Glu Cys Leu Asn Glu Phe Val Pro Ile Lys Pro Phe Ser Met Glu
        115                 120                 125

Ala Ile Ser Asp Glu Arg Tyr Pro Leu Leu Gly Val Gln Val Asn Val
    130                 135                 140

Phe Asp Ser Gly Ile Ala Ile Gly Val Ser Val Ser His Lys Leu Ile
145                 150                 155                 160

Asp Gly Gly Thr Ala Asp Cys Phe Leu Lys Ser Trp Gly Ala Val Phe
                165                 170                 175

Arg Gly Cys Arg Glu Asn Ile Ile His Pro Ser Leu Ser Glu Ala Ala
            180                 185                 190

Leu Leu Phe Pro Pro Arg Asp Leu Pro Glu Lys Tyr Val Asp Gln
        195                 200                 205

Met Glu Ala Leu Trp Phe Ala Gly Lys Lys Val Ala Thr Arg Arg Phe
    210                 215                 220

Val Phe Gly Val Lys Ala Ile Ser Ser Ile Gln Asp Glu Ala Lys Ser
225                 230                 235                 240

Glu Ser Val Pro Lys Pro Ser Arg Val His Ala Val Thr Gly Phe Leu
                245                 250                 255

Trp Lys His Leu Ile Ala Ala Ser Arg Ala Leu Thr Ser Gly Thr Thr
            260                 265                 270

Ser Thr Arg Leu Ser Ile Ala Ala Gln Ala Val Asn Leu Arg Thr Arg
        275                 280                 285

Met Asn Met Glu Thr Val Leu Asp Asn Ala Thr Gly Asn Leu Phe Trp
    290                 295                 300

Trp Ala Gln Ala Ile Leu Glu Leu Ser His Thr Thr Pro Glu Ile Ser
305                 310                 315                 320

Asp Leu Lys Leu Cys Asp Leu Val Asn Leu Asn Gly Ser Val Lys
                325                 330                 335

Gln Cys Asn Gly Asp Tyr Phe Glu Thr Phe Lys Gly Lys Glu Gly Tyr
            340                 345                 350

Gly Arg Met Cys Glu Tyr Leu Asp Phe Gln Arg Thr Met Ser Ser Met
        355                 360                 365
```

```
Glu Pro Ala Pro Asp Ile Tyr Leu Phe Ser Ser Trp Thr Asn Phe Phe
    370                 375                 380

Asn Pro Leu Asp Phe Gly Trp Gly Arg Thr Ser Trp Ile Gly Val Ala
385                 390                 395                 400

Gly Lys Ile Glu Ser Ala Ser Cys Lys Phe Ile Ile Leu Val Pro Thr
                405                 410                 415

Gln Cys Gly Ser Gly Ile Glu Ala Trp Val Asn Leu Glu Glu Glu Lys
            420                 425                 430

Met Ala Met Leu Glu Gln Asp Pro His Phe Leu Ala Leu Ala Ser Pro
        435                 440                 445

Lys Thr Leu Ile
    450

<210> SEQ ID NO 61
<211> LENGTH: 459
<212> TYPE: PRT
<213> ORGANISM: Rosa rugosa

<400> SEQUENCE: 61

Met Glu Lys Ile Glu Val Ser Ile Ile Ser Arg Asp Thr Ile Lys Pro
1               5                   10                  15

Ser Ala Ala Ser Ser Leu His Pro Tyr Lys Leu Ser Ile Ile Asp
            20                  25                  30

Gln Phe Thr Pro Thr Thr Tyr Phe Pro Val Ile Phe Phe Tyr Pro Ile
            35                  40                  45

Thr Asp Pro Val Phe Asn Leu Pro Gln Thr Leu Thr Asp Leu Lys Ile
50                  55                  60

Thr Val Ser Gln Thr Leu Thr Leu Tyr Tyr Pro Leu Ser Gly Arg Ile
65                  70                  75                  80

Lys Asn Asn Leu Tyr Ile Asp Asp Phe Glu Ala Gly Ile Pro Tyr Leu
                85                  90                  95

Glu Ala Arg Val Asn Cys His Met Ile Asp Phe Leu Arg Leu Pro Lys
            100                 105                 110

Ile Glu Trp Leu Asn Glu Phe Val Pro Ile Ala Pro Tyr Arg Lys Glu
        115                 120                 125

Thr Ile Ser Glu Leu Leu Pro Leu Leu Gly Ile Gln Val Asn Ile Phe
    130                 135                 140

Asp Ser Gly Ile Ala Ile Gly Val Ser Phe Ser His Lys Ile Asn Asp
145                 150                 155                 160

Gly Glu Thr Ala Asn Cys Phe Leu Lys Ser Trp Val Ala Ile Phe Arg
                165                 170                 175

Gly Tyr Arg Asn Lys Ile Ile His Pro Asn Leu Ser Gln Ala Ala Leu
            180                 185                 190

Leu Phe Pro Ser Arg Asp Asp Leu Ser Glu Lys Tyr Val Ala Met Met
        195                 200                 205

Glu Arg Trp Trp Phe Gly Glu Lys Lys Val Val Thr Arg Phe Val
    210                 215                 220

Phe Asp Thr Lys Ala Ile Ser Ala Leu Gln His Glu Gly Lys Ser Glu
225                 230                 235                 240

Tyr Val Pro Lys Pro Ser Arg Val Gln Ala Leu Thr Gly Phe Leu Trp
                245                 250                 255

Lys His Gln Leu Ala Ala Thr Arg Ala Leu Ser Ser Gly Thr Ser Thr
            260                 265                 270

Arg Phe Ser Leu Ala Ile Gln Ala Val Asn Leu Arg Ser Arg Met Asn
```

-continued

```
                275                 280                 285
Met Lys Thr Thr Leu Asp Asn Ala Ile Gly Asn Ile Phe Leu Trp Ala
            290                 295                 300
Pro Ala Phe Leu Glu Leu Asn Tyr Thr Thr Pro Glu Ser Ser Asp His
305                 310                 315                 320
Lys Leu Cys Asp Leu Val Asn Leu Leu Lys Glu Ser Val Lys Glu Tyr
                325                 330                 335
Asn Ser Asp Tyr Leu Glu Thr Leu Lys Gly Lys Gly Tyr Gly Gly
            340                 345                 350
Met Cys Asp Trp Leu Asp Leu Met Asp Glu Gly Ser Ser Ile Glu Pro
            355                 360                 365
Ala Leu Glu Ile Tyr Ser Phe Ser Ser Trp Thr Arg Met Phe Asp Gln
            370                 375                 380
Val Asp Phe Gly Trp Gly Lys Pro Phe Trp Ile Gly Val Thr Gly Lys
385                 390                 395                 400
Val Gln Thr Thr Tyr Thr Asn Ser Thr Val Leu Val Glu Thr Gln Cys
                405                 410                 415
Glu Asn Gly Ile Glu Ala Trp Val Thr Leu Asp Gln Lys Arg Met Ala
            420                 425                 430
Met Leu Glu Gln Asp Pro Gln Phe Leu Ala Phe Ala Ser Pro Thr Pro
            435                 440                 445
Gly Ile Ser Met Ala Ser Ser Val Gly Ile Asp
            450                 455

<210> SEQ ID NO 62
<211> LENGTH: 452
<212> TYPE: PRT
<213> ORGANISM: Ricinus communis

<400> SEQUENCE: 62

Met Val Thr Lys Met Gln Val Asp Ile Ile Ser Arg Glu Val Ile Lys
1               5                   10                  15
Pro Ser Ser Pro Thr Ile His His Tyr Lys Pro Phe Lys Phe Pro Leu
            20                  25                  30
Phe Ser Gln Leu Thr Pro Thr Thr Tyr Ser Pro Val Ile Phe Phe Tyr
        35                  40                  45
Pro Thr Thr Lys Pro Asn Leu Asn Ile Thr Gln Thr Leu Ile His Leu
    50                  55                  60
Lys Lys Thr Leu Ala Glu Thr Leu Thr Leu Tyr Tyr Pro Phe Ser Gly
65              70                  75                  80
Arg Val Val Asp Asn Leu Ser Ile Asp His Phe Asp Glu Gly Val Pro
                85                  90                  95
Phe Phe Ile Ala Arg Val Thr Gly Leu Val Leu Ser Asp Phe Leu Lys
            100                 105                 110
Asn Pro Glu Ile Glu Leu Leu Asn Gly Phe Leu Pro Tyr Lys Pro Phe
        115                 120                 125
Thr Lys Glu Thr Asp Lys Gly Val Pro Gln Met Ala Phe Gln Val Asn
    130                 135                 140
Val Phe Ser Cys Gly Gly Ile Val Ile Gly Trp Ser Ser His Lys
145                 150                 155                 160
Leu Val Asp Gly Pro Thr Gly Ala Ala Phe Ile His Ala Trp Ala Thr
                165                 170                 175
Met Ser Arg Thr Gly Ser Leu Ser Asp Val Ile Lys Pro Asn Cys Asp
            180                 185                 190
```

```
Glu Ala Ser Ile Phe Phe Pro Pro Arg Asn Pro Phe Pro Glu Glu His
            195                 200                 205

Leu Ser Leu Met Glu Ser Leu Trp Phe Thr Lys Gly Asn Tyr Ile Ser
    210                 215                 220

Lys Arg Phe Val Phe Asp Ser Lys Ala Ile Ala Ser Leu Arg Val Lys
225                 230                 235                 240

Ala Arg Gly Glu Gly Asn Glu Lys Lys Asn Met Pro Ser Arg Val Glu
                245                 250                 255

Ala Leu Ser Cys Phe Ile Trp Lys Cys Cys Met Ala Ala Ser Arg Ala
            260                 265                 270

Ala Ser Gly Thr Pro Lys Pro Ser Ile Leu Val Glu Ala Val Asn Leu
    275                 280                 285

Arg Thr Arg Thr Lys Pro Pro Met Ser Lys Val Ser Ile Gly Asp Ile
290                 295                 300

Phe Trp Trp Ala Thr Ala Val Ala Asp Pro Ser Leu His Asn Lys Glu
305                 310                 315                 320

Leu His Glu Leu Ala Thr Leu Leu Asp Glu Ala Ile Ala Leu Tyr Asp
                325                 330                 335

Ser Asp Tyr Met Glu Ser Leu Gln Gly Glu Asp Gly Phe Glu Thr Met
            340                 345                 350

Ser Glu Tyr Cys Asn Gln Leu Arg Gly Leu Phe Ser Ile Glu Glu Pro
    355                 360                 365

Asp Ile Phe Ala Phe Thr Ser Trp Ser Arg Leu Gly Ile Tyr Asp Met
370                 375                 380

Asp Phe Gly Phe Gly Asn Pro Phe Trp Ile Gly Ile Leu Gly Lys Val
385                 390                 395                 400

Gly Pro Ala Phe Arg Asn Leu Thr Val Phe Leu Glu Thr Arg Asp Gly
                405                 410                 415

Lys Gly Ile Glu Ala Trp Ile Thr Leu Asp Glu Glu Arg Met Ala Leu
            420                 425                 430

Leu Glu Arg Asp Pro Glu Phe Leu Ala Asn Ala Ser Pro Asn Pro Arg
    435                 440                 445

Phe Ser Ser Leu
    450

<210> SEQ ID NO 63
<211> LENGTH: 443
<212> TYPE: PRT
<213> ORGANISM: Erythroxylum coca

<400> SEQUENCE: 63

Met Glu Val His Ile Val Ser Arg Glu Thr Val Lys Pro Ser Ser Pro
1               5                   10                  15

Ala Thr Leu Thr Lys Lys Pro Tyr Lys Leu Ser Leu Phe Asp Gln Leu
            20                  25                  30

Thr Pro Gly Thr Tyr Thr Pro Thr Ile Phe Phe Tyr Pro Lys Asn Arg
        35                  40                  45

Pro Asn Ser Asp Thr Thr Gln Val Leu Ala Arg Leu Lys Arg Ser Leu
    50                  55                  60

Ser Glu Thr Leu Asp Ser Tyr Phe Phe Leu Ser Gly Thr Arg Thr Asp
65                  70                  75                  80

Asn Arg Phe Ile Asp Cys Phe Asp Glu Gly Val Pro Phe Phe Glu Ala
                85                  90                  95

Ser Val Ser Val Gly Leu Ser Asp Phe Leu Lys His His Glu His Glu
            100                 105                 110
```

Trp Leu Asn Arg Leu Val Ala Tyr Arg Pro Tyr Thr Lys Glu Ala Leu
            115                 120                 125

Asp Ser Pro Leu Leu Ser Ile Gln Val Ser Val Phe Ala Cys Gly Gly
        130                 135                 140

Ile Val Ile Gly Thr Ser Ala Ser His Lys Leu Ile Asp Ala Leu Thr
145                 150                 155                 160

Gly Ser Phe Ile Leu Lys Thr Trp Ala Met Phe Arg Gly Asp Val
                165                 170                 175

Ser Asp Gly Ile Ser Pro Gln Ile Asp Glu Ala Ser Met Tyr Phe Pro
            180                 185                 190

Thr Arg Asp Ser Phe Pro Gln Asn His Leu Ser Leu Met Glu Ser Leu
        195                 200                 205

Trp Phe Thr Glu Ala Asn Tyr Val Thr Arg Arg Phe Val Phe Gly Ala
    210                 215                 220

Lys Ser Ile Ser Ala Ile Lys Glu Met Ala Lys Ser Lys Pro Glu Ser
225                 230                 235                 240

Lys Gln Ser Arg Ile Glu Ala Leu Ser Cys Phe Ile Trp Lys His Cys
                245                 250                 255

Met Ser Ala Ser Lys Ala Val Ser Gly Ser Pro Gln Val Ser Ile Leu
            260                 265                 270

Val Glu Ala Val Asn Leu Arg Thr Arg Thr Thr Pro Pro Met Ser Ser
        275                 280                 285

Ser Ser Ile Gly Asp Leu Phe Trp Trp Ala Thr Ala Ala Ser Asn Asn
    290                 295                 300

Asp Asp Thr Lys Ser Thr Glu Leu Pro Glu Leu Ala Asn Leu Leu Lys
305                 310                 315                 320

Glu Ala Ile Glu Leu Tyr Asp Thr Asp Phe Thr Lys Ser Leu Gln Gly
                325                 330                 335

Asn Glu Gly Asp Glu Ala Ile Tyr Gln Tyr Cys Glu Gln Leu Glu Gly
            340                 345                 350

Leu Phe Ser Leu Glu Lys Pro Asp Ile Phe Ala Phe Thr Ser Trp Cys
        355                 360                 365

Tyr Val Gly Phe Thr Lys Leu Asn Phe Gly Trp Gly Glu Pro Ile Trp
    370                 375                 380

Val Gly Thr Val Gly Lys Ala Gly Pro Ala Phe Arg Asn Leu Thr Val
385                 390                 395                 400

Phe Ile Glu Thr Arg Asp Gly Lys Gly Ile Glu Ala Trp Ile Thr Leu
                405                 410                 415

Asp Gln Lys Arg Met Ser Val Leu Glu His Asp Pro Gln Phe Leu Ala
            420                 425                 430

Phe Ala Ser Leu Asn Pro Lys Ile Ser Ser Leu
        435                 440

<210> SEQ ID NO 64
<211> LENGTH: 443
<212> TYPE: PRT
<213> ORGANISM: Ricinus communis

<400> SEQUENCE: 64

Met Glu Val His Ile Val Ser Arg Glu Met Met Lys Pro Ser Ser Pro
1               5                   10                  15

Ala Ile Lys His Gln Lys Pro Tyr Lys Leu Cys Leu Leu Asp Gln Leu
                20                  25                  30

Thr Pro Thr Thr Tyr Ile Pro Ile Ile Phe Phe Tyr Pro Met Asn Asn

-continued

```
             35                  40                  45
Leu Phe Thr Lys Ser Thr Leu Ala His Leu Lys Glu Ser Leu Val Lys
 50                  55                  60
Thr Leu Asn Phe Tyr Tyr Pro Phe Ser Gly Arg Ala Lys Asp Asn Leu
 65                  70                  75                  80
Tyr Ile Asp Arg Phe Glu Glu Gly Val Pro Phe Phe Glu Ala Lys Val
                 85                  90                  95
Asn Cys Ser Met Ser Tyr Phe Leu Lys His Tyr Glu Thr Glu Ser Leu
                100                 105                 110
Ser Asn Leu Phe Ile Pro Ser His Pro Phe Ser Lys Glu Ile Asp Met
            115                 120                 125
Ser Ile Ala Leu Val Ala Val Gln Val Ser Met Phe Thr Cys Gly Gly
            130                 135                 140
Ile Ala Val Gly Leu Cys Leu Ser His Lys Leu Ile Asp Ala Ala Thr
145                 150                 155                 160
Ala Ser Ser Phe Val Thr Thr Trp Ala Ser Phe Cys Arg Gly Asp Pro
                165                 170                 175
Lys Asn Val Ile Gln Pro Asp Phe Glu Gln Pro Ser Thr Phe Phe Pro
            180                 185                 190
Ser Ser Thr Ser Leu Pro Gln Asn Tyr Leu Ser Leu Met Glu Arg Ile
            195                 200                 205
Trp Phe Val Lys Ala Asn Tyr Ile Thr Lys Arg Phe Val Phe Asp Ala
210                 215                 220
Lys Ala Ile Ala Ala Leu Arg Val Lys Ala Lys Ala Lys Leu Glu Ala
225                 230                 235                 240
Glu Pro Thr Arg Ile Ala Thr Leu Ser Cys Phe Ile Trp Lys Cys Ser
                245                 250                 255
Met Ala Ala Ser Arg Ala Ile Ser Gly Ala Pro Lys Pro Ser Ile Leu
            260                 265                 270
Val Glu Ala Val Asn Leu Arg Gln Lys Thr Lys Pro Pro Met Lys Asp
            275                 280                 285
Ser Ser Thr Gly Asn Leu Phe Trp Trp Ala Val Ala Leu Ala Ser Pro
            290                 295                 300
Thr Asp Thr Asn Ser Thr Glu Leu Asn Glu Leu Val Ser Met Leu Ser
305                 310                 315                 320
Glu Ala Ile Ala Val Tyr Lys Ser Asp Tyr Thr His Ser Leu Gln Gly
                325                 330                 335
Glu Asn Gly Leu Lys Ile Met Ser Glu Tyr Cys Glu Gln Leu Glu Gly
            340                 345                 350
Met Phe Ser Leu Glu Glu Pro Asp Ile Phe Gly Phe Thr Ser Trp Ser
            355                 360                 365
Lys Met Pro Val Thr Arg Pro Asn Phe Gly Trp Gly Glu Pro Phe Trp
            370                 375                 380
Val Gly Leu Met Ala Lys Ala Gly Pro Glu Phe Arg Asn Phe Thr Val
385                 390                 395                 400
Phe Ile Asp Thr Lys Asp Gly Lys Gly Ile Glu Ala Trp Ile Thr Leu
                405                 410                 415
Asp Glu Ala Arg Met Ala Ile Leu Gln Arg Asp Pro Gly Phe Leu Ala
            420                 425                 430
Phe Ala Ser Pro Asn Pro Lys Ile Ser Ser Leu
            435                 440

<210> SEQ ID NO 65
```

```
<211> LENGTH: 445
<212> TYPE: PRT
<213> ORGANISM: Vitis vinifera

<400> SEQUENCE: 65

Met Glu Val Thr Ile Ile Ser Arg Glu Thr Ile Lys Pro Ser Pro
1               5                   10                  15

Thr Pro His His Leu Arg Ala Phe Lys Leu Ser Leu Leu Asp Gln Leu
                20                  25                  30

Val Pro Cys Cys Tyr Thr Gln Val Leu Leu Phe Tyr Leu Ile Asp Gly
            35                  40                  45

Phe His Gly Gln Ser Ile Glu Thr Ser His Ile Ser Thr Arg Leu Lys
    50                  55                  60

Asp Ser Leu Ser Glu Thr Leu Thr His Phe Tyr Pro Leu Ala Gly Ser
65                  70                  75                  80

Ile Gly Asp Asp Glu Leu Gln Ile Asp Cys Asn Asp Glu Gly Val Pro
                85                  90                  95

Tyr Phe Glu Ala Arg Val Asp Cys Asn Leu Ser Glu Phe Leu Gln Glu
            100                 105                 110

Pro Glu Leu Glu Leu Leu Asn Gln Phe Phe Pro Cys Asp Pro Leu Asn
        115                 120                 125

Thr Pro Pro Met Ala Lys Leu His Leu Ala Met Ile Gln Val Asn Ile
130                 135                 140

Phe Asn Arg Gly Gly Ile Ala Ile Gly Val Cys Leu Ser His Lys Ile
145                 150                 155                 160

Ala Asp Gly Val Ser Ile Ser Ala Phe Leu Lys Ala Trp Ala Ala Ile
                165                 170                 175

Ala Arg Gly Cys Phe Glu Glu Tyr Pro Ser Phe Glu Ala Lys Ser Leu
            180                 185                 190

Phe Pro Gln Asn Glu Ser Leu Pro Gln Asp Tyr Ser Met Val Leu Gly
        195                 200                 205

Lys Cys Leu Ile Arg Thr Gly Lys Cys Val Thr Lys Arg Val Val Phe
210                 215                 220

Asp Ala Ser Ala Ile Ala Ala Leu Lys Ala Lys Ala Ser Val Asp Cys
225                 230                 235                 240

Thr Arg Val Glu Val Val Ser Ala Phe Ile Trp Lys Arg Ala Met Ala
                245                 250                 255

Ala Ala Lys Gln Lys Leu Gly Phe Gln Arg Ser Ser Ile Leu Thr His
            260                 265                 270

Ala Val Asn Leu Arg Lys Lys Thr Ile Leu Ser Leu Pro Glu Ser Ser
        275                 280                 285

Met Gly Asn Leu Phe Trp Ile Ala Ile Thr Glu Gly Arg Val Asp Asp
290                 295                 300

Glu Ala Glu Leu Asp Leu Leu Val Asp Lys Thr Arg Lys Ala Ile Ser
305                 310                 315                 320

Lys Ile Ser Cys Asp Phe Ala Lys Lys Leu Gln Gly Glu Glu Gly Phe
                325                 330                 335

Ala Val Ala Phe Glu His Val Lys Glu Val Lys Ala Ala Phe Glu Glu
            340                 345                 350

Asp Gly Val Asp Phe Tyr Gly Phe Ser Ser Trp Cys Lys Phe Glu Val
        355                 360                 365

Tyr Glu Gly Asp Phe Gly Trp Gly Arg Pro Ile Trp Val Ser Ser Phe
370                 375                 380

Ser Gly Lys Gly Ser Val Tyr Lys Asn Leu Ile Phe Phe Met Asp Thr
```

```
                385                 390                 395                 400
Arg Cys Gly Asn Gly Ile Glu Glu Trp Val Thr Leu Asp Glu Glu
                    405                 410                 415

Leu Gly Ile Leu Glu Cys Asp Pro Glu Phe Leu Ser Phe Gly Ser Met
                420                 425                 430

Asp Pro Ser Pro Leu Lys Leu Ala His Phe Gly Gln Val
                435                 440                 445

<210> SEQ ID NO 66
<211> LENGTH: 562
<212> TYPE: PRT
<213> ORGANISM: Saccharomyces cerevisiae

<400> SEQUENCE: 66

Met Asp Leu Trp Lys Arg Leu Phe Glu Ala Asn Pro Thr Lys Ile Arg
1               5                   10                  15

Asp Lys Lys Ile Lys Asn Gly His Phe Ile Ser Ile Thr Asn Thr Ile
                20                  25                  30

Asn Leu Ser Ala Leu Met Asn Glu Ile Asp Glu Lys Asn Gln Ala Pro
            35                  40                  45

Val Gln Gln Glu Cys Leu Lys Glu Met Ile Gln Asn Gly His Ala Arg
        50                  55                  60

Arg Met Gly Ser Val Glu Asp Leu Tyr Val Ala Leu Asn Arg Gln Asn
65                  70                  75                  80

Leu Tyr Arg Asn Phe Cys Thr Tyr Gly Glu Leu Ser Asp Tyr Cys Thr
                85                  90                  95

Arg Asp Gln Leu Thr Leu Ala Leu Arg Glu Ile Cys Leu Lys Asn Pro
                100                 105                 110

Thr Leu Leu His Ile Val Leu Pro Thr Arg Trp Pro Asn His Glu Asn
            115                 120                 125

Tyr Tyr Arg Ser Ser Glu Tyr Tyr Ser Arg Pro His Pro Val His Asp
        130                 135                 140

Tyr Ile Ser Val Leu Gln Glu Leu Lys Leu Ser Gly Val Val Leu Asn
145                 150                 155                 160

Glu Gln Pro Glu Tyr Ser Ala Val Met Lys Gln Ile Leu Glu Glu Phe
                165                 170                 175

Lys Asn Ser Lys Gly Ser Tyr Thr Ala Lys Ile Phe Lys Leu Thr Thr
                180                 185                 190

Thr Leu Thr Ile Pro Tyr Phe Gly Pro Thr Gly Pro Ser Trp Arg Leu
            195                 200                 205

Ile Cys Leu Pro Glu Glu His Thr Glu Lys Trp Lys Lys Phe Ile Phe
        210                 215                 220

Val Ser Asn His Cys Met Ser Asp Gly Arg Ser Ser Ile His Phe Phe
225                 230                 235                 240

His Asp Leu Arg Asp Glu Leu Asn Asn Ile Lys Thr Pro Pro Lys Lys
                245                 250                 255

Leu Asp Tyr Ile Phe Lys Tyr Glu Glu Asp Tyr Gln Leu Leu Arg Lys
                260                 265                 270

Leu Pro Glu Pro Ile Glu Lys Val Ile Asp Phe Arg Pro Pro Tyr Leu
            275                 280                 285

Phe Ile Pro Lys Ser Leu Leu Ser Gly Phe Ile Tyr Asn His Leu Arg
        290                 295                 300

Phe Ser Ser Lys Gly Val Cys Met Arg Met Asp Asp Val Glu Lys Thr
305                 310                 315                 320
```

```
Asp Asp Val Val Thr Glu Ile Ile Asn Ile Ser Pro Thr Glu Phe Gln
            325                 330                 335

Ala Ile Lys Ala Asn Ile Lys Ser Asn Ile Gln Gly Lys Cys Thr Ile
            340                 345                 350

Thr Pro Phe Leu His Val Cys Trp Phe Val Ser Leu His Arg Trp Gly
            355                 360                 365

Lys Phe Phe Lys Pro Leu Asn Phe Glu Trp Leu Thr Asp Ile Phe Ile
            370                 375                 380

Pro Ala Asp Cys Arg Ser Gln Leu Pro Asp Asp Glu Met Arg Gln
385                 390                 395                 400

Met Tyr Arg Tyr Gly Ala Asn Val Gly Phe Ile Asp Phe Thr Pro Trp
                405                 410                 415

Ile Ser Glu Phe Asp Met Asn Asp Asn Lys Glu Asn Phe Trp Pro Leu
                420                 425                 430

Ile Glu His Tyr His Glu Val Ile Ser Glu Ala Leu Arg Asn Lys Lys
                435                 440                 445

His Leu His Gly Leu Gly Phe Asn Ile Gln Gly Phe Val Gln Lys Tyr
                450                 455                 460

Val Asn Ile Asp Lys Val Met Cys Asp Arg Ala Ile Gly Lys Arg Arg
465                 470                 475                 480

Gly Gly Thr Leu Leu Ser Asn Val Gly Leu Phe Asn Gln Leu Glu Glu
                485                 490                 495

Pro Asp Ala Lys Tyr Ser Ile Cys Asp Leu Ala Phe Gly Gln Phe Gln
                500                 505                 510

Gly Ser Trp His Gln Ala Phe Ser Leu Gly Val Cys Ser Thr Asn Val
                515                 520                 525

Lys Gly Met Asn Ile Val Val Ala Ser Thr Lys Asn Val Val Gly Ser
                530                 535                 540

Gln Glu Ser Leu Glu Glu Leu Cys Ser Ile Tyr Lys Ala Leu Leu Leu
545                 550                 555                 560

Gly Pro

<210> SEQ ID NO 67
<211> LENGTH: 545
<212> TYPE: PRT
<213> ORGANISM: Saccharomyces pastorianus

<400> SEQUENCE: 67

Met Glu Thr Glu Glu Ser Gln Phe Ser Ser Ile Thr Lys Ile Ile Asn
1               5                   10                  15

Pro Lys Thr Leu Met Asn Thr Tyr Ser Glu Lys Thr Ser Leu Val Gln
                20                  25                  30

Asp Glu Cys Leu Val Lys Met Ile Gln Asn Gly His Ser Arg Arg Met
            35                  40                  45

Gly Ser Val Glu Asp Leu Tyr Ala Ala Leu Asn Arg Gln Lys Leu Tyr
        50                  55                  60

Arg Asn Phe Ser Thr Tyr Ser Glu Leu Asn Asp Tyr Cys Thr Lys Asp
65                  70                  75                  80

Gln Leu Ala Leu Ala Leu Arg Asn Ile Cys Leu Lys Asn Pro Thr Leu
                85                  90                  95

Leu His Ile Val Leu Pro Ala Arg Trp Pro Asp His Lys Lys Tyr Tyr
                100                 105                 110

Leu Ser Ser Glu Tyr Tyr Ser Gln Pro Arg Pro Lys His Asp Tyr Ile
            115                 120                 125
```

```
Ser Val Leu Pro Glu Leu Lys Leu Asp Gly Val Ile Leu Asn Glu Gln
    130                 135                 140

Pro Glu His Asn Ala Leu Met Lys Gln Ile Leu Glu Glu Phe Ala Asn
145                 150                 155                 160

Ser Asn Gly Ser Tyr Thr Ala Lys Ile Phe Lys Leu Thr Thr Ala Leu
                165                 170                 175

Thr Ile Pro Tyr Thr Gly Pro Thr Ser Pro Thr Trp Arg Leu Ile Cys
            180                 185                 190

Leu Pro Glu Glu Asp Asp Thr Asn Lys Trp Lys Lys Phe Ile Phe Val
        195                 200                 205

Ser Asn His Cys Met Cys Asp Gly Arg Ser Ser Ile His Phe Phe Gln
210                 215                 220

Asp Leu Arg Asp Glu Leu Asn Asn Ile Lys Thr Leu Pro Lys Lys Leu
225                 230                 235                 240

Asp Tyr Ile Phe Glu Tyr Glu Lys Asp Tyr Gln Leu Leu Arg Lys Leu
                245                 250                 255

Pro Glu Pro Ile Glu Asn Met Ile Asp Phe Arg Pro Tyr Leu Phe
            260                 265                 270

Ile Pro Lys Ser Leu Leu Ser Gly Phe Ile Tyr Ser His Leu Arg Phe
        275                 280                 285

Ser Ser Lys Gly Val Cys Thr Arg Met Asp Glu Ile Glu Lys Ser Asp
    290                 295                 300

Glu Ile Val Thr Glu Ile Ile Asn Ile Ser Pro Ser Glu Phe Gln Lys
305                 310                 315                 320

Ile Arg Thr Lys Ile Lys Leu Asn Ile Pro Gly Lys Cys Thr Ile Thr
                325                 330                 335

Pro Phe Leu Glu Val Cys Trp Phe Val Thr Leu His Lys Trp Gly Lys
            340                 345                 350

Phe Phe Lys Pro Leu Lys Phe Glu Trp Leu Thr Asp Val Phe Ile Pro
        355                 360                 365

Ala Asp Cys Arg Ser Leu Leu Pro Glu Asp Glu Val Arg Ala Met
370                 375                 380

Tyr Arg Tyr Gly Ala Asn Val Gly Phe Val Asp Phe Thr Pro Trp Ile
385                 390                 395                 400

Ser Lys Phe Asn Met Asn Asp Ser Lys Glu Asn Phe Trp Pro Leu Ile
                405                 410                 415

Ala His Tyr His Glu Val Ile Ser Gly Ala Ile Lys Asp Lys Lys His
            420                 425                 430

Leu Asn Gly Leu Gly Phe Asn Ile Gln Ser Leu Val Gln Lys Tyr Val
        435                 440                 445

Asn Ile Asp Lys Val Met Arg Asp Arg Ala Leu Gly Lys Ser Arg Gly
450                 455                 460

Gly Thr Leu Leu Ser Asn Val Gly Met Phe His Gln Ser Glu Glu Thr
465                 470                 475                 480

Glu His Lys Tyr Arg Ile Arg Asp Leu Ala Phe Gly Gln Phe Gln Gly
                485                 490                 495

Ser Trp His Gln Ala Phe Ser Leu Gly Val Ser Ser Thr Asn Val Lys
            500                 505                 510

Gly Met Asn Ile Leu Ile Ser Ser Thr Lys Asn Val Val Gly Ser Gln
        515                 520                 525

Glu Leu Leu Glu Glu Leu Cys Ala Met Tyr Lys Ala Leu Leu Leu Asn
530                 535                 540

Pro
```

545

<210> SEQ ID NO 68
<211> LENGTH: 471
<212> TYPE: PRT
<213> ORGANISM: Saccharomyces cerevisiae x Saccharomyces kudriavzevii

<400> SEQUENCE: 68

```
Met Ile Gln Asn Gly His Ala Arg Arg Met Gly Ser Val Glu Asp Leu
1               5                   10                  15

Tyr Val Ala Leu Asn Arg Gln Asn Leu Tyr Arg Asn Phe Ser Ala Tyr
                20                  25                  30

Ala Glu Leu Ser Asp Tyr Cys Ser Lys Asp Gln Leu Thr Leu Ala Leu
            35                  40                  45

Arg Asn Ile Cys Leu Lys Asn Pro Thr Leu Leu His Ile Val Leu Pro
50                  55                  60

Thr Arg Trp Pro Asp His Glu Asn Tyr Tyr Leu Ser Ser Glu Tyr Tyr
65                  70                  75                  80

Ser His Pro His Pro Lys His Asp Tyr Ile Ser Val Leu Pro Glu Leu
                85                  90                  95

Lys Leu Asp Gly Val Ile Ile Asn Glu Gln Pro Glu Asn Gly Lys Ile
            100                 105                 110

Val Arg Gln Ile Leu Glu Glu Phe Arg Asn Ser Asn Gly Thr Tyr Asn
        115                 120                 125

Ala Lys Ile Phe Lys Leu Thr Thr Ala Leu Thr Ile Pro Tyr Phe Gly
130                 135                 140

Pro Thr Ser Pro Asn Trp Arg Leu Ile Cys Leu Pro Glu Glu His Thr
145                 150                 155                 160

Asp Lys Trp Lys Lys Phe Ile Phe Val Ser Asn His Cys Met Ser Asp
                165                 170                 175

Gly Arg Ser Ser Ile His Phe His Asp Leu Arg Ala Glu Leu Asn
            180                 185                 190

Asp Ile Lys Thr Pro Pro Lys Lys Leu Asp Tyr Leu Phe Lys Tyr Glu
        195                 200                 205

Asn Asp Tyr Gln Leu Leu Arg Lys Leu Pro Glu Pro Ile Glu Lys Val
    210                 215                 220

Ile Asp Phe Arg Pro Pro Tyr Leu Phe Ile Pro Lys Ser Leu Leu Ser
225                 230                 235                 240

Gly Phe Ile Tyr Asn His Leu Arg Phe Ala Ser Arg Gly Ile Cys Thr
                245                 250                 255

Arg Met Asp Asp Met Glu Lys Ser Asp Asp Val Val Ala Glu Ile Ile
            260                 265                 270

Thr Ile Ser Pro Ser Glu Leu Gln Glu Ile Arg Thr Lys Ile Lys Ser
        275                 280                 285

Asn Ile Gln Gly Lys Cys Thr Leu Thr Pro Phe Leu Gln Val Cys Trp
    290                 295                 300

Phe Val Ser Leu His Gln Trp Gly Lys Phe Phe Lys Pro Leu Asn Phe
305                 310                 315                 320

Glu Trp Leu Thr Asp Ile Phe Ile Pro Ala Asp Cys Arg Pro Gln Leu
                325                 330                 335

Pro Asp Asp Glu Glu Val Arg Gln Met Tyr Arg Tyr Gly Ala Asn Val
            340                 345                 350

Gly Phe Val Asp Phe Thr Pro Trp Ile Cys Glu Ser Asn Met Asn Glu
        355                 360                 365
```

```
Asn Lys Glu Asn Phe Trp Pro Leu Ile Glu His Tyr His Gln Val Ile
370                 375                 380
Ser Gly Ala Leu Arg Asp Asn Lys His Leu His Gly Leu Gly Leu Asn
385                 390                 395                 400
Ile Gln Gly Phe Val Gln Lys Tyr Val Asn Ile Asp Lys Ala Met Cys
            405                 410                 415
Asp Arg Ala Ile Gly Lys Ala Arg Gly Gly Thr Leu Leu Ser Asn Val
            420                 425                 430
Gly Met Phe Lys Gln Leu Asp Ser Ser Asn Cys Asn Tyr Ser Ile Lys
            435                 440                 445
Thr Trp Leu Leu Gly Asn Phe Lys Gly His Gly Thr Lys His Phe His
450                 455                 460
Trp Val Phe Val Arg Leu Met
465                 470

<210> SEQ ID NO 69
<211> LENGTH: 508
<212> TYPE: PRT
<213> ORGANISM: Lachancea thermotolerans

<400> SEQUENCE: 69

Met Asp Ser Leu Lys Glu Arg Gly His Ala Arg Pro Leu Gly His Leu
1               5                   10                  15
Glu Asn Tyr Phe Ser Ile Thr Gln Arg Gln Lys Leu Tyr Ala Asn Phe
            20                  25                  30
Ser Met Tyr Cys Glu Leu Ser Lys Pro Cys Ser Pro Lys Gln Leu Ala
        35                  40                  45
Tyr Ala Leu Arg Ser Ile Cys Leu Gln Asn Pro Ile Leu Val His Gln
    50                  55                  60
Val Leu Pro Lys His Trp Pro Asn His Leu Glu Tyr Tyr Ala Ser Asp
65                  70                  75                  80
Glu Phe Leu Ala Gln Pro Thr Leu Gln His Glu Asp Met Arg Leu Leu
                85                  90                  95
Asp Asn Val Leu Leu Ser Asp Ile Val Met Asn Glu Gln Glu Glu Tyr
            100                 105                 110
Gly Thr Val Val Ser Glu Ala Ile Glu Glu Phe Ser Gln Asn Gly Gly
        115                 120                 125
Gln Tyr Ser Lys Lys Ile Phe Asp Ile Ile Ala Asp Ile Arg Ile Pro
    130                 135                 140
Tyr Gly Asp Pro Leu Lys Pro Asn Trp Arg Leu Leu Cys Phe Pro Glu
145                 150                 155                 160
Gly Glu Ser Asn Leu Trp Arg Lys Phe Ile Tyr Ile Thr Asn His Cys
                165                 170                 175
Ser Ser Asp Gly Arg Ser Ala Ala Asn Leu Met Arg Asp Leu Ser Glu
            180                 185                 190
Gln Leu Asn His Val Pro Glu Thr Leu Pro Asp Ser Asp Ile Ile Phe
        195                 200                 205
Asn Tyr Ser Ser Asp Tyr Glu Gly Leu Arg Lys Leu Pro Asp Pro Ile
    210                 215                 220
Glu Asn Arg Ile Asp Tyr Lys Pro Pro Ile Ser Tyr Leu Leu Gln Leu
225                 230                 235                 240
Leu Ser Ser Ser Tyr Val Arg Asp Tyr Leu Gly Tyr Tyr Ser Lys Gly
                245                 250                 255
Pro Leu Val Thr Arg Ile Asp Glu Val Gly Glu Asn Lys Thr Tyr Tyr
            260                 265                 270
```

```
Ser Tyr Phe Leu Asn Phe Ser Ala Glu Gln Met Lys Thr Ile Lys Gln
        275                 280                 285

Lys Leu Lys Ser Arg Leu Pro Gly Cys Thr Met Thr Pro Phe Leu Gln
    290                 295                 300

Ala Cys Trp Leu Thr Ser Met Tyr Lys Ser Gly Arg Val Phe Ser Lys
305                 310                 315                 320

Ser Met Arg Glu Trp Phe Phe Asp Val Val Ile Thr Met Asn Thr Ala
                325                 330                 335

Gln Met Leu Pro Asp Asp Pro Glu Leu Arg Ser Met Tyr Lys Tyr Gly
            340                 345                 350

Ser Asn Val Gly Gly Thr Arg Tyr Asn Tyr Leu Ile Ser Ser Phe Asn
        355                 360                 365

Val Gly Glu Asp Lys Asp Ala Phe Trp Ser Leu Val Asp Tyr Tyr Gln
370                 375                 380

Gly Val Phe Asn Ser Ala Met Glu Lys Lys His Tyr Leu Phe Pro Leu
385                 390                 395                 400

Gly Ala Leu Met Leu Asp Ser Leu Arg Glu Lys Ser Asn Met Asp Lys
                405                 410                 415

Val Ile Met Asp Asp Leu Leu Gly Lys Pro Arg Gln Gly Val Ile Leu
            420                 425                 430

Ser Asn Val Gly Tyr Phe Gln Gln Lys Glu Thr Asp Gly Tyr Tyr
        435                 440                 445

Val Arg Asp Leu Val Phe Ala Gln Ser Leu Gly Ser Leu Arg His Thr
    450                 455                 460

Phe Val Cys Asn Ser Cys Thr Thr Asp Val Gly Met Asn Ile Val
465                 470                 475                 480

Ala Cys Ala Ala Gln Gly Ser Val Ala Ser Glu His Asp Trp Ala Asp
                485                 490                 495

Val Cys Glu Leu Phe Lys Glu Gln Thr Leu Ala Leu
            500                 505

<210> SEQ ID NO 70
<211> LENGTH: 523
<212> TYPE: PRT
<213> ORGANISM: Vanderwaltozyma polyspora

<400> SEQUENCE: 70

Met Glu Glu Tyr Ala Pro Phe Ile Thr Gln Glu Leu Val Asp Arg Gly
1               5                   10                  15

His Ala Arg Arg Met Gly Gln Leu Glu Asn Tyr Phe Ala Leu Leu Gln
            20                  25                  30

Arg Gln Asn Leu Tyr Lys Asn Phe Asn Val Tyr Gly Glu Ile Asn Glu
        35                  40                  45

Pro Ile Asp Lys Phe Gln Leu Gly Thr Ala Phe Arg Gln Met Leu Leu
    50                  55                  60

Lys Tyr Pro Ile Leu Met His Val Ile Val Pro Arg Lys Tyr Pro His
65                  70                  75                  80

His Glu Glu Tyr Tyr Ala Ser Asp Glu Tyr Leu Asn Asn Pro Gln Pro
                85                  90                  95

Ile Asn Asp Tyr Ile Lys Val Met Glu Asn Ile Asp Leu Glu Asp Ile
            100                 105                 110

Leu Leu Asn Ser Gln Pro Glu Tyr Glu Ala Ile Val Gly Lys Leu Leu
        115                 120                 125

Asp Gln Tyr Lys Ser Asp Gly Tyr Lys Tyr Thr Asn Arg Met Ile Glu
```

```
            130                 135                 140
Ile Ile Gly Asp Ile Ser Ile Pro Ile Cys Asp Gln Thr Lys Pro Asn
145                 150                 155                 160

Trp Arg Leu Leu Cys Leu Pro Thr Lys Glu Ser Asp Lys Lys Trp His
                165                 170                 175

Ala Phe Val Tyr Ile Ser Asn His Cys Ala Ala Asp Gly Met Thr Ser
                180                 185                 190

Met Asn Phe Phe His Asp Ile Val Asn Gly Leu Asn Asp Lys Ser Ser
            195                 200                 205

Glu Thr Val Thr Glu Val Asn Gly Arg Met Asn Leu Val Asn Tyr Ala
        210                 215                 220

Lys Asp His Lys Asn Ile Ser Lys Phe Pro Lys Pro Ile Thr Glu Arg
225                 230                 235                 240

Val Glu Tyr Arg Pro Ser Leu Ser Gln Leu Pro Lys Phe Met Ile Gly
                245                 250                 255

Asn Ile Ala Arg Thr Lys Leu Asn Tyr Lys Ser Pro Cys Ala Leu Thr
                260                 265                 270

Thr Thr Val Asp Lys Val Asp Met Gln Thr Phe Asp Tyr Ile Leu Asn
            275                 280                 285

Phe Thr Asn Glu Glu Val Gly Lys Ile Arg Lys His Ile Lys Ala Asn
        290                 295                 300

Thr His Asn Gly Val Thr Leu Thr Pro Phe Leu Gln Thr Cys Leu Phe
305                 310                 315                 320

Val Thr Leu Tyr Gln Phe Gly Thr Ile Phe Gln Lys Thr Leu Leu Glu
                325                 330                 335

Trp Gly Leu Asp Ser Val Leu Pro Val Asn Ala Arg Lys Tyr Leu Pro
                340                 345                 350

Glu Asp Ala Glu Leu Arg Asp Ser Tyr Lys Tyr Gly Ser Asn Val Gly
            355                 360                 365

Gly Ile His Tyr Phe Asn Leu Ile Ser Ser Phe Asn Ile Lys Asn Asp
        370                 375                 380

Glu Ala Glu Thr Phe Trp Ser Leu Val Asp Tyr Tyr His Ala Asn Tyr
385                 390                 395                 400

Gln Lys Ala Tyr His Asn Gly Asp Thr Phe Val Gly Phe Gly Leu Leu
                405                 410                 415

Met Ser Asp Phe Ile Val Lys Asn Lys Asn Val Asp Lys Leu Ile Lys
                420                 425                 430

Glu Asp Tyr Val Asn Gln Lys Arg Gly Gly Val Ile Leu Ser Asn Leu
            435                 440                 445

Gly Phe Phe Pro Gln Asp Thr Arg Asn Glu Tyr Tyr Leu Asn Asp Leu
        450                 455                 460

Ile Phe Ala Gln Thr Phe Gly Ser Met Lys Phe Thr Phe Gly Leu Ser
465                 470                 475                 480

Leu Cys Ser Thr Asn Val Asn Gly Leu Asn Ile Gly Ile Ser Val Val
                485                 490                 495

Arg Asp Ala Phe Asn Asp Arg Glu Thr Phe Glu Lys Phe Cys Lys His
                500                 505                 510

Tyr Lys Glu Thr Ile Ile Asn Phe Ala Asn Leu
            515                 520

<210> SEQ ID NO 71
<211> LENGTH: 522
<212> TYPE: PRT
<213> ORGANISM: Lachancea thermotolerans
```

<400> SEQUENCE: 71

Met Thr Thr Ser Gln Ala Asp Thr Lys Leu Glu Glu Leu Glu Lys Arg
1               5                   10                  15

Gly His Ala Arg Arg Leu Gly Asn Leu Glu Asn Tyr Phe Ala Leu Gly
            20                  25                  30

Gln Arg Gln Asp Leu Tyr Ser Asn Phe Gly Met Phe Cys Glu Leu Asp
        35                  40                  45

Arg Ala Cys Ser Glu Asn Glu Leu Ala Glu Ala Leu Arg Gly Met Cys
    50                  55                  60

Leu Glu Tyr Pro Leu Leu Leu His Thr Val Leu Glu Lys Lys Glu Ala
65                  70                  75                  80

Gln Asp Val Asn Phe Tyr Gln Thr Ser Glu Tyr Leu Ser Lys Pro Trp
                85                  90                  95

Pro Gln His Asp Tyr Ile Arg Val Leu Gln Arg Val Arg Phe Ala Asp
            100                 105                 110

Val Leu Leu Asn Asp Gln Glu Glu Tyr Ala Glu Ile Val Asn Ala Ala
        115                 120                 125

Leu Lys Glu Phe Ala Ser Asn Gly Gly Gln Tyr Ser Ser Glu Val Phe
130                 135                 140

Glu Leu Ile Asn Lys Val Arg Ile Pro Tyr Cys His Asn Ser Arg Pro
145                 150                 155                 160

Asn Trp Arg Ile Met Cys Phe Pro Glu Glu Gly Asn Ala Gln Ser Arg
                165                 170                 175

Glu Trp Arg Lys Ile Leu Leu Leu Ser Asn His Cys Ser Ser Asp Gly
            180                 185                 190

Met Ser Ser Ala Asn Phe Phe His Asp Leu Gln Asp His Leu Asn Asn
        195                 200                 205

Leu Pro Pro Ser Leu Pro Gln Ala Asp Val Ile Phe Asp Tyr Ser Gln
210                 215                 220

Asp His Glu Thr Leu Gly Lys Leu Pro Ala Pro Ile Glu Thr Gln Ile
225                 230                 235                 240

Ser Tyr Val Gly Pro Lys Ser Tyr Phe Ala Gln Leu Val Gly Asn Gln
                245                 250                 255

Val Leu Arg Glu Tyr Phe Gly Tyr Lys Ser Pro Thr Pro Pro Ile Pro
            260                 265                 270

Arg Val Asn Glu Pro Gly Gly Asn Asp Phe Tyr Ser Tyr Phe Leu Lys
        275                 280                 285

Ile Thr Pro Ser Glu Val Ala Ala Val Lys Lys Leu Lys Asn Lys
290                 295                 300

Leu Asp Pro Ser Cys Thr Leu Thr Pro Phe Phe Gln Ala Cys Trp Phe
305                 310                 315                 320

Ala Ala Leu Tyr Lys Ser Gly Ile Val Phe Ser Lys Ser Phe Ser Gln
                325                 330                 335

Gln Leu Ser Asn Ile Met Val Ala Met Asn Thr Ala Gln Leu Leu Pro
            340                 345                 350

Glu Asp Lys Gln Leu Lys Lys Gln Tyr Arg Tyr Gly Ala Asn Val Gly
        355                 360                 365

Gly Ser His Tyr Asn Tyr Gln Ile Ser Ser Phe Asn Val Ala Asp Lys
    370                 375                 380

Pro Glu Ala Phe Trp Lys Leu Val Arg Tyr Tyr Gln Asp Val Phe Val
385                 390                 395                 400

Asp Ala Lys Arg Lys Lys His Phe Leu Tyr Pro Leu Gly Ala Leu Met

```
            405                 410                 415
Ile Asp Ser Ile Tyr Lys Thr Lys Asn Ile Asp Leu Ala Val Thr Asn
            420                 425                 430

Ser Ile Leu Gly Lys Ser Arg Leu Gly Thr Met Leu Ser Asn Val Gly
            435                 440                 445

Tyr Phe Pro Gln Lys Ala Arg Ala Thr Val Gly Gly Phe His Ile Gln
            450                 455                 460

Asp Leu Ile Phe Ala Gln Thr Thr Gly Ser Phe Arg Phe Thr Phe Asp
465                 470                 475                 480

Ile Asn Leu Cys Ala Thr Asp Ile Gly Gly Leu Asn Ile Thr Ala Cys
            485                 490                 495

Val Ala Glu Gly Ala Leu Pro Thr Arg Glu Asp Trp Lys Lys Leu Cys
            500                 505                 510

Glu Leu Phe Lys Thr Ile Ile Leu Glu Ser
            515                 520

<210> SEQ ID NO 72
<211> LENGTH: 535
<212> TYPE: PRT
<213> ORGANISM: Saccharomyces cerevisiae

<400> SEQUENCE: 72

Met Glu Asp Ile Glu Gly Tyr Glu Pro His Ile Thr Gln Glu Leu Ile
1               5                   10                  15

Asp Arg Gly His Ala Arg Arg Met Gly His Leu Glu Asn Tyr Phe Ala
            20                  25                  30

Val Leu Ser Arg Gln Lys Met Tyr Ser Asn Phe Thr Val Tyr Ala Glu
        35                  40                  45

Leu Asn Lys Gly Val Asn Lys Arg Gln Leu Met Leu Val Leu Lys Val
    50                  55                  60

Leu Leu Gln Lys Tyr Ser Thr Leu Ala His Thr Ile Ile Pro Lys His
65                  70                  75                  80

Tyr Pro His His Glu Ala Tyr Tyr Ser Ser Glu Glu Tyr Leu Ser Lys
                85                  90                  95

Pro Phe Pro Gln His Asp Phe Ile Lys Val Ile Ser His Leu Glu Phe
            100                 105                 110

Asp Asp Leu Ile Met Asn Asn Gln Pro Glu Tyr Arg Glu Val Met Glu
        115                 120                 125

Lys Ile Ser Glu Gln Phe Lys Lys Asp Asp Phe Lys Val Thr Asn Arg
130                 135                 140

Leu Ile Glu Leu Ile Ser Pro Val Ile Pro Leu Gly Asn Pro Lys
145                 150                 155                 160

Arg Pro Asn Trp Arg Leu Ile Cys Leu Pro Gly Lys Asp Thr Asp Gly
                165                 170                 175

Phe Glu Thr Trp Lys Asn Phe Val Tyr Val Thr Asn His Cys Gly Ser
            180                 185                 190

Asp Gly Val Ser Gly Ser Asn Phe Phe Lys Asp Leu Ala Leu Leu Phe
        195                 200                 205

Cys Lys Ile Glu Glu Lys Gly Phe Asp Tyr Asp Glu Glu Phe Ile Glu
    210                 215                 220

Asp Gln Val Ile Ile Asp Tyr Asp Arg Asp Tyr Thr Glu Ile Ser Lys
225                 230                 235                 240

Leu Pro Lys Pro Ile Thr Asp Arg Ile Asp Tyr Lys Pro Ala Leu Thr
                245                 250                 255
```

```
Ser Leu Pro Lys Phe Leu Thr Thr Phe Ile Tyr Glu His Cys Asn
            260                 265                 270

Phe Lys Thr Ser Ser Glu Ser Thr Leu Thr Ala Arg Tyr Ser Pro Ser
        275                 280                 285

Ser Asn Ala Asn Ala Ser Tyr Asn Tyr Leu Leu His Phe Ser Thr Lys
    290                 295                 300

Gln Val Glu Gln Ile Arg Ala Gln Ile Lys Lys Asn Val His Asp Gly
305                 310                 315                 320

Cys Thr Leu Thr Pro Phe Ile Gln Ala Cys Phe Leu Val Ala Leu Tyr
                325                 330                 335

Arg Leu Asp Lys Leu Phe Thr Lys Ser Leu Leu Glu Tyr Gly Phe Asp
            340                 345                 350

Val Ala Ile Pro Ser Asn Ala Arg Arg Phe Leu Pro Asn Asp Glu Glu
        355                 360                 365

Leu Arg Asp Ser Tyr Lys Tyr Gly Ser Asn Val Gly Gly Ser His Tyr
    370                 375                 380

Ala Tyr Leu Ile Ser Ser Phe Asp Ile Pro Glu Gly Asp Asn Asp Lys
385                 390                 395                 400

Phe Trp Ser Leu Val Glu Tyr Tyr Asp Arg Phe Leu Glu Ser Tyr
                405                 410                 415

Asp Asn Gly Asp His Leu Ile Gly Leu Gly Val Leu Gln Leu Asp Phe
            420                 425                 430

Ile Val Glu Asn Lys Asn Ile Asp Ser Leu Leu Ala Asn Ser Tyr Leu
        435                 440                 445

His Gln Gln Arg Gly Gly Ala Ile Ile Ser Asn Thr Gly Leu Val Ser
    450                 455                 460

Gln Asp Thr Thr Lys Pro Tyr Tyr Val Arg Asp Leu Ile Phe Ser Gln
465                 470                 475                 480

Ser Ala Gly Ala Leu Arg Phe Ala Phe Gly Leu Asn Val Cys Ser Thr
                485                 490                 495

Asn Val Asn Gly Met Asn Met Asp Met Ser Val Val Gln Gly Thr Leu
            500                 505                 510

Arg Asp Arg Gly Glu Trp Glu Ser Phe Cys Lys Leu Phe Tyr Gln Thr
        515                 520                 525

Ile Gly Glu Phe Ala Ser Leu
    530                 535

<210> SEQ ID NO 73
<211> LENGTH: 523
<212> TYPE: PRT
<213> ORGANISM: Vanderwaltozyma polyspora

<400> SEQUENCE: 73

Met Glu Glu Tyr Ala Pro Phe Ile Thr Gln Glu Leu Val Asp Arg Gly
1               5                   10                  15

His Ala Arg Arg Met Gly Gln Leu Glu Asn Tyr Phe Ala Leu Leu Gln
            20                  25                  30

Arg Gln Asn Leu Tyr Lys Asn Phe Asn Val Tyr Gly Glu Ile Asn Glu
        35                  40                  45

Pro Ile Asp Lys Phe Gln Leu Gly Thr Ala Phe Arg Gln Met Leu Leu
    50                  55                  60

Lys Tyr Pro Ile Leu Met His Val Ile Val Pro Arg Lys Tyr Pro His
65                  70                  75                  80

His Glu Glu Tyr Tyr Ala Ser Asp Glu Tyr Leu Asn Asn Pro Gln Pro
                85                  90                  95
```

-continued

```
Ile Asn Asp Tyr Ile Lys Val Met Glu Asn Ile Asp Leu Glu Asp Ile
                100                 105                 110

Leu Leu Asn Ser Gln Pro Glu Tyr Glu Ala Ile Val Gly Lys Leu Leu
            115                 120                 125

Asp Gln Tyr Lys Ser Asp Gly Tyr Lys Tyr Thr Asn Arg Met Ile Glu
        130                 135                 140

Ile Ile Gly Asp Ile Ser Ile Pro Ile Cys Asp Gln Thr Lys Pro Asn
145                 150                 155                 160

Trp Arg Leu Leu Cys Leu Pro Thr Lys Glu Ser Asp Lys Lys Trp His
                165                 170                 175

Ala Phe Val Tyr Ile Ser Asn His Cys Ala Ala Asp Gly Met Thr Ser
            180                 185                 190

Met Asn Phe Phe His Asp Ile Val Asn Gly Leu Asn Asp Lys Ser Ser
        195                 200                 205

Glu Thr Val Thr Glu Val Asn Gly Arg Met Asn Leu Val Asn Tyr Ala
    210                 215                 220

Lys Asp His Lys Asn Ile Ser Lys Phe Pro Lys Pro Ile Thr Glu Arg
225                 230                 235                 240

Val Glu Tyr Arg Pro Ser Leu Ser Gln Leu Pro Lys Phe Met Ile Gly
                245                 250                 255

Asn Ile Ala Arg Thr Lys Leu Asn Tyr Lys Ser Pro Cys Ala Leu Thr
            260                 265                 270

Thr Thr Val Asp Lys Val Asp Met Gln Thr Phe Asp Tyr Ile Leu Asn
        275                 280                 285

Phe Thr Asn Glu Glu Val Gly Lys Ile Arg Lys His Ile Lys Ala Asn
    290                 295                 300

Thr His Asn Gly Val Thr Leu Thr Pro Phe Leu Gln Thr Cys Leu Phe
305                 310                 315                 320

Val Thr Leu Tyr Gln Phe Gly Thr Ile Phe Gln Lys Thr Leu Leu Glu
                325                 330                 335

Trp Gly Leu Asp Ser Val Leu Pro Val Asn Ala Arg Lys Tyr Leu Pro
            340                 345                 350

Glu Asp Ala Glu Leu Arg Asp Ser Tyr Lys Tyr Gly Ser Asn Val Gly
        355                 360                 365

Gly Ile His Tyr Phe Asn Leu Ile Ser Ser Phe Asn Ile Lys Asn Asp
    370                 375                 380

Glu Ala Glu Thr Phe Trp Ser Leu Val Asp Tyr Tyr His Ala Asn Tyr
385                 390                 395                 400

Gln Lys Ala Tyr His Asn Gly Asp Thr Phe Val Gly Phe Gly Leu Leu
                405                 410                 415

Met Ser Asp Phe Ile Val Lys Asn Lys Asn Val Asp Lys Leu Ile Lys
            420                 425                 430

Glu Asp Tyr Val Asn Gln Lys Arg Gly Gly Val Ile Leu Ser Asn Leu
        435                 440                 445

Gly Phe Phe Pro Gln Asp Thr Arg Asn Glu Tyr Tyr Leu Asn Asp Leu
    450                 455                 460

Ile Phe Ala Gln Thr Phe Gly Ser Met Lys Phe Thr Phe Gly Leu Ser
465                 470                 475                 480

Leu Cys Ser Thr Asn Val Asn Gly Leu Asn Ile Gly Ile Ser Val Val
                485                 490                 495

Arg Asp Ala Phe Asn Asp Arg Glu Thr Phe Lys Phe Cys Lys His
            500                 505                 510
```

```
Tyr Lys Glu Thr Ile Ile Asn Phe Ala Asn Leu
        515                 520
```

<210> SEQ ID NO 74
<211> LENGTH: 564
<212> TYPE: PRT
<213> ORGANISM: Candida glabrata

<400> SEQUENCE: 74

```
Met Ala Pro Asn Thr Lys Ser Ile Glu Gln Pro Leu Ile Ser Lys Ala
1               5                   10                  15

Lys Ile Ser Gly Lys Gly Pro Asp Gly Phe Ala Ile Glu Glu Ser Leu
            20                  25                  30

Leu Glu Arg Gly His Ser Arg Arg Met Gly His Leu Glu Asn Tyr Phe
        35                  40                  45

Ala Ile Met Gln Arg Gln Lys Leu Tyr Thr Asn Phe Asn Met Tyr Gly
    50                  55                  60

Glu Leu Asn Lys Glu Val Thr Arg Glu Gln Leu Ala Val Ala Ile Arg
65                  70                  75                  80

Gln Ile Leu Leu Arg His Pro Ile Met Met Gln Ala Ile Ile Pro Lys
                85                  90                  95

Lys Phe Pro Glu His Glu Glu Tyr Tyr Thr Ser Asp Asp Tyr Tyr Asn
            100                 105                 110

Thr Pro Phe Pro Glu Asn Asp Phe Leu Arg Val Ile Thr Ser Lys Ile
        115                 120                 125

Lys Leu Ser Asp Ile Ile Asn Glu Gln Ser Glu Asp Tyr Gly Glu
    130                 135                 140

Ile Ile Asp Met Ile Leu Ser Glu Tyr Lys Lys Asn Gly Tyr Lys Phe
145                 150                 155                 160

Asp Ala Tyr Met Gln Glu Leu Ile Gly Asn Ile Val Ile Pro Ile Gly
                165                 170                 175

Asn Pro Asn Lys Pro Asn Trp Arg Leu Leu Cys Leu Pro Ser Ala Glu
            180                 185                 190

Gly Gly Gly Ala Gln Trp Lys Lys Phe Val Tyr Ile Ser Asn His Cys
        195                 200                 205

Cys Ser Asp Ala Ile Ser Ala Val Asn Leu Phe Gln Asp Ile Ala Glu
    210                 215                 220

Asn Val Ser Leu Ile Glu Gln Asn Ser Trp Ala Val Pro Tyr Ala Asp
225                 230                 235                 240

Asp Val Ile Val Asp Tyr Glu Gln Asp Val Ala Asp Ile Ala Lys Leu
                245                 250                 255

Pro Ala Pro Ile Thr Glu Arg Val Glu Tyr Arg Pro Pro Leu Ser Lys
            260                 265                 270

Leu Pro Lys Ile Met Leu Val Ser Phe Leu Lys Thr Ala Leu Asn Phe
        275                 280                 285

Lys Ser Asp Ala Leu Glu Thr Arg Cys Asn Asp Glu Tyr Ser Gly Glu
    290                 295                 300

Pro Glu Thr Ser Ala Val Gln Met Gly Asp Val Cys Tyr Asp Ser Ile
305                 310                 315                 320

Leu Asn Tyr Thr Cys Glu Glu Val Ala Val Ile Arg Asp Arg Ile Lys
                325                 330                 335

His Asn Val His Gly Lys Cys Thr Val Thr Pro Phe Ile Gln Ala Ala
            340                 345                 350

Phe Phe Val Ala Met His Gln Ser Arg Lys Leu Leu Gly Gln Lys Gln
        355                 360                 365
```

```
Gly Phe Lys Glu Trp Met Ser Glu Trp Gly Val Asp Met Ala Thr Pro
        370                 375                 380

Ser Ser Thr Arg Arg Tyr Leu Pro Glu Asp Pro Glu Val Arg Asp Met
385                 390                 395                 400

Tyr Lys Tyr Gly Ser Asn Val Gly Gly Ile His Tyr Leu Tyr Met Ile
                405                 410                 415

Ser Gly Met Lys Val Glu Arg Glu Thr Glu Lys Phe Trp Ser Leu
            420                 425                 430

Val Glu Tyr Tyr His Asp Ile Leu Leu Ala Ser His Ser Asn Gly Asp
            435                 440                 445

Gln Thr Val Gly Leu Gly Thr Leu Met Leu Asp Val Ile Val Asp Lys
    450                 455                 460

Lys Asn Val Asp Lys Leu Ile Arg Asp Glu Tyr Leu Tyr Gln Lys Arg
465                 470                 475                 480

Gly Gly Val Ile Met Ser Asn Ala Gly Tyr Phe His Gln Asp Pro Ala
                485                 490                 495

Gln Ala Tyr His Val Thr Asp Leu Val Phe Gly Gln Arg Pro Gly Ala
                500                 505                 510

Leu Lys Phe Ser Phe Gly Val Asn Val Val Ser Thr Asn Ile Gly Gly
            515                 520                 525

Met Asn Leu Asn Val Gly Met Val Arg Arg Thr Leu Arg Asp Arg Ala
530                 535                 540

Glu Phe Arg Glu Phe Ile Gly Ile Leu Asp Arg Val Ile Arg Asp Phe
545                 550                 555                 560

Thr Gly Leu Asn

<210> SEQ ID NO 75
<211> LENGTH: 534
<212> TYPE: PRT
<213> ORGANISM: Tetrapisispora phaffii

<400> SEQUENCE: 75

Met Ser Leu Glu Ala Leu Ser Phe Asp Glu Tyr Lys Pro Tyr Ile Thr
1               5                   10                  15

Glu Glu Leu Ile Glu Arg Gly His Ala Arg Arg Met Gly His Leu Gln
                20                  25                  30

Asp Tyr Phe Ala Ile Ile Gln Arg Gln Lys Leu Tyr Asn Asn Phe Asn
            35                  40                  45

Ile Tyr Cys Glu Leu Asn Glu Lys Val Asn Lys Val Gln Leu Ser His
        50                  55                  60

Ala Phe Arg Glu Met Phe Leu Gln Tyr Pro Ala Leu Ile Glu Tyr Ile
65                  70                  75                  80

Val Pro Lys Phe Tyr Pro Lys His Glu Ala Tyr Tyr Arg Ser Glu Glu
                85                  90                  95

Tyr Leu Ser Lys Pro Cys Pro Ile His Asp Tyr Ile Arg Val Leu Asn
            100                 105                 110

Glu Val Asn Ile Asn Asp Ile Met Asn Glu Gln Asp Glu Tyr Lys
        115                 120                 125

Ser Ile Thr Thr Lys Ile Ser Asp Ile Phe Val Lys Asn Asp Tyr Lys
    130                 135                 140

Phe Ser Asn Glu Ile Ser Glu Met Val Ser Thr Ile Lys Ile Ala Ile
145                 150                 155                 160

Cys Asp Pro Lys Lys Pro Asn Trp Arg Ile Ile Cys Leu Pro Ser Lys
                165                 170                 175
```

```
Thr Ser Ser Thr Glu Trp Lys Asp Phe Ile Leu Val Ser Asn His Phe
            180                 185                 190

Asp Ser Asp Gly Thr Ser Ala Val Asn Phe Phe Glu Asp Leu Thr Asn
        195                 200                 205

Ile Leu Ser Lys Gln Ala Asn Val Glu Asn Asp Thr Ile Val Ile Gly
    210                 215                 220

Asn Asp Ile Asn Ile Asn Tyr Ser Lys Asp Tyr Lys Leu Ile Ser
225                 230                 235                 240

Lys Leu Pro Ile Pro Ile Thr Glu Arg Ile Ser Tyr Thr Pro Thr Leu
                245                 250                 255

Ser Ser Ile Pro Lys Phe Ile Val Gly Asn Ile Cys Lys Thr Lys Leu
            260                 265                 270

Gln Tyr Thr Ser Asp Gly Gly Asp Thr Pro Ala Glu Phe Val Ser Glu
        275                 280                 285

Asp Pro Leu Thr Tyr Asp Tyr Leu Ile Asn Phe Ser Ser Glu Glu Val
    290                 295                 300

Ala Lys Met Lys Lys Thr Ile Lys Asn Cys Leu Tyr Asn Ser Val Thr
305                 310                 315                 320

Leu Thr Pro Phe Ile Gln Ala Cys Phe Phe Val Ala Met Tyr Lys Tyr
                325                 330                 335

Asn Lys Ile Leu Asn Leu Asn Asn Trp Trp Gln Trp Gly Val Asp Cys
            340                 345                 350

Ala Leu Ala Thr Asn Ala Arg Arg Leu Leu Pro Asp Pro Glu Thr
        355                 360                 365

Arg Asp Leu Tyr Arg Tyr Gly Ser Asn Val Gly Thr His Tyr Phe
370                 375                 380

Asn Leu Ile Ser Gln Phe Asn Ile Asn Glu Phe Glu Tyr Asp Lys Phe
385                 390                 395                 400

Phe Lys Leu Val Asp Tyr Tyr His Lys Asn Tyr Gln Asn Ser Tyr Arg
                405                 410                 415

Asn Gly Asp Glu Leu Val Gly Phe Gly Val Leu Phe Ser Asp Leu Ile
            420                 425                 430

Ile Asn Asn Thr Asn Met Asp Lys Thr Ile Lys Asp Asp Tyr Thr Asn
        435                 440                 445

His Lys Arg Gly Gly Leu Leu Phe Ser Asn Val Gly Tyr Arg Asn Glu
    450                 455                 460

Asp Leu Thr Lys Lys Val His Val Asn Asn Ile Ile Phe Ser Gln Ser
465                 470                 475                 480

Pro Gly Cys Met Lys Phe Thr Phe Gly Leu Asn Leu Ile Ser Thr Asp
                485                 490                 495

Lys Cys Gly Met Asn Ile Leu Met Asn Gly Val Arg Gly Ser Val Lys
            500                 505                 510

Ser Arg Glu Asn Phe Glu Asp Phe Cys Arg Phe Phe Arg Lys Thr Val
        515                 520                 525

Glu Asn Phe Ala Lys Leu
    530

<210> SEQ ID NO 76
<211> LENGTH: 518
<212> TYPE: PRT
<213> ORGANISM: Naumovozyma castellii

<400> SEQUENCE: 76

Met Thr Gln Asp Gln Val Thr Leu Asp Glu Tyr Lys Pro Tyr Ile Ala
```

-continued

```
  1               5                   10                  15
Asp Glu Leu Ile Glu Arg Gly His Ala Arg Arg Met Gly His Leu Glu
                 20                  25                  30
Asn Tyr Phe Ala Leu Leu Gln Arg Gln Lys Leu Tyr Thr Asn Phe Ser
                 35                  40                  45
Ile Tyr Gly Glu Leu Asn Lys Glu Val Lys Asp Val Asp Leu Thr Arg
                 50                  55                  60
Ala Leu Arg Ser Ile Ile Phe Lys Asn Pro Ile Leu Ala His Thr Ile
 65                  70                  75                  80
Val Pro Lys Lys Tyr Pro Asp Gln Glu Pro Phe Tyr Gln Ser Glu Glu
                 85                  90                  95
Tyr Leu Asn Ala Pro Tyr Pro Glu His Asp Phe Ile Lys Val Leu Pro
                100                 105                 110
Lys Leu Ser Leu Ser Asp Ile Leu Ile Asn Glu Gln Glu Glu Phe Arg
                115                 120                 125
Glu Ile Val Asp Asp Ile Leu Thr Gln Phe Lys Glu Ala Asn Gly Val
                130                 135                 140
Ile Thr Pro Asp Ile Met Lys Ala Val Ala Tyr Val Ile Ile Pro Ile
145                 150                 155                 160
Cys Asp Pro Ser Arg Pro Asn Trp Arg Leu Phe Arg Leu Ser Pro Thr
                165                 170                 175
Lys Phe Phe Tyr Ile Ser Asn His Cys Thr Ser Asp Ala Ile Ser Gly
                180                 185                 190
Val Asn Ile Phe Gln Asp Ile Cys Thr Glu Leu Ser Gln Asn Asp Glu
                195                 200                 205
Glu Pro Phe Arg Asp Asp Leu Gln Ile Phe Asn Tyr Glu Glu Asp Trp
                210                 215                 220
Glu Ser Phe His Lys Ile Tyr Ile Pro Ile Thr Asp Ile Glu Tyr
225                 230                 235                 240
Arg Pro Ala Leu Thr Ser Leu Pro Lys Ile Ile Ala Ser Ala Leu Val
                245                 250                 255
Lys Gly Phe Leu Asn Tyr Arg Asn Trp Pro Thr Glu Leu Thr Ser Thr
                260                 265                 270
Asn Asp Lys Gly Ile Pro Phe Asp Phe Asn Ile Ile Thr Phe Thr Asn
                275                 280                 285
Asp Glu Val Asn Ser Ile Arg Glu Thr Val Lys Lys Tyr Asn Cys Thr
                290                 295                 300
Phe Thr Pro Phe Leu Gln Ala Cys Trp Phe Val Ala Met Phe Asn Asn
305                 310                 315                 320
Gly Lys Ile Phe His Met Asp Ser Trp Arg Glu Trp Gly Leu Asp Val
                325                 330                 335
Ala Ile Pro Ser Asn Ser Arg Arg Phe Leu Ala Asp Glu Glu Leu Lys
                340                 345                 350
Asp Ile Tyr Lys Tyr Gly Ser Asn Val Gly Gly Leu His Tyr Thr His
                355                 360                 365
Leu Ile Ser Ser Phe Asn Ile Gln Leu Asp Glu Lys Glu Lys Phe Trp
                370                 375                 380
Asp Leu Val Gln Tyr Tyr Gln Asp Gly Tyr Thr Lys Ser Tyr Glu Asn
385                 390                 395                 400
Gly Asp His Phe Ser Gly Leu Gly Leu Leu Met Met Asp Gly Leu Val
                405                 410                 415
Lys Arg Gln Asn Ile Asp Lys Val Ile Ser Ser Asp Tyr Leu His Lys
                420                 425                 430
```

```
Thr Arg Ala Gly Val Leu Phe Ser Asn Ala Gly Phe Pro Gln Asp
        435                 440                 445

Arg Thr Gln Ala Tyr His Val Asn Asp Leu Leu Phe Thr Gln Ser Gln
    450                 455                 460

Gly Ala Met Lys Phe Ser Phe Gly Leu Asn Ile Ala Thr Thr Asn Ile
465                 470                 475                 480

Gly Gly Met Asn Ile Ala Ile Asn Val Ala Gln Gly Thr Phe Asp Asp
                485                 490                 495

Glu Glu Gly Ile Ile Asp Leu Ser Gln Asp Phe Tyr Arg Asn Ile Lys
                500                 505                 510

Ser Phe Ser Asn Ile Ala
                515

<210> SEQ ID NO 77
<211> LENGTH: 534
<212> TYPE: PRT
<213> ORGANISM: Kazachstania africana

<400> SEQUENCE: 77

Met Gly Leu Ser Thr Lys Val Glu Ser Val Arg Glu Val Gln Ser
1               5                   10                  15

Gln Ser Asp Ala Ser Ser Ile Ala Leu Leu Glu Asp Pro Val Ala Glu
                20                  25                  30

Tyr Asp Ile Pro Gln Glu Leu Ile Asp Arg Gly His Ala Arg Arg Met
            35                  40                  45

Gly His Leu Glu Asn Tyr Phe Ala Met Leu Gln Arg Gln Glu Leu Tyr
        50                  55                  60

Ser Asn Phe Ala Val Tyr Leu Lys Met Asn Lys Ser Val Ser Arg Asn
65                  70                  75                  80

Asp Leu Lys His Ala Leu Arg Glu Val Ile Leu Glu Asn Ser Val Leu
                85                  90                  95

Ala His Thr Ile Val Pro Lys Tyr Tyr Pro Asp His Glu Ala Phe Tyr
            100                 105                 110

Lys Ser Glu Lys Tyr Leu Asn Val Pro Tyr Pro Lys His Asp Phe Met
        115                 120                 125

Lys Ile Leu Pro Ser Leu Ser Leu Glu Asp Ile Ile Asn Asp Gln
130                 135                 140

Ser Glu Tyr Thr Glu Val Val Asn Ser Ile Ile Asp Gln Phe Val Lys
145                 150                 155                 160

Asp Asn Gly Lys Ile Thr Asn Lys Leu Ser Glu Ile Val Ser Asn Ile
                165                 170                 175

Cys Ile Pro Ile Tyr Asp Gln Ser Arg Pro Asn Trp Arg Leu Leu Cys
            180                 185                 190

Leu Pro Asp Asn Thr Asp Glu Tyr Ser Asn Phe Val Tyr Ile Ser Asn
        195                 200                 205

His Cys Cys Ser Asp Gly Thr Gly Ile Asn Leu Phe Gln Asp Leu
        210                 215                 220

Val Lys Ser Leu Asn Gly Lys Lys Ser Pro Glu Met Thr Ser Pro Asp
225                 230                 235                 240

Ser Leu Ile Tyr Asn Tyr Glu Lys Asp Phe Asp Lys Ile Ser Lys Leu
                245                 250                 255

Pro Ala Ala Ile Thr Asp Arg Val Asp Tyr Arg Pro Ala Leu Trp Lys
            260                 265                 270

Leu Pro Gln Phe Met Leu Ser Thr Leu Gly Lys Val Phe Phe Ser Tyr
```

```
              275                 280                 285
Lys Ser Pro Ala Pro Val Ser Thr Lys Ile Asn Met Ser Lys Pro Gln
    290                 295                 300

Pro Ser Phe His Asn Ile Leu Asn Phe Thr Pro Asp Glu Leu Asn Lys
305                 310                 315                 320

Ile Arg Ile Ala Ile Lys Lys Asn Ala Cys Thr Met Thr Ser Phe Leu
                325                 330                 335

Gln Thr Cys Leu Phe Ile Thr Leu Lys Glu His Gly Ile Phe Ala Asn
            340                 345                 350

Arg Lys Trp Asn Glu Phe Gly Phe Asp Ile Thr Val Pro Ser Asn Thr
        355                 360                 365

Arg Lys Asp Leu Pro Glu Glu Leu Val Thr Ser Gln Tyr Lys Tyr Gly
    370                 375                 380

Ser Asn Val Gly Gly Leu His Tyr Ser Phe Leu Ile Ser Phe Ile
385                 390                 395                 400

Ala Glu Asn Phe Trp Lys Leu Cys Ser Tyr Tyr Ser Ala Val Leu Lys
                405                 410                 415

Gln Ala Asp Phe Leu Arg Pro Leu Gly Thr Ile Met Leu Asp Phe Val
            420                 425                 430

Val Asn Lys Gln Asn Ile Asp Ser Met Ile Ser Asp Ser Tyr Leu Asn
        435                 440                 445

Lys Lys Arg Gly Gly Ile Ile Leu Ser Asn Val Gly Tyr Phe Glu Gln
    450                 455                 460

Asn Asp Asp Glu Cys Glu Ile Leu Asp Leu Met Leu Met Gln Asn Val
465                 470                 475                 480

Gly Gly Leu Asn Phe Ser Tyr Ala Val Asn Ile Cys Ser Thr Asn Leu
                485                 490                 495

Gly Gly Met Asn Ile Cys Leu Ser Ile Val Glu Gly Thr Leu Lys Asp
            500                 505                 510

Arg Asp Asp Phe Asn Ala Phe Cys Asp Glu Leu Lys Thr Thr Val Arg
        515                 520                 525

Gln Phe Cys Asp Ile Asn
    530

<210> SEQ ID NO 78
<211> LENGTH: 410
<212> TYPE: PRT
<213> ORGANISM: Pseudomonas putida

<400> SEQUENCE: 78

Met Asn Glu Tyr Ala Pro Leu Arg Leu His Val Pro Glu Pro Thr Gly
1               5                   10                  15

Arg Pro Gly Cys Gln Thr Asp Phe Ser Tyr Leu Arg Leu Asn Asp Ala
            20                  25                  30

Gly Gln Ala Arg Lys Pro Ala Ile Asp Val Asp Ala Ala Asp Thr Ala
        35                  40                  45

Asp Leu Ser Tyr Ser Leu Val Arg Val Leu Asp Glu Gln Gly Asp Ala
    50                  55                  60

Gln Gly Pro Trp Ala Glu Asp Ile Asp Pro Gln Ile Leu Arg Gln Gly
65                  70                  75                  80

Met Arg Ala Met Leu Lys Thr Arg Ile Phe Asp Ser Arg Met Val Val
                85                  90                  95

Ala Gln Arg Gln Lys Lys Met Ser Phe Tyr Met Gln Ser Leu Gly Glu
            100                 105                 110
```

Glu Ala Ile Gly Ser Gly Gln Ala Leu Ala Leu Asn Arg Thr Asp Met
             115                 120                 125

Cys Phe Pro Thr Tyr Arg Gln Gln Ser Ile Leu Met Ala Arg Asp Val
130                 135                 140

Ser Leu Val Glu Met Ile Cys Gln Leu Leu Ser Asn Glu Arg Asp Pro
145                 150                 155                 160

Leu Lys Gly Arg Gln Leu Pro Ile Met Tyr Ser Val Arg Glu Ala Gly
                165                 170                 175

Phe Phe Thr Ile Ser Gly Asn Leu Ala Thr Gln Phe Val Gln Ala Val
            180                 185                 190

Gly Trp Ala Met Ala Ser Ala Ile Lys Gly Asp Thr Lys Ile Ala Ser
        195                 200                 205

Ala Trp Ile Gly Asp Gly Ala Thr Ala Glu Ser Asp Phe His Thr Ala
    210                 215                 220

Leu Thr Phe Ala His Val Tyr Arg Ala Pro Val Ile Leu Asn Val Val
225                 230                 235                 240

Asn Asn Gln Trp Ala Ile Ser Thr Phe Gln Ala Ile Ala Gly Gly Glu
                245                 250                 255

Ser Thr Thr Phe Ala Gly Arg Gly Val Gly Cys Gly Ile Ala Ser Leu
            260                 265                 270

Arg Val Asp Gly Asn Asp Phe Ala Val Tyr Ala Ala Ser Arg Trp
        275                 280                 285

Ala Ala Glu Arg Ala Arg Arg Gly Leu Gly Pro Ser Leu Ile Glu Trp
    290                 295                 300

Val Thr Tyr Arg Ala Gly Pro His Ser Thr Ser Asp Asp Pro Ser Lys
305                 310                 315                 320

Tyr Arg Pro Ala Asp Asp Trp Ser His Phe Pro Leu Gly Asp Pro Ile
                325                 330                 335

Ala Arg Leu Lys Gln His Leu Ile Lys Ile Gly His Trp Ser Glu Glu
            340                 345                 350

Glu His Gln Ala Val Thr Ala Glu Leu Glu Ala Ala Val Ile Ala Ala
        355                 360                 365

Gln Lys Glu Ala Glu Gln Tyr Gly Thr Leu Ala Asn Gly His Ile Pro
    370                 375                 380

Ser Ala Ala Ser Met Phe Glu Asp Val Tyr Lys Glu Met Pro Asp His
385                 390                 395                 400

Leu Arg Arg Gln Arg Gln Glu Leu Gly Val
                405                 410

<210> SEQ ID NO 79
<211> LENGTH: 339
<212> TYPE: PRT
<213> ORGANISM: Pseudomonas putida

<400> SEQUENCE: 79

Met Ala Thr Thr Thr Met Thr Met Ile Gln Ala Leu Arg Ser Ala Met
1               5                   10                  15

Asp Val Met Leu Glu Arg Asp Asp Asn Val Val Tyr Gly Gln Asp
                20                  25                  30

Val Gly Tyr Phe Gly Gly Val Phe Arg Cys Thr Glu Gly Leu Gln Asn
            35                  40                  45

Lys Tyr Gly Lys Ser Arg Val Phe Asp Ala Pro Ile Ser Glu Ser Gly
        50                  55                  60

Ile Val Gly Thr Ala Val Gly Met Gly Ala Tyr Gly Leu Arg Pro Val
65                  70                  75                  80

Val Glu Ile Gln Phe Ala Asp Tyr Phe Tyr Pro Ala Ser Asp Gln Ile
             85                  90                  95

Val Ser Glu Leu Ala Arg Leu Arg Tyr Arg Ser Ala Gly Glu Phe Ile
            100                 105                 110

Ala Pro Leu Thr Leu Arg Met Pro Cys Gly Gly Gly Ile Tyr Gly Gly
            115                 120                 125

Gln Thr His Ser Gln Ser Pro Glu Ala Met Phe Thr Gln Val Cys Gly
            130                 135                 140

Leu Arg Thr Val Met Pro Ser Asn Pro Tyr Asp Ala Lys Gly Leu Leu
145                 150                 155                 160

Ile Ala Ser Ile Glu Cys Asp Asp Pro Val Ile Phe Leu Glu Pro Lys
                165                 170                 175

Arg Leu Tyr Asn Gly Pro Phe Asp Gly His His Asp Arg Pro Val Thr
                180                 185                 190

Pro Trp Ser Lys His Pro His Ser Ala Val Pro Asp Gly Tyr Tyr Thr
                195                 200                 205

Val Pro Leu Asp Lys Ala Ala Ile Thr Arg Pro Gly Asn Asp Val Thr
            210                 215                 220

Val Leu Thr Tyr Gly Thr Thr Val Tyr Val Ala Gln Val Ala Ala Glu
225                 230                 235                 240

Glu Ser Gly Val Asp Ala Glu Val Ile Asp Leu Arg Ser Leu Trp Pro
                245                 250                 255

Leu Asp Leu Asp Thr Ile Val Glu Ser Val Lys Lys Thr Gly Arg Cys
                260                 265                 270

Val Val Val His Glu Ala Thr Arg Thr Cys Gly Phe Gly Ala Glu Leu
            275                 280                 285

Val Ser Leu Val Gln Glu His Cys Phe His His Leu Glu Ala Pro Ile
            290                 295                 300

Glu Arg Val Thr Gly Trp Asp Thr Pro Tyr Pro His Ala Gln Glu Trp
305                 310                 315                 320

Ala Tyr Phe Pro Gly Pro Ser Arg Val Gly Ala Ala Leu Lys Lys Val
                325                 330                 335

Met Glu Val

<210> SEQ ID NO 80
<211> LENGTH: 423
<212> TYPE: PRT
<213> ORGANISM: Pseudomonas putida

<400> SEQUENCE: 80

Met Gly Thr His Val Ile Lys Met Pro Asp Ile Gly Glu Gly Ile Ala
1               5                   10                  15

Gln Val Glu Leu Val Glu Trp Phe Lys Val Gly Asp Ile Ile Ala
            20                  25                  30

Glu Asp Gln Val Val Ala Asp Val Met Thr Asp Lys Ala Thr Val Glu
            35                  40                  45

Ile Pro Ser Pro Val Ser Gly Lys Val Leu Ala Leu Gly Gly Gln Pro
        50                  55                  60

Gly Glu Val Met Ala Val Gly Ser Glu Leu Ile Arg Ile Glu Val Glu
65                  70                  75                  80

Gly Ser Gly Asn His Val Asp Val Pro Gln Pro Lys Pro Val Glu Ala
            85                  90                  95

Pro Ala Ala Pro Ile Ala Ala Lys Pro Glu Pro Gln Lys Asp Val Lys
            100                 105                 110

```
Pro Ala Val Tyr Gln Ala Pro Ala Asn His Glu Ala Ala Pro Ile Val
            115                 120                 125

Pro Arg Gln Pro Gly Asp Lys Pro Leu Ala Ser Pro Ala Val Arg Lys
        130                 135                 140

Arg Ala Leu Asp Ala Gly Ile Glu Leu Arg Tyr Val His Gly Ser Gly
145                 150                 155                 160

Pro Ala Gly Arg Ile Leu His Glu Asp Leu Asp Ala Phe Met Ser Lys
                165                 170                 175

Pro Gln Ser Asn Ala Gly Gln Ala Pro Asp Gly Tyr Ala Lys Arg Thr
            180                 185                 190

Asp Ser Glu Gln Val Pro Val Ile Gly Leu Arg Arg Lys Ile Ala Gln
        195                 200                 205

Arg Met Gln Asp Ala Lys Arg Arg Val Ala His Phe Ser Tyr Val Glu
210                 215                 220

Glu Ile Asp Val Thr Ala Leu Glu Ala Leu Arg Gln Gln Leu Asn Ser
225                 230                 235                 240

Lys His Gly Asp Ser Arg Gly Lys Leu Thr Leu Leu Pro Phe Leu Val
                245                 250                 255

Arg Ala Leu Val Val Ala Leu Arg Asp Phe Pro Gln Ile Asn Ala Thr
            260                 265                 270

Tyr Asp Asp Glu Ala Gln Ile Ile Thr Arg His Gly Ala Val His Val
        275                 280                 285

Gly Ile Ala Thr Gln Gly Asp Asn Gly Leu Met Val Pro Val Leu Arg
290                 295                 300

His Ala Glu Ala Gly Ser Leu Trp Ala Asn Ala Gly Glu Ile Ser Arg
305                 310                 315                 320

Leu Ala Asn Ala Ala Arg Asn Asn Lys Ala Ser Arg Glu Glu Leu Ser
                325                 330                 335

Gly Ser Thr Ile Thr Leu Thr Ser Leu Gly Ala Leu Gly Gly Ile Val
            340                 345                 350

Ser Thr Pro Val Val Asn Thr Pro Glu Val Ala Ile Val Gly Val Asn
        355                 360                 365

Arg Met Val Glu Arg Pro Val Val Ile Asp Gly Gln Ile Val Val Arg
370                 375                 380

Lys Met Met Asn Leu Ser Ser Ser Phe Asp His Arg Val Val Asp Gly
385                 390                 395                 400

Met Asp Ala Ala Leu Phe Ile Gln Ala Val Arg Gly Leu Leu Glu Gln
                405                 410                 415

Pro Ala Cys Leu Phe Val Glu
            420

<210> SEQ ID NO 81
<211> LENGTH: 60
<212> TYPE: DNA
<213> ORGANISM: artificial
<220> FEATURE:
<223> OTHER INFORMATION: synthetic oligonucleotide primer

<400> SEQUENCE: 81
gaaaacgaaa gctctctaag ctgagcagga gaaattaact atggcgcatg atcagagcct    60

<210> SEQ ID NO 82
<211> LENGTH: 60
<212> TYPE: DNA
<213> ORGANISM: artificial
<220> FEATURE:
```

```
<223> OTHER INFORMATION: synthetic oligonucleotide primer

<400> SEQUENCE: 82
agcctttcgt tttatttgat gcctctagag ctcagcttac aggctgctct gggtgaaatg    60

<210> SEQ ID NO 83
<211> LENGTH: 60
<212> TYPE: DNA
<213> ORGANISM: artificial
<220> FEATURE:
<223> OTHER INFORMATION: synthetic oligonucleotide primer

<400> SEQUENCE: 83
cgaaagctct ctaagctgag caggagaaat taactatgaa tgaaatcgat gagaaaaatc    60

<210> SEQ ID NO 84
<211> LENGTH: 60
<212> TYPE: DNA
<213> ORGANISM: artificial
<220> FEATURE:
<223> OTHER INFORMATION: synthetic oligonucleotide primer

<400> SEQUENCE: 84
agcctttcgt tttatttgat gcctctagag ctcagcttaa gggcctaaaa ggagagcttt    60

<210> SEQ ID NO 85
<211> LENGTH: 60
<212> TYPE: DNA
<213> ORGANISM: artificial
<220> FEATURE:
<223> OTHER INFORMATION: synthetic oligonucleotide primer

<400> SEQUENCE: 85
cgaaagctct ctaagctgag caggagaaat taactatgga agatatagaa ggatacgaac    60

<210> SEQ ID NO 86
<211> LENGTH: 60
<212> TYPE: DNA
<213> ORGANISM: artificial
<220> FEATURE:
<223> OTHER INFORMATION: synthetic oligonucleotide primer

<400> SEQUENCE: 86
cctttcgttt tatttgatgc ctctagagct cagcttaaag cgacgcaaat tcgccgatgg    60

<210> SEQ ID NO 87
<211> LENGTH: 60
<212> TYPE: DNA
<213> ORGANISM: artificial
<220> FEATURE:
<223> OTHER INFORMATION: synthetic oligonucleotide primer

<400> SEQUENCE: 87
aaacgaaagc tctctaagct gagcaggaga aattaactat ggacagcaaa cagagcagcg    60

<210> SEQ ID NO 88
<211> LENGTH: 60
<212> TYPE: DNA
<213> ORGANISM: artificial
<220> FEATURE:
<223> OTHER INFORMATION: synthetic oligonucleotide primer

<400> SEQUENCE: 88
cctttcgttt tatttgatgc ctctagagct cagcttaaag cgctggggtg atgaacgcat    60
```

```
<210> SEQ ID NO 89
<211> LENGTH: 60
<212> TYPE: DNA
<213> ORGANISM: artificial
<220> FEATURE:
<223> OTHER INFORMATION: synthetic oligonucleotide primer

<400> SEQUENCE: 89
aaacgaaagc tctctaagct gagcaggaga aattaactat ggagaaaata gaagtgagca         60

<210> SEQ ID NO 90
<211> LENGTH: 60
<212> TYPE: DNA
<213> ORGANISM: artificial
<220> FEATURE:
<223> OTHER INFORMATION: synthetic oligonucleotide primer

<400> SEQUENCE: 90
cctttcgttt tatttgatgc ctctagagct cagcttagat cagcgtcttt ggactcgcca         60

<210> SEQ ID NO 91
<211> LENGTH: 52
<212> TYPE: DNA
<213> ORGANISM: artificial
<220> FEATURE:
<223> OTHER INFORMATION: synthetic oligonucleotide primer

<400> SEQUENCE: 91
gggcccgcat gcaggagaaa ttaactatga caaactttaa tctgcacacc cc                 52

<210> SEQ ID NO 92
<211> LENGTH: 38
<212> TYPE: DNA
<213> ORGANISM: artificial
<220> FEATURE:
<223> OTHER INFORMATION: synthetic oligonucleotide primer

<400> SEQUENCE: 92
gggccctcta gattagcggg cggcttcgta tatacggc                                 38
```

BIOSYNTHETIC PATHWAYS, RECOMBINANT CELLS, AND METHODS

CROSS-REFERENCE TO RELATED APPLICATION

This application is a U.S. National Stage Application of International Application No. PCT/US2013/031470, filed on Mar. 14, 2013, which claims priority to U.S. Provisional Patent Application Ser. No. 61/652,505, filed May 29, 2012, each of which is incorporated herein by reference.

SUMMARY

This disclosure describes, in one aspect, a recombinant cell modified to exhibit increased biosynthesis of an ester compared to a wild-type control. The recombinant cell may be a eukaryotic cell or a prokaryotic cell. In some cases, the microbial cell may be photosynthetic. In some cases, the microbial cell may be cellulolytic. In some embodiments, the recombinant cell can exhibit an increase in conversion of an organic acid to an acyl-CoA compared to a wild-type control, an increase in conversion of ketoacids to an acyl-CoA compared to a wild-type control, an increase in conversion of an aldehyde to an organic acid compared to a wild-type control, an increase in conversion of an aldehyde to an alcohol compared to a wild-type control, or an increase in combining an acyl-CoA with an alcohol to form an ester compared to a wild-type control.

In another aspect, this disclosure describes a method that generally includes incubating a recombinant cell modified to exhibit increased biosynthesis of an ester compared to a wild-type control in medium that includes a carbon source under conditions effective for the recombinant cell to produce an ester, wherein the carbon source comprises one or more of: glucose, pyruvate, ketovaline, $CO_2$, cellulose, xylose, sucrose, arabinose, or glycerol.

In another aspect, this disclosure describes a method that generally includes introducing into a host cell a heterologous polynucleotide encoding at least one polypeptide that catalyzes a step in converting a carbon source to an ester, wherein the at least one polynucleotide is operably linked to a promoter so that the modified host cell catalyzes conversion of the carbon source to an ester. In some embodiments, the carbon source can include one or more of: glucose, pyruvate, ketovaline, $CO_2$, cellulose, xylose, sucrose, arabinose, or glycerol. In some embodiments, the host cell can be a eukaryotic cell. In other embodiments, the host cell can be a prokaryotic cell. In some embodiments, the host cell can be photosynthetic. In some embodiments, the host cell can be cellulolytic.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. (a) Proposed artificial biosynthetic pathway to esters. (b) Example molecules. (c) Advantages of ester approach to fuels and chemicals.

DETAILED DESCRIPTION OF ILLUSTRATIVE EMBODIMENTS

Figure 2:
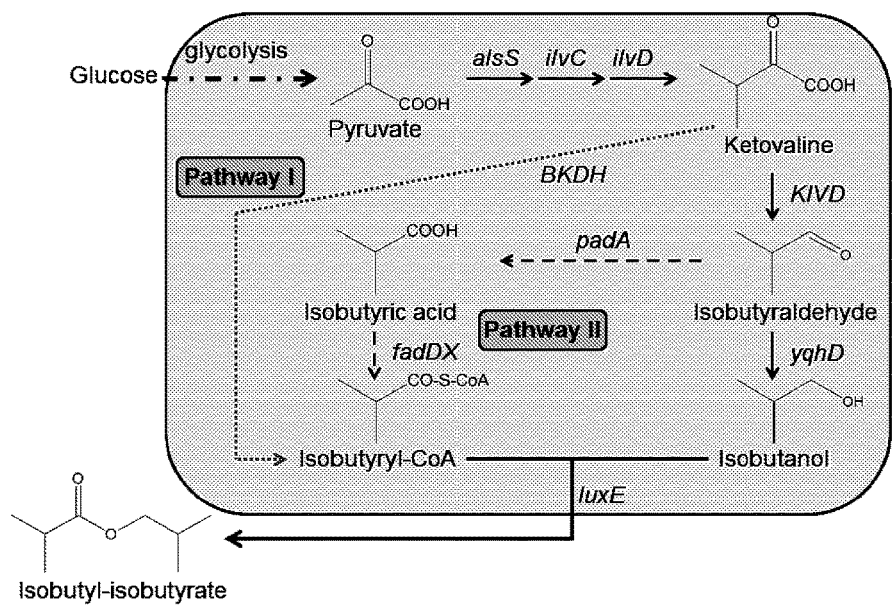
FIG. 2. An exemplary synthetic pathway to ester isobutyl-isobutyrate. Two independent pathways can lead to the production of isobutyryl-CoA.
Figure 3A:
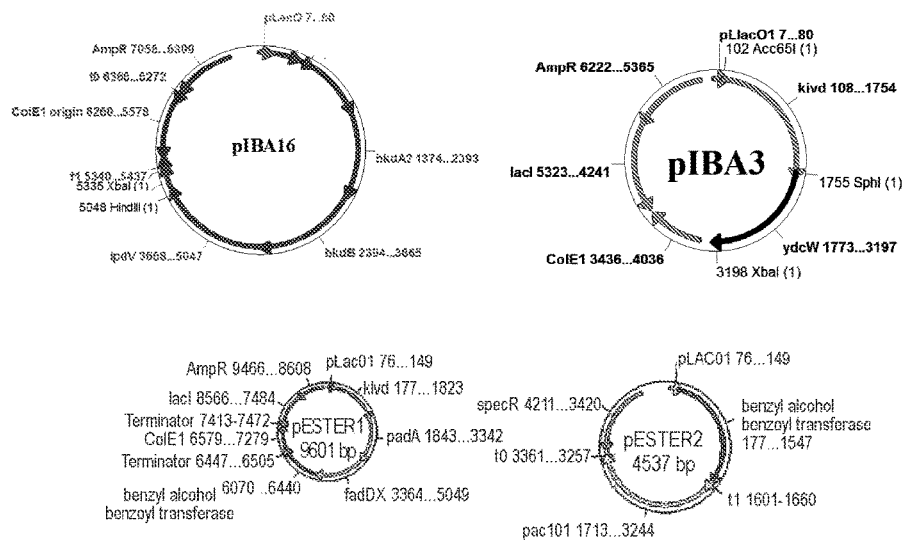
FIG. 3. (a) Plasmids and (b) gas chromatography data result showing biosynthesis of isobutyl isobutyrate.
Figure 3B:
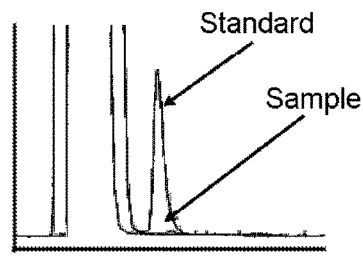

In the description of exemplary embodiments that follow, certain metabolic enzymes, and the natural source of those enzymes, are specified. These are merely examples of suitable enzymes and suitable sources of the specified enzymes. Alternative enzymes with similar catalytic activities are possible, as are homologs that are obtainable from different microbial species or strains. Accordingly, the exemplary embodiments described herein should not be construed as limiting the scope of the microbes or methods that are reflected in the claims. The search for renewable resources to replace petroleum is a significant challenge facing science, industry, and society. Biosynthesis can provide a sustainable supply of fuels and chemicals from biomass resources. Factors that can influence the viability of a fermentation process include, for example, feedstock availability, fermentation performance (e.g., yield, titer, productivity), and the cost of recovering the fermentation product. While great advances have been made in feedstock development, current fermentation approaches to the production of alcohols or organic acids is not ideal. First, alcohols and organic acids can be very toxic to cells, which can limit the concentration to which these products can accumulate in a fermentation culture before they have a deleterious effect on the viability of the microbes in the culture. Second, alcohols and acids tend to be very soluble in aqueous media (e.g., culture media) and therefore can require an energy-intensive distillation purification scheme to recover these products from an aqueous fermentation medium. As a result, while higher alcohols such as, for example, butanol can offer advantages as fuels compared to, for example, ethanol, it is difficult for higher alcohols to compete with ethanol as a commercially viable biofuel because of the high purification cost from low fermentation titers (<20 g/L). Third, fermentation to produce organic acids often involves adding a base to the fermentation in order to neutralize the pH of the medium in which the organic acid accumulates. The recovery of the organic acid often involves subsequent addition of sulfuric acid and disposal of salts, each of which can involve significant cost.

To provide a general solution, we have developed an ester platform for the production of alcohols, organic acids, or other biofuels. As shown in FIG. 1(a), one embodiment of this approach has three components: 1) a metabolic pathway for the biosynthesis of carboxylic acids and then acyl-CoAs; 2) a parallel metabolic pathway for the biosynthesis of alcohols; and 3) an engineered pathway for the production of esters from acyl-CoAs and alcohols. The successful implementation of this platform has enabled the bio-based production of esters. In some alternative embodiments, the approach may include a metabolic pathway for the biosynthesis of carboxylic acids (and then acyl-CoAs) and an engineered pathway for the production of esters from the biosynthesized acyl-CoAs and alcohols provided as a co-reactant (e.g., in the culture medium). In other alternative embodiments, the approach can include a metabolic pathway for the biosynthesis of alcohols and an engineered pathway for the production of esters from the biosynthesized alcohol and acyl-CoAs provided as a co-reactant (e.g., in the culture medium).

An ester produced by using our platform technology may be used as a biofuel, an industrial chemical, or a raw material for the production of other compounds. For example, esters can be readily hydrolyzed to make alcohols and organic acids. In principle, this approach can be used to manufacture any alcohol and/or organic acid from an appropriate ester produced by a microbe engineered according to our platform. Several exemplary organic acids and alcohols are listed in FIG. 1(b). Exemplary organic acid products include, for example, acetate, isobutyrate, 3-hydroxypropionate, butyrate, lactate, methacrylate, acrylate, and isopentanoate. Exemplary alcohol products include, for example, ethanol, methanol, butanol, isobutanol, propanol, isopropanol, pentanol, isopentanol, hexanol, heptanol, and octanol. The combination of any of these acids with any of these alcohols could generate an ester metabolite.

An ester produced as described herein can be used as a biofuel. Esters, in general, can provide certain advantages over, for example, ethanol as a fuel. As shown in Table 1, ester fuels have similar energy density to higher alcohols such as, for example, isobutanol and isopentanol. Esters also can exhibit less solubility in water compared to corresponding alcohol compounds, allowing one to recover an ester from aqueous medium using phase separation rather than distillation. As a result, recovering esters can be simpler, more efficient, and less costly than recovering alcohols from fermentations. While fatty acids and alkanes also have very low water solubility, long chain fatty acids typically are not efficiently secreted to the extracellular milieu and fuels prepared from these compounds may not perform well at low temperatures because they may be prone to gelling.

Bioproduction of esters can produce higher theoretical yields than bioproduction of higher alcohols, alkanes, and fatty acids. In $E.$ $coli$, for example, isobutanol accumulation can reach approximately 22 g/L without in situ recovery during fermentation (Baez et al., Appl. Microbiol. Biotechnol. 2011, 90 (5), 1681-1690). In contrast, we can produce 90 g/L isobutyrate, which is comparable to fermentation of lactate (Wang et al., Proc. Natl. Acad. Sci. USA. 2011, 108 (47), 18920-18925) or succinate (Lin et al., Metab. Eng. 2005, 7 (2), 116-127), two of the most promising renewable chemicals under commercial production. Also, C5 isovalerate can accumulate to 32 g/L, much higher than isopentanol (4.4 g/L) (Connor et al., Appl. Microbiol. Biotechnol. 2010, 86 (4), 1155-1164) and fatty acid (4.5 g/L) (Liu et al., Metab. Eng. 2010, 12 (4), 378-386). Finally, esters are not toxic to cells, allowing one to observe higher accumulations in fermentation broths compared to other compounds.

TABLE 1

Comparison of biosynthesis profile, physical properties, and fuel properties of various compounds.

| Fuel | Energy density (MJ/L) | Theoretical yield (g/g glucose) | Titer (g/L) | Solubility (g/L) |
|---|---|---|---|---|
| Ethanol | 21 | 0.51 | 200 | miscible |
| Fatty acid | 33 | 0.36 | 4.5 | insoluble |
| Farnesene | 31 | 0.29 | 104 | insoluble |
| Isobutanol | 26 | 0.41 | 22 | 85 |
| Isopentanol | 27 | 0.33 | 4.4 | 27 |
| Isobutyric acid | x | 0.49 | 90 | 200 |
| Isovaleric acid | x | 0.38 | 32 | 25 |
| Ethyl acetate | 19 | 0.49 | | 83 |
| Ethyl isobutyrate | 25 | 0.43 | | 3.2 |
| Ethyl isovalerate | 26 | 0.36 | | 2 |
| isobutyl isobutyrate | 27 | 0.40 | | 0.5 |
| isovaleryl isovalerate | 29 | 0.32 | | insoluble |
| Gasoline | 32 | | | |
| Jet fuel | 35 | | | |
| Diesel | 39 | | | |

FIG. 2 shows an exemplary, generalized engineered pathway for producing an exemplary ester compound, isobutyl-isobutyrate. To catalyze the esterification enzymatically, a carboxylic acid is activated to an acyl-CoA. Then, the acyl-CoA can react with an alcohol to produce an esters. The esterification reaction is catalyzed by an acyltransferase (FIG. 2). We have engineered two ester-producing strains of $E.$ $coli$, Ester strain 1 and Ester strain 2, each of which employs an independent pathway for the generation of the acyl-CoA intermediate. One pathway to producing an acyl-CoA converts isobutyrate into isobutyryl-CoA by an acyl-CoA synthetase (Acs). We cloned FadDx from $Pseudomonas$ $putida$, an exemplary acyl-CoA synthetase, to catalyze the production of the acyl-CoA in this manner (Ester strain 1, shown in FIG. 2 as "Pathway II"). Another pathway to acyl-CoA is to employ branched-chain keto acid dehydrogenase complex BKDH from $Pseudomonas$ $putida$. We employed this strategy in a separate strain (Ester strain 2, shown in FIG. 2 as "Pathway I").

We then cloned benzoyl-coenzyme A (CoA):benzyl alcohol benzoyl transferase (BEBT, or LuxE) from $Clarkia$ $breweri$ (D'Auria et al., Plant Physiol. 2002, 130(1):466) into both Ester strain 1 and Ester strain 2.

According to gas chromatography analysis, 3.5 mg/L isobutyl isobutyrate was obtained during shake flask fermentations for Ester 1 strain and 200 mg/L for Ester 2 strain. Without LuxE, no isobutyl isobutyrate was detected in the fermentation broth.

This embodiment establishes a basic platform in which microbes can be engineered to produce an ester compound. The particular enzymes we have used are merely exemplary, establishing that the platform can be effective for biosynthesis of ester compounds. One can use any suitable combination of acyl-CoA-generating enzymes—either acyl-CoA synthetase or branched-chain keto acid dehydrogenase complex, BKDH—and acyltransferase to produce a desired ester product from a given feedstock. Exemplary acyl-CoA synthetases that may be used in our platform include, for example, those reflected in any one of SEQ ID NO:5-28, regardless of the enzyme's common name or native substrate. Certain exemplary acyl-CoA synthetases are listed in Table 2. Exemplary branched-chain keto acid dehydrogenase complex enzymes that may be used in our platform include, for example, any one or more of the amino acid sequences reflected in SEQ ID NO:29 and 78-80, regardless of the enzyme's common name or native function. Certain exemplary branched-chain keto acid dehydrogenase complex enzymes are listed in Table 2. Exemplary acyltransferases that may be used in our platform include, for example, those reflected in any one of SEQ ID NO:30-77, regardless of the enzyme's common name or native function. Certain exemplary acyltransferases include, for example, those listed in Table 2.

TABLE 2

Exemplary alternative acyl-CoA synthetases and acyl-transferases

| Common Name | Organism | Encoding gene | Accession No. | Native Substrate | Comment | SEQ ID NO |
|---|---|---|---|---|---|---|
| Exemplary Acyl-CoA synthetases | | | | | | |
| Acyl-CoA synthetase | P. Putida | Acs | NP_746598.1 | aliphatic acids | Synthesizes isobutyl isobutyrate | 5 |
| Acyl-CoA synthetase | S. cerevisiae | Faa2P | NP_010931.1 | medium chain acids | Activate C4-C22 substrates | 11 |
| Acyl-CoA synthetase | S. cerevisiae | Acs1p | NP_009347.1 | acetate | Activate propionate | 17 |
| Acyl-activating enzyme 11 | A. thaliana | AAE11 | AAP03024.1 | Fatty acids | Activate C4-C8 acids | 23 |
| Branched-chain alpha-keto acid dehydrogenase comlex enzymes | | | | | | |
| branched-chain alpha-keto acid dehydrogenase | P. putida KT2440 | bkdA1 | NP_746515.1 | Branched chain alpha-keto acids | Activate C4-C6 keto acids | 78 |
| branched-chain alpha-keto acid dehydrogenase | P. putida KT2440 | bkdA2 | NP_746516.1 | Branched-chain alpha-keto acids | Activate C4-C6 keto acids | 79 |
| branched-chain alpha-keto acid dehydrogenase | P. putida KT2440 | bkdB | NP_746517.1 | Branched-chain alpha-keto acids | Activate C4-C6 keto acids | 80 |
| branched-chain alpha-keto acid dehydrogenase | P. putida KT2440 | lpdV | NP_746518.1 | Branched-chain alpha-keto acids | Activate C4-C6 keto acids | 29 |
| Exemplary Acyltransferases | | | | | | |
| Acyl-transferase | S. cerevisiae | EEB1 | NP_015230.1 | acyl-CoA & ethanol | Produce ethyl esters | 30 |
| benzyl alcohol benzoyl transferase | C. breweri | BEBT (luxE) | Q8GT21.1 | benzoyl CoA & benzyl alcohol | Synthesize isobutyl isobutyrate in our preliminary study | 36 |
| alcohol acyl-transferases | C. melo | CmAAT3 | AAW51125.1 | acetyl CoA & benzyl alcohol | Accept a broad range of acyl-CoA and alcohols | 42 |
| benzyl alcohol benzoyl transferase | P. hybrida | BPBT | AAT68601.1 | benzoyl CoA & phenylethanol | Accept a broad range of acyl-CoA and alcohols | 48 |
| alcohol acyl transferase | M. domestica | MpAAT1 | AAU14879.2 | alcohol | Produce medium-chain aliphatic volatile esters | 54 |
| alcohol acyltransferase | Fragaria spp. and hybrids | SAAT | AAG13130.1 | medium-chain aliphatic alcohols | Produce butyl butyrate | 60 |
| alcohol acetyltransferase | S. cerevisiae | ATF1 | EGA72844.1 | alcohol acetyl acetate | Produce | 66 |
| alcohol acetyltransferase | S. cerevisiae | ATF2 acetyl acetate | | alcohol | Produce | 72 |

Figure 4:
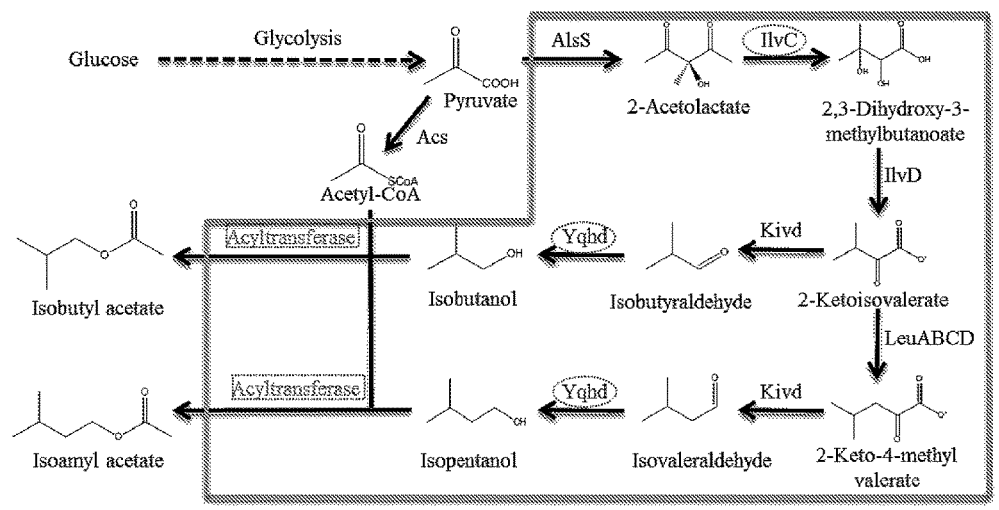
FIG. 4. Synthetic pathways for the production of isobutyl acetate (IBAC) and isoamyl acetate (IVAC). The engineered steps of the pathways are shown in the box. NADPH-dependent enzymes are indicated with a dotted circle and key enzyme acyltransferase are indicated with dotted rectangles. Abbreviation: PDC (pyruvate dehydrogenase complex), AAT (alcohol acyltransferase); other enzymes and are specified in FIG. 5.

FIG. 4 illustrates an alternative embodiment of our platform for ester biosynthesis. In this embodiment, isobutyl acetate (IBAC) and/or isoamyl acetate (IVAC, banana oil) may be produced by a microbe in which the native valine biosynthetic pathway is modified. Acetyl-CoA is natively and readily available in, for example, *E. coli.* as a component of the TCA cycle. To produce either IBAC and IVAC, the microbe is first constructed to overexpress AlsS and IlvD to promote biosynthesis of 2-ketoisovalerate. The microbe also is constructed to express Kivd and Yqhd, which together can convert 2-ketoisovalerate to isobutanol, which can be esterified to isobutyl acetate in a reaction catalyzed by an acyltransferase. To produce isoamyl acetate, the microbe may be constructed to further express the "+1" pathway (LeuABCD), which can elongate 2-ketoisovalerate by one carbon to form 2-keto-4-methylvalerate. In these embodiments, the combination of KivD and Yqhd can convert 2-keto-4-methylvalerate to isopentanol, which can be esterified to isoamyl acetate by an acyltransferase.

We characterized five exemplary alcohol acyltransferases (AAT), LuxE, ATF1, ATF2, BPBT, and SAAT (as shown in Table 3). Each was cloned and transformed into *E. coli* strain BW25113 for analysis.

TABLE 3

Exemplary alcohol acyltransferases (AAT) in medium-chain esters biosynthesis.

| Gene | Enzyme | Native Function | Organism |
| --- | --- | --- | --- |
| luxE | Benzyl alcohol O-benzoyltransferase | Uses benzoyl-CoA and benzyl alcohol to make benzyl benzoate | *C. breweri* |
| ATF1 | Alcohol acetyltransferase | Acetate ester production | *S. cerevisiae* |
| ATF2 | Alcohol acetyltransferase | Acetate ester production | *S. cerevisiae* |
| BPBT | Benzyl alcohol O-benzoyltransferase | Uses benzoyl-CoA and benzyl alcohol to make benzyl benzoate | *P. hybrida* |
| SAAT | Strawberry alcohol acetyltransferase | Uses aliphatic medium-chain alcohols and broad ranges of acyl-CoA to make esters | Strawberry |

Figure 5A:
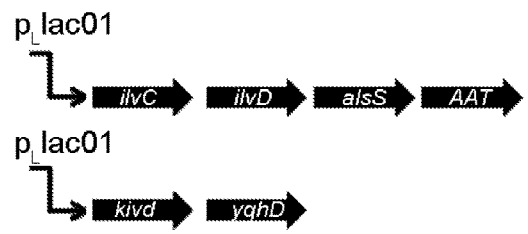
FIG. 5. Synthetic operons for (a) isobutyl acetate (IBAC) (b) isoamyl acetate (IVAC) production. Abbreviation: AAT (alcohol acyltransferase).
Figure 5B:
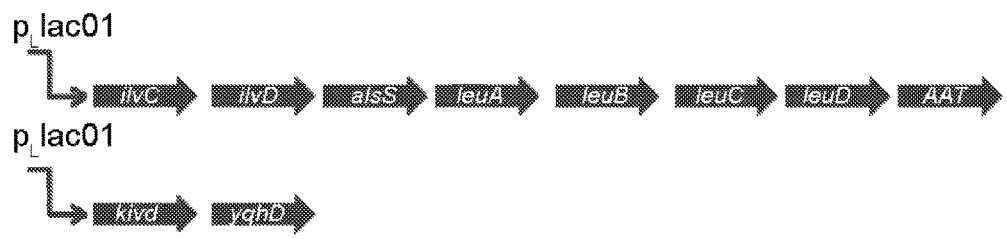

Three synthetic operons were constructed for gene expression to produce isobutyl acetate and isoamyl acetate (FIG. 5). All the plasmids were constructed to be under the regulation of $P_L$lacO1 promoter. To produce isobutyl acetate, the first operon included four coding regions on a medium copy plasmid carrying kanamycin resistance marker in a transcriptional order ilvC-ilvD-alsS-AAT, with the ATT position being occupied by the coding region of one of the five exemplary acyltransferases (AAT) being analyzed. (FIG. 5(*a*)). The second operon included two coding regions on a high copy plasmid with an ampicillin resistance maker in a transcriptional order kivd-yqhD. For the synthesis of isoamyl acetate, the coding regions of leuA, leuB, leuC, and leuD involved in leucine biosynthesis were introduced in the first medium copy plasmid between alsS and AAT, and the same second high copy plasmid was used. (FIG. 5(*b*)).

We assessed the effect of each of the five exemplary acyltransferases on the production titers for isobutyl acetate and isoamyl acetate. Coding regions for ATF1 and ATF2 were amplified by PCR from *S. cerevisiae* genomic DNA. Coding regions for LuxE, BPBT, and SAAT were artificially synthesized by annealing based connection of oligonucleotides. Recombinant strains were constructed with the synthetic operons as shown in FIG. 2.

Shake flask fermentations and products analyses were carried as described in Example 2 and three independent colonies were streaked for inoculation to get standard deviation. All strains were identical except for the alcohol acyltransferase that was expressed. Therefore, with the same fermentation conditions, the strain with the highest production titer of the target compound would have the most active alcohol acyltransfersase. The activity here represents the combined effects of kinetic parameters and protein expression levels.

Figure 6A:
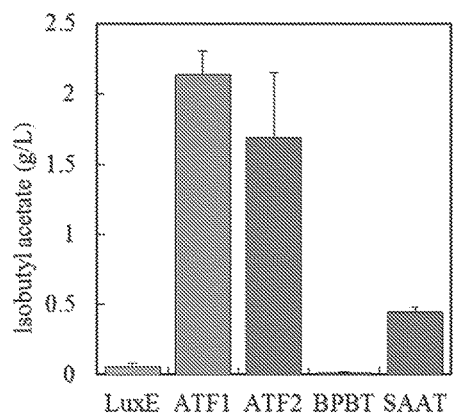
FIG. 6. Fermentation results with the introduction of five candidate acyltransferases (AAT) for (a) isobutyl acetate production and (b) isoamyl acetate production. Error bars indicate standard deviation. These five AATs and their natural substrates are shown as in Table 3.
Figure 6B:
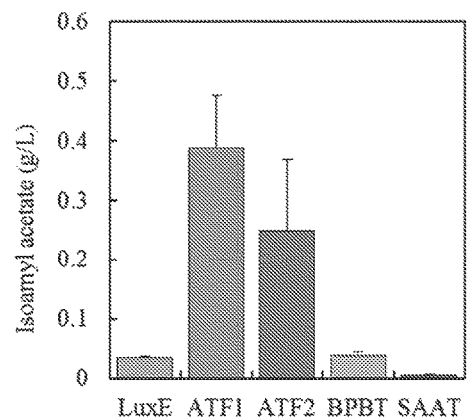

FIG. 6(*a*) provides data for isobutyl acetate production. ATF1 produced the highest titer (2.14±0.17 g/L). ATF2 produced a titer of 1.69±0.46 g/L. FIG. 6(*b*) shows data for the production of isoamyl acetate and reveals a similar trend. ATF1 and ATF2 produced the highest production titers.

Coding regions for any heterologous enzyme introduced into a host cell can be PCR amplified from the genomic DNA of a native host if commercially available (e.g., from American Type Culture Collection). Otherwise, one can artificially synthesize a coding region by PCR assembly using multiple primers. A synthetic coding region can be codon optimized for expression in a host cell such as, for example, *E. coli* or *S. cerevisiae*. Cells transformed with plasmids harboring the coding region for a heterologous enzyme can be cultured in medium that includes carboxylic acid and/or alcohol precursors.

Thus, in one aspect, the invention provides recombinant microbial cell modified to exhibit increased biosynthesis of an ester compared to a wild-type control. In some cases, the wild-type control may be unable to produce ester and, therefore, an increase in the biosynthesis of an ester may reflect any measurable biosynthesis of the ester. In certain embodiments, an increase in the biosynthesis of an ester can include biosynthesis sufficient for a culture of the microbial cell to accumulate the ester to a predetermine concentration.

The predetermined concentration may be any predetermined concentration of the product suitable for a given application. Thus, a predetermined concentration may be, for example, a concentration of at least 3 mg/L such as, for example, at least 10 mg/L, at least 100 mg/L, at least 200 mg/L, at least 500 mg/L, at least 1.0 g/L, at least 2.0 g/L, at least 3.0 g/L, at least 4.0 g/L, at least 5.0 g/L, at least 6.0 g/L, at least 7.0 g/L, at least 8.0 g/L, at least 9.0 g/L, at least 10 g/L, at least 20 g/L, at least 50 g/L, at least 100 g/L, or at least 200 g/L.

The recombinant cell can be, or be derived from, any suitable microbe including, for example, a prokaryotic microbe or a eukaryotic microbe. As used herein, the term "or derived from" in connection with a microbe simply allows for the "host cell" to possess one or more genetic modifications before being further modified to exhibit the indicated increased biosynthetic activity. Thus, the term "recombinant cell" encompasses a "host cell" that may contain nucleic acid material from more than one species before being modified to exhibit the indicated biosynthetic activity.

In some embodiments, the host cell may be selected to possess one or more natural physiological activities. For example, the host cell may be photosynthetic (e.g., cyanobacteria) or may be cellulolytic (e.g., *Clostridium cellulolyticum*).

In some embodiments, the recombinant cell may be, or be derived from, a eukaryotic microbe such as, for example, a fungal cell. In some of these embodiments, the fungal cell may be, or be derived from, a member of the Saccharomycetaceae family such as, for example, *Saccharomyces cerevisiae, Candida rugosa,* or *Candida albicans.*

In other embodiments, the recombinant cell may be, or be derived from, a prokaryotic microbe such as, for example, a bacterium. In some of these embodiments, the bacterium may be a member of the phylum Protobacteria. Exemplary members of the phylum Protobacteria include, for example, members of the Enterobacteriaceae family (e.g., *Escherichia coli*) and, for example, members of the Pseudomonaceae family (e.g., *Pseudomonas putida*). In other cases, the bacterium may be a member of the phylum Firmicutes. Exemplary members of the phylum Firmicutes include, for example, members of the Bacillaceae family (e.g., *Bacillus subtilis*), members of the Clostridiaceae family (e.g., *Clostridium cellulolyticum*) and, for example, members of the Streptococcaceae family (e.g., *Lactococcus lactis*). In other cases, the bacterium may be a member of the phylum Cyanobacteria.

In some embodiments, the increased biosynthesis of an ester compared to a wild-type control can include one or more of the following: an increase in conversion of an organic acid to an acyl-CoA compared to a wild-type control, an increase in conversion of ketoacids to an acyl-CoA compared to a wild-type control, an increase in conversion of an aldehyde to an organic acid compared to a wild-type control, an increase in conversion of an aldehyde to an alcohol compared to a wild-type control, or an increase in combining an acyl-CoA with an alcohol to form an ester compared to a wild-type control. The particular acyl-CoA synthetase, branched-chain keto acid dehydrogenase (BKDH) complex enzyme(s), and/or acyltransferase can be selected based on one or more criteria such as, for example, the metabolic substrate in the designed pathway, the available feedstock, and/or the efficiency at which the enzyme is expressed in the host microbe.

In other embodiments, the increased biosynthesis of an ester compared to a wild-type control can include one or more of the following: an increase in conversion of 2-ketoisovalerate to isobutyraldehyde, and increase in conversion of isobutyraldehyde to isobutanol, an increase in synthesis of isobutyl acetate from isobutanol and an acyl-CoA, an increase in elongation of 2-ketoisovalerate to 2-keto-4-methylvalerate, an increase in conversion of 2-keto-4-methylvalerate to isovaleraldehyde, an increase in conversion of isovaleraldehyde to isopentanol, or an increase in synthesis of isoamyl acetate from isopentanol and an acyl-CoA.

In some cases, increased biosynthesis of an ester compared to a wild-type control can include a decrease in catalytic activity of one or more enzymes such as, for example, an esterase and/or a lipase that can otherwise divert an intermediate of the designed pathway to an alternative pathway that does not result in biosynthesis of the desired ester.

As used herein, the terms "activity" with regard to particular enzyme refers to the ability of a polypeptide, regardless of its common name or native function, to catalyze the conversion of the enzyme's substrate to a product, regardless of whether the "activity" is less than, equal to, or greater than the native activity of the identified enzyme. Methods for measuring the biosynthetic activities of cells and enzymatic activities of acyl-CoA synthetase and acyltransferase are routine and well known to those of ordinary skill in the art. In the context of a genetically-modified cell, the term "activity" refers to the ability of the genetically-modified cell to synthesize an identified product compound, regardless of whether the "activity" is less than, equal to, or greater than the native activity of a wild-type strain of the cell.

As used herein, an increase in catalytic activity of an enzyme or an increase in the biosynthetic activity of a genetically-modified cell can be quantitatively measured and described as a percentage of the catalytic activity of an appropriate wild-type control. The catalytic activity exhibited by a genetically-modified polypeptide or the biosynthetic activity of a genetically-modified cell can be, for example, at least 110%, at least 125%, at least 150%, at least 175%, at least 200% (two-fold), at least 250%, at least 300% (three-fold), at least 400% (four-fold), at least 500% (five-fold), at least 600% (six-fold), at least 700% (seven-fold), at least 800% (eight-fold), at least 900% (nine-fold), at least 1000% (10-fold), at least 2000% (20-fold), at least 3000% (30-fold), at least 4000% (40-fold), at least 5000% (50-fold), at least 6000% (60-fold), at least 7000% (70-fold), at least 8000% (80-fold), at least 9000% (90-fold), at least 10,000% (100-fold), or at least 100,000% (1000-fold) of the activity of an appropriate wild-type control.

Alternatively, an increase in catalytic activity may be expressed as at an increase in $k_{cat}$ such as, for example, at least a two-fold increase, at least a three-fold increase, at least a four-fold increase, at least a five-fold increase, at least a six-fold increase, at least a seven-fold increase, at least an eight-fold increase, at least a nine-fold increase, at least a 10-fold increase, at least a 15-fold increase, or at least a 20-fold increase in the $K_{cat}$ value of the enzymatic conversion.

An increase in catalytic activity also may be expressed in terms of a decrease in $K_m$ such as, for example, at least a two-fold decrease, at least a three-fold decrease, at least a four-fold decrease, at least a five-fold decrease, at least a six-fold decrease, at least a seven-fold decrease, at least an eight-fold decrease, at least a nine-fold decrease, at least a 10-fold decrease, at least a 15-fold decrease, or at least a 20-fold decrease in the $K_m$ value of the enzymatic conversion.

A decrease in catalytic activity of an enzyme or an increase in the biosynthetic activity of a genetically-modified cell can be quantitatively measured and described as a percentage of the catalytic activity of an appropriate wild-type control. The catalytic activity exhibited by a genetically-modified polypeptide or the biosynthetic activity of a genetically-modified cell can be, for example, no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, no more than 5%, no more than 4%, no more than 3%, no more than 2%, no more than 1% of the activity, or 0% of the activity of a suitable wild-type control.

Alternatively, a decrease in catalytic activity can be expressed as a decrease in $k_{cat}$ such as, for example, at least a two-fold decrease, at least a three-fold decrease, at least a four-fold decrease, at least a five-fold decrease, at least a six-fold decrease, at least a seven-fold decrease, at least an eight-fold decrease, at least a nine-fold decrease, at least a 10-fold decrease, at least a 15-fold decrease, or at least a 20-fold decrease in the $k_{cat}$ value of the enzymatic conversion.

A decrease in catalytic activity also may be expressed in terms of an increase in $K_m$ such as, for example, an increase in $K_m$ of at least two-fold, at least three-fold, at least four-fold, at least five-fold, at least six-fold, at least seven-fold, at least an eight-fold, at least nine-fold, at least 10-fold, at least 15-fold, at least 20-fold, at least 25-fold, at least 30-fold, at least 35-fold, at least 40-fold, at least 45-fold, at least 50-fold, at least 75-fold, at least 100-fold, at least 150-fold, at least 200-fold, at least 230-fold, at least 250-fold, at least 300-fold, at least 350-fold, or at least 400-fold.

Thus, in another aspect, we describe herein methods for biosynthesis of an ester. The ester may be any desired ester. As noted above, the ester may be used as a biofuel, an industrial chemical, or a raw material for the production of other compounds. Our approach can be used to prepare an ester from combining any organic acid—e.g., the exemplary organic acids identified in FIG. 1(b)—with any alcohol—e.g., the exemplary alcohols identified in FIG. 1(b). The combination of any of these acids and any of these alcohols could generate an ester metabolite. In various applications, the organic acid, the alcohol, or both may be synthesized by the cell. In some of these embodiments, the cell may be genetically modified to promote the biosynthesis of the organic acid or the alcohol. Also in various applications, the organic acid or the alcohol may be provided in culture medium so that its biosynthesis is unnecessary to produce the ester.

In some cases, the ester can be an ester having no more than 12 carbon atoms (C12) such as, for example, a C11 ester, a C10 ester, a C9 ester, a C8 ester, a C7 ester, a C6 ester, a C5 ester, a C4 ester, or a C3 ester. In other cases, the ester can be an ester having any number of carbons and a predetermined degree of branching. The degree of branching may be characterized by the number of branched carbons and/or the length of one or more—or, cumulatively, all—of the branches. As used herein, branching refers to the number of carbons that are covalently bound to at least three other carbons. In certain specific embodiments, the ester can be, for example, isobutyl isobutyrate, isovaleryl isovalerate, or ethyl lactate.

Generally, the methods include incubating a recombinant cell as described herein in medium that includes a carbon source under conditions effective for the recombinant cell to produce the ester. Thus, the carbon source can include one or more of: glucose, pyruvate, or ketovaline. In addition, the carbon sources for cell growth can be $CO_2$, cellulose, glucose, xylose, sucrose, arabinose, glycerol, alginate, glucarate, galacturonate, etc. as long as the related carbon assimilation pathways are introduced in the engineered microbe. Also, the carbon source can include the organic acid—or a metabolic precursor of the organic acid—to be activated to produced the desired ester. In the exemplary pathway shown in FIG. 2, the organic acid is isobutyric acid. In other pathways in which the ester is formed from a different organic acid, the different organic acid may be a component of the culture medium. Similarly, the carbon source can include the alcohol—or a metabolic precursor of the alcohol—from which the desired ester is synthesized. In the exemplary pathway shown in FIG. 2, the alcohol is isobutanol and metabolic precursors include, for example, isobutyraldehyde and ketovaline. In pathways in which the ester is formed from a different alcohol, the different alcohol and/or precursors to the different alcohol may be components of the culture medium.

As noted above, the ester may be the desired end product or may be used as a precursor to produce another compound. In some cases, the ester may be hydrolyzed to the alcohol and organic acid from which it was biosynthesized. In this way, one can use the platform described herein to produce greater amounts of an alcohol and/or organic acid than can be accumulated if the alcohol and/or organic acid is the fermentation end product. The ester may be biosynthesized and recovered from aqueous culture by phase separation—a process that can be simpler, more efficient, and/or less costly than recovery of an alcohol and/or an organic acid form an aqueous medium by, for example, distillation. The recovered ester can be hydrolyzed in a controlled volume of water, in most cases without any additional enzymatic or activating treatment, to yield the constituent alcohol and organic acid.

In yet another aspect, we describe herein methods for introducing a heterologous polynucleotide into cell so that the host cell exhibits an increased ability to convert a carbon source to an ester. The heterologous polynucleotide can encode a polypeptide operably linked to a promoter so that the modified cell catalyzes conversion of the carbon source to an ester. In some of these embodiments, the carbon source can include one or more of glucose, pyruvate, ketovaline, and organic acid (or precursor thereof), or an alcohol (or precursor thereof). The host cells for such methods can include, for example, any of the microbial species identified above with regard to the recombinant cells described herein.

As used in the preceding description, the term "and/or" means one or all of the listed elements or a combination of any two or more of the listed elements; the term "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiment can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Plasmid Construction

BKDH enzyme complex coding regions and fadDX were amplified from *Pseudomonas Putida* KT2440 genomic DNA with primers bkdh_ecofwd (TgcatcgaattcAGGA-GAAATT AACTatgAACGAGTACGCCC CCCT-GCGTTTGC, SEQ ID NO:1) and bkdh_hindrev (Tgcatc aagcttTCAGATATGCAAGGCGTGGCCCAG, SEQ ID NO:2), fadDXsalI-F (tgtacggtat taatgtcgac AGGAGAAAT-TAACTATGCTTCAACTCCAAAAACAAGAAAC, SEQ ID NO:3) and fadDXbam-R (TGATCATGCGCCATAGT-TAATTTCTCCTGGATCCTTAGACGC TGGCA-GGGGTGGCCTGTT, SEQ ID NO:4), respectively. The PCR product of BKDH was then digestion with EcoRI and HindIII, and inserted into pZE12 to make pIBA16. To construct plasmid pESTER1, the coding region of BEBT from *Clarkia breweri* was synthesized by DNAworks (Hoover and Lubkowski, Nucleic Acids Res 2002, 30 (10), e43), and then the linear plasmid of pIBA7 was obtained after XbaI digestion. Finally, the plasmid of pESTER1 was formed after combination of fadDX, BEBT, and linear pIBA7 by as described in Gibson et al., Nat Meth 2009, 6(5):343-345. The BEBT coding region, digested with Acc65I and HindIII, was inserted into the corresponding site of pZS plasmid, to form plasmid pESTER2.

Fermentation Results

E. coli host BW25113 was used for fermentation. One strain Ester 1 was BW25113 transformed with pIBA1 (International Patent Publication No. WO 2012/109534) and pESTER1, and the other strain Ester 2 was BW25113 transformed with pIBA1, pIBA16 and pESTER2.

Overnight cultures incubated in LB medium were diluted 25-fold into 5 mL M9 medium supplemented with 0.5% yeast extract and 4% glucose in 125-mL conical flasks. Antibiotics were added appropriately (ampicillin 100 mg/L and kanamycin 25 mg/L). 0.1 mM isopropyl-b-D-thiogalactoside (IPTG) was added to induce protein expression. The culture medium was buffered by adding 0.5 g $CaCO_3$. Cultures were placed in a 30° C. shaker (250 rpm) and incubated for 48 hours. Fermentation products were quantified by HPLC or GC analysis. Results are shown in FIG. 2(b).

Example 2

Acyltransferases LuxE, ATF1, ATF2, BPBT, and SAAT were amplified from *Clarkia breweri* with primers:

```
luxEalsS-F
(gaaaacgaaagctctctaa GCTGAGCAGG AGAAATTAAC
TATGGCGCAT GATCAGAGCCT, SEQ ID NO: 81)
and luxEvec-R
(agcctttcgttttatttgatgcctctaga GCTCAGCTTA
CAGGCTGCTC TGGGTGAAATG, SEQ ID NO: 82)
from S. cerevisiae;

ATF1alsS-F
(cgaaagctctctaa GCTGAGCAGG AGAAATTAAC
TATGAATGAA ATCGATGAGAAAAATC, SEQ ID NO: 83)
and ATF1vec-R
(agcctttcgttttatttgatgcctctaga GCTCAGCTTA
AGGGCCTAAA AGGAGAGCTTT, SEQ ID NO: 84)
from S. cerevisiae;

ATF2alsS-F
(cgaaagctctctaa GCTGAGCAGG AGAAATTAAC
TATGGAAGAT ATAGAAGGAT ACGAAC, SEQ ID NO: 85)
and ATF2vec-R
(cctttcgttttatttgatgcctctaga GCTCAGCTTA
AAGCGACGCA AATTCGCCGA TGG, SEQ ID NO: 86)
from P. hybrida;

BPBTalsS-F
(aaacgaaagctctctaa GCTGAGCAGG AGAAATTAAC
TATGGACAGC AAACAGAGCA GCG, SEQ ID NO: 87)
and BPBTvec-R
(cctttcgttttatttgatgcctctaga GCTCAGCTTA
AAGCGCTGGG GTGATGAACG CAT, SEQ ID NO: 88)
from Strawberry;
and SAATalsS-F
(aaacgaaagctctctaa GCTGAGCAGG AGAAATTAAC
TATGGAGAAA ATAGAAGTGA GCA, SEQ ID NO: 89)
and SAATvec-R
(cctttcgttttatttgatgcctctaga GCTCAGCTTA
GATCAGCGTC TTTGGACTCG CCA,, SEQ ID NO: 90)
from Strawberry.
```

The different acyltransferases were ligated with BlpI digested plasmids of pIBA1 (International Patent Publication No. WO 2012/109534) and pIVC1 (Xiong et al. Sci Rep 2012, 2:311) as described in Gibson et al., Nat Meth 2009, 6(5):343-345, to form plasmids of pZA-ilvD-alsS-LuxE, pZA-ilvD-alsS-ATF1, pZA-ilvD-alsS-ATF2, pZA-ilvD-alsS-BTBT, pZA-ilvD-alsS-SAAT, pZA-leuABCD-ilvD-alsS-LuxE, pZA-leuABCD-ilvD-alsS-ATF1, pZA-leuABCD-ilvD-alsS-ATF2, pZA-leuABCD-ilvD-alsS-BTBT and pZA-leuABCD-ilvD-alsS-SAAT, respectively. To construct plasmid of pZE-KivD-yqhD, yqhD was PCR amplified with primers yqhDSphI-F (GGGCCCgcatgc AGGAGAAATT AACTATGAAC AACTTTAATC TGCA-CACCCC, SEQ ID NO:91) and yqhDXbaI-R (GGGC-CCtctaga TTAGCGGGCG GCTTCGTATA TACGGC, SEQ ID NO:92), and then replaced the padA of plasmid pIBA7 (International Patent Publication No. WO 2012/109534) to form pZE-KivD-yqhD.

Fermentation Results

Shake flask fermentations were carried out for the recombinant strains. Cells were inoculated in test tubes overnight and 200 µL cells were transferred into 10 mL of fermentation medium in a 150-mL screw-cap conical flask. Fermentation medium consisted of 20 g/L glucose in M9 minimum medium (5 g/L yeast extract) supplemented with thiamine (10 mg/L), ampicillin (100 µg/mL), kanamycin (25 µg mL), and 0.5 g calcium carbonate for neutralization. Protein expression was induced by addition of 0.1 mM isopropyl-β-D-1-thiogalactoside (IPTG). Flasks were sealed with Parafilm before fermentations started to create a micoraerobic environment. Samples were collected after incubation at 30° C. on a rotary shaker (250 r.p.m.) for 48 hours. The produced medium-chain ester compounds were quantified by GC-FID (gas chromatography-flame ionization detector) analysis. Their byproducts and remaining glucose were identified by HPLC-RID (high-performance liquid chromatography-refractive index detector) analysis. Results are shown in FIG. 6.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

| Sequence Listing Free Text |
|---|

SEQ ID NO: 1

Tgcatc gaattc AGGAGAAATT AACTatg AACGAGTACGCCC CCCTGCGTTTGC

SEQ ID NO: 2

Tgcatc aagctt TCAGATATGCAAGGCGTGGC CCAG

SEQ ID NO: 3 tgtacggtat taatgtcgac AGGAGAAATT AACTATGCTT CAACTCCAAA AACAAGAAAC

SEQ ID NO: 4

TGATCATGCGCCATAGTTAATTTCTCCTGGATCCTTAGACGC TGGCAGGGGTGGCCTGTT

GI:26991173, Protein name: acetyl-CoA synthetase ACS_ [*Pseudomonas putida* KT2440]

SEQ ID NO: 5

```
  1   msaaplypvr pevaattltd eatykamyqq svinpdgfwr eqagridwik
      pftkvkqtsf 61   ddhhvdikwf adgtlnvssn cldrhleerg dqlaiiwegd dpsehrnity
      relheqvckf 121   analrgqdvh rgdvvtiymp mipeavvaml acarigaihs vvfggfspea
      lagriidcks 181   kvvitadegv rggrrtplka nvdlaltnpe tssvgkiivc krtggdiawh
      qhrdiwyedl 241   mkvasshcap kemgaeealf ilytsgstgk pkgvlhttgg ylvyaalthe
      rvfdyrpgev 301   ywctadvgwv tghsyivygp langattllf egvpnypdit rvskivdkhk
      vnilytapta 361   irammaegqa avegadgssl rllgsvgepi npeawnwyyk tvgkercpiv
      dtwwqtetgg 421   ilisplpgat glkpgsatrp ffgvvpalvd nlgnlidgaa egnlvildsw
      pgqsrslygd 481   hdrfvdtyfk tfrgmyftgd garrdedgyy witgrvddvl nvsghrmgta
      eiesamvahs 541   kvaeaavvgv phdikgqgiy vyvtlnagie aseqlrlelk nwvrkeigpi
      aspdviqwap 601   glpktrsgki mrrilrkiat geydalgdis tladpgvvqh lidthkamnl
      asa
```

GI:260770658, Protein name: acetyl-CoA synthetase [*Vibrio fumissii* CIP 102972]

SEQ ID NO: 6

```
  1   mseahiypvk enikahthad detylamyqq sysdpegfws ehgkivdwmk
      pftqvkhtsf 61   dtghvdirwf edgtlnvsan cidrhlaerg ddvaiiwegd dpaddktltf
      nelhrdvcrf 121   snalkaqgvr kgdvvclymp mvpeaavaml actrigavht vvfggfspea
      lagriidsds 181   kvvitadegv rggravplkk nvdealtnpe vktiskvivf krtggevawh
      ehrdvwwhda
```

| | |
|---|---|
| 241 | vaaasdvcpp eemnaedplf ilytsgstgk pkgvlhttgg ylvyatmtfk yvfdyqpget |
| 301 | fwctadvgwi tghtyliygp lsngaktilf egvpnypsta rmsevvdkhq vnilytapta |
| 361 | iralmakgde avkgtsrssl rimgsvgepi npeawewyyk tignekspiv dtwwqtetgg |
| 421 | ilitplpgat alkpgsatrp ffgvqpalvd nmgevidgaa egnlvildsw pgqmrtvygd |
| 481 | herfeqtyfs tfkgmyftgd garrdedgyy witgrvddvl nvsghrmgta eiesalvafd |
| 541 | kiaeaavvgv phdikgqaiy ayitlndgvy psaelhkevk dwvrkeigpi atpdvlhwtd |
| 601 | alpktrsgki mrrilrkiat gdtgnlgdts tladpsvvdk liaekaqlv |

GI:167623628, Protein name: acetyl-CoA synthetase
[*Shewanella halifaxensis* HAW-EB4]

SEQ ID NO: 7

| | |
|---|---|
| 1 | mstqslykvp seiaanalvn degykkmyge sivnpegfwr ehgnridwik pftkvkktsf |
| 61 | ddhnlfikwf ydgtlnasan cldrhlenna dklaiiwegd dakdqrtlty gqlhtqvckf |
| 121 | analrsqgvr rgdvvtiymp mvpeaavaml acarigaihs vvfggfspds iasrvidgns |
| 181 | kvvitadegv ragriiplka nidealshpd vncvekvivm krtggdinwv egrdiwwdsl |
| 241 | mdtasehcia eemgaedplf llytsgstgn pkgvlhttgg ymvyaamthe yvfdykenev |
| 301 | ywctadvgwi tghsymvygp langatvlih egvpnypspa rlgemvdrhk vnilytaptl |
| 361 | iralmaegke qfagfdgssl rimgsvgepi npeawrwynd vighekcpiv dtwwqtetgg |
| 421 | ilitplpgat dtkpgsatrp ffgvqpalvd nmgnivdgas egnlvildsw pgqmrtvfgd |
| 481 | hdrfvltyfk tfrgmyftgd gakrdedgyy witgrvddvi nvsghrlgta evesalvahe |
| 541 | fvaeaavvgy phdikgqgiy ayvtltkgsv eteelrgelr qwvrkeigal atpdliqwag |
| 601 | glpktrsgki mrrflrkiaa nevsnlgdss tladpavidt lietrinrse |

GI:330830937, Protein name: acetyl-CoA synthetase
[*Aeromonas veronii* B565]

SEQ ID NO: 8

| | |
|---|---|
| 1 | mstqslykvp seiaanalvn degykkmyge sivnpegfwr ehgnridwik pftkvkktsf |
| 61 | ddhnlfikwf ydgtlnasan cldrhlenna dklaiiwegd dakdqrtlty gqlhtqvckf |
| 121 | analrsqgvr rgdvvtiymp mvpeaavaml acarigaihs vvfggfspds iasrvidgns |
| 181 | kvvitadegv ragriiplka nidealshpd vncvekvivm krtggdinwv egrdiwwdsl |
| 241 | mdtasehcia eemgaedplf llytsgstgn pkgvlhttgg ymvyaamthe yvfdykenev |
| 301 | ywctadvgwi tghsymvygp langatvlih egvpnypspa rlgemvdrhk vnilytaptl |

Sequence Listing Free Text -continued

```
361    iralmaegke gfagfdgssl rvmgsvgepi npeawrwynd vighekcpiv
       dtwwqtetgg 421    ilisplpgat dtkpgsatrp ffgvqpalvd nmgnivdgas egnlvildsw
       pgqmrtvfgd 481    hdrfvltyfk tfrgmyftgd gakrdedgyy witgrvddvi nvsghrlgta
       evesalvahe 541    fvaeaavvgy phdikgqgiy ayvtltkgsv eteelrgelr qwvrkeigal
       atpdliqwag 601    glpktrsgki mrrflrkiaa nevsnlgdss tladpavidt lietrinrse
```

GI:209696237, Protein name: acetyl-CoA synthetase
[*Aliivibrio salmonicida* LFI1238]

SEQ ID NO: 9

```
  1    msdihvypvn qdiaknahad edkyremyqq svinpegfwr ehgqivdwmt
       pytkvkntsf 61    dtghvdikwf edgelnvsan cidrhlaarg devaiiwegd dpqddasitf
       nelheqvckf 121    snalksqgvr kgdvvciymp mvaeaaiaml actrigavht vvfggfspea
       lagrivdsda 181    kvvitadegv rggrtvplkk nvddalnnpe vttiekvvvf qrtgndidwn
       eerdvwwhea 241    tavasahcep eamnaedplf ilytsgstgk pkgvlhttgg ylvyaamtfk
       yifdygegev 301    fwctadvgwi tghtyliygp langaktilf egvpnypsts rmsevvdkhn
       vnilytapta 361    iralmahgnd avegtsrssl rvmgsvgepi npeawewyyn tigdarcpiv
       dtwwqtetgg 421    ilisplpgat alkpgsatrp ffgvqpalvd nmgnliegaa dgnlvitdsw
       pgqmrtiygd 481    hdrfeqtyfs tfkgmyftsd garrdedgyy witgrvddvl nvsghrmgta
       evesalvsfs 541    kiaeaaivgv phdikggaiy ayitlnsgey psaelhkevk dwvrkeigpi
       atpdflhwtd 601    slpktrsgki mrrilrkiat gdtsnlgdts tladpsvvnk lieegrkia
```

GI:54310469, Protein name: acetyl-CoA synthetase
[*Photobacterium profundum* SS9]

SEQ ID NO: 10

```
  1    msevhvypvn qeiaatahvn degyremyqg svinpegfwr ehgqivdwik
       pftkvkhtsf 61    dtghvsvkwf edgtlnvsan cidrhlatrg dqpaiiwegd dptddatfty
       nelheqvckf 121    snalksqgvr kgdvvclymp mvaeaaiaml actrigavht ivfggfspea
       lagrivdsna 181    klvitadegv ragravplkk nvddalankn vtsiekvivl krtggnvewh
       serdvwwhea 241    tavasshcep eemnaedplf ilytsgstgk pkgvlhttgg ylvyatmtfk
       yvfdygegdv 301    ywctadvgwi tghsylvygp langattvlf egvpnypsts rmsevvdkhn
       vsilytapta 361    iralmakgte aikgtsrssl rimgsvgepi npeawewyhh tigdsrcpiv
       dtwwqtetgg 421    ilitplpgat alkpgsatrp ffgvqpaivd nmgnilegva egnlvmvdsw
       pgqmrtlwgd
```

| | |
|---|---|
| 481 | herfeqtyfs tfqgmyftgd garrdedgyy witgrvddvl nisghrmgta eiesalvafd |
| 541 | kiaeaaivgv phdikgqaiy ayitlndgei psaelhkevk dwvrkeigpi atpdflhwtd |
| 601 | alpktrsgki mrrilrkiat gdtgslgdts tladpsvvdk liaekqtil |

GI:6320852, Protein name: acetyl-CoA synthetase Faa2p
[S. cerevisiae]

SEQ ID NO: 11

| | |
|---|---|
| 1 | maapdyaltd liesdprfes lktrlagytk gsdeyieely sqlpltsypr yktflkkqav |
| 61 | aisnpdneag fssiyrssls senlvscvdk nlrtaydhfm fsarrwpqrd clgsrpidka |
| 121 | tgtweetfrf esystvskrc hnigsgilsl vntkrkrple andfvvails hnnpewiltd |
| 181 | lacqaysltn talyetlgpn tseyilnite apilifaksn myhvlkmvpd mkfvntivcm |
| 241 | delthdelrm lnesllpvkc nslnekitff sleqveqvgc fnkipaippt pdslytisft |
| 301 | sgttglpkgv emshrniasg iafafstfri ppdkrnqqly dmcflplahi fermviaydl |
| 361 | aigfgigflh kpdptvlved lkilkpyava lvpriltrfe agiknaldks tvqrnvanti |
| 421 | ldsksarfta rggpdksimn flvyhrvlid kirdslglsn nsfiitgsap iskdtllflr |
| 481 | saldigirqg ygltetfagv clsepfekdv gscgaigisa ecrlksvpem gyhadkdlkg |
| 541 | elqirgpqvf eryfknpnet skavdqdgwf stgdvafidg kgrisvidry knffklahge |
| 601 | yiapekieni ylsscpyitq ifvfgdplkt flvgivgvdv daaqpilaak hpevktwtke |
| 661 | vlvenlnrnk klrkeflnki nkctdglqgf eklhnikvgl epltleddvv tptfkikrak |
| 721 | askffkdtld qlyaegslvk tekl |

GI:255717016, Protein name: acetyl-CoA synthetase
[Lachancea thermotolerans]

SEQ ID NO: 12

| | |
|---|---|
| 1 | mskqdgyisl selietdkrf qnlreelavy dknskeylsn lisklpltnh vsyrqflkeq |
| 61 | ayslesskkh gyspvfrssl speclvsnvh prlstffelf nfsverfpdn dclgqrsqdr |
| 121 | vtghwgqhye fesyreiger sqnlgsgimt vvnlkrkrrf gsndfivsfl stnrkewvis |
| 181 | dlacqgyslg ntalyetlgl dtseyilnvt espvlilske niyrvmemvp klphlstivc |
| 241 | mdelsdlela qlngpllpqh tnskgerisi lnfrqverig asnkvplipp tpdslytisf |
| 301 | tsgttgtpkg vqmkqshvaa avafvlstlr mprlkhrsqa ydlcflplah iferqivafd |
| 361 | lssgtaigfl hkpdpsvlve dlkllkpdvf psvpriltkf eagiknslqn gdgsavtknv |
| 421 | astilnkrle rtthhggkdh silntvvfhr vlidkirssl glenldvvit gsapisndtl |

| Sequence Listing Free Text |
|---|

| 481 | lfmksaldcg vrqgygltet fagiclsear erdsgtcggm avttecrlrs ipemgydaeh |
| 541 | dlkgevqlrg sqvfrgyykn pqetsralge dgwystgdvg fidskgrlsi idrvknffkl |
| 601 | aggeyiapek iesvylsscp yltqisvhgd slqtflvavi gleldtapi ihkkipelrg |
| 661 | fsgkdlvdei nksrahrkal ivlinsfieg lqgfekihnl yvgieplkvt ddtitptlkv |
| 721 | kranaakhfr kilenlyeeg slikvekl |

GI:45187925, Protein name: acetyl-CoA synthetase
[*Ashbya gossypii* ATCC 10895]

SEQ ID NO: 13

| 1 | msnetevnry pgmgpislve virtdarfae lwkrlslfqg gsvefykely dnmplfagmd |
| 61 | gmalsapvpg sgkkgyspvf rnvlvpegkl lsaidegvdt gyhvfklsar mypdnhclgm |
| 121 | raydeatgkw ldeyrwetys qverraenlg aglvvvnvk rskpldtndf ivammsansk |
| 181 | ewvltdlacq tfslvntaly etlgpntsey imnitespvv vvskpnllri falasklral |
| 241 | ntivimddmd lgevdrlasl lpvtknakge tisvltlrqv ekigelnnia pippspdsfh |
| 301 | tisftsgtts lpkgvqlthr aycaalafac shvrcepnkq ryalcllplt hiyqrqmtgl |
| 361 | nlmhafgigf lhkpnpdlfi eamcvlrpam vslvprvltk leagiknsiq gadvstfkrk |
| 421 | laktvidakd krfsaysgpd dsymnrfiyr kifvdkirdk lgftnvplvt tgsapispet |
| 481 | lrfiqcamdi gilqgyglte tfggnflsvp yetdcgscgp pamttevrlr dvpgmsynae |
| 541 | kdhmgevvvr sqqqferyyk mpektaevld kdgwfstgdv gyidkkgrlf itdrvknifk |
| 601 | lsqgeyiape kvencylssc pfitqifvhg nslnnylvgv vgidvvpfka ildsrtskws |
| 661 | klpleevipt inkdpalkql tlkiinsfvt aelqgfekig nlyadvepls vdgetltptf |
| 721 | kvkrevctkv fkdilsslyd eghilkagkl |

GI:380351855, Protein name: acetyl-CoA synthetase
[*Candida orthopsilosis*]

SEQ ID NO: 14

| 1 | maslfnekpe hiwktitesf pldqsvtsra lplpnsevpg fspiyrnays qkelktvpyp |
| 61 | gittlhdtfe lsvannghkr alghrvkkad gsfgeyvwqd yktvqqrrnn lgsgiffvlq |
| 121 | nnpyktdsea hkklkydpls ddsfvltifa hnrpewvlad vtstaysitn talydtlgpd |
| 181 | tskyilnite cpiilcskdk vkslvelkeq npeelsnlic lvsmddltte davlknychd |
| 241 | hnislfdykq veklgeinpl apippkpetk fsitftsgtt ganpkgvllt hetavagitf |
| 301 | vysgitlpra davfysflpl ahiyerggih faltygaaig fpcopspltl lediqvlepd |

TABLE-continued

Sequence Listing Free Text

```
361    ylalvprvlt kleagikaqt inndekpilk slftkaintk lalqsnpane
       ntnpshllyd 421    rvlgllrkkl gmknlkiims gsapispetl kflkaslntg vgvvygmset
       fagvmasstf 481    etdasscgpi svttecktrd lpamgytskd eggprgellv rgpqifleyy
       knpeetaksf 541    dedgwfytgd varidsktgr tyiidrvknf fklaggeyvt perientyls
       cfpyiaqlfv 601    hgdslrthlv gvvgvdpasi tgyikgrhge titdaadlvr ffqdpkrkre
       llvdmnaslg 661    nklqgfeklh nievdvepls veknlitptm kikrpictky fkdtldklye
       egslirndkl
```

GI:126136683,Protein name: acetyl-CoA synthetase
[*Scheffersomyces stipitis* CBS 6054]

SEQ ID NO: 15

```
  1    mslfqedpkn ihnfiraslp ldpkklcesv plpysekpgy savyrnkysv
       dglitrphps 61    latlfdlhev aarsqpdspc fgvrhkqadg tygpyqwiny qevydrkvhf
       gsgvffilqn 121    npyrtnspvh qkihydpqat espfvlsifs anraewvttd macsayslts
       talydslgaq 181    tskyilsste spivvsskdk lksliklkae dpetlsnlit lvsmdpldpk
       tdealvkyan 241    dnritlfdfd qvlklgeink lpqippkpet iytisftsgt tganpkgvll
       thanavcavt 301    fcysnitlpe sptvycflpl ahiyermsis falsmcaaig fpgspspltl
       mddikhlrph 361    flnlvprvyt kleaalkaqt fnsdkpiiks lfsaainkkm elqavedgaq
       gkhivydqvv 421    qllrkkigfd rliavttgsa pispetlkfi kaslntgmsq gygltesfag
       vctslkyean 481    pgscgaisit temrlrevpe mnyhandkgg prgelmlrgp qifreyfknp
       eetakaidse 541    gwfatgdiar idatngnriy iidrvknffk laqgeyitpe kientylsqf
       pfiqqlyvhg 601    dplkthlvai vgldpatvds yikrkfndil snqddivdff rnpkhrlall
       edmnssvggl 661    lggyerihni kvdfnpltie dnvitptlki krpiavkffk edfdalyeeg
       slikpdahkl
```

GI:294656605, Protein name: acetyl-CoA synthetase
[*Debaryomyces hansenii* CBS767]

SEQ ID NO: 16

```
  1    mtssdvydhg dspyvfkpsk tpasqlirdh lplpekmfkd syslpgteke
       gysaiyrnkm 61    fpgrlkealt peldtyyrlf knsvltfgdk sclayrkydy vnkksaddys
       fltyrevdem 121    kqrygsgfly llqnnpfkns ekfeshrkid nhvkdyknfd isdmsfvati
       ysanrmewvl 181    sdlmcssysi tntalydtlg adtseyilqt tqspvviatk ehvmdivnlk
       ekypeklehv 241    isiveldpld lknetslsae dqalvtacks hritivdinq vmkvgeifpt
       pelppspetl
```

```
301    ytisftsgtt  gahpkgvlls  qkictagvtf  vltqlpripd  arsfsflpla
       hiferqvcaf 361    glscgncigf  pqnggtpltl  iedlklfkpn  ymcnvprvft  kyeaaiksat
       vdhptstfkr 421    gifdkvistk  igagekydga  dgshlvydrl  flssirkafg  fdnmefivtg
       sapispstvk 481    flkaticvgm  pqgygstesf  agfaigipye  aepgscgsvg  vtvemklrel
       pamgynlddp 541    egprgelllr  gpgifkqyfh  neeetkksfd  degwfhtgdv  arfsknngrl
       fiidrvknff 601    klsvveyvtp  ekvenkylss  ssilnglyvh  gdslrhflvg  ivgidpegav
       nflvekckvs 661    ksqlssseqi  lneinkkenr  ellvayinsr  isnqlsgfek  lhniyvefep
       lrldrdvvta 721    tqklkrpvaf  kffkpaidvm  ydegslvkgp  kl
```

GI:6319264, Protein name: Acs1p
[*Saccharomyces cerevisiae* S288c]

SEQ ID NO: 17

```
  1    mspsavqssk  leegsseidk  lkakmsqsaa  taqqkkehey  ehltsvkivp
       grpisdrlqp 61    aiathysphl  dglqdyqrlh  kesiedpakf  fgskatqfln  wskpfdkvfi
       pdpktgrpsf 121    qnnawflngq  lnacyncvdr  halktpnkka  iifegdepgq  gysitykell
       eevcqvaqvl 181    tysmgvrkgd  tvavympmvp  eaiitllais  rigaihsvvf  agfssnslrd
       rindgdskvv 241    ittdesnrgg  kvietkrivd  dalretpgvr  hvlvyrktnn  psvafhaprd
       ldwatekkky 301    ktyypctpvd  sedplfllyt  sgstgapkgv  qhstagyllg  alltmrytfd
       thqedvffta 361    gdigwitght  yvvygpllyg  cativfegtp  aypnysrywd  iidehkvtqf
       yvaptalrll 421    kragdsyien  hslkslrclg  svgepiaaev  wewysekigk  neipivdtyw
       qtesgshlvt 481    plaggvtpmk  pgsasfpffg  idavvldpnt  geelntshae  gvlavkaawp
       sfartiwknh 541    dryldtylnp  ypgyyftgdg  aakdkdgyiw  ilgrvddvvn  vsghrlstae
       ieaaiiedpi 601    vaecavvgfn  ddleggavaa  fvvlknkssw  statddelqd  ikkhlvftvr
       kdigpfaapk 661    liilvddlpk  trsgkimrri  lrkilagesd  qlgdvstlsn  pgivrhlids
       vkl
```

GI:254579411, Protein name: ZYRO0C00682p
[*Zygosaccharomyces rouxii*]

SEQ ID NO: 18

```
  1    mtvnyvyagm  wrnlfpesic  rlrdkrkehi  pysmspstta  tgtsptggti
       gdlkarlvha 61    aerentspat  tnnvstekdh  eaetntpttd  ydhlisvhtv  qqkpithrlq
       selschycph 121    isgfreyekl  yresidqpse  ffgnkarqfl  nwfkdfdqvf  ipdprtgkps
       lnnnawflng 181    qtnacyncvd  rhaletpdkp  aiiyetdepg  qgytltysel  leqvcqlaqv
       lrysmgvrkg
```

-continued

Sequence Listing Free Text

| | |
|---|---|
| 241 | dtvavympmi pqavislmai arigaihsvv fagfscnslr drindadshv vittdetkrg |
| 301 | gkivetkriv ddalketpgv snvlvyrrtn nprvprqvsr dldwdgelrk ykgycpcepv |
| 361 | dsehplflly tsgstgtpkg vqhstagyll salltmrysf dthredvfft agdvgwitgh |
| 421 | tyvvygplly gcttivfegt payptyaryw diidqykvtq fyvaptalrl lkragdsfie |
| 481 | ghslqslral gtvgepiaae vwewysekig knelpivdty wqtesgshml tpmaggvtpm |
| 541 | kpgsagfpfi gidscildpt tgqeltkplv egvlavrcgw psfartiwkd hdrfldtylk |
| 601 | pypgyyftgd gaardkdgyi wilgrvddvv nisghrlsta eiesavldda ivaecavvgf |
| 661 | nddltgqava afvvlknkss wstaseeell dikkhlilav rkdigpfaap klivlvddlp |
| 721 | ktrsgkimrr ilrkilagec dqlgdvstls npgvvrhlid svkl |

GI:45188280, Protein name: ADR408Wp
[*Ashbya gossypii* ATCC 10895]

SEQ ID NO: 19

| | |
|---|---|
| 1 | mvtsagvgha eynngadvqh adyahltsvg qveqkplggr lgalaeyykp nvasmeeyra |
| 61 | mhaqsitdpa afygerarty vdwfrpfdav flpgpdgrps fdnnawfvng qlnacynlvd |
| 121 | rhaartpdkv aiiyeadepg egysltyrel laqvckvaqv lqysmgvrkg dtvavympmi |
| 181 | pqalvtllai srigaihsvv fagfscnslr drindarsev vvttdeskrg gkiietkriv |
| 241 | ddaiketpql rkvlvykrtc npsysyvadr dldwdtevkk yksycpcepv dsehplflly |
| 301 | tsgstgapkg vqhstagyll qaylsmlysf dvhsddifft agdigwitgh tyvvygplly |
| 361 | gcttvvfegt paypsysryw diidkysvtq fyvaptalrl lkragdsyvd gyslifirsl |
| 421 | gtvgepiaae vwewyytvig kreipvidty wqtesgahlv tplaggstpm kpgsasfpff |
| 481 | gidlaildpq tgeellgpnv egvlavkqpw psftrtiwnn hdryldtyln pykgyyfagd |
| 541 | gaardsqgfi wilgrvddvv nvsghrlsta eveaaiiges mvaecavvgf adeltgqaia |
| 601 | afvvlkqkss wntaserelq eikkhlilsv rrdigpfaap klivlvddlp ktrsgkimrr |
| 661 | ilrkilagea dqlgdvstls npgivkhlie svkf |

GI:3139035, Protein name: acetyl-CoA synthetase
[*Kluyveromyces lactis*]

SEQ ID NO: 20

| | |
|---|---|
| 1 | mksnasaaaa dqiktheyeh ltsvpivqpl pitdrlssea aqkykpnlpg gfeeykslhk |
| 61 | eslenpakfy heraqllnwf kpydqvfipd tegkptfenn awftngqlna cynlvdrhaf |
| 121 | tqpnkvaily eadepgqgys ltyaelleqv ckvaqilqys mnvkkgdtva vympmipqal |

-continued

| | Sequence Listing Free Text |
|---|---|
| 181 | itllaitrig aihsvvfagf ssnslrdrin daysktvitt deskrggkti etkrivdeal |
| 241 | kdtpgvtnvl vfkrthneni kyipgrdldw deevkkyksy tpcepvdseh plfllytsgs |
| 301 | tgapkgvqhs tagyllqall smkytfdiqn ddifftagdi gwitghtycv ygpllqgctt |
| 361 | lvfegtpayp nfsryweivd kyqvtqfyva ptalrllkra gdsftegfsl kslrslgsvg |
| 421 | epiaaevwew ysekigknel pivdtywqte sgshlvtpla ggatpmkpga aafpffgidl |
| 481 | avldpttgie qtgehaegvl aikrpwpsfa rtiwknndrf ldtylkpypg yyftgdgvar |
| 541 | dkdgffwilg rvddvvnvsg hrlstaeiea aiieddmvae cavvgfndel tgqavaafvv |
| 601 | lknkssltaa seselqdikk hliitvrkdi gpfaapkliv lvddlpktrs gkimrrilrk |
| 661 | ilagesdqla tsphyptivs lst |

GI:320580699, Protein name: Acetyl-coA synthetase isoform
[*Ogataea parapolymorpha* DL-1]

SEQ ID NO: 21

| | |
|---|---|
| 1 | mpekhleneh lmreralepp agflerhpsk pylssldeyk kmyeesirdp gsffggmaeq |
| 61 | hlswfkpftv pkvpnapflk dnngepsawf vdgelnacyn cvdrwaiknp dkpaiiyead |
| 121 | epdggeiity gellkqvckv sqvllnlgvk kgdtvavylp mipeaivtlm aivrigaihs |
| 181 | vvfagfssgs lrdrindans kvvittdesk rggkiietkk ivddallacp qvtnvlvykr |
| 241 | tgnshipwte grdlwwheev kkypsyypat pvsaedtlfl lytsgstgkp kgiqhstagy |
| 301 | llgallttky vfdvhpedil ftagdvgwit ghsyvvygpl lngattvvfe gtpaypnysr |
| 361 | yweivdkykv tqfyvaptal rllkragesy iepyslqslr vlgsvgepia kdvwewynah |
| 421 | igrgkahicd tywqtesgsh litplagvtp tkpgsaslpf fgidpaiidp vsgkelegne |
| 481 | vegvlairss wpsmartiwr dysrfldtyl rpyhgyyfsg dgaardkdgf ywilgrvddv |
| 541 | vnvsghrlst aeieaalieh smvaesavvg fpdeltgsav aafvslknrs iedpsaikke |
| 601 | liltvrkeig pfaapklill vndlpktrsg kimrrilrki lsgeedqlgd tstlsnpqvv |
| 661 | shlievvkak |

GI:190348910, Protein name: acetyl-coenzyme A synthetase 1
[*Meyerozyma guilliermondii* ATCC 6260]

SEQ ID NO: 22

| | |
|---|---|
| 1 | mpestdhldh ekmldppkgf ferstskpnl asldeykkly kqsiedpatf fgnaaksfld |
| 61 | wdrpfdytrf pvdpkddfkn gdipswfing qlnasynavd rwamknpekp aiiyeadevn |
| 121 | egrtitygel lkdvsklaat ltnlgvkkgd svavylpmip eaivtllaiv rigalhsvvf |

| | |
|---|---|
| 181 | agfsstslrd riidadsriv itadeskrgg ktietkkivd dalkecphvr nvlvfkrtgn |
| 241 | shvpfsagrd lwwhdelqky gpyfppvpvn sedplfllyt sgstgkpkgv qhntagyllg |
| 301 | almtakytfd lheediifta gdvgwitght yvvygpllcg attvvfegtp aypdysrywd |
| 361 | vvdkykvnqf yvaptalrll kragtkyvek hdlsslrvlg svgepiaaev whwyndnigr |
| 421 | gkahivdtyw qtesgshllt plagvtptkp gsaslpffgi darildpvsg kdlvdnnveg |
| 481 | vlcvksawps itrgiyhdya ryietylkpy pnhyfsgdga ardkdgffwi lgrvddvvnv |
| 541 | sghrlstaei eaaliehelv gesavvgyad eltgqavaay vslksnvevd dleaikkeli |
| 601 | ltvrkeigpf aapklillvd dlpktrsgki mrrilrkvla geedqlgdis tlsnpqvvsq |
| 661 | vievvkasrk |

GI:29893231, Protein name: acyl-activating enzyme 11-AAE11 [Arabidopsis thaliana]

SEQ ID NO: 23

| | |
|---|---|
| 1 | mdnlvlcean nvpltpitfl krasecypnr tsiiygqtrf twpqtydrcc rlaasllsln |
| 61 | itrndvvsil apnvpamyem hfsvpmtgav lnpintrlda ktiaiilrha epkilfvdye |
| 121 | fapliqevlr liptdqsqah priilineid sttkpfskel dyeglirkge ptpsssasmf |
| 181 | rvhnehdpis lnytsgttad pkgvvishrg aylsalssii gwemgifpvy lwtlpmfhcn |
| 241 | gwthtwsvaa rggtnvcirh vtapeiykni elhgvthmsc vptvfrflle gsrtdqspks |
| 301 | spvqvltggs sppavlikkv eqlgfhvmhg yglteatgpv lfcewqdewn klpehqqmel |
| 361 | qqrqgvrnit ladvdvkntk tlesvprdgk tmgeivikgs slmkgylknp katseafkhg |
| 421 | wlntgdigvi hpdgyveikd rskdiiisgg enissievek vlymyqqvle aavvamphpl |
| 481 | wgetpcafvv lkkgdeesvt segdlikycr enmphfmcpk kvvffqelpk nsngkilksk |
| 541 | lrdiakalvv reddagskkv hqrsiehvss rl |

GI:29893229, Protein name: acyl-activating enzyme 12 [Arabidopsis thaliana]

SEQ ID NO: 24

| | |
|---|---|
| 1 | mdnlalcean nvpltpitfl krasecypnr tsiiygktrf twpqtydrcc rlaaslisln |
| 61 | igkndvvsvv apntpamyem hfavpmagav lnpintrlda tsiaailrha kpkilfidrs |
| 121 | feplareilq llssedsnln lpvifiheid fpkrvssees dyecliqrge ptpsllarmf |
| 181 | cigdehdpis lnytsgttad pkgvvishrg aylstlsaii gwemgtcpvy lwtlpmfhcn |
| 241 | gwtftwgtaa rggtsvcmrh vtapeiykni emhnvthmcc vptvfnillk gnsldlshrs |

Sequence Listing Free Text

```
301    gpvhvltggs pppaalvkkv grlgfqvmha yglteatgpv lfcewqdewn
       rlpenqqmel 361    karcolsilg ltevdvrnke tqesvprdgk tmgeivmkgs simkgylknp
       katyeafkhg 421    wlnsgdvgvi hpdghveikd rskdiiisgg enissveven iiykypkvle
       tavvamphpt 481    wgetpcafvv lekgetnned redklvtker dlieycrenl phfmcprkvv
       fldelpkngn 541    gkilkpklrd iakglvaede vnvrskvqrp vehftsrl
```

GI:224065064, Protein name: acyl:coa ligase acetate-coa synthetase-like protein [*Populus trichocarpa*]

SEQ ID NO: 25

```
  1    mdqllkcdan yvpltpitfl kranavyanr tsviyegtrf twsqtyercc
       rladslrsln 61    vgkndvvsvl apnipavyem hfavpmagav lntinirlda kniatilshs
       gakvffvdyq 121    ykelaskals fldgavpsii aciddidtpt gvqfgqleye qlvqrgnpgy
       tgelvqdewd 181    pialnytsgt tsapkgvvys hrgaylssls lilgwemgna pvylwslpmf
       hcngwtftwg 241    vaarggtnvc irntsakdmy hniaehavth mccapivfnv llearpherr
       eitspveilt 301    ggapppasll qdierlgfhv thaygltead gpalvcewqk kwnklpqqdq
       aklkarqgis 361    iltladadvk dldtmvsvpr dgktmgeivl rgssimkgyf kdpeatskaf
       rngwfatgdv 421    gvihpdgyle ikdrskdvii sggenissve lesvlyrhpr vleaavvamp
       hpkwgespca 481    fisvkknsng dtndvkesdi iayckknlph ftvpkrvefm aelpktstgk
       iqkfqlrala 541    qnfvvneilp skkinghsqp sasgrvntev teyaqgheqv lalsrl
```

GI:226508754, Protein name: acyl-activating enzyme 11 [*Zea mays*]

SEQ ID NO: 26

```
  1    mdqlpkrpan yvplspvgfl pranavygdr tsviyrgvrf twrqtyarcr
       rlasallslg 61    vvrrgdvvsv lapnvpamye mhfavpmaga vintintrld aaavatilrh
       sgaklffvdy 121    dyvrlasdal rlldaadvpl vaviddihsp tgarlgeley eallahgdpd
       adlpplqdew 181    davtlsytsg ttsapkgvvy shrgaylstt slllqwgvpa epvylwtlpm
       fhcngwtftw 241    gmaarggvnv cirdarpadi yraiarhrvt hmccapvvfs illdgdgdsd
       gaarqlqapv 301    hvltggappp aallerveri gfnvthaygl teatgpalac ewrdqwdrlp
       lperarlkar 361    qgvsvlslad advknadtml svprdgrtvg eivlrgssvm kgylnnpean
       esafragwfl 421    tgdvgvvhpd gyieikdrsk dviisggeni cskeleevlf rhpavadaav
       vamphprwge 481    tpcafvvprd kaavlsegdv lafcskrmar fmvpkkvevv galprnalgk
       vekvklreaa
```

| Sequence Listing Free Text |
|---|

541  rklaptvaaa qkpkaktttv ggrrdgqpva hvmaysrl

GI:357491641, Protein name: 2-succinylbenzoate-CoA ligase
[*Medicago truncatula*]

SEQ ID NO: 27

1  mnqltrnqan staltpltfl eraatvygns isiiynntsf twsqthkrcl
     glasslss1g 61  iqkgdvvsvl spntpamyel hfsvpmsgai lnnlnfrldh ktlsvllihs
     esklifvdil 121  slsltlnals lfptniqqpk lvlimdetla phqipplpkn vniintyegl
     vakgdpyfkw 181  irpdsewdpi tlnytsgtts spkgvvhchr atfivsldsl idwsvpvqpv
     flwtlpmfhs 241  ngwsypwama avgginictr rtdaptiytl ieshgvthmc aapvvinmls
     nfnkteplkk 301  pvhvltggss pptailtrae rlgfevshgf gmtevigviv scawkrewdr
     fpatekarmk 361  arqgvrkvgv aevdvvgptg esvkndgvtv geivvkgacv mlgyfkdeia
     tsqcikkngw 421  fytgdvavmh edgyleikdr skdliisgge nmssvevegv lymhsavkea
     avvarpddfw 481  getpcgfvsl kdelkkndip tdneikefck eklphfmmpk tivfmkelpk
     tstgkvqkhv 541  lrkvakkmgs lslppprli sri GI:149375957, Protein name: acyl-CoA synthase
[*Marinobacter algicola* DG893]

SEQ ID NO: 28

1  mnsifdkgle ptdannatlt pldflartas vypeypavih gatrrnwqqt
     yercrrlasa 61  ladrgvgkgd tvaamlpnip pmlechfgip mlgavinaln trldakaiaf
     mlehgeakvl 121  iadrefgdvi neavgmldnp pqvidvndpe fsgagtqvsd ldydafvasg
     dpafdwqmpa 181  dewdaislcy tsgttgnpkg vvyhhrgaye namgnqavws mgmhpvylwt
     lpmfhcngwc 241  fpwtitafag thvclrkvep ekilqliseh kvshmcgapi vintllgase
     aakssfshtv 301  qamtagaapp akvieaienm gfrvthvygl tevygpvtvc awksewddlp
     vedrarikar 361  qgvryhtlag mmvgdpetme avpkdgntig eiflrgntvm kgylknpkat
     eeafrggwfh 421  tgdlavwhad gyaeikdrlk diiisggeni stievedvly rhpdileaav
     varpdekwge 481  tpcafvtlkp eagevseddi iafcrermak fkvpktivfs elpktstgki
     qkfvlrddak 541  kl GI:26991093, Protein name: lpdV gene product
[*Pseudomonas putida* KT2440]

SEQ ID NO: 29

1  mqqiiqttll iigggpggyv aairagqlgi ptvlvegqal ggtclnigci
     pskalihvae 61  qfhqasrfte psplgisvas prldigqsvt wkdgivdrlt tgvaallkkh
     gvkvvhgwak

| | |
|---|---|
| 121 | vldgkqvevd gqriqcehll latgsssvel pmlplggpvi sstealapkt lpqhlvvvgg |
| 181 | gyiglelgia yrklgaqvsv vearerilpt ydseltapva eslkklgial hlghsvegye |
| 241 | ngcllasdgk gggqlrleadq vlvavgrrpr tkgfnlecld lkmngaaiai derchtsmhn |
| 301 | vwaigdvage pmlahramaq gemvaeiiag karrfeptai aavcftdpev vvvgktpeqa |
| 361 | sqqgldciva qfpfaangra mslesksgfv rvvarrdnhl ivgwqavgva vselstafaq |
| 421 | slemgacled vagtihahpt lgeavqeaal ralghalhi |

GI:6325162, Protein name: Eeb1p
[*Saccharomyces cerevisiae* S288c]

SEQ ID NO: 30

| | |
|---|---|
| 1 | mfrsgyyptv tpshwgyngt vkhvlgekgt kslafrdskr qiplhefvtk hvptlkdgan |
| 61 | frinsllftg ylqtlylsag dfskkfqvfy greiikfsdg gvctadwvmp eweqtyslna |
| 121 | ekasfnekqf sndekathpk gwprlhprtr ylsseelekc hskgysyplv vvlhglaggs |
| 181 | hepliralse dlskvgdgkf qvvvinargc srskvttrri ftalhtgdvr eflnhqkalf |
| 241 | pqrkiyavgt sfgaamltny lgeegdncpl naavalsnpw dfvhtwdkla hdwwsnhifs |
| 301 | rtltqfltrt vkvnmnelqv penfevshkp tvekpvfyty trenlekaek ftdilefdnl |
| 361 | ftapsmglpd gltyyrkass inrlpnikip tliinatddp vtgenvipyk qarenpcvll |
| 421 | cetdlgghla yldnesnswl tkqaaeflgs fdelvl, |

GI:207340567, Protein name: YPL095Cp-like protein
[*Saccharomyces cerevisiae* AWRI1631]

SEQ ID NO: 31

| | |
|---|---|
| 1 | mfrsgyyptv tpshwgyngt vkhvlgekgt rslafrdskr qiplhefvtk hvptlkdgan |
| 61 | frinsllftg ylqtlylsag dfskkfqvfy greiikfsdg gvctadwvmp eweqtyslna |
| 121 | ekasfnekqf sndekathpk gwprlhprtr ylsseelekc hskgysyplv vvlhglaggs |
| 181 | hepliralse dlskvgdgkf qvvvinargc srskvttrri ftalhtgdvr eflnhqkalf |
| 241 | pqrkiyavgt sfgaamltny lgeegdnepl naavalsnpw dfvhtwdkla hdwwsnhifs |
| 301 | rtltqfltrt vkvnmnelqv penfevshkp tvekpsfiri pekiwkrlkn lqty |

GI:255715549, Proteinname: KLTH0E13310p
[*Lachancea thermotolerans*]

SEQ ID NO: 32

| | |
|---|---|
| 1 | mplpifnpfh wgyhgtieqv snpngtvalt lkdekkpvqf sdfvsreipg lkdkakfevn |
| 61 | pllftgylqt lylggadfsk sfpvyygrei vkfsdggict adwvmkswks kygadtssfk |
| 121 | tdeqathpen wprlhprtrf leesekkdvh nsekplvvvl hglaggshep iirsltqdls |

-continued

| Sequence Listing Free Text |
|---|

```
181   nagdskfdvv vincrgcars kittrklfya vftsdirefi arekarhpsr
      kiyavgfsfg 241   atmlghylge egekapieaa sflcnpwdly qsalkmnqdw wsrnlfskni
      aqflirlvkv 301   nikelefkeg dvmpaepasl ehpsfcvfts knlrkarefg staefdnlft
      apclgfdnam 361   dyykacgsih qlpnikvpsl iinskddpvv gedsipykca kesdnlvlcv
      sdlgghlafl 421   dkkynswats kiaaffdkfe elvq
```

GI:254584546, Protein name: ZYROOF14740p
[*Zygosaccharomyces rouxii*]

SEQ ID NO: 33

```
  1   msnlpiinpf hwgsrgtlkh tsapsgttkl tlnhdktkid fqhfvsqyvp
      alkdgskfkl 61   nnflftgilq tmylsgadyt kwfpvfygre ilelsdggvc tvdnvmvswe
      ekyqlrqnsg 121   sfnklefekd ekdthpqnwp rlqartrylt akelaevhgd grplvvvlhg
      laggshetii 181   rsltsklski dggkfqvavl ncrgcarski tnkklfsafq tgdlkeylar
      eksrnpnrki 241   yavgfsfgas llanylgetg sesnitaavt lccpwdfllc aekmkkdyws
      knlfskaitq 301   flvrlvkvnm gelespegsk pefqpdienp clymctksnl eraksftqml
      efdgtftaps 361   mgfssaeeyy ragsainnlh kvqvptliin stddpiidas sipysqvkmn
      pnllllatdl 421   gghlayldet wdswmnthia sffstfdefl v
```

GI:45185426, Protein name: ABR194Cp
[*Ashbya gossypii* ATCC 10895]

SEQ ID NO: 34

```
  1   mglptfaprs wgyrgtithr pheeglvklp lkdkekepvt lsdllnehvp
      elkdgarfyl 61   hpylyngilq tmylygadfs qqykpfygre ivsysdggvs tadwamrewd
      dlyaapegyn 121   kekfdadaak thpenwprlq pntrfldeee lakipkdtrp livvahglag
      gsheniiral 181   vtellsvgng qfnvvvinsr gcarskiank klfsafhtmd irefinreha
      rqperkiygl 241   gfsfgsvifg nylgeegdks plsgavccag pwdmfasskm lnddfwisrl
      fgknlvkhls 301   rllhvnrkel eydgskgddv edasptnpas hiftkenlar astmactrdf
      dnfftapalg 361   fknandyyka aspvnivgki rvptllinal ddpmvgaegf lpieklrsnk
      hillcttdig 421   ghlayldkny tpwmagrvae flskmdtiva
```

GI:294659670, Protein name: DEHA2G12430p
[*Debaryomyces hansenii* CBS767]

SEQ ID NO: 35

```
  1   mvfpwgfrsn vkihqsnsdk sidlplrnge ktikyadfik delpiideke
      klwlnpllfn 61   gllqtlyyss anlshkfqvy ygreiftyed ggvcsidhvi pqpenteefk
      alhdktlpeg
```

```
121   wpklhprsry fsneelegvn spsegsqstk picvvlhgla ggsheplirn
      laeylstgkn 181   enkwdtivin srgccrtkit ngklftalst gdihevlvel kkrnpnrpiy
      tvgfsfgaai 241   lanylaeikd dtmitaaclv gcpwdlidsa yhiekswsgs ylfnpaltsf
      lnklvknnft 301   elnhhnpelf neenlkrgmk qtktwqfdsv ytchtigysn pfeyyrdasp
      vnriskihtp 361   tlilnstddp avgvrlpwme vennphlcmv etdlgghlgy vgssgkfwcv
      qlveeffakf 421   delias
```

GI:75150384, Protein name: Benzoyl coenzyme A: benzyl alcohol benzoyl transferase [*Clarkia breweri*]

SEQ ID NO: 36

```
  1   mandqslsfe vcrrkpelir pakqtphefk klsdvedgeg lrfqipviqf
      ykhnnesmqe 61   rdpvqvireg iaralvyyyp fagrlrevdg rklvvectge gvmfieadad
      vtleqfgdal 121   qppfpcfdql lfdvpgsggi ldsplliqv trlkcgsfif alrinhtmad
      aagivlfmka 181   vgemargaat pstlpvwdrh ilnarvppqv tfnhreyeev kgtiftpfdd
      lahrsfffgs 241   teisamrkqi pphlrscstt ievltaclwr crtlaikpnp deevrmiciv
      narskfnppl 301   pdgyygnafa ipaavttagk lcnnplgfal elirkakrev teeymhsvad
      lmvatgrphf 361   tvvntylvsd vtragfgevd fgwgeavygg pakggvgvip gvtsfyiplr
      nrggekgivl 421   piclpsaame ifaealnntl ngkeieiakh ftqssl
```

GI:49798480, Protein name: benzoyl coenzyme A: benzyl alcohol benzoyl transferase [*Petunia x hybrida*]

SEQ ID NO: 37

```
  1   mdskqsselv ftvrrqepel iapakptpre tkflsdiddq eglrfqipvi
      nfyrkdssmg 61   gkdpvevikk aiaetivfyy pfagrlregn drklmvdctg egvmfveana
      dvtleefgde 121   lqppfpclee llydvpgsag vlhcpllliq vtrlrcggfi falrinhtms
      dapglvqfmt 181   avgemargat apstlpvwcr ellnarnppq vtcthheyee vpdtkgtlip
      lddmvhrsff 241   fgptevsalr rfvpphlhnc stfevltaal wrcrtisikp dpeeevrvlc
      ivnarsrfnp 301   qlpsgyygna fafpvavtta eklcknplgy alelvkktks dvteeymksv
      adlmvikgrp 361   hftvvrtylv sdvtragfge vdfgwgkavy ggpakggvga ipgvasfyip
      frnkkgengi 421   vvpiclpgfa mekfvkelds mlkgdaqldn kkyafitpal
```

GI:1171577, Protein name: hsr201 [*Nicotiana tabacum*]

SEQ ID NO: 38

```
  1   mdskqsselv ftvrrqkpel iapakptpre tkflsdiddq eglrfqipvi
      qfyhkdssmg 61   rkdpvkvikk aiaetivfyy pfagrlregn grklmvdctg egimfveada
      dvtleqfgde
```

```
121   lqppfpclee llydvpdsag vincpllliq vtrlrcggfi falrinhtms
      dapglvqfmt 181   avgemarggs apsilpvwcr ellnarnppq vtcthheyde vrdtkgtiip
      lddmvhksff 241   fgpsevsalr rfvphhlrkc stfelltavl wrcrtmslkp dpeeevralc
      ivnarsrfnp 301   plptgyygna fafpvavtta aklsknplgy alelvkktks dvteeymksv
      adlmvlkgrp 361   hftvvrtflv sdvtrggfge vdfgwgkavy ggpakggvga ipgvasfyip
      fknkkgengi 421   vvpiclpgfa metfvkeldg mlkvdaplvn snyaiirpal
```

GI:84578877, Protein name: benzoyl CoA benzoic acid benzoyltransferase [*Verbena x hybrida*]

SEQ ID NO: 39

```
  1   maqnntlltf tvrrnepeli apakptprel kplsdiddqe glrfqipviq
      fyrhdpkmrn 61   knparvirea lakvlvfyyp fagrlkegpa kklmvdcsge gvlfieaead
      vtlnqfgdal 121   qppfpcleel lydvpgsggv ldspllliqv trllcggfif alrinhtmsd
      apglvqfmta 181   lgemaggapr psilpvwqre llfarvqphv tcthheydev kdtkgtiipl
      ddmahrsfff 241   gptevaalrr fvpsslqkcs tfevltaclw rcrtialkpd peeemriici
      vnarakfnpp 301   lpkgyygngf afpvaisrag dlstkplgha lklvmqakna vndeymrslt
      dlmvikgrph 361   ftvvrsylvs dvtragfdav dfgwgnaayg gpakggvgai pgvasfyipf
      tnhkgetgiv 421   lpiclpnaam etfvkelnnm lakgnndqvl kehnynvlsr l
```

GI:254771941, Protein name: alcohol acyltransferase [*Vasconcellea cundinamarcensis*]

SEQ ID NO: 40

```
  1   maekasslmf nvrrhepeli tpakptprei kllsdiddqd glrfqvpiiq
      fyknnssmqg 61   knpakiiksa laetivhyyp lagrlregfg rklmvectge gilfieadad
      vtlhefgddl 121   pppfpclvel lydvpgssgi idtpllliqv trlkcggfif alrinhtmsd
      asglvqfmta 181   vgemargqrs lsiqpvwerh llnardppry thihheyddl edtkgtiipl
      ddmvhrsfff 241   gpsemaairr lvpahfhrst tsevltaylw rcytialqpd peeemrvicv
      vnsrtklnpp 301   lptgfygngi afpaaisqak kicenpfgyt lqlvkqtkvd vteeymrsaa
      dlmamkgrph 361   ftvvrrymvs dvtragfglv dfgwgrpepv yggpakggvg pipgvtsffv
      pfknrkgekg 421   ivvptclptp amerfaklmn eilqnqllvs aeenksvfiv sai
```

GI: 161089458, Protein name: acyltransferase [*Vanda hybrid cultivar*]

SEQ ID NO: 41

```
  1   masstlhfsv rrrppqlvap asptprelkr lsdiddgegl rfqipviqfy
      rhepamagqn
```

```
 61    pasvirdala  rtivfyypfa  grlregagkk  lfvdctgegv  lfieaeadvk
       lkdfgdalhp 121    pfpcleellf  dvdgssavin  tplliqvtl   lscggfilal  rinhtmsdap
       glvqlmtavg 181    elargsssps  vipvwrrell  earpspapff  phpeyeqvpd  tegtitpldn
       tahrsfifgp 241    reisilrsrl  psqlrgasst  fdiltacvwr  srtralqpad  pkenfriici
       vnirgrinpp 301    lpsgfygnaf  glpvaiatag  elcsrpldya  velvkraksq  vsgdylhsva
       dymvmkgrph 361    ftvvrtyvis  dltragfgdv  dfgwgkpvyg  gpakggvgvs  pgvfnffipf
       vnasgekgiv 421    vpiclpppam  rrfvaeigsl  lsaqsal GI:57471999, Protein name: putative alcohol
acyl-transferases CmAAT3 [Cucumis melo]
                                                       SEQ ID NO: 42
  1    masslvfqvq  rsqpqlipps  dptphefkql  sdiddgeglr  fqipviqfyr
       hdprmagtdp 61    arvikeaiak  alvfyypfag  rlregpgrkl  fvectgegvm  fieadadvsl
       eqfgdalqpp 121    fpcleeplfd  vpnssgvldc  plliqvtrl   kcggfifalr  lnhtmsdasg
       lvqfmmavge 181    margatapsv  rpvwqralln  ardppkvtch  hreydevvdt  kgtiiplddm
       ahrsfffgps 241    eisairkalp  shlrqcssfe  vltaclwrfr  tislqpdpee  evrvlcivns
       rskfnpplpt 301    gyygnafafp  valttagklc  qnplgyalel  vrkakadvte  dymksvadlm
       vikgrphftv 361    vrtylvsdvt  ragfedvdfg  wgkamyggpa  kggvgaipgv  asfyipfknk
       kgergilvpl 421    clpapamerf  vkeldallka  gktidgvdnk  kplfiasal GI:49798480, Protein name: benzoyl coenzyme A: benzyl
alcohol benzoyl transferase [Petunia x hybrida]
                                                       SEQ ID NO: 43
  1    mdskqsselv  ftvrrqepel  iapakptpre  tkflsdiddq  eglrfqipvi
       nfyrkdssmg 61    gkdpvevikk  aiaetivfyy  pfagrlregn  drklmvdctg  egvmfveana
       dvtleefgde 121    lqppfpclee  llydvpgsag  vlhcplliq   vtrlrcggfi  falrinhtms
       dapglvqfmt 181    avgemargat  apstlpvwcr  ellnarnppq  vtcthheyee  vpdtkgtlip
       lddmvhrsff 241    fgptevsalr  rfvpphlhnc  stfevltaal  wrcrtisikp  dpeeevrvlc
       ivnarsrfnp 301    qlpsgyygna  fafpvavtta  eklcknplgy  alelvkktks  dvteeymksv
       adlmvikgrp 361    hftvvrtylv  sdvtragfge  vdfgwgkavy  ggpakggvga  ipgvasfyip
       frnkkgengi 421    vvpiclpgfa  mekfvkelds  mlkgdaqldn  kkyafitpal
```

Sequence Listing Free Text

GI:75150383, Protein name: Benzoyl coenzyme A: benzyl alcohol benzoyl transferase [*Nicotiana tabacum*]

SEQ ID NO: 44

```
  1  mdskqsselv ftvrrqkpel iapakptpre ikflsdiddq eglrfqipvi
     qfyhkdssmg
 61  rkdpvkvikk aiaetivfyy pfagrlregn grklmvdctg egimfveada
     dvtleqfgde
121  lqppfpclee llydvpdsag vincpllliq vtrlrcggfi falrinhtms
     dapglvqfmt
181  avgemargas apsilpvwcr ellnarnppq vtcthheyde vrdtkgtiip
     lddmvhksff
241  fgpsevsalr rfvphhlrkc stfelltavl wrcrtmslkp dpeeevralc
     ivnarsrfnp
301  plptgyygna fafpvavtta aklsknplgy alelvkktks dvteeymksv
     adlmvlkgrp
361  hftvvrtflv sdvtrggfge vdfgwgkavy ggpakggvga ipgvasfyip
     fknkkgengi
421  vvpiclpgfa metfvkeldg mlkvdapldn snyaiirpal
```

GI:224144897, Protein name: predicted protein [*Populus trichocarpa*]

SEQ ID NO: 45

```
  1  masspasllf kvhrrepeli kpakptphef kllsdiddqe glrfhipvmq
     fyrnnpsmqg
 61  kdpvkiirea laktivfyyp fagrlregpn rklmvectge gilfieadad
     vtleqfgdal
121  qppfpcleel lfdvpgssgv lncpllliqv trlkcggflf alrinhtmsd
     avglvqfmaa
181  vgemargana psvpavwerq vinasdppry tcthreyeev adtkgtiipl
     ddmahrsfff
241  gpsemsalrk fvpphlshcs tfeiltaclw kcrtialqpd pteemrilci
     vnarekfnpp
301  lprgyygngf afpvavatae elsknpfgya lelvrkakad vteeymrsys
     slmvikgrph
361  ftvvraylvs dlrragfeev dfgwgnaiyg gaakggvgai pgvasfyipf
     tnkkgengvv
421  vpfclpapam erfvkeldgm lkddqtvsaq tkskfivssl
```

GI:356500043, Protein name: PREDICTED: benzyl alcohol O-benzoyltransferase-like [*Glycine max*]

SEQ ID NO: 46

```
  1  mdtslvftvr rseaeliapa kptprevkll sdiddqdglr fqipviqfyr
     hdpsmagkdp
 61  vdvirkavak tivfyypfag rlreglgrkl mvdctgegvl fieadadvtl
     kqfgdalqpp
121  fpcweellyd vpgsqgvint pllliqvtrl kcggfilavr lnhtmsdaag
     lvqfmsalge
181  iargrqepsi ppvwrrelln ardpprvtct hreyehvpdt kgtiipldhm
     ahrsfffgps
241  evaairslip qtdqrcsnfe vltaclwrcr tialqpdkde evrilcivna
     rskfdpplps
301  gyygnafafp vavttagklc dnplgyalel vrkakadvte eymhsvadlm
     vtkgrphftv
```

| Sequence Listing Free Text |
|---|

```
361   vrsylvsdvt ragfgniefg wgkavyggpa kggvgaipgv asfyipfkna
      kgeeglvipv 421   clpseamerf qkeldcvinh hivqpsaiap nsrfivssl
```

GI:133874202, Protein name: putative acyltransferase [*Clitoria ternatea*]

SEQ ID NO: 47

```
  1   matstsssl mfqvqkreae liapakptpr evkllsdidd qeglrfqipv
      iqfyrynetm 61   agkdpvevir kalaktivfy ypfagrlreg pgrklmvdct gegvlfieah
      advtlqqfgd 121   slqppfpgld hllynlpnsd gvinspllli qvtrlkcggf ilalrinhtm
      sdaaglvqfm 181   savgeiargm eepsippvwr rellnarnpp kvtcthreye qvpdskgtii
      plddmahrsf 241   ffgpaeisai rrlipaqqqr qcsnfeilta clwrcrtial qpdsdeevri
      lcivnargkf 301   npplpagyyg nafafpvavt tagklcgnpl gyalelvrka kgdvseeymh
      sladlmvtkg 361   rphftvvrsy lvsdvtragf gdvdfgwgkp vyggpakggv gaipgvasfy
      ipfrnskgee 421   glvipvclps qamdrfvrel dtilnhhlqp ppksplvlss l
```

GI:49798480, Protein name: benzyl alcohol benzoyl transferase(BPBT) [*Petunia x hybrida*]

SEQ ID NO: 48

```
  1   mdskqsselv ftvrrgepel iapakptpre tkflsdiddq eglrfqipvi
      nfyrkdssmg 61   gkdpvevikk aiaetivfyy pfagrlregn drklmvdctg egvmfveana
      dvtleefgde 121   lqppfpclee llydvpgsag vlhcpllliq vtrlrcggfi falrinhtms
      dapglvqfmt 181   avgemargat apstlpvwcr ellnarnppq vtcthheyee vpdtkgtlip
      lddmvhrsff 241   fgptevsalr rfvpphlhnc stfevltaal wrcrtisikp dpeeevrvlc
      ivnarsrfnp 301   qlpsgyygna fafpvavtta eklcknplgy alelvkktks dvteeymksv
      adlmvikgrp 361   hftvvrtylv sdvtragfge vdfgwgkavy ggpakggvga ipgvasfyip
      frnkkgengi 421   vvpiclpgfa mekfvkelds mlkgdaqldn kkyafitpal
```

GI:1171577, Protein name. hsr201 [*Nicotiana tabacum*]

SEQ ID NO: 49

```
  1   mdskqsselv ftvrrqkpel iapakptpre tkflsdiddq eglrfqipvi
      qfyhkdssmg 61   rkdpvkvikk aiaetivfyy pfagrlregn grklmvdctg egimfveada
      dvtleqfgde 121   lqppfpclee llydvpdsag vincpllliq vtrlrcggfi falrinhtms
      dapglvqfmt 181   avgemarggs apsilpvwcr ellnarnppq vtcthheyde vrdtkgtiip
      lddmvhksff 241   fgpsevsalr rfvphhlrkc stfelltavl wrcrtmslkp dpeeevralc
      ivnarsrfnp 301   plptgyygna fafpvavtta aklsknplgy alelvkktks dvteeymksv
      adlmvlkgrp
```

Sequence Listing Free Text

```
361    hftvvrtflv sdvtrggfge vdfgwgkavy ggpakggvga ipgvasfyip
       fknkkgengi 421    vvpiclpgfa metfvkeldg mlkvdaplvn snyaiirpal
```

GI:57471999, Protein name: putative alcohol
acyl-transferases [*Cucumis melo*]

SEQ ID NO: 50

```
  1    masslvfqvq rsqpqlipps dptphefkql sdiddqeglr fqipviqfyr
       hdprmagtdp 61    arvikeaiak alvfyypfag rlregpgrkl fvectgegvm fieadadvsl
       eqfgdalqpp 121    fpcleeplfd vpnssgvldc pllliqvtrl kcggfifalr lnhtmsdasg
       lvqfmmavge 181    margatapsv rpvwqralln ardppkvtch hreydevvdt kgtiiplddm
       ahrsfffgps 241    eisairkalp shlrqcssfe vltaclwrfr tislqpdpee evrvlcivns
       rskfnpplpt 301    gyygnafafp valttagklc qnplgyalel vrkakadvte dymksvadlm
       vikgrphftv 361    vrtylvsdvt ragfedvdfg wgkamyggpa kggvgaipgv asfyipfknk
       kgergilvpl 421    clpapamerf vkeldallka gktidgvdnk kplfiasal
```

GI:133874202, Protein name: putative acyltransferase
[*Clitoria ternatea*]

SEQ ID NO: 51

```
  1    matstssssl mfqvqkreae liapakptpr evkllsdidd geglrfqipv
       iqfyrynetm 61    agkdpvevir kalaktivfy ypfagrlreg pgrklmvdct gegvlfieah
       advtlqqfgd 121    slqppfpgld hllynlpnsd gvinspllli qvtrlkcggf ilalrinhtm
       sdaaglvqfm 181    savgeiargm eepsippvwr rellnarnpp kvtcthreye qvpdskgtii
       plddmahrsf 241    ffgpaeisai rrlipaqqqr qcsnfeilta clwrcrtial qpdsdeevri
       lcivnargkf 301    npplpagyyg nafafpvavt tagklcgnpl gyalelvrka kgdvseeymh
       sladlmvtkg 361    rphftvvrsy lvsdvtragf gdvdfgwgkp vyggpakggv gaipgvasfy
       ipfrnskgee 421    glvipvclps qamdrfvrel dtilnhhlqp ppksplvlss l
```

GI:224144897, Protein name: predicted protein
[*Populus trichocarpa*]

SEQ ID NO: 52

```
  1    masspasllf kvhrrepeli kpakptphef kllsdiddqe glrfhipvmq
       fyrnnpsmqg 61    kdpvkiirea laktivfyyp fagrlregpn rklmvectge gilfieadad
       vtleqfgdal 121    qppfpcleel lfdvpgssgv lncplliqv trlkcggflf alrinhtmsd
       avglvqfmaa 181    vgemargana psvpavwerq vinasdppry tcthreyeev adtkgtiipl
       ddmahrsfff 241    gpsemsalrk fvpphlshcs tfeiltaclw kcrtialqpd pteemrilci
       vnarekfnpp
```

Sequence Listing Free Text

```
301    lprgyygngf afpvavatae elsknpfgya lelvrkakad vteeymrsys
       slmvikgrph 361    ftvvraylvs dlrragfeev dfgwgnaiyg gaakggvgai pgvasfyipf
       tnkkgengvv 421    vpfclpapam erfvkeldgm lkddqtvsaq tkskfivssl
```

GI:225454593, Protein name: benzyl alcohol
O-benzoyltransferase [*Vitis vinifera*]

SEQ ID NO: 53

```
  1    mapppslvfs vrrskpelva pakptphefk plsdiddgeg lrfqipviqf
       ykkvpsmhgr 61    dpakvikdav aralvfyypf agrlreeagr klvvectgeg ivfieadadv
       tleqfgdalq 121    ppfpgleeli ydapgsggvl nsplliqvt rlqcggfifg lrinhtmsda
       aglvqfmsav 181    gemargasap sippvwrrdl lnardpprvt rthheydeva dtkgtiipld
       dmehrsfffg 241    ptefaalrrl lsphlrtcst felltaclwr crtialrpdp eeevrvlciv
       narsrlqppl 301    pagyygnvfg fpvalssagk lcrnpleyal dlvkgaknsv dqeymksvad
       lmvstgrrhf 361    tvvrsylvsd ltragfgdvd fgwgkavygg aakggvgaip gvasfyipfr
       nhkgedgivv 421    pfclpaaame ifvkelnsll keehplpsnk sstfiisal
```

GI:52139953, Protein name: alcohol acyl transferase
(MpAAT1) [*Malus x domestica*]

SEQ ID NO: 54

```
  1    mmsfsvlqvk rlqpelitpa kstpqetkfl sdiddqeslr vgipiimcyk
       dnpslnknrn 61    pvkaireals ralvyyypla grlregpnrk lvvdcngegi lfveasadvt
       leqlgdkilp 121    pcplleefly nfpgsdgiid cpllliqvtc ltcggfilal rinhtmcdaa
       glllfltaia 181    emargahaps ilpvwerell fardppritc ahheyedvig hsdgsyassn
       qsnmvqrsfy 241    fgakemrvlr kqipphlist cstfdlitac lwkcrtlaln inpkeavrvs
       civnargkhn 301    nvrlplgyyg nafafpaais kaeplcknpl gyalelvkka katmneeylr
       svadllvlrg 361    rpqysstgsy livsdntrvg fgdvnfgwgq pvfagpvkal dlisfyvqhk
       nntedgilvp 421    mclpssamer fqqeleritq epkedicnnl rstsq
```

GI:44887628, Protein name: alcohol acyl transferase
[*Pyrus communis*]

SEQ ID NO: 55

```
  1    mmslsvlqvk rlqpelitpa kptpqetkfl sdiddqeglr fqlpvimcyk
       dnpslnknrn 61    pikvikeals ralvyyypla grlregpnrk lmvncngegi lfveasadvt
       leqlgdkilp 121    pcplleeflf nfpgsdgiig cplllvqvtc ltcggfilal rinhtmcdat
       gllmfltait 181    emgrgadaps ilpvwerell fardppritc ahyeyedvid hsdgsyafsn
       qsnmvqrsfy
```

Sequence Listing Free Text

```
241   fgakemrvlr kqipphlist cstfdlitac lwkcrtivlk inpkgavrvs
      civnargkhn 301   nvhiplgyyg nafafpaays kaeplcknpl gyalelvkka katmneeylr
      svadllvlrg 361   rpqysstgsy livsdntrag fgdvnfgwgq pvfagpakal dlisfyvqhk
      nntedgilvp 421   mclpssamer fqqeleritt gt
```

GI:147801410, Protein name: hypothetical protein
VITISV_042062 [*Vitis vinifera*]

SEQ ID NO: 56

```
  1   masswsplvf svkrcapefv rptnitprev kqlsdiddqe glrfqipvim
      fypnnplmkg 61   kdpvkvirea lgkalvyyyp fagrliegdn rklmvdctge gvlfieadad
      ttlenlgdai 121   qpmcpcfeel lydvpgsggi lgspliliqv trlrcggfif alrinhtmsd
      algliqflna 181   isemaqglsv psllpiwere llnarnppri trihheyeev tnnkgtlmam
      dennlvhrsf 241   ffgpkeiral rnrlpaslga cstfevltay vwrcrtiafa vdpdevvris
      clinmrgkrg 301   fdlppgyygn afvypasitk agmlcknple yairllkkak aemsqeyiks
      vadlmvikgr 361   psftqpgnyf vsdvtragfg evnfgwgkpv ygglaralsi isfctrfrns
      kgeegnvipi 421   clpppvmerf eqelkrmtke aepvrliksm l
```

GI:49798480, Protein name: benzyl alcohol benzoyl
transferase [*Petunia x hybrida*]

SEQ ID NO: 57

```
  1   mdskqsselv ftvrrqepel iapakptpre tkflsdiddq eglrfqipvi
      nfyrkdssmg 61   gkdpvevikk aiaetivfyy pfagrlregn drklmvdctg egvmfveana
      dvtleefgde 121   lqppfpclee llydvpgsag vlhcpllliq vtrlrcggfi falrinhtms
      dapglvqfmt 181   avgemargat apstlpvwcr ellnarnppq vtcthheyee vpdtkgtlip
      lddmvhrsff 241   fgptevsalr rfvpphlhnc stfevltaal wrcrtisikp dpeeevrvlc
      ivnarsrfnp 301   qlpsgyygna fafpvavtta eklcknplgy alelvkktks dvteeymksv
      adlmvikgrp 361   hftvvrtyiv sdvtragfge vdfgwgkavy ggpakggvga ipgvasfyip
      frnkkgengi 421   vvpiclpgfa mekfvkelds mlkgdaqldn kkyafitpal
```

GI:158828372, Protein name: alcohol acyl transferase
[*Citrus sinensis*]

SEQ ID NO: 58

```
  1   mvftfsqgll vtrkapeliv perptprevk qisdiddges lrfqiplllf
      ykndpspsmq 61   grdpvkvire aiskalvfyy plagrlkegy nrklmvecna egvlfieada
      nftleqlrdd 121   vqppcpylnq liydvpgseg ilgcpllliq vtrltcggfi fairfnhtmc
      dafglvqflk
```

| | | |
|---|---|---|
| 181 | aiedmarger sptlfpiwqr lilnarnppq vtcihheyde intnevpsdn mahksfffsl | |
| 241 | kgikalrnql pfqlkdcstf elllaflwkc rtialklqpe eiakvccivn vrgksyemdi | |
| 301 | ppgyygnaft fsavcskaeq lcknpigyav elvkkakaqm neeyirsaad lmvikgrrik | |
| 361 | fstrgnfivs dlrnvglgdv dfgwgkpiya gtagavavis fftkyqnkng epgilvpicl | |
| 421 | pqsamerlqe elkglmiqgs aedlcninqt gifskl | |

GI:255552914, Protein name: Taxadien-5-alpha-ol
O-acetyltransferase, putative [Ricinus communis]

SEQ ID NO: 59

| | | |
|---|---|---|
| 1 | malppppftf avrrsppeli vparptprel kkvsdiddqe glrfqisfvm fyrslpsmkg | |
| 61 | rdpveiirka lsealvfyyp fagrliegpn rklivdcnge gilfieadad itieqlgdsm | |
| 121 | qppcpcieel lydvpgssgi igcpllliqi trlacggfvf avrinhvmsd svglakffka | |
| 181 | tgeiakgacm pslfpvwqre ilsarnppqv thkleeyeei khtddksilt ldspdmvqra | |
| 241 | fffgpkemrs lrrqlpshlr ncssfemlaa clwrcrtiaf dippnevvrl scimnvrgkk | |
| 301 | glqlpdgycg nsfifpavls raehlcknpl gyavelvrks kskmseeyir stidlmeikg | |
| 361 | rphyvtawnl llvdmshvgl advdfgwgnp vyfgptgsfp nismfsrfkn skgengfvvp | |
| 421 | mwlprtvmek fqdeflkmte esaenlndar rqriistl | |

GI:10121328, Protein name: alcohol acyltransferase (SAAT)
[Fragaria x ananassa]

SEQ ID NO: 60

| | | |
|---|---|---|
| 1 | mekievsins khtikpstss tplqpykltl ldqltppayv pivffypitd hdfnlpqtla | |
| 61 | dlrgalsetl tlyyplsgry knnlyiddfe egvpyleary ncdmtdflrl rkieclnefv | |
| 121 | pikpfsmeai sderypllgv qvnvfdsgia igvsyshkli dggtadcflk swgavfrgcr | |
| 181 | eniihpslse aallfpprdd lpekyvdqme alwfagkkva trrfvfgvka issiqdeaks | |
| 241 | esvpkpsrvh avtgflwkhl iaasraltsg ttstrlsiaa qavnlrtrmn metvldnatg | |
| 301 | nlfwwaqail elshttpeis dlklcdlvnl lngsvkqcng dyfetfkgke gygrmceyld | |
| 361 | fqrtmssmep apdiylfssw tnffnpldfg wgrtswigva gkiesasckf iilvptqcgs | |
| 421 | gieawvnlee ekmamleqdp hflalaspkt li | |

GI:374498907, Protein name: alcohol acyl-transferase
[Rosa rugosa]

SEQ ID NO: 61

| | | |
|---|---|---|
| 1 | mekievsiis rdtikpsaas sslhpyklsi idqftpttyf pviffypitd pvfnlpqtlt | |
| 61 | dlkitvsqtl tlyyplsgri knnlyiddfe agipyleary nchmidflrl pkiewlnefv | |

```
121    piapyrketi sellpllgiq vnifdsgiai gvsfshkind getancflks
       wvaifrgyrn 181    kiihpnlsqa allfpsrddl sekyvammer wwfgekkvvt rrfvfdtkai
       salqhegkse 241    yvpkpsrvqa ltgflwkhql aatralssgt strfslaiqa vnlrsrmnmk
       ttldnaigni 301    flwapaflel nyttpessdh klcdlvnllk esvkeynsdy letlkgekgy
       ggmcdwldlm 361    degssiepal eiysfsswtr mfdqvdfgwg kpfwigvtgk vqttytnstv
       lvetqcengi 421    eawvtldqkr mamleqdpqf lafasptpgi smassvgid
```

GI:255585363, Protein name: Anthranilate N-benzoyltransferase protein, putative [*Ricinus communis*]

SEQ ID NO: 62

```
  1    mvtkmqvdii srevikpssp tihhykpfkf plfsqltptt yspviffypt
       tkpnlnitqt 61    lihlkktlae tltlyypfsg rvvdnlsidh fdegvpffia rvtglvlsdf
       lknpeielln 121    gflpykpftk etdkgvpqma fqvnvfscgg ivigwssshk lvdgptgaaf
       ihawatmsrt 181    gslsdvikpn cdeasiffpp rnpfpeehls lmeslwftkg nyiskrfvfd
       skaiaslrvk 241    argegnekkn mpsrvealsc fiwkccmaas raasgtpkps ilveavnlrt
       rtkppmskvs 301    igdifwwata vadpslhnke lhelatllde aialydsdym eslqgedgfe
       tmseycnqlr 361    glfsieepdi faftswsrlg iydmdfgfgn pfwigilgkv gpafrnitvf
       letrdgkgie 421    awitldeerm allerdpefl anaspnprfs sl
```

GI:380863876, Protein name: BAHD acyltransferase [*Erythroxylum coca*]

SEQ ID NO: 63

```
  1    mevhivsret vkpsspatlt kkpyklslfd qltpgtytpt iffypknrpn
       sdttqvlarl 61    krslsetlds yfflsgrtrd nrfidcfdeg vpffeasysv glsdflkhhe
       hewlnrlvay 121    rpytkealds pllsiqvsvf acggivigts ashklidalt gsfilktwaa
       mfrgdvsdgi 181    spqideasmy fptrdsfpqn hlslmeslwf teanyvtrrf vfgaksisai
       kemakskpes 241    kqsriealsc fiwkhcmsas kaysgspqvs ilveavnlrt rttppmssss
       igdlfwwata 301    asnnddtkst elpelanllk eaielydtdf tkslqgnegd eaiyqyceql
       eglfslekpd 361    ifaftswcyv gftklnfgwg epiwvgtvgk agpafrnitv fietrdgkgi
       eawitldqkr 421    msvlehdpqf lafaslnpki ssl
```

GI:255577416, Protein name: Anthranilate N-benzoyltransferase protein, putative [*Ricinus communis*]

SEQ ID NO: 64

```
  1    mevhivsrem mkpsspaikh qkpyklclld qltpttyipi iffypmnnlf
       tkstlahlke
```

| Sequence Listing Free Text |
|---|

```
 61    slvktlnfyy pfsgrakdnl yidrfeegvp ffeakvncsm syflkhyete
       slsnlfipsh 121    pfskeidmsi alvavqvsmf tcggiavglc lshklidaat assfvttwas
       fcrgdpknvi 181    qpdfeqpstf fpsstslpqn ylslmeriwf vkanyitkrf vfdakaiaal
       rvkakaklea 241    eptriatlsc fiwkcsmaas raisgapkps ilveavnlrq ktkppmkdss
       tgnlfwwava 301    lasptdtnst elnelvsmls eaiavyksdy thslqgengl kimseyceql
       egmfsleepd 361    ifgftswskm pvtrpnfgwg epfwvglmak agpefrnftv fidtkdgkgi
       eawitldear 421    mailqrdpef lafaspnpki ssl
```

GI:359492333, Protein name: PREDICTED: vinorine synthase-like [*Vitis vinifera*]

SEQ ID NO: 65

```
  1    mevtiisret ikpssptphh lrafklslld qlvpccytqv llfylidgfh
       gqsietshis 61    trlkdslset lthfyplags igddelqidc ndegvpyfea rvdcnlsefl
       qepelellnq 121    ffpcdpintp pmaklhlami qvnifnrggi aigvclshki adgvsisafl
       kawaaiargc 181    feeypsfeak slfpqneslp qdysmvlgkc lirtgkcvtk rvvfdasaia
       alkakasvdc 241    trvevvsafi wkramaaakq klgfqrssil thavnlrkkt ilslpessmg
       nlfwiaiteg 301    rvddeaeldl lvdktrkais kiscdfakkl qgeegfavaf ehvkevkaaf
       eedgvdfygf 361    sswckfevye gdfgwgrpiw vssfsgkgsv ykniliffmdt rcgngieewv
       tldeeelgil 421    ecdpeflsfg smdpsplkla hfgqv
```

GI:323331427, Protein name: Atf1p [*Saccharomyces cerevisiae* AWRI796]

SEQ ID NO: 66

```
  1    mdlwkrlfea nptkirdkki knghfisitn tinlsalmne ideknqapvq
       qeclkemiqn 61    gharrmgsve dlyvalnrqn lyrnfctyge lsdyctrdql tlalreiclk
       nptllhivlp 121    trwpnhenyy rsseyysrph pvhdyisvlq elklsgvvin eqpeysavmk
       qileefknsk 181    gsytakifkl tttltipyfg ptgpswrlic lpeehtekwk kfifvsnhcm
       sdgrssihff 241    hdlrdelnni ktppkkldyi fkyeedyqll rklpepiekv idfrppylfi
       pksllsgfiy 301    nhlrfsskgv cmrmddvekt ddvvteiini sptefqaika niksniggkc
       titpflhvcw 361    fvslhrwgkf fkpinfewlt difipadcrs qlpdddemrq myryganvgf
       idftpwisef 421    dmndnkenfw pliehyhevi sealrnkkhl hglgfniqgf vqkyvnidkv
       mcdraigkrr
```

| | |
|---|---|
| 481 | ggtllsnvgl fnqleepdak ysicdlafgq fqgswhqafs lgvcstnvkg mnivvastkn |
| 541 | vvgsqeslee lcsiykalll gp |

GI:34485580, Protein name: lager alcohol acetyltransferase I [*Saccharomyces pastorianus*]

SEQ ID NO: 67

| | |
|---|---|
| 1 | meteesqfss itkiinpktl mntysektsl vgdeclvkmi qnghsrrmgs vedlyaalnr |
| 61 | qklyrnfsty selndyctkd glalalrnic lknptllhiv lparwpdhkk yylsseyysq |
| 121 | prpkhdyisv lpelkldgvi lneqpehnal mkqileefan sngsytakif klttaltipy |
| 181 | tgptsptwrl iclpeeddtn kwkkfifvsn hcmcdgrssi hffqdlrdel nniktlpkkl |
| 241 | dyifeyekdy qllrklpepi enmidfrppy lfipksllsg fiyshlrfss kgvctrmdei |
| 301 | eksdeivtei inispsefqk irtkiklnip gkctitpfle vcwfvtlhkw gkffkplkfe |
| 361 | wltdvfipad crsllpedee vramyrygan vgfvdftpwi skfnmndske nfwpliahyh |
| 421 | evisgaikdk khlnglgfni gslvqkyvni dkvmrdralg ksrggtllsn vgmfhqseet |
| 481 | ehkyrirdla fgqfqgswhq afslgvsstn vkgmniliss tknvvgsgel leelcamyka |
| 541 | lllnp |

GI:365758173, Protein name: Atf1p [*Saccharomyces cerevisiae x Saccharomyces kudriavzevii* VIN7]

SEQ ID NO: 68

| | |
|---|---|
| 1 | miqngharrm gsvedlyval nrqnlyrnfs ayaelsdycs kdqltlalrn iclknptllh |
| 61 | ivlptrwpdh enyylsseyy shphpkhdyi svlpelkldg viineqpeng kivrqileef |
| 121 | rnsngtynak ifklttalti pyfgptspnw rliclpeeht dkwkkfifvs nhcmsdgrss |
| 181 | ihffhdlrae lndiktppkk ldylfkyend yqllrklpep iekvidfrpp ylfipkslls |
| 241 | gfiynhlrfa srgictrmdd meksddvvae iitispselq eirtkiksni qgkctltpfl |
| 301 | qvcwfvslhq wgkffkpinf ewltdifipa dcrpqlpdde evrqmyryga nvgfvdftpw |
| 361 | icesnmnenk enfwpliehy hqvisgalrd nkhlhglgln iqgfvqkyvn idkamcdrai |
| 421 | gkarggtlls nvgmfkqlds sncnysiktw llgnfkghgt khfhwvfvrl m |

GI:255712859, Protein name: KLTH0C11440p [*Lachancea thermotolerans*]

SEQ ID NO: 69

| | |
|---|---|
| 1 | mdslkergha rplghlenyf sitqrqklya nfsmycelsk pcspkqlaya lrsiclgnpi |
| 61 | lvhqvlpkhw pnhleyyasd eflaqptlqh edmrlldnvl lsdivmneqe eygtvvseai |
| 121 | eefsqnggqy skkifdiiad iripygdplk pnwrllcfpe gesnlwrkfi yitnhcssdg |

|     | -continued |
| --- | --- |
|     | Sequence Listing Free Text |

```
 181   rsaanlmrdl seqlnhvpet lpdsdiifny ssdyeglrkl pdpienridy
       kppisyllql 241   lsssyvrdyl gyyskgplvt ridevgenkt yysyflnfsa eqmktikqkl
       ksrlpgctmt 301   pflqacwlts myksgrvfsk smrewffdvv itmntagmlp ddpelrsmyk
       ygsnvggtry 361   nylissfnvg edkdafwslv dyyqgvfnsa mekkhylfpl galmldslre
       ksnmdkvimd 421   dllgkprqgv ilsnvgyfqq kketdgyyvr dlvfaqslgs lrhtfvcnsc
       ttdvggmniv 481   acaaqgsvas ehdwadvcel fkeqtlal
```

GI:156847986, Protein name: hypothetical protein
Kpol_2002p89 [*Vanderwaltozyma polyspora* DSM 70294]

SEQ ID NO: 70
```
   1   meeyapfitq elvdrgharr mgqlenyfal lqrqnlyknf nvygeinepi
       dkfqlgtafr 61   qmllkypilm hvivprkyph heeyyasdey lnnpqpindy ikvmenidle
       dillnsqpey 121   eaivgklldq yksdgykytn rmieiigdis ipicdqtkpn wrllclptke
       sdkkwhafvy 181   isnhcaadgm tsmnffhdiv nglndksset vtevngrmnl vnyakdhkni
       skfpkpiter 241   veyrpslsql pkfmigniar tklnykspca ltttvdkvdm qtfdyilnft
       neevgkirkh 301   ikanthngvt ltpflqtclf vtlyqfgtif qktllewgld svlpvnarky
       lpedaelrds 361   ykygsnvggi hyfnlissfn ikndeaetfw slvdyyhany qkayhngdtf
       vgfgllmsdf 421   ivknknvdkl ikedyvnqkr ggvilsnlgf fpqdtrneyy lndlifaqtf
       gsmkftfgls 481   lcstnvngln igisvvrdaf ndretfekfc khyketiinf anl
```

GI:255711342, Protein name: KLTH0B03806p
[*Lachancea thermotolerans*]

SEQ ID NO: 71
```
   1   mttsqadtkl eelekrghar rlgnlenyfa lgqrqdlysn fgmfceldra
       csenelaeal 61   rgmcleypll lhtvlekkea qdvnfyqtse ylskpwpqhd yirvlqrvrf
       advllndgee 121   yaeivnaalk efasnggqys sevfelinkv ripychnsrp nwrimcfpee
       gnaqsrewrk 181   illlsnhcss dgmssanffh dlqdhlnnlp pslpqadvif dysqdhetlg
       klpapietqi 241   syvgpksyfa qlvgnqvlre yfgyksptpp iprvnepggn dfysyflkit
       psevaavkkk 301   lknkldpsct ltpffqacwf aalyksgivf sksfsqqlsn imvamntaql
       lpedkglkkq 361   yryganvggs hynygissfn vadkpeafwk lvryyqdvfv dakrkkhfly
       plgalmidsi
```

```
421   yktknidlav tnsilgksrl gtmlsnvgyf pqkaratvgg fhiqdlifaq
      ttgsfrftfd 481   inlcatdigg lnitacvaeg alptredwkk lcelfktiil es
```

GI:6321616, Protein name: Atf2p
[*Saccharomyces cerevisiae* S288c]

SEQ ID NO: 72

```
  1   mediegyeph itqelidrgh arrmghleny favlsrqkmy snftvyaeln
      kgvnkrqlml 61   vlkvalqkys tlahtiipkh yphheayyss eeylskpfpq hdfikvishl
      efddlimnnq 121   peyrevmeki seqfkkddfk vtnrlielis pviiplgnpk rpnwrliclp
      gkdtdgfetw 181   knfvyvtnhc gsdgvsgsnf fkdlallfck ieekgfdyde efiedqviid
      ydrdyteisk 241   lpkpitdrid ykpaltslpk fflttfiyeh cnfktssest ltaryspssn
      anasynyllh 301   fstkgvegir aqikknvhdg ctltpfiqac flvalyrldk lftkslleyg
      fdvaipsnar 361   rflpndeelr dsykygsnvg gshyayliss fdipegdndk fwslveyyyd
      rflesydngd 421   hliglgvlql dfivenknid sllansylhq grggaiisnt glvsqdttkp
      yyvrdlifsq 481   sagalrfafg lnvcstnvng mnmdmsvvqg tlrdrgewes fcklfyqtig
      efasl
```

GI:156847986, Protein name: hypothetical protein
Kpol_2002p89 [*Vanderwaltozyma polyspora* DSM 70294]

SEQ ID NO: 73

```
  1   meeyapfitq elvdrgharr mgqlenyfal lqrqnlyknf nvygeinepi
      dkfqlgtafr 61   qmllkypilm hvivprkyph heeyyasdey lnnpqpindy ikvmenidle
      dillnsqpey 121   eaivgklldq yksdgykytn rmieiigdis ipicdqtkpn wrllclptke
      sdkkwhafvy 181   isnhcaadgm tsmnffhdiv nglndksset vtevngrmnl vnyakdhkni
      skfpkpiter 241   veyrpslsql pkfmigniar tklnykspca ltttvdkvdm qtfdyilnft
      neevgkirkh 301   ikanthngvt ltpflqtclf vtlyqfgtif qktllewgld svlpvnarky
      lpedaelrds 361   ykygsnvggi hyfnlissfn ikndeaetfw slvdyyhany qkayhngdtf
      vgfgllmsdf 421   ivknknvdkl ikedyvngkr ggvilsnlgf fpqdtrneyy lndlifaqtf
      gsmkftfgls 481   lcstnvngln igisvvrdaf ndretfekfc khyketiinf anl
```

GI:50286475, Protein name: hypothetical protein
[*Candida glabrata* CBS 138]

SEQ ID NO: 74

```
  1   mapntksieq pliskakisg kgpdgfaiee sllerghsrr mghlenyfai
      mqrqklytnf 61   nmygelnkev treqlavair qillrhpimm qaiipkkfpe heeyytsddy
      yntpfpendf 121   lrvitskikl sdiiineqse dygeiidmil seykkngykf daymqelign
      ivipignpnk
```

Sequence Listing Free Text

```
181   pnwrllclps  aegggaqwkk  fvyisnhccs  daisavnlfq  diaenvslie
      qnswavpyad 241   dvivdyeqdv  adiaklpapi  terveyrppl  sklpkimlvs  flktalnfks
      daletrcnde 301   ysgepetsav  qmgdvcydsi  lnytceevav  irdrikhnvh  gkctvtpfiq
      aaffvamhqs 361   rkllgqkqgf  kewmsewgvd  matpsstrry  lpedpevrdm  ykygsnvggi
      hylymisgmk 421   vereetekfw  slveyyhdil  lashsngdqt  vglgtlmldv  ivdkknvdkl
      irdeylyqkr 481   ggvimsnagy  fhqdpaqayh  vtdlvfgqrp  galkfsfgvn  vvstniggmn
      lnvgmvrrtl 541   rdraefrefi  gildrvirdf  tgln
```

GI:367002213, Protein name: hypothetical protein TPHA_0E03170 [*Tetrapisispora phaffii* CBS 4417]

SEQ ID NO: 75

```
  1   mslealsfde  ykpyiteeli  ergharrmgh  lqdyfaiiqr  qklynnfniy
      celnekvnkv 61   qlshafremf  lqypalieyi  vpkfypkhea  yyrseeylsk  pcpihdyiry
      lnevnindii 121   mneqdeyksi  ttkisdifvk  ndykfsneis  emvstikiai  cdpkkpnwri
      iclpsktsst 181   ewkdfilvsn  hfdsdgtsav  nffedltnil  skqanvendt  ivigndinii
      nyskdyklis 241   klpipiteri  sytptlssip  kfivgnickt  klqytsdggd  tpaefvsedp
      ltydylinfs 301   seevakmkkt  iknclynsvt  ltpfiqacff  vamykynkil  nlnnwwqwgv
      dcalatnarr 361   llpddpetrd  lyrygsnvgg  thyfnlisqf  ninefeydkf  fklvdyyhkn
      yqnsyrngde 421   lvgfgvlfsd  liinntnmdk  tikddytnhk  rggllfsnvg  yrnedltkkv
      hvnniifsqs 481   pgcmkftfgl  nlistdkcgm  nilmngvrgs  vksrenfedf  crffrktven
      fakl
```

GI:366987729, Protein name: hypothetical protein NCAS_0A06920 [*Naumovozyma castellii* CBS 4309]

SEQ ID NO: 76

```
  1   mtqdqvtlde  ykpyiadeli  ergharrmgh  lenyfallqr  qklytnfsiy
      gelnkevkdv 61   dltralrsii  fknpilahti  vpkkypdgep  fyqseeylna  pypehdfikv
      lpklslsdil 121   ineqeefrei  vddiltqfke  angvitpdim  kavayviipi  cdpsrpnwrl
      frlsptkffy 181   isnhctsdai  sgvnifqdic  telsqndeep  frddlqifny  eedwesfhki
      yipitdiiey 241   rpaltslpki  iasalvkgfl  nyrnwptelt  stndkgipfd  fniitftnde
      vnsiretvkk 301   ynctftpflq  acwfvamfnn  gkifhmdswr  ewgldvaips  nsrrfladee
      lkdiykygsn 361   vgglhythli  ssfniqldek  ekfwdlvqyy  qdgytksyen  gdhfsglgll
      mmdglvkrqn
```

| | |
|---|---|
| 421 | idkvissdyl hktragvlfs nagffpqdrt qayhvndllf tqsqgamkfs fglniattni |
| 481 | ggmniainva qgtfddeegi idlsqdfyrn iksfsnia |

GI:372463540, Protein name: hypothetical protein
KAFR_0D01730 [*Kazachstania africana* CBS 2517]

SEQ ID NO: 77

| | |
|---|---|
| 1 | mglstkvees vrevqsqsda ssialledpv aeydipqeli drgharrmgh lenyfamlqr |
| 61 | qelysnfavy lkmnksysrn dlkhalrevi lensvlahti vpkyypdhea fyksekylnv |
| 121 | pypkhdfmki lpslsledii indqseytev vnsiidqfvk dngkitnkls eivsnicipi |
| 181 | ydqsrpnwrl lclpdntdey snfvyisnhc csdgtsginl fqdlvkslng kkspemtspd |
| 241 | sliynyekdf dkisklpaai tdrvdyrpal wklpqfmlst lgkvffsyks papvstkinm |
| 301 | skpqpsfhni lnftpdelnk iriaikknac tmtsflqtcl fitlkehgif anrkwnefgf |
| 361 | ditvpsntrk dlpeelvtsq ykygsnvggl hysflissfi aenfwklcsy ysavlkqadf |
| 421 | lrplgtimld fvvnkqnids misdsylnkk rggiilsnvg yfeqnddece ildlmlmqnv |
| 481 | gglnfsyavn icstnlggmn iclsivegtl kdrddfnafc delkttvrqf cdin |

GI:26991090, Protein name: bkdA1 gene product
[*Pseudomonas putida* KT2440]

SEQ ID NO: 78

| | |
|---|---|
| 1 | mneyaplrlh vpeptgrpgc qtdfsylrin dagqarkpai dvdaadtadl syslvrvlde |
| 61 | qgdaqgpwae didpqilrqg mramlktrif dsrmvvaqrq kkmsfymqsl geeaigsgqa |
| 121 | lalnrtdmcf ptyrqqsilm ardvslvemi cqllsnerdp lkgrqlpimy svreagffti |
| 181 | sgnlatqfvq avgwamasai kgdtkiasaw igdgataesd fhtaltfahv yrapvilnvv |
| 241 | nnqwaistfq aiaggesttf agrgvgcgia slrvdgndfv avyaasrwaa erarrglgps |
| 301 | liewvtyrag phstsddpsk yrpaddwshf plgdpiarlk qhlikighws eeehqavtae |
| 361 | leaaviaaqk eaeqygtlan ghipsaasmf edvykempdh lrrqrelgv |

GI:26991091, Protein name: bkdA2 gene product
[*Pseudomonas putida* KT2440]

SEQ ID NO: 79

| | |
|---|---|
| 1 | matttmtmiq alrsamdvml erddnvvvyg qdvgyfggvf rcteglqnky gksrvfdapi |
| 61 | sesgivgtav gmgayglrpv veiqfadyfy pasdqivsel arlryrsage fiapltlrmp |
| 121 | cgggiyggqt hsgspeamft qvcglrtvmp snpydakgll iasiecddpv iflepkrlyn |
| 181 | gpfdghhdrp vtpwskhphs avpdgyytvp ldkaaitrpg ndvtvltygt tvyvaqvaae |

```
241  esgvdaevid lrslwpldld tivesvkktg rcvvvheatr tcgfgaelvs
     lvgehcfhhl 301  eapiervtgw dtpyphagew ayfpgpsrvg aalkkvmev
```

GI:26991092, Protein name: bkdB gene product
[*Pseudomonas putida* KT2440]

SEQ ID NO: 80
```
  1  mgthvikmpd igegiaqvel vewfvkvgdi iaedqvvadv mtdkatveip
     spvsgkvlal 61  ggqpgevmav gselirieve gsgnhvdvpq pkpveapaap iaakpepqkd
     vkpavyqapa 121  nheaapivpr qpgdkplasp avrkraldag ielryvhgsg pagrilhedl
     dafmskpqsn 181  agqapdgyak rtdseqvpvi glrrkiaqrm qdakrrvahf syveeidvta
     lealrqqlns 241  khgdsrgklt llpflvralv valrdfpqin atyddeaqii trhgavhvgi
     atqgdnglmv 301  pvlrhaeags lwanageisr lanaarnnka sreelsgsti tltslgalgg
     ivstpvvntp 361  evaivgvnrm verpvvidgq ivvrkmmnls ssfdhrvvdg mdaalfiqav
     rgllegpacl 421  fve
```

SEQ ID NO: 81
gaaaacgaaagctctctaaGCTGAGCAGGAGAAATTAACTATGGCGCATGATCAGAGCCT

SEQ ID NO: 82
agcctttcgttttatttgatgcctctagaGCTCAGCTTACAGGCTGCTCTGGGTGAAATG

SEQ ID NO: 83
cgaaagctctctaaGCTGAGCAGGAGAAATTAACTATGAATGAAATCGATGAGAAAAATC

SEQ ID NO: 84
agcctttcgttttatttgatgcctctagaGCTCAGCTTAAGGGCCTAAAAGGAGAGCTTT

SEQ ID NO: 85
cgaaagctctctaaGCTGAGCAGGAGAAATTAACTATGGAAGATATAGAAGGATACGAAC

SEQ ID NO: 86
cctttcgattatttgatgcctctagaGCTCAGCTTAAAGCGACGCAAATTCGCCGATGG

SEQ ID NO: 87
aaacgaaagctctctaaGCTGAGCAGGAGAAATTAACTATGGACAGCAAACAGAGCAGCG

SEQ ID NO: 88
cctttcgttttatttgatgcctctagaGCTCAGCTTAAAGCGCTGGGGTGATGAACGCAT

SEQ ID NO: 89
aaacgaaagctctctaaGCTGAGCAGGAGAAATTAACTATGGAGAAAATAGAAGTGAGCA

SEQ ID NO: 90
cctttcgttttatttgatgcctctagaGCTCAGCTTAGATCAGCGTCTTTGGACTCGCCA

SEQ ID NO: 91
GGGCCCgcatgcAGGAGAAATTAACTATGAACAACTTTAATCTGCACACCCC

SEQ ID NO: 92
GGGCCCtctagaTTAGCGGGCGGCTTCGTATATACGGC

What is claimed is:

1. A method comprising:
   introducing into a host cell a first heterologous polynucleotide operably linked to a promoter, wherein the first heterologous polynucleotide encodes at least one of:
   an acyl-CoA synthetase or a branched-chain keto acid dehydrogenase;
   introducing into a host cell a second heterologous polynucleotide operably linked to a promoter, wherein the second heterologous polynucleotide encodes an alpha-ketoisovalerate decarboxylase; and
   introducing into a host cell a third heterologous polynucleotide operably linked to a promoter, wherein the third heterologous polynucleotide encodes at least one of:
   an acyl transferase; or
   an acyl-CoA synthetase.

2. The method of claim 1 wherein the carbon source comprises one or more of:
   glucose, pyruvate, ketovaline, $CO_2$, cellulose, xylose, sucrose, arabinose, glycerol, alginate, glucarate, or galacturonate.

3. The method of claim 1 wherein the host cell is a fungal cell.

4. The method of claim 1 wherein the host cell is a bacterial cell.

5. The method of claim 1 wherein the host cell is photosynthetic.

6. The method of claim 1 wherein the host cell is cellulolytic.

7. The method of claim 1 wherein more than one heterologous polynucleotide is provided in a single molecule.

* * * * *